United States Patent
Kim et al.

(10) Patent No.: US 10,221,138 B2
(45) Date of Patent: Mar. 5, 2019

(54) BIARYL DERIVATIVES AS GPR120 AGONISTS

(71) Applicant: LG CHEM, LTD., Seoul (KR)

(72) Inventors: Young Kwan Kim, Daejeon (KR); Sang Yun Park, Daejeon (KR); Hyun Woo Joo, Daejeon (KR); Eun Sil Choi, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/894,928

(22) PCT Filed: Jun. 26, 2014

(86) PCT No.: PCT/KR2014/005688
§ 371 (c)(1),
(2) Date: Nov. 30, 2015

(87) PCT Pub. No.: WO2014/209034
PCT Pub. Date: Dec. 31, 2014

(65) Prior Publication Data
US 2016/0168096 A1    Jun. 16, 2016

(30) Foreign Application Priority Data

Jun. 27, 2013 (KR) .................. 10-2013-0074927

(51) Int. Cl.
| | |
|---|---|
| C07C 59/68 | (2006.01) |
| C07C 59/72 | (2006.01) |
| C07C 217/80 | (2006.01) |
| C07C 323/52 | (2006.01) |
| C07C 323/53 | (2006.01) |
| C07D 213/30 | (2006.01) |
| C07D 213/64 | (2006.01) |
| C07D 213/65 | (2006.01) |
| C07D 213/70 | (2006.01) |
| C07D 213/74 | (2006.01) |
| C07D 401/04 | (2006.01) |
| C07D 401/12 | (2006.01) |
| C07D 405/12 | (2006.01) |
| C07D 413/12 | (2006.01) |
| C07D 213/643 | (2006.01) |

(52) U.S. Cl.
CPC .......... *C07D 213/643* (2013.01); *C07C 59/68* (2013.01); *C07C 59/72* (2013.01); *C07C 217/80* (2013.01); *C07C 323/52* (2013.01); *C07C 323/53* (2013.01); *C07D 213/30* (2013.01); *C07D 213/64* (2013.01); *C07D 213/65* (2013.01); *C07D 213/70* (2013.01); *C07D 213/74* (2013.01); *C07D 401/04* (2013.01); *C07D 401/12* (2013.01); *C07D 405/12* (2013.01); *C07D 413/12* (2013.01); *C07C 2601/02* (2017.05); *C07C 2601/04* (2017.05); *C07C 2601/08* (2017.05)

(58) Field of Classification Search
None
See application file for complete search history.

(56) References Cited

U.S. PATENT DOCUMENTS

| | | | |
|---|---|---|---|
| 4,440,787 A | | 4/1984 | de Vincentiis |
| 5,665,777 A | | 9/1997 | Fesik et al. |
| 6,300,514 B1 | | 10/2001 | Takahashi et al. |
| 6,605,604 B1 | * | 8/2003 | Casara ............ C07C 233/82 514/173 |
| 2001/0041715 A1 | | 11/2001 | Malamas et al. |
| 2003/0166687 A1 | | 9/2003 | Warpehoski et al. |
| 2003/0207889 A1 | | 11/2003 | Owen et al. |
| 2004/0147755 A1 | | 7/2004 | Malamas |
| 2005/0027013 A1 | | 2/2005 | Danvy et al. |
| 2005/0187277 A1 | | 8/2005 | Mjalli et al. |
| 2006/0128807 A1 | | 6/2006 | Kobayashi et al. |
| 2008/0167378 A1 | | 7/2008 | Fukatsu et al. |
| 2009/0111730 A1 | | 4/2009 | Dorwald et al. |
| 2010/0004159 A1 | | 1/2010 | Bouey et al. |
| 2010/0022592 A1 | | 1/2010 | Epple et al. |
| 2010/0130559 A1 | | 5/2010 | Hashimoto et al. |
| 2010/0274022 A1 | | 10/2010 | Tsujimoto et al. |
| 2011/0065739 A1 | | 3/2011 | Ishikawa et al. |
| 2011/0184031 A1 | | 7/2011 | Tsujimoto et al. |
| 2012/0035196 A1 | | 2/2012 | Negoro et al. |
| 2012/0225061 A1 | * | 9/2012 | Burger ............ A61K 31/444 424/133.1 |
| 2014/0148459 A1 | * | 5/2014 | Khera ............ C07D 237/32 514/243 |

FOREIGN PATENT DOCUMENTS

| | | | | |
|---|---|---|---|---|
| CA | 2 504 207 A1 | 5/2004 | | |
| EP | 0 080 010 A1 | 6/1983 | | |
| EP | 0 317 204 A2 | 5/1989 | | |
| EP | 2 415 755 A1 | 2/2012 | | |
| GB | 916242 A | 1/1963 | | |
| JP | 2005-247822 A | 9/2005 | | |
| JP | WO 2013187496 A1 | * | 12/2013 | ........... C07D 401/14 |
| WO | WO 92/01675 A2 | 2/1992 | | |
| WO | WO 95/02580 A2 | 1/1995 | | |
| WO | WO 97/18188 A1 | 5/1997 | | |

(Continued)

OTHER PUBLICATIONS

Chollet et al. Bioorganic & Medicinal Chemistry 10 (2002) 531-544.*

(Continued)

*Primary Examiner* — Joseph R Kosack
(74) *Attorney, Agent, or Firm* — Rothwell, Figg, Ernst & Manbeck, P.C.

(57) ABSTRACT

The present invention relates to biaryl derivatives of Formula 1, a method for preparing the same, a pharmaceutical composition comprising the same and use thereof. The biaryl derivatives of Formula 1 according to the present invention promote GLP-1 formation in the gastrointestinal tract and improve insulin resistance in the liver or in muscle due to anti-inflammatory action in macrophages, lipocytes, etc., and can accordingly be effectively used for preventing or treating diabetes, complications of diabetes, obesity, non-alcoholic fatty liver, steatohepatitis, osteoporosis or inflammation.

10 Claims, No Drawings

(56) References Cited

FOREIGN PATENT DOCUMENTS

| | | |
|---|---|---|
| WO | WO 99/58518 A2 | 11/1999 |
| WO | WO 00/59864 A1 | 10/2000 |
| WO | WO 02/060875 A1 | 8/2002 |
| WO | WO 03/099805 A1 | 12/2003 |
| WO | WO 2004/000814 A1 | 12/2003 |
| WO | WO 2004/010996 A1 | 2/2004 |
| WO | WO 2004/039764 A1 | 5/2004 |
| WO | WO 2004/089885 A1 | 10/2004 |
| WO | WO 2004/099170 A2 | 11/2004 |
| WO | WO 2004/113266 A1 | 12/2004 |
| WO | WO 2005/105724 A1 | 11/2005 |
| WO | WO 2006/005667 A2 | 1/2006 |
| WO | WO 2006/037982 A2 | 4/2006 |
| WO | WO 2007/055417 A1 | 5/2007 |
| WO | WO 2008/002676 A2 | 1/2008 |
| WO | WO 2008/034600 A1 | 3/2008 |
| WO | WO 2008/066131 A1 | 6/2008 |
| WO | WO 2008/139879 A1 | 11/2008 |
| WO | WO 2008/139987 A1 | 11/2008 |
| WO | WO 2009/011285 A1 | 1/2009 |
| WO | WO 2009/147990 A1 | 12/2009 |
| WO | WO 2009/151800 A1 | 12/2009 |
| WO | WO 2010/048207 A2 | 4/2010 |
| WO | WO 2010048149 A2 * 4/2010 | ........... A61K 31/506 |
| WO | WO 2010/080537 A1 | 7/2010 |
| WO | WO 2010/104195 A1 | 9/2010 |
| WO | WO 2010/123016 A1 | 10/2010 |
| WO | WO 2011/054530 A1 | 5/2011 |
| WO | WO 2011/159297 A1 | 12/2011 |
| WO | WO 2011/159839 A2 | 12/2011 |
| WO | WO 2012038942 A1 * 3/2012 | ........... C07D 237/32 |
| WO | WO 2012/081736 A1 | 6/2012 |
| WO | WO 2013/056679 A1 | 4/2013 |

OTHER PUBLICATIONS

Jepsen et al. "Synthesis of Functionalized Dibenzothiophenes—An Efficient Three-Step Approach Based on Pd-Catalyzed C—C and C—S Bond Formations" European Journal of Organic Chemistry, 2011, pp. 53-57.*

Finch et al. "Synthesis of 2-methyl and 2-phenyl-5-thiopyridines" Journal of Organic Chemistry, 1975, vol. 40, pp. 569-574.*

Australian Office Action, dated May 20, 2016, for Australian Application No. 2014299457.

English translation of the Chinese Office Action, dated Oct. 21, 2016, for Chinese Application No. 201480036409.7.

Luker et al., "Switching between agonists and antagonists at CRTh2 in a series of highly potent and selective biaryl phenoxyacetic acids," Elsevier, Bioorganic & Medicinal Chemistry Letters, vol. 21, Issue 12, Jun. 15, 2011 (available online Apr. 28, 2011), pp. 3616-3621.

Supplementary European Search Report, dated Oct. 21, 2016, for European Application No. 14 81 8620.

STN Registry Database, Reg Nos. 1182268-18-3, 1182245-58-4, 1182244-95-6, 1182222-49-6, Entered STN: Sep. 10, 2009, 2 pages.

International Search Report, issued in PCT/KR2014/005688, dated Sep. 30, 2014.

Suzuki et al., "Identification of G protein-coupled receptor 120-selective agonists derived from PPAR-gamma agonists", J. Med. Chem. 2008, vol. 51, pp. 7640-7644.

Chen et al., "A Mixed Cyclodextrin-Biphenyl Thermotropic Liquid Crystal: Synthesis, Liquid-Crystalline Properties, and Supramolecular Organization," Journal of Polymer Science: Part A: Polymer Chemistry, vol. 48, 2010, pp. 2838-2845.

Weiser et al., "3,3'-Disubstituted bipolar biphenyls as inhibitors of nuclear receptor coactivator binding," Bioorganic & Medicinal Chemistry Letters, vol. 22, 2012 (Available online Sep. 13, 2012), pp. 6587-6590.

Australian Office Action for Appl. No. 2014299457 dated May 17, 2017.

Geiger et al., "Self-Assembly of Aromatic-Derivatized Amphiphiles: Phenyl, Biphenyl, and Terphenyl Fatty Acids and Phospholipids", vol. 15, No. 17, 1999 (Published online Jun. 16, 1999), pp. 5606-5616, Langmuir.

Hirani et al., "Liquid crystallinity of newly synthesized glucose derivatives with mesogenic side chains", vol. 23, No. 1, 1997, pp. 59-67 (pp. 59-60 provided only), Liquid Crystals.

STN Registry Database, Reg. No. 1026324-23-1, Entered STN: Jun. 8, 2008, 1 page.

STN Registry Database, Reg. No. 1181723-08-9, Entered STN: Sep. 9, 2009, 1 page.

STN Registry Database, Reg. No. 890534-53-9, Entered STN: Jul. 5, 2006, 1 page.

STN Registry Database, Reg. Nos. 1182241-89-9, 1182071-50-6, 1182253-77-5, 1182268-13-8, 1182026-98-7, Entered STN: Sep. 10, 2009, 2 pages.

* cited by examiner

BIARYL DERIVATIVES AS GPR120 AGONISTS

TECHNICAL FIELD

The present invention relates to novel biaryl derivatives as GPR120 agonists, a method for preparing the same, a pharmaceutical composition comprising the same as active components and use thereof. Herein a GPR120 agonist means a compound which can be effectively used for preventing or treating diabetes, complications of diabetes, obesity, non-alcoholic fatty liver, steatohepatitis, osteoporosis or inflammation, by promoting GLP-1 in the gastrointestinal tract and anti-inflammatory action.

BACKGROUND ART

Diabetes is divided into two types—i.e., insulin-dependent type 1 diabetes and insulin-independent (insulin-resistant) type 2 diabetes which is found in 90% or more of diabetic patients.

GPR120 agonists, which are noted for possible treatment of type 2 diabetes, are known to have (1) an antidiabetic effect caused by the actions of increasing incretin hormone in intestinal cells, (2) anti-inflammatory action in macrophages, and (3) an action of improvement on insulin resistance in lipocytes. They are also known as a possible treatment of type 1 diabetes due to the improvement on proliferation of pancreas cells by anti-inflammatory action.

G protein-coupled receptor 120 (GPR120) is expressed copiously in the intestines, lungs, adipose tissue, and macrophages which induce inflammation, and is activated by long-chain free fatty acid (FFA). GPR120 stimulates the secretion of glucagon-like peptide-1 (GLP-1) by FFA. GLP-1, an incretin hormone, is known to stimulate the secretion of insulin in the pancreas dependently on blood glucose level, and also to have the effect of improvement of insulin resistance, proliferation of β-cells, appetite loss and increase of satiety. Recently, GPR120 is known to relate with improvement of insulin resistance and anti-inflammatory effect, and therefore, it is regarded as a target for developing a drug to effectively improve insulin resistance, type 2 diabetes and obesity involving low-level chronic inflammation. Furthermore, in animal experiments of type 1 diabetes, GPR120 agonists are reported to improve the secretion of insulin by the action of proliferation of β-cells.

Since GPR 120 agonists also have anti-inflammatory action, they are reported to be a possible treatment of inflammation-related diseases for example, steatohepatitis, rheumatoid arthritis, etc.

Considering the above, researches on GPR120 agonists are actively in progress. In the representative compounds presented as GPR120 agonists, two aryl groups are connected with a center bridge structure, and the characteristic feature is that one of two aryl groups is substituted by carboxylic acid. GPR120 agonist compounds are disclosed in WO2011/159297, WO2010/080537, WO2010/104195, WO2010/048207, WO2009/147990, WO2008/066131, WO2008/103500 and WO2008/139879.

DISCLOSURE OF INVENTION

Technical Problem

The object of the present invention is to provide novel biaryl derivatives as GPR120 agonists.

Another object of the present invention is to provide a method for preparing the biaryl derivatives.

Still another object of the present invention is to provide a pharmaceutical composition for the prevention and treatment of diabetes, complications of diabetes, obesity, non-alcoholic fatty liver, steatohepatitis, osteoporosis or inflammation which comprises as active components the biaryl derivatives, and a method for preparing the composition.

A still further object of the present invention is to provide a method for preventing and treating diabetes, complications of diabetes, obesity, non-alcoholic fatty liver, steatohepatitis, osteoporosis or inflammation which use the biaryl derivatives as active components.

Solution to Problem

Therefore, the present invention provides biaryl derivatives of Formula 1, or pharmaceutically acceptable salts or isomers thereof:

[Formula 1]

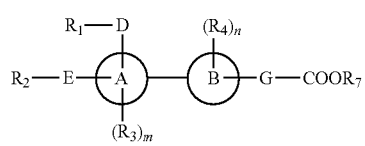

wherein,

A and B represent independently phenyl or pyridine, any one of $R_1$-D- and $R_2$-E- cannot exist, D and E represent independently carbon, nitrogen, oxygen or sulfur, or represent direct bond, and any one of $R_1$ and $R_2$ cannot exist, or $R_1$ and $R_2$ represent independently hydrogen, halogen, optionally substituted $C_1$-$C_6$-alkyl, $C_3$-$C_{10}$-cycloalkyl, $C_2$-$C_6$-alkenyl, $C_2$-$C_6$-alkynyl, $C_3$-$C_{10}$-heterocycloalkyl, $C_1$-$C_6$-alkyl-$C_3$-$C_{10}$-cycloalkyl, $C_1$-$C_6$-alkyl-$C_3$-$C_{10}$-heterocycloalkyl, aryl, $C_1$-$C_6$ alkylaryl, heteroaryl or $C_1$-$C_6$-alkyl-$C_5$-$C_6$-heteroaryl, and when D and E represent nitrogen or carbon, $R_1$ and $R_2$ can represent two or three optionally substituted $C_1$-$C_6$ alkyl, $C_3$-$C_{10}$-cycloalkyl, $C_2$-$C_6$-alkenyl, $C_2$-$C_6$-alkynyl, $C_1$-$C_6$-alkyl-$C_3$-$C_{10}$-cycloalkyl, aryl or $C_1$-$C_6$-alkylaryl which may be the same or different, G represents -J-$(CR_5R_6)_p$, wherein J represents oxygen or sulfur, $R_5$ and $R_6$ represent independently hydrogen, halogen, optionally substituted alkyl or cycloalkyl, hydroxyl or amine, and $R_5$ and $R_6$ which are substituted at the same or different carbon may be connected to form optionally substituted cycloalkyl or cycloheteroalkyl, $R_3$ and $R_4$ cannot independently exist depending on the number of m or n, or represent independently hydrogen, halogen or optionally substituted $C_1$-$C_6$-alkyl or $C_1$-$C_6$-alkoxy, $R_7$ represents hydrogen, alkyl or cycloalkyl, m and n represent independently an integer of 0 to 5, and p represents an integer of 1 to 6.

The compounds of Formula 1 according to the present invention can form pharmaceutically acceptable salts, which include acid-addition salts which are formed from inorganic acids such as hydrochloric acid, sulfuric acid, nitric acid, phosphoric acid, hydrobromic acid and hydroiodic acid; organic acids such as tartaric acid, formic acid, citric acid, acetic acid, trichloroacetic acid, trifluoroacetic acid, gluconic acid, benzoic acid, lactic acid, fumaric acid, maleic acid and salicylic acid; or sulfonic acids such as methanesulfonic acid, ethanesulfonic acid, benzenesulfonic acid and p-toluenesulfonic acid, which form non-toxic acid-addition salts including pharmaceutically acceptable anions. For example, the pharmaceutically acceptable carboxylic acid salts include the salts with alkali metal or alkali earth metal such as lithium, sodium, potassium, calcium and magnesium; salts with amino acid such as lysine, arginine and guanidine; organic salts such as dicyclohexylamine, N-methyl-D-glucamine, tris(hydroxymethyl)methylamine, diethanolamine, choline and triethylamine. The compounds of Formula 1 according to the present invention can be converted into their salts by conventional methods.

Furthermore, since the compounds of Formula 1 according to the present invention can have an asymmetric carbon center and asymmetric axis or plane, they can exist as E- or Z-isomer, R- or S-isomer, racemic mixtures or diastereoisomer mixtures and each diastereoisomer, all of which are within the scope of the present invention.

Herein, unless indicated otherwise, the term "the compounds of Formula 1" is used to mean all the compounds of Formula 1, including the pharmaceutically acceptable salts and isomers thereof.

The terms used herein are defined as follows.

Halogen or halo means fluoride (F), chlorine (Cl), bromine (Br) or iodine (I).

Alkyl means straight or branched hydrocarbons, and is preferably $C_1$-$C_6$-alkyl. Examples of alkyl include, but are not limited to, methyl, ethyl, n-propyl, i-propyl, n-butyl, i-butyl, tert-butyl, acetylene, vinyl, trifluoromethyl and the like.

Cycloalkyl means partially or fully saturated single or fused ring hydrocarbons, and is preferably $C_3$-$C_{10}$-cycloalkyl. Examples of cycloalkyl include, but are not limited to, cyclopropyl, cyclobutyl, cyclopentyl, cyclohexyl, cyclohexenyl and the like.

Aryl means aromatic hydrocarbons, preferably $C_5$-$C_{10}$-aryl, and includes, but is not limited to, phenyl, naphthyl and the like.

Heteroaryl means aromatic hydrocarbons which form a single or fused ring including at least one hetero atom selected from N, O and S, and is preferably $C_3$-$C_9$-heteroaryl. Examples of heteroaryl include, but are not limited to, pyridinyl, pyrimidinyl, pyridazinyl, oxadiazolyl, isoxadiazolyl, tetrazolyl, triazolyl, indolyl, isoxazolyl, oxazolyl, thiazolyl, imidazolyl, thiophenyl, benzthiazole, benzimidazole, 1,2,3,4-tetrahydroisoquinolyl, thiazolopyridyl and the like.

Heterocyclyl means partially or fully saturated hydrocarbons which form a single or fused ring including at least one hetero atom selected from N, O and S, and is preferably $C_3$-$C_{10}$-heterocyclyl. Examples of heterocyclyl include, but are not limited to, pyrrolidinyl, piperidinyl, morpholinyl, imidazolinyl, piperazinyl, tetrahydrofuran, tetrahydrothiofuran and the like.

Arylalkyl and heteroarylalkyl mean groups which are formed by the combination of the above-mentioned aryl with alkyl or heteroaryl with alkyl. Examples include, but are not limited to, benzyl, thiophene methyl, pyrimidine methyl and the like.

The above-mentioned amine, alkyl, cycloalkyl, aryl, heteroaryl, heterocyclyl, arylalkyl and heteroarylalkyl may be substituted by at least one group selected from the following groups: alkyl, cycloalkyl, heterocyclyl, aryl, heteroaryl, arylalkyl, heteroarylalkyl, heterocyclylalkyl, oxo, cyano, halo, nitro, —OR, —OC(O)R, —OC(O)OR, SR, —S(O)R, —S(O)$_2$R, —C(O)R, —C(O)OR, —C(S)R, —C(O)NRR, —NR$_2$, —NRCHO, —NRC(O)R, —NRC(O)NRR, —C(S) NRR, —NRC(S)R and —NRC(S)NRR, wherein R is independently selected from hydrogen, alkyl, cycloalkyl, heterocyclyl, aryl, heteroaryl, arylalkyl and heteroarylalkyl, and when two Rs are substituted, they may be connected to form cycloalkyl or heterocyclyl.

Representative compounds of Formula 1 according to the present invention include, but are not limited to, the following compounds:

4-[4-(6-phenoxy-2-pyridyl)phenoxy]butyric acid;
4-[2,6-difluoro-4-(6-isopropylsulfanyl-2-pyridyl)phenoxy] butyric acid;
4-[2,6-difluoro-4-(6-phenoxy-2-pyridyl)phenoxy]butyric acid;
4-[2-chloro-4-(6-isopropylsulfanyl-2-pyridyl)phenoxy]butyric acid;
4-[2-fluoro-4-(6-isopropylsulfanyl-2-pyridyl)phenoxy]butyric acid;
4-[4-(6-cyclopentylsulfanyl-2-pyridyl)-2,6-difluoro-phenoxy]butyric acid;
4-[4-(2-cyclobutylsulfanyl-pyridin-3-yl)-2-methoxy-phenoxy]-butyric acid;
4-[2,6-difluoro-4-(2-isopropylsulfanyl-4-pyridyl)phenoxy] butyric acid;
4-[4-[6-(cyclopentoxy)-2-pyridyl]-2,6-difluoro-phenoxy] butyric acid;
4-[4-(2-cyclobutylsulfanyl-pyridin-3-yl)-2,6-dimethyl-phenoxy]-butyric acid;
4-[4-[3-(cyclopentoxy)phenyl]-2,6-difluoro-phenoxy]butyric acid;
4-[2,6-difluoro-4-(6-pyrrolidin-1-yl-2-pyridyl)phenoxy]butyric acid;
4-[4-(2-sec-butylsulfanyl-pyridin-3-yl)-2,6-difluoro-phenoxy]-butyric acid;
4-[4-[3-(cyclopentoxy)phenyl]-2,3-difluoro-phenoxy]butyric acid;
4-[2,6-difluoro-4-[6-(1-piperidyl)-2-pyridyl]phenoxy]butyric acid;
4-[4-(6-anilino-2-pyridyl)-2,6-difluoro-phenoxy]butyric acid;
4-[2,6-difluoro-4-[6-(N-methylanilino)-2-pyridyl]phenoxy] butyric acid;
4-[4-[6-(cyclopentylamino)-2-pyridyl]-2,6-difluoro-phenoxy]butyric acid;
4-[4-[6-(cyclopropylmethylsulfanyl)-2-pyridyl]-2,6-difluoro-phenoxy]butyric acid;
4-[4-(6-cyclobutylsulfanyl-2-pyridyl)-2,6-difluoro-phenoxy]butyric acid;
4-[2,6-difluoro-4-(6-propylsulfanyl-2-pyridyl)phenoxy]butyric acid;
4-[2,6-difluoro-4-(6-isopropoxy-2-pyridyl)phenoxy]butyric acid;
4-[2,6-difluoro-4-(6-propoxy-2-pyridyl)phenoxy]butyric acid;
4-[4-[6-(cyclopropylmethoxy)-2-pyridyl]-2,6-difluoro-phenoxy]butyric acid;
4-[4-[6-(cyclobutoxy)-2-pyridyl]-2,6-difluoro-phenoxy]butyric acid;
4-[4-[6-(cyclobutoxy)-2-pyridyl]-2-methyl-phenoxy]butyric acid;
4-[4-[6-(cyclobutoxy)-2-pyridyl]-2-(trifluoromethyl)phenoxy]butyric acid;
4-[4-(2-cyclobutylsulfanyl-3-pyridyl)-2,6-difluoro-phenoxy]pentanoic acid;
4-[4-[6-(cyclobutoxy)-2-pyridyl]-2,6-difluoro-phenoxy] pentanoic acid;
4-[[5-(2-cyclobutylsulfanyl-3-pyridyl)-2-pyridyl]oxy]pentanoic acid;
4-{2,6-difluoro-4-[2-(3-methyl-butylsulfanyl)-pyridin-3-yl]-phenoxy}-butyric acid;

4-{2,6-difluoro-4-[2-(2-fluoro-ethoxy)-pyridin-3-yl]-phenoxy}-butyric acid;
2-[1-[[4-(2-cyclobutylsulfanyl-3-pyridyl)-2,6-difluoro-phenoxy]methyl]cyclopropyl]acetic acid;
2-[1-[[4-[3-(cyclobutoxy)phenyl]-2,6-difluoro-phenoxy]methyl]cyclopropyl]acetic acid;
4-[[6-[3-(cyclobutoxy)phenyl]-3-pyridyl]oxy]butyric acid;
4-[[6-[3-(cyclopentoxy)phenyl]-3-pyridyl]oxy]butyric acid;
4-(2'-phenoxy-biphenyl-4-yloxy)-butyric acid;
4-[4-(2-isopropylsulfanyl-pyridin-3-yl)-phenoxy]-butyric acid;
4-(3,5-difluoro-2'-phenoxy-biphenyl-4-yloxy)-butyric acid;
4-[4-(2-cyclopentylsulfanyl-pyridin-3-yl)-phenoxy]-butyric acid;
4-[2,6-difluoro-4-(2-isopropylsulfanyl-pyridin-3-yl)-phenoxy]-butyric acid;
4-[2,6-difluoro-4-(2-phenoxy-pyridin-3-yl)-phenoxy]-butyric acid;
4-[2,6-difluoro-4-(2-isopropoxy-pyridin-3-yl)-phenoxy]-butyric acid;
4-[4-(2-cyclopentyloxy-pyridin-3-yl)-2,6-difluoro-phenoxy]-butyric acid;
4-[4-(2-cyclopentylsulfanyl-pyridin-3-yl)-2,6-difluoro-phenoxy]-butyric acid;
4-[4-(2-cyclopropylmethoxy-pyridin-3-yl)-2,6-difluoro-phenoxy]-butyric acid;
4-[4-(2-cyclopropylmethylsulfanyl-pyridin-3-yl)-2,6-difluoro-phenoxy]-butyric acid;
4-[4-(2-cyclobutylsulfanyl-pyridin-3-yl)-phenoxy]-butyric acid;
4-[4-(2-cyclopropylmethylsulfanyl-pyridin-3-yl)-phenoxy]-butyric acid;
4-[4-(2-cyclobutylsulfanyl-pyridin-3-yl)-2,6-difluoro-phenoxy]-butyric acid;
4-[4-(2-propylsulfanyl-pyridin-3-yl)-phenoxy]-butyric acid;
4-(3,5-difluoro-2'-isopropoxy-biphenyl-4-yloxy)-butyric acid;
4-(2'-cyclobutoxy-3,5-difluoro-biphenyl-4-yloxy)-butyric acid;
4-(2'-cyclopropylmethoxy-3,5-difluoro-biphenyl-4-yloxy)-butyric acid;
4-(2'-cyclopentyloxy-3,5-difluoro-biphenyl-4-yloxy)-butyric acid;
4-(2'-cyclopentyloxy-biphenyl-4-yloxy)-butyric acid;
4-(2'-isopropoxy-biphenyl-4-yloxy)-butyric acid;
4-(2'-cyclopropylmethoxy-biphenyl-4-yloxy)-butyric acid;
4-[4-(2-cyclobutylsulfanyl-pyridin-3-yl)-2,6-difluoro-phenoxy]-2-methyl-butyric acid;
2-[4-(2-cyclobutylsulfanyl-pyridin-3-yl)-2,6-difluoro-phenoxymethyl]-cyclopropane carboxylic acid;
4-[4-(2-cyclobutylsulfanyl-pyridin-3-yl)-2,5-difluoro-phenoxy]-butyric acid;
4-[4-(6-cyclobutylsulfanyl-pyridin-2-yl)-2,5-difluoro-phenoxy]-butyric acid;
4-[4-(2-tert-butylsulfanyl-pyridin-3-yl)-2,6-difluoro-phenoxy]-butyric acid;
6-[2,6-difluoro-4-(2-propylsulfanyl-3-pyridyl)phenoxy] hexanoic acid;
4-{2,6-difluoro-4-[6-(2-methyl-propenyl)-pyridin-2-yl]-phenoxy}-butyric acid;
4-[2,6-difluoro-4-(6-isobutyl-pyridin-2-yl)-phenoxy]-butyric acid;
4-[4-(2-cyclobutylsulfanyl-pyridin-3-yl)-3,5-difluoro-phenoxy]-butyric acid;
4-{2,6-difluoro-4-[2-(tetrahydro-pyran-4-yloxy)-pyridin-3-yl]-phenoxy}-butyric acid;
4-{2,6-difluoro-4-[2-(tetrahydro-furan-3-yloxy)-pyridin-3-yl]-phenoxy}-butyric acid;
4-[4-(2-cyclobutoxy-pyridin-3-yl)-2,6-difluoro-phenoxy]-butyric acid;
4-{2,6-difluoro-4-[2-(2-methoxy-ethoxy)-pyridin-3-yl]-phenoxy}-butyric acid;
4-[2,6-difluoro-4-(2-pyrrolidin-1-yl-3-pyridyl)phenoxy]butanoic acid;
4-[4-[2-(cyclopentylamino)-3-pyridyl]-2,6-difluoro-phenoxy]butanoic acid;
4-[4-[2-(cyclopropylmethylamino)-3-pyridyl]-2,6-difluoro-phenoxy]butanoic acid;
4-[4-[6-(cyclopropylmethylamino)-2-pyridyl]-2,6-difluoro-phenoxy]butanoic acid;
4-[2,6-difluoro-4-[2-(isopropylamino)-3-pyridyl]phenoxy]butanoic acid;
4-[4-[2-(cyclopropylamino)-3-pyridyl]-2,6-difluoro-phenoxy]butanoic acid;
4-[2,6-difluoro-4-[6-(isopropylamino)-2-pyridyl]phenoxy]butanoic acid;
4-[4-[2-(cyclopentylamino)phenyl]-2,6-difluoro-phenoxy]butanoic acid;
4-[4-[3-(cyclopentylamino)phenyl]-2,6-difluoro-phenoxy]butanoic acid;
4-[2,6-difluoro-4-[2-(propylamino)phenyl]phenoxy]butanoic acid;
4-[4-[2-(cyclopropylmethylamino)phenyl]-2,6-difluoro-phenoxy]butanoic acid;
4-[2,6-difluoro-4-[2-(isopropylamino)phenyl]phenoxy]butanoic acid;
4-[4-[2-(cyclopentylamino)phenyl]phenoxy]butanoic acid;
4-[4-[2-(cyclopropylmethylamino)phenyl]phenoxy]butanoic acid;
4-[4-[2-(propylamino)phenyl]phenoxy]butanoic acid;
4-[4-[2-(isopropylamino)phenyl]phenoxy]butanoic acid;
4-[4-[2-(cyclobutylamino)phenyl]phenoxy]butanoic acid;
4-[4-[2-(cyclobutylamino)phenyl]-2,6-difluoro-phenoxy]butanoic acid;
4-[4-[3-(cyclopropylmethylamino)phenyl]-2,6-difluoro-phenoxy]butanoic acid;
4-[2,6-difluoro-4-[3-(isopropylamino)phenyl]phenoxy]butanoic acid;
4-[2,6-difluoro-4-(3-pyrrolidin-1-ylphenyl)phenoxy]butanoic acid;
4-[4-[3-(cyclobutylamino)phenyl]-2,6-difluoro-phenoxy]butanoic acid;
4-[2,6-difluoro-4-[3-(propylamino)phenyl]phenoxy]butanoic acid;
4-[4-[5-chloro-2-(cyclopentylamino)phenyl]-2,6-difluoro-phenoxy]butanoic acid;
4-[4-[2-(cyclopentylamino)-5-fluoro-phenyl]-2,6-difluoro-phenoxy]butanoic acid;
4-[4-(3-cyclopentylphenyl)-2,6-difluoro-phenoxy]butanoic acid;
4-[4-[3-(cyclopentylmethyl)phenyl]-2,6-difluoro-phenoxy]butanoic acid;
4-[4-[2-(cyclopentylmethyl)phenyl]-2,6-difluoro-phenoxy]butanoic acid;
4-[4-[6-(cyclopentylmethyl)-2-pyridyl]-2,6-difluoro-phenoxy]butanoic acid;
4-[4-[2-(cyclobutylmethyl)phenyl]-2,6-difluoro-phenoxy]butanoic acid;
4-[4-[3-(cyclobutylmethyl)phenyl]-2,6-difluoro-phenoxy]butanoic acid;
4-[4-[6-(cyclobutylmethyl)-2-pyridyl]-2,6-difluoro-phenoxy]butanoic acid;

4-[4-(2-cyclopentylphenyl)-2,6-difluoro-phenoxy]butanoic acid;
4-[4-(6-cyclopentyl-2-pyridyl)-2,6-difluoro-phenoxy]butanoic acid;
4-[2,6-difluoro-4-(2-isobutyl-3-pyridyl)phenoxy]butanoic acid;
4-[4-(2-cyclopentyl-3-pyridyl)-2,6-difluoro-phenoxy]butanoic acid;
4-[4-[2-(cyclopentylmethyl)-3-pyridyl]-2,6-difluoro-phenoxy]butanoic acid;
4-[2,6-difluoro-4-(2-pyrrol-1-yl-3-pyridyl)phenoxy]butanoic acid;
4-[2,6-difluoro-4-[2-(4-methylpyrazol-1-yl)-3-pyridyl]phenoxy]butanoic acid;
4-[2,6-difluoro-4-(2-morpholino-3-pyridyl)phenoxy]butanoic acid;
4-[2,6-difluoro-4-[2-(tetrahydropyran-4-ylmethylamino)-3-pyridyl]phenoxy]butanoic acid;
4-[2,6-difluoro-4-[2-(1-piperidyl)-3-pyridyl]phenoxy]butanoic acid;
(4S)-4-[4-(2-cyclobutylsulfanyl-3-pyridyl)-2,6-difluoro-phenoxy]pentanoic acid;
(4R)-4-[4-(2-cyclobutylsulfanyl-3-pyridyl)-2,6-difluoro-phenoxy]pentanoic acid;
(4R)-4-[4-[3-(cyclobutoxy)phenyl]-2,6-difluoro-phenoxy]pentanoic acid;
(4R)-4-[4-(2-cyclopentylsulfanyl-3-pyridyl)-2,6-difluoro-phenoxy]pentanoic acid;
(4R)-4-[2,6-difluoro-4-(3-phenoxyphenyl)phenoxy]pentanoic acid;
4-(3'-cyclobutoxy-biphenyl-4-ylsulfanyl)-butyric acid;
4-(3'-isopropoxy-biphenyl-4-ylsulfanyl)-butyric acid;
[1-(3,5-difluoro-3'-isopropoxy-biphenyl-4-ylsulfanylmethyl)-cyclopropyl]-acetic acid;
4-(3'-cyclopentyloxy-3,5-difluoro-biphenyl-4-ylsulfanyl)-butyric acid;
4-[4-(2-cyclopentyloxy-pyridin-3-yl)-phenylsulfanyl]-butyric acid;
4-[4-(2-cyclopropylmethoxy-pyridin-3-yl)-phenylsulfanyl]-butyric acid;
4-(3'-phenoxy-biphenyl-4-ylsulfanyl)-butyric acid;
4-(3'-cyclopentyloxy-biphenyl-4-ylsulfanyl)-butyric acid;
4-(3'-propoxy-biphenyl-4-ylsulfanyl)-butyric acid;
4-[4-(6-cyclobutoxy-pyridin-2-yl)-phenylsulfanyl]-butyric acid;
4-[4-(6-cyclopentyloxy-pyridin-2-yl)-phenylsulfanyl]-butyric acid;
4-[4-(6-isopropoxy-pyridin-2-yl)-phenylsulfanyl]-butyric acid;
4-[4-(2-isopropoxy-pyridin-3-yl)-phenylsulfanyl]-butyric acid;
4-[4-(6-propoxy-pyridin-2-yl)-phenylsulfanyl]-butyric acid;
4-[4-(6-cyclopentylsulfanyl-pyridin-2-yl)-phenylsulfanyl]-butyric acid;
4-(3'-cyclobutoxy-3,5-difluoro-biphenyl-4-ylsulfanyl)-butyric acid;
4-(3,5-difluoro-3'-isopropoxy-biphenyl-4-ylsulfanyl)-butyric acid;
4-[2,6-difluoro-4-(6-propoxy-pyridin-2-yl)-phenylsulfanyl]-butyric acid;
4-[2,6-difluoro-4-(6-isopropoxy-pyridin-2-yl)-phenylsulfanyl]-butyric acid;
4-[2,6-difluoro-4-(2-isopropoxy-pyridin-3-yl)-phenylsulfanyl]-butyric acid;
4-[2,6-difluoro-4-(2-propoxy-pyridin-3-yl)-phenylsulfanyl]-butyric acid;
4-[2,6-difluoro-4-(6-isopropylsulfanyl-pyridin-2-yl)-phenylsulfanyl]-butyric acid;
4-[2,6-difluoro-4-(6-propylsulfanyl-pyridin-2-yl)-phenylsulfanyl]-butyric acid;
4-[4-(2-cyclobutylsulfanyl-pyridin-3-yl)-2,6-difluoro-phenylsulfanyl]-butyric acid;
4-[4-(2-cyclobutoxy-pyridin-3-yl)-phenylsulfanyl]-butyric acid;
4-[4-(2-cyclobutoxy-pyridin-3-yl)-2,6-difluoro-phenylsulfanyl]-butyric acid;
4-[4-(2-cyclopentyloxy-pyridin-3-yl)-2,6-difluoro-phenylsulfanyl]-butyric acid;
4-[2,6-difluoro-4-(2-isopropylsulfanyl-pyridin-3-yl)-phenylsulfanyl]-butyric acid;
4-[4-(2-cyclopentylsulfanyl-pyridin-3-yl)-2,6-difluoro-phenylsulfanyl]-butyric acid;
4-[4-(2-isopropylsulfanyl-pyridin-3-yl)-phenylsulfanyl]-butyric acid;
4-[4-(2-cyclopentylsulfanyl-pyridin-3-yl)-phenylsulfanyl]-butyric acid;
4-[2-fluoro-4-(6-isopropoxy-pyridin-2-yl)-phenylsulfanyl]-butyric acid;
4-[4-(2-cyclopentyloxy-pyridin-3-yl)-2-fluoro-phenylsulfanyl]-butyric acid;
4-[4-(2-cyclobutylsulfanyl-pyridin-3-yl)-2-fluoro-phenylsulfanyl]-butyric acid;
4-[4-(2-cyclobutylsulfanyl-pyridin-3-yl)-phenylsulfanyl]-butyric acid;
4-[4-(6-cyclobutoxy-pyridin-2-yl)-2,6-difluoro-phenylsulfanyl]-butyric acid;
4-[4-(6-cyclopentyloxy-pyridin-2-yl)-2,6-difluoro-phenylsulfanyl]-butyric acid;
4-[4-(6-cyclobutylsulfanyl-pyridin-2-yl)-phenylsulfanyl]-butyric acid;
4-[4-(6-cyclopropylmethoxy-pyridin-2-yl)-2,6-difluoro-phenylsulfanyl]-butyric acid;
4-[4-(6-cyclobutylsulfanyl-pyridin-2-yl)-2,6-difluoro-phenylsulfanyl]-butyric acid;
4-[4-(6-cyclopentylsulfanyl-pyridin-2-yl)-2,6-difluoro-phenylsulfanyl]-butyric acid;
4-(2'-cyclopentylamino-3-fluoro-biphenyl-4-ylsulfanyl)-butyric acid;
4-(2'-cyclopentylamino-3,5-difluoro-biphenyl-4-ylsulfanyl)-butyric acid;
4-[2'-(cyclopropylmethyl-amino)-3,5-difluoro-biphenyl-4-ylsulfanyl]-butyric acid;
4-[2-fluoro-4-(2-isopropylsulfanyl-pyridin-3-yl)-phenylsulfanyl]-butyric acid;
4-[4-(2-cyclopentylsulfanyl-pyridin-3-yl)-2-fluoro-phenylsulfanyl]-butyric acid;
4-(3,5-difluoro-2'-isopropylamino-biphenyl-4-ylsulfanyl)-butyric acid;
4-(3,5-difluoro-2'-propylamino-biphenyl-4-ylsulfanyl)-butyric acid;
4-[4-(2-cyclopropylmethoxy-pyridin-3-yl)-2,6-difluoro-phenylsulfanyl]-butyric acid;
4-[2,6-difluoro-4-(2-propylsulfanyl-pyridin-3-yl)-phenylsulfanyl]-butyric acid;
4-[4-(6-cyclobutylsulfanyl-pyridin-2-yl)-2-fluoro-phenylsulfanyl]-butyric acid;
4-[4-(2-cyclopentylamino-pyridin-3-yl)-2-fluoro-phenylsulfanyl]-butyric acid;
4-[2-fluoro-4-(2-isopropoxy-pyridin-3-yl)-phenylsulfanyl]-butyric acid;
4-[4-(2-cyclobutoxy-pyridin-3-yl)-2-fluoro-phenylsulfanyl]-butyric acid;

4-[2-fluoro-4-(2-pyrrolidin-1-yl-pyridin-3-yl)-phenylsulfanyl]-butyric acid;
4-[2-fluoro-4-(2-isopropylamino-pyridin-3-yl)-phenylsulfanyl]-butyric acid;
4-(2'-cyclopentylamino-3,5'-difluoro-biphenyl-4-ylsulfanyl)-butyric acid;
4-(2'-cyclopentylamino-5'-fluoro-biphenyl-4-ylsulfanyl)-butyric acid;
4-(2'-cyclopentyloxy-5'-methyl-biphenyl-4-ylsulfanyl)-butyric acid;
4-(2'-cyclopentyloxy-4'-methoxy-biphenyl-4-ylsulfanyl)-butyric acid;
4-(2'-cyclopentyloxy-5'-fluoro-biphenyl-4-ylsulfanyl)-butyric acid;
4-(2'-cyclopentyloxy-3,5'-difluoro-biphenyl-4-ylsulfanyl)-butyric acid;
4-[4-(2-cyclopentyloxy-5-methyl-pyridin-3-yl)-phenylsulfanyl]-butyric acid;
4-(2'-cyclopentyloxy-3,5,5'-trifluoro-biphenyl-4-ylsulfanyl)-butyric acid;
4-(2'-cyclopentyloxy-3-fluoro-4'-methoxy-biphenyl-4-ylsulfanyl)-butyric acid;
4-(2'-cyclopentyloxy-3,5-difluoro-4'-methoxy-biphenyl-4-ylsulfanyl)-butyric acid;
4-(3-fluoro-2'-isopropoxy-4'-methoxy-biphenyl-4-ylsulfanyl)-butyric acid;
4-[4-(2-cyclopentyloxy-5-methyl-pyridin-3-yl)-2-fluoro-phenylsulfanyl]-butyric acid;
4-[2-fluoro-4-(2-isopropoxy-5-methyl-pyridin-3-yl)-phenylsulfanyl]-butyric acid;
4-(3,5'-difluoro-2'-isopropoxy-biphenyl-4-ylsulfanyl)-butyric acid;
4-[4-(2-cyclopentyloxy-6-methyl-pyridin-3-yl)-2-fluoro-phenylsulfanyl]-butyric acid;
4-(3,3'-difluoro-2'-isopropoxy-5'-methyl-biphenyl-4-ylsulfanyl)-butyric acid;
4-(3,3'-difluoro-5'-methyl-2'-propoxy-biphenyl-4-ylsulfanyl)-butyric acid;
4-(3-fluoro-2',4'-dipropoxy-biphenyl-4-ylsulfanyl)-butyric acid;
4-(6'-cyclopentyloxy-3,2'-difluoro-3'-methyl-biphenyl-4-ylsulfanyl)-butyric acid;
4-(2'-cyclopentyloxy-3,3'-difluoro-biphenyl-4-ylsulfanyl)-butyric acid;
4-(2'-cyclopentyloxy-3,3'-difluoro-5'-methyl-biphenyl-4-ylsulfanyl)-butyric acid;
5-[4-(2-cyclobutylmethoxy-pyridin-3-yl)-2,6-difluoro-phenoxy]-pentanoic acid;
5-[4-(2-cyclopropoxy-pyridin-3-yl)-2,6-difluoro-phenoxy]-pentanoic acid;
4-[4-(2-cyclopentyloxy-5-methyl-pyridin-3-yl)-2,6-difluoro-phenylsulfanyl]-butyric acid;
4-[4-(2-cyclopentyloxy-pyridin-3-yl)-phenylsulfanyl]-pentanoic acid;
4-[4-(2-isopropoxy-pyridin-3-yl)-phenylsulfanyl]-pentanoic acid;
4-[4-(2-cyclopentyloxy-pyridin-3-yl)-2,6-difluoro-phenylsulfanyl]-pentanoic acid;
4-[4-(2-cyclopentylsulfanyl-pyridin-3-yl)-2,6-difluoro-phenylsulfanyl]-pentanoic acid;
4-[4-[2-(2-dimethylaminoethyloxy)-3-pyridyl]-2,6-difluoro-phenoxy]butanoic acid;
4-[2,6-difluoro-4-(2-propylsulfanyl-pyridin-3-yl)-phenoxy]-butanoic acid;
4-[4-(2-cyclopropylsulfanyl-pyridin-3-yl)-2,6-difluoro-phenoxy]-butanoic acid;
4-[4-(2-ethylsulfanyl-pyridin-3-yl)-2,6-difluoro-phenoxy]-butanoic acid;
4-[4-(2-butylsulfanyl-pyridin-3-yl)-2,6-difluoro-phenoxy]-butanoic acid;
4-(2'-cyclopentylamino-biphenyl-4-ylsulfanyl)-butyric acid;
4-[4-(2-cyclopentyloxy-5-methyl-pyridin-3-yl)-2,6-difluoro-phenoxy]-butyric acid;
4-[4-(6-isopropylsulfanyl-2-pyridyl)phenoxy]butanoic acid;
4-[2,6-difluoro-4-(3-phenoxyphenyl)phenoxy]butanoic acid;
4-[4-[6-[3-(dimethylamino)pyrrolidin-1-yl]-2-pyridyl]-2,6-difluoro-phenoxy]butanoic acid;
5-[2,6-difluoro-4-(2-isopropoxy-pyridin-3-yl)-phenoxy]-pentanoic acid;
5-[4-(2-cyclobutoxy-pyridin-3-yl)-2,6-difluoro-phenoxy]-pentanoic acid;
4-[4-[2-(3,3-difluoropyrrolidin-1-yl)-3-pyridyl]-2,6-difluoro-phenoxy]butanoic acid;
4-[2,6-difluoro-4-[2-(4-methylpiperazin-1-yl)-3-pyridyl]phenoxy]butanoic acid;
4-[2,6-difluoro-4-[2-(5-methylisoxazol-3-yl)oxy-3-pyridyl]phenoxy]butanoic acid;
4-[4-[2-[2-(aziridin-1-yl)ethoxy]-3-pyridyl]-2,6-difluoro-phenoxy]butanoic acid;
4-[2,6-difluoro-4-[2-(3-furylmethoxy)-3-pyridyl]phenoxy]butanoic acid;
4-[2,6-difluoro-4-[2-(2-furylmethoxy)-3-pyridyl]phenoxy]butanoic acid;
4-[2,6-difluoro-4-[2-[(3-methyloxetan-3-yl)methoxy]-3-pyridyl]phenoxy]butanoic acid;
4-[2,6-difluoro-4-[2-(tetrahydrofuran-3-ylmethoxy)-3-pyridyl]phenoxy]butanoic acid;
4-[2,6-difluoro-4-[2-(tetrahydrofuran-2-ylmethoxy)-3-pyridyl]phenoxy]butanoic acid;
4-[4-(2-cyclobutylmethoxy-pyridin-3-yl)-2,6-difluoro-phenoxy]-butyric acid;
4-[4-(2-cyclopropoxy-pyridin-3-yl)-2,6-difluoro-phenoxy]-butyric acid;
4-(4-{2-[3-(tert-butyl-dimethyl-silanyloxy)-cyclopentyloxy]-pyridin-3-yl}-2,6-difluoro-phenoxy)-butyric acid;
4-{2,6-difluoro-4-[2-(3-hydroxy-cyclopentyloxy)-pyridin-3-yl]-phenoxy}-butyric acid;
4-[4-(2-cyclohexyloxy-pyridin-3-yl)-2,6-difluoro-phenoxy]-butyric acid;
4-[4-(2-cyclopentylmethoxy-pyridin-3-yl)-2,6-difluoro-phenoxy]-butyric acid;
4-[2,6-difluoro-4-(2-isobutoxy-pyridin-3-yl)-phenoxy]-butyric acid;
4-{4-[2-(2,2-dimethy-propoxy)-pyridin-3-yl]-2,6-difluoro-phenoxy}-butyric acid;
5-[4-(2-cyclopentyloxy-pyridin-3-yl)-2,6-difluoro-phenoxy]-pentanoic acid;
5-[4-(2-cyclobutylsulfanyl-3-pyridyl)-2,6-difluoro-phenoxy]pentanoic acid;
5-[4-(2-cyclopentylsulfanyl-3-pyridyl)-2,6-difluoro-phenoxy]pentanoic acid;
5-[2,6-difluoro-4-(2-isopropylsulfanyl-3-pyridyl)phenoxy]pentanoic acid;
5-[2,6-difluoro-4-(2-propylsulfanyl-3-pyridyl)phenoxy]pentanoic acid;
5-[2,6-difluoro-4-(6-isopropylsulfanyl-2-pyridyl)phenoxy]pentanoic acid;
5-[2,6-difluoro-4-(6-isopropoxy-2-pyridyl)phenoxy]pentanoic acid;
5-[4-[2-(cyclopropylmethoxy)-3-pyridyl]-2,6-difluoro-phenoxy]pentanoic acid;

5-[2,6-difluoro-4-(2-tetrahydrofuran-3-yloxy-3-pyridyl) phenoxy]pentanoic acid;
5-[2,6-difluoro-4-(2-tetrahydropyran-4-yloxy-3-pyridyl) phenoxy]pentanoic acid;
4-[2,6-difluoro-4-(2-isopropoxy-pyridin-3-yl)-phenylsulfanyl]-pentanoic acid;
4-[4-(2-cyclopentylsulfanyl-pyridin-3-yl)-phenylsulfanyl]-pentanoic acid;
4-{2-fluoro-4-[2-(tetrahydro-pyran-4-yloxy)-pyridin-3-yl]-phenylsulfanyl}-butyric acid;
4-{2-fluoro-4-[2-(tetrahydrofuran-3-yloxy)-pyridin-3-yl]-phenylsulfanyl}-butyric acid;
4-[4-(2-cyclobutylmethoxy-pyridin-3-yl)-2-fluoro-phenylsulfanyl]-butyric acid;
4-{2,6-difluoro-4-[2-(2,2,2-trifluoro-ethoxy)-pyridin-3-yl]-phenylsulfanyl}-butyric acid;
4-[4-(2-cyclobutylmethoxy-pyridin-3-yl)-2,6-difluoro-phenylsulfanyl]-butyric acid;
4-[4-(2-cyclopentylamino-pyridin-3-yl)-2,6-difluoro-phenylsulfanyl]-butyric acid;
4-[2,6-difluoro-4-(2-isopropylamino-pyridin-3-yl)-phenylsulfanyl]-butyric acid;
4-{4-[2-(cyclopropylmethyl-amino)-pyridin-3-yl]-2,6-difluoro-phenylsulfanyl}-butyric acid;
5-[4-(2-cyclopentyloxy-pyridin-3-yl)-2,6-difluoro-phenylsulfanyl]-pentanoic acid;
5-[2,6-difluoro-4-(2-isopropoxy-pyridin-3-yl)-phenylsulfanyl]-pentanoic acid;
5-[4-(2-cyclopentyloxy-pyridin-3-yl)-phenylsulfanyl]-pentanoic acid;
5-[4-(2-isopropoxy-pyridin-3-yl)-phenylsulfanyl]-pentanoic acid;
5-[4-(2-cyclopentylsulfanyl-pyridin-3-yl)-2,6-difluoro-phenylsulfanyl]-pentanoic acid;
5-[2,6-difluoro-4-(2-propylsulfanyl-pyridin-3-yl)-phenylsulfanyl]-pentanoic acid;
5-[4-(2-cyclopentylsulfanyl-pyridin-3-yl)-phenylsulfanyl]-pentanoic acid;
5-[4-(2-cyclobutylsulfanyl-pyridin-3-yl)-phenylsulfanyl]-pentanoic acid;
5-[4-(2-cyclobutylmethoxy-pyridin-3-yl)-2,6-difluoro-phenylsulfanyl]-pentanoic acid;
5-[4-(2-cyclobutoxy-pyridin-3-yl)-2,6-difluoro-phenylsulfanyl]-pentanoic acid;
6-[4-(2-cyclopentyloxy-pyridin-3-yl)-2,6-difluoro-phenoxy]-hexanoic acid;
7-[4-(2-cyclopentyloxy-pyridin-3-yl)-2,6-difluoro-phenoxy]-heptanoic acid;
5-[2-fluoro-4-(2-isopropoxy-pyridin-3-yl)-phenoxy]-pentanoic acid;
5-[4-(2-cyclopentylsulfanyl-pyridin-3-yl)-2-fluoro-phenoxy]-pentanoic acid;
5-[4-(2-cyclobutylsulfanyl-pyridin-3-yl)-2-fluoro-phenoxy]-pentanoic acid;
5-[4-(2-cyclopentyloxy-pyridin-3-yl)-2-fluoro-phenoxy]-pentanoic acid;
4-[2,6-difluoro-4-(2-methoxy-pyridin-3-yl)-phenoxy]-butyric acid;
4-[4-(2-allyloxy-pyridin-3-yl)-2,6-difluoro-phenoxy]-butyric acid;
4-[4-(2-but-2-ynyloxy-pyridin-3-yl)-2,6-difluoro-phenoxy]-butyric acid;
6-[4-[2-(cyclobutoxy)-3-pyridyl]-2,6-difluoro-phenoxy] hexanoic acid;
6-[4-[2-(cyclobutylmethoxy)-3-pyridyl]-2,6-difluoro-phenoxy]hexanoic acid;
6-[4-[2-(cyclopropylmethoxy)-3-pyridyl]-2,6-difluoro-phenoxy]hexanoic acid;
6-[4-(2-cyclobutylsulfanyl-3-pyridyl)-2,6-difluoro-phenoxy]hexanoic acid;
6-[4-(2-cyclopentylsulfanyl-3-pyridyl)-2,6-difluoro-phenoxy]hexanoic acid;
6-[4-(2-cyclopentyloxy-pyridin-3-yl)-2,6-difluoro-phenylsulfanyl]-hexanoic acid;
6-[4-(2-cyclopentylsulfanyl-pyridin-3-yl)-2,6-difluoro-phenylsulfanyl]-hexanoic acid;
6-[4-(2-cyclobutylsulfanyl-pyridin-3-yl)-2,6-difluoro-phenylsulfanyl]-hexanoic acid; and
6-[2,6-difluoro-4-(2-propylsulfanyl-pyridin-3-yl)-phenylsulfanyl]-hexanoic acid.

The terms and abbreviations used herein retain their original meanings unless indicated otherwise.

The present invention also provides a method for preparing the compounds of Formula 1. Hereinafter, the method for preparing the compounds of Formula 1 is explained based on exemplary reactions in order to illustrate the present invention. However, a person skilled in the art could prepare the compounds of Formula 1 by various methods based on the structure of Formula 1, and such methods should be interpreted as being within the scope of the present invention. That is, the compounds of Formula 1 may be prepared by the methods described herein or by combining various methods disclosed in the prior art, which should be interpreted as being within the scope of the present invention. Accordingly, a method for preparing the compounds of Formula 1 is not limited to the following methods.

As represented in the following reaction scheme 1, the compounds of Formula 1 according to the present invention can be produced by C—C coupling reaction of Compound 2 and Compound 3 in the presence of a conventional metal catalyst, and, if necessary, additional hydrolysis.

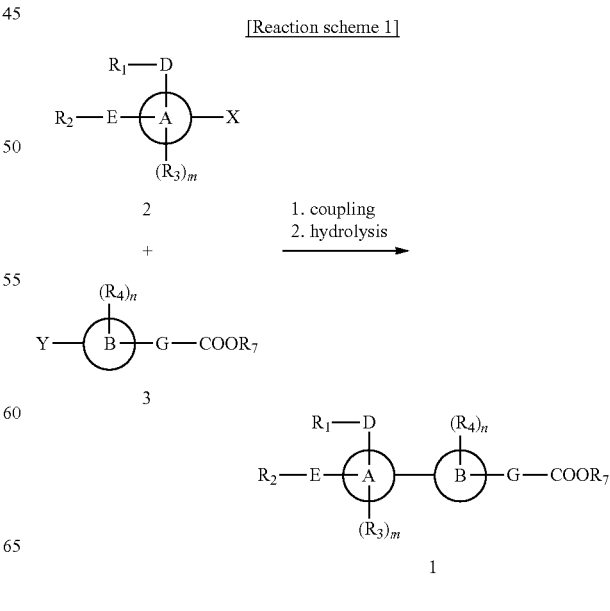

Furthermore, the compounds of Formula 1 according to the present invention can b produced by coupling reaction of Compound 4 and Compound 5, Compound 6 or Compound 7 in the presence of conventional base or coupling reagents and, if necessary, additional hydrolysis, as represented in the following reaction scheme 2. In the reaction scheme 2, Z—$R_7$ and J of Compounds 4 and 7 represent independently halogen, OH, SH or O-alkyl. When Z—$R_7$ is O-alkyl, it is converted to OH by dealkylation reaction before being subjected to coupling reaction.

The compounds of Formula 1 according to the present invention can be produced by reacting Compound 8 substituted with J radical with Compound 9 or Compound 10 in the presence of conventional base, metal catalysts or coupling reagents, as represented in the following reaction scheme 4. In reaction scheme 4, J and Y represent independently halogen, OH, SH or $NH_2$. When J is amine, "reductive-amination reaction" can be carried out between Compound 8 and Compound 11.

[Reaction scheme 2]

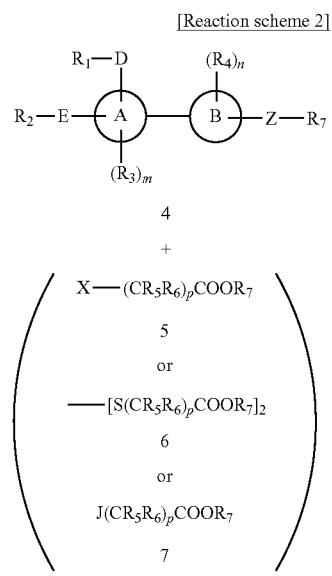

[Reaction scheme 4]

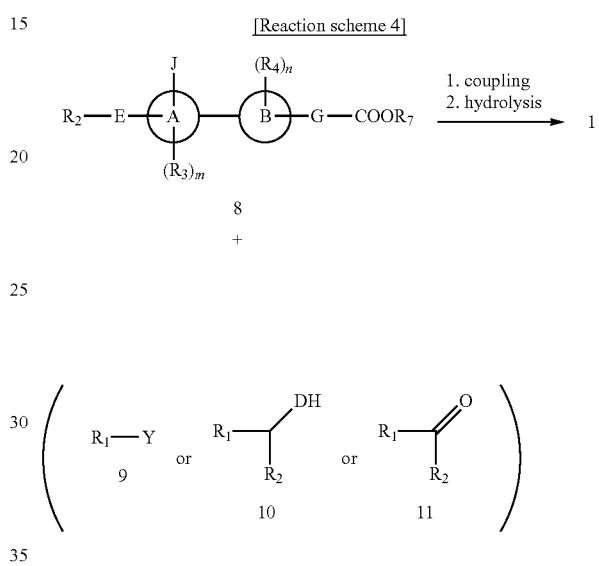

The compounds of Formula 1 having various substituents can also be produced through a series of reaction steps, as represented in the following reaction scheme 3. Specifically, the compounds of Formula I can be reduced to Compound I-1 by using conventional reducing agents, and Compound I-1 can be oxidized to aldehyde compounds (Compound I-2) by using oxidizing agents. Compound I-3 can be produced by using conventional olefination reaction such as HWE (Horner-Wadsworth-Emmons) reaction. Compound I-3 can be converted via reduction and hydrolysis to the compounds of Formula I having various substituents.

In the above reaction scheme 1, Compound 3 can be produced by coupling reaction of Compound 12 and Compound 5, Compound 6 or Compound 7 in the presence of conventional base or coupling reagents, as represented in the following reaction scheme 5. In reaction scheme 5, J and Z—$R_7$ are as defined in the above reaction scheme 2.

[Reaction scheme 3]

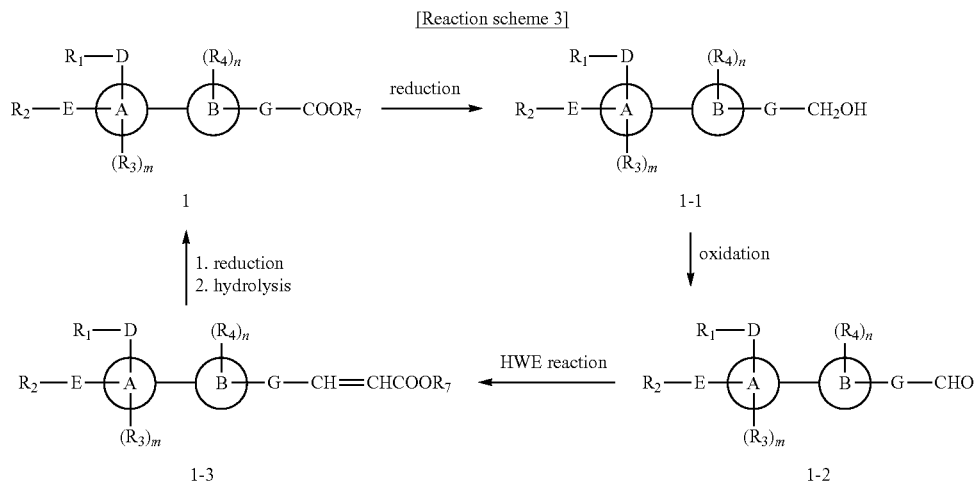

[Reaction scheme 5]

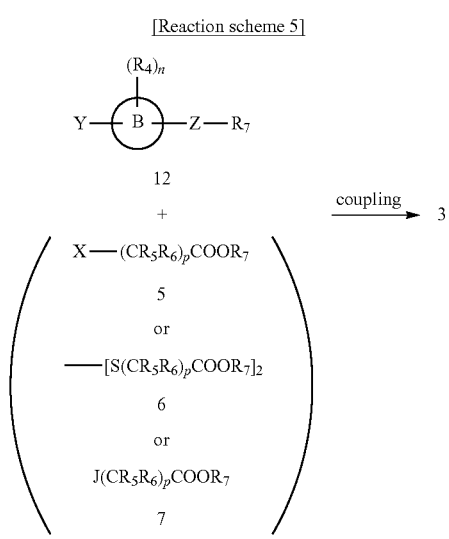

In the above reaction scheme 2, Compound 4 can be produced by coupling reaction of Compound 2 and Compound 12 in the presence of conventional coupling reagents such as metal catalysts, as represented in the following reaction scheme 6.

[Reaction scheme 6]

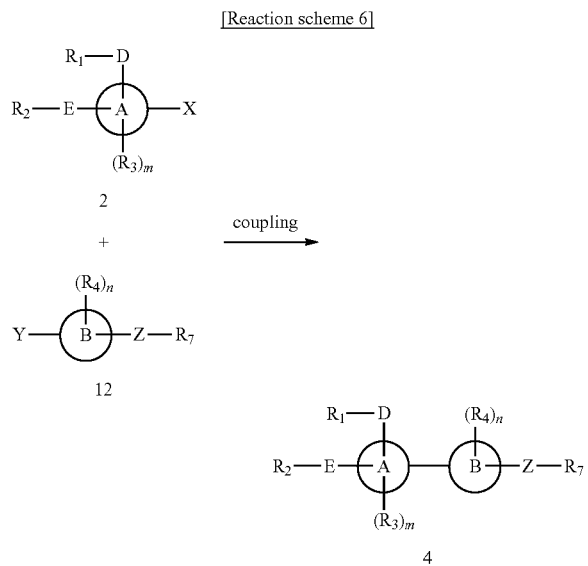

In the above reaction schemes 1 to 6,
X represents halogen, boronic acid or —OSO$_2$CF$_3$,
Y represents boronic acid, halogen or boronic acid ester, and
A, B, D, E, G, R$_1$, R$_2$, R$_3$, R$_4$, R$_7$, m, n and p are as described in the definition of the compounds of Formula 1.

In the above reaction, transition metal such as palladium (Pd) can be used as a conventional metal catalyst. The above reactions can be carried out in conventional solvents which do not have an adverse effect on the reactions. Preferable solvents include, but are not limited to, dimethylformamide, dimethylacetamide, tetrahydrofuran, acetonitrile, methanol, ethanol, water, 1,2-dichloroethane, dimethylsulfoxide, ethylether, methyl tert-butylether, methylene chloride, chloroform and mixtures thereof.

In the above reactions, unexplained compounds are known compounds or compounds easily obtainable from known compounds by known methods or similar methods.

The compounds of Formula 1 obtained by the above methods can be separated or purified from the reaction products by conventional methods such as recrystallization, ionospheresis, silica gel column chromatography or ion-exchange chromatography.

As described above, the compounds according to the present invention, starting materials or intermediates for the preparation thereof can be prepared by a variety of methods, which should be interpreted as being within the scope of the present invention.

The compounds of Formula 1 according to the present invention have the effect of GPR120 agonists. Accordingly, the present invention provides a pharmaceutical composition as GPR120 agonists comprising the compounds of Formula 1, pharmaceutically acceptable salts or isomers thereof as an active component. Various kinds of prodrugs, which are converted into the compounds of Formula I in vivo, are also within the scope of the present invention.

Exemplary diseases which can be prevented or treated by the pharmaceutical composition according to the present invention as GPR120 agonists include, but are not limited to, metabolic disorders such as diabetes, complications of diabetes, obesity, non-alcoholic fatty liver, steatohepatitis, osteoporosis and inflammation.

In addition, the present invention provides a method for preparing the composition for preventing or treating metabolic disorders such as diabetes, complications of diabetes, obesity, non-alcoholic fatty liver, steatohepatitis, osteoporosis or inflammation which comprises the step of mixing the compound of Formula 1, a pharmaceutically acceptable salt or isomer thereof as an active component and a pharmaceutically acceptable carrier.

According to the present invention, the "pharmaceutical composition" or the "composition for lowering blood glucose level" can include other components such as carriers, diluents, excipients, etc., in addition to the active component of the present invention. Accordingly, the pharmaceutical composition can include pharmaceutically acceptable carriers, diluents, excipients or combinations thereof as necessary. The pharmaceutical composition facilitates the administration of compounds into the body. Various methods for administering the compounds include, but are not limited to, oral, injection, aerosol, parenteral and local administration.

Herein, "carriers" mean compounds that facilitate the addition of compounds into the cell or tissue. For example, dimethylsulfoxide (DMSO) is a conventional carrier facilitating the administration of many organic compounds into living cells or tissues.

Herein, "diluents" mean compounds that not only stabilize a biologically active form but are diluted in solvent dissolving the compounds. Dissolved salts in buffer are used as diluents in this field. A conventionally used buffer is a phosphate buffer saline mimicking salt form in body fluid. Since buffer solution can control the pH of the solution at low concentration, buffer diluents hardly modify the biological activity of compounds.

Herein, "pharmaceutically acceptable" means such property that does not impair the biological activity and physical property of compounds.

The compounds according to the present invention can be formulated as various pharmaceutically administered dosage forms. In the preparation of the pharmaceutical composition of the present invention, an active component—specifically, the compound of Formula 1 or a pharmaceutically acceptable salt or isomer thereof—is mixed with selected pharmaceutically acceptable carriers considering the dosage form to be prepared. For example, the pharmaceutical composition of the present invention can be formulated as injections, oral preparations and the like, as needed.

The compounds of the present invention can be formulated by conventional methods using known pharmaceutical carriers and excipients, and inserted into a unit or multiunit containers. The formulations may be solution, suspension or emulsion in oil or aqueous solvent and include conventional dispersing agents, suspending agents or stabilizing agents. In addition, the compounds may be, for example, dry powder form which is dissolved in sterilized pyrogen-free water before use. The compounds of the present invention can be formulated into suppositories by using a conventional suppository base such as cocoa butter or other glycerides. Solid forms for oral administration include capsules, tablets, pills, powders and granules. Capsules and tablets are preferred. Tablets and pills are preferably enteric-coated. Solid forms are manufactured by mixing the compounds of the present invention with at least one carrier selected from inert diluents such as sucrose, lactose or starch, lubricants such as magnesium stearate, disintegrating agents, binders and the like.

The compounds according to the present invention can be administered in combination with other drugs—for example, other antidiabetics—as required.

The dose of the compounds according to the present invention is determined by a physician's prescription considering the patient's body weight, age and disease condition. A typical dose for adults is in the range of about 0.3 to 500 mg per day according to the frequency and intensity of administration. A typical daily dose of intramuscular or intravenous administration for adults is in the range of about 1 to 300 mg per day which can be administered in divided unit dosages. Some patients need a higher daily dose.

The present invention also provides a method for preventing or treating diseases by using an effective amount of the compound of Formula 1 or a pharmaceutically acceptable salt or isomer thereof as an active component of GPR120 agonists. Representative diseases to be treated by GPR120 agonists include, but are not limited to, metabolic disorders such as the above-mentioned diabetes, complications of diabetes, obesity, non-alcoholic fatty liver, steatohepatitis, osteoporosis, inflammation and the like. Herein, the term "treatment" is used to mean deterring, delaying or ameliorating the progress of diseases in a subject exhibiting symptoms of diseases. The term "prevention" is used to mean deterring, delaying or ameliorating the sign of diseases in a subject at risk of exhibiting symptoms of diseases, even if he or she does not exhibit the symptoms.

Advantageous Effects of Invention

The biaryl derivatives of Formula 1 according to the present invention promote GLP-1 formation in the gastrointestinal tract and improve insulin resistance in the liver or in muscle due to anti-inflammatory action in macrophages, lipocytes, etc., and can accordingly be effectively used for preventing or treating metabolic disorders such as diabetes, complications of diabetes, obesity, non-alcoholic fatty liver, steatohepatitis, osteoporosis or inflammation.

MODE FOR THE INVENTION

The present invention is explained in more detail by the following Examples. However, these Examples seek to illustrate the present invention only, and the scope of the present invention is not limited by them.

Hereinafter, M means molar concentration and N means normal concentration. Furthermore, abbreviations used in the following Preparations and Examples are as follows:
$BBr_3$: boron tribromide
BINAP: 2,2'-bis(diphenylphosphino)-1,1'-binaphthyl
$Br_2$: bromine
$CH_3CN$: acetonitrile
$Cs_2CO_3$: cesium carbonate
DCM: dichloromethane
DMF: N,N-dimethylformamide
DMSO: dimethylsulfoxide
DPPF: 1,1'-bis(diphenylphosphino)ferrocene
EtOAc: ethyl acetate
EtOH: ethanol
$Et_2O$: diethyl ether
HCl: hydrochloric acid
Hex: n-hexane
$K_2CO_3$: potassium carbonate
LAH: lithium aluminum hydride
MeOH: methanol
$MgSO_4$: magnesium sulfate
$NaBH_4$: sodium borohydride
NaCl: sodium chloride
$Na_2CO_3$: sodium carbonate
NaH: sodium hydride
NaOH: sodium hydroxide
NBS: N-bromosuccinimide
Pd/C: palladium/carbon
$PdCl_2$(dppf)-DCM: 1,1'-bis(diphenylphosphino)ferrocene-palladium(II) dichloride dichloromethane
$PdCl_2(PPh_3)_2$: bis(triphenylphosphine)palladium(II) dichloride
$Pd_2(dba)_3$: tris(dibenzylideneacetone)dipalladium(0)
$Pd(PPh_3)_4$: tetrakis(triphenylphosphine)palladium(0)
$SOCl_2$: thionyl chloride
SPhos: 2-dicyclohexylphosphino-2',6'-dimethoxybiphenyl
TBAF: tetrabutylammonium fluoride hydrate
TEA: triethylamine
TFA: trifluoroacetic acid
THF: tetrahydrofuran
XPhos: 2-dicyclohexylphosphino-2',4',6'-triisopropylbiphenyl Preparation Example 1

4-[4-(4,4,5,5-tetramethyl-1,3,2-dioxaborolan-2-yl) phenoxy]butyric acid ethyl ester Step A: 4-(4,4,5,5-tetramethyl-1,3,2-dioxaborolan-2-yl)phenol 4-Chlorophenol (2 g, 15.5 mmol), bis(pinacolato)diboron (5.92 g, 23.3 mmol), potassium acetate (4.58 g, 46.6 mmol) and Xphos (0.3 g, 0.62 mmol) were dissolved in 30 mL of 1,4-dioxane, and the mixture was charged with $N_2$ gas for 5 minutes. $Pd_2$ (dba)$_3$ (0.14 g, 0.15 mmol) was added thereto, and the mixture was stirred for 1 hour at 110° C. The mixture was filtered through Celite and then purified by column chromatography to obtain the title compound (3.4 g, 99%).
$^1$H NMR (CDCl$_3$) δ 7.71 (2H, d), 6.82 (2H, d), 5.00 (1H, s), 1.33 (12H, s)

Step B: 4-[4-(4,4,5,5-tetramethyl-1,3,2-dioxaborolan-2-yl)phenoxy]butyric acid ethyl ester 4-(4,4,5,5-Tetramethyl-1,3,2-dioxaborolan-2-yl)phenol obtained from Step A (0.32 g, 1.4 mmol) was dissolved in 5 mL of DMF. K$_2$CO$_3$ (0.39 g, 2.8 mmol) and 4-butyric acid ethyl ester (0.22 mL, 1.54 mmol) were added thereto, and the mixture was stirred for 1 hour at 60° C. Solids were removed and the mixture was purified by column chromatography to obtain the title compound (0.38 g, 82%).

$^1$H NMR (CDCl$_3$) δ 7.73 (2H, d), 6.87 (2H, d), 4.14 (2H, q), 4.03 (2H, t), 2.51 (2H, t), 2.11 (2H, m), 1.32 (12H, s), 1.25 (3H, t)

Preparation Example 2

4-[2,6-Difluoro-4-(4,4,5,5-tetramethyl-1,3,2-dioxaborolan-2-yl)phenoxy]butyric acid ethyl ester Step A: 4-bromo-2,6-difluoro-phenol 2,6-Difluorophenol (1.02 g, 7.8 mmol) was dissolved in 15 mL of DMF, and at 0° C. NBS (1.40 g, 7.84 mmol) was added thereto. The reaction mixture was stirred for 24 hours at room temperature and concentrated. 50 mL of water was added thereto, and the mixture was extracted with Et$_2$O. The extract was dried with MgSO$_4$ to obtain the title compound (1.41 g, 86%).

$^1$H NMR (CDCl$_3$) δ 7.08 (2H, m), 5.42 (1H, brs)

Step B: 2,6-difluoro-4-(4,4,5,5-tetramethyl-1,3,2-dioxaborolan-2-yl)phenol

4-Bromo-2,6-difluoro-phenol obtained from Step A (1.414 g, 6.76 mmol), bis(pinacolato)diboron (1.8 g, 7.09 mmol), potassium acetate (2.66 g, 27 mmol) and DPPF (0.19 g, 0.34 mmol) were dissolved in 23 mL of 1,4-dioxane, and the mixture was charged with N$_2$ gas for 5 minutes. PdCl$_2$(dppf)-DCM (0.27 g, 0.34 mmol) was added thereto, and the mixture was stirred for 3 hours at 80° C. The mixture was filtered through Celite and purified by column chromatography to obtain the title compound (1.366 g, 79%).

$^1$H NMR (CDCl$_3$) δ 7.33 (2H, m), 5.25 (1H, s), 1.32 (12H, s)

Step C: 4-[2,6-difluoro-4-(4,4,5,5-tetramethyl-1,3,2-dioxaborolan-2-yl)phenoxy]butyric acid ethyl ester 2,6-Difluoro-4-(4,4,5,5-tetramethyl-1,3,2-dioxaborolan-2-yl)phenol obtained from Step B (1.87 g, 7.3 mmol), Cs$_2$CO$_3$ (4.76 g, 14.6 mmol) and 4-bromo-butyric acid ethyl ester (1.42 g, 7.3 mmol) were dissolved in 24 mL of DMF. The mixture was stirred for 24 hours at room temperature. Solids were filtered, and the filtrate was purified by column chromatography to obtain the title compound (1.66 g, 61%).

$^1$H NMR (CDCl$_3$) δ 7.29 (2H, m), 4.21 (2H, t), 4.14 (2H, q), 2.56 (2H, t), 2.07 (2H, m), 1.32 (12H, s), 1.25 (3H, t)

Preparation Example 3

4-[2-chloro-4-(4,4,5,5-tetramethyl-1,3,2-dioxaborolan-2-yl)phenoxy]butyric acid ethyl ester Step A: 2-chloro-4-(4,4,5,5-tetramethyl-1,3,2-dioxaborolan-2-yl)phenol 4-Bromo-2-chlorophenol (2.0 g, 9.6 mmol), bis(pinacolato)diboron (2.81 g, 11 mmol), potassium acetate (3.78 g, 38.5 mmol) and DPPF (0.27 g, 0.49 mmol) were dissolved in 32 mL of 1,4-dioxane. The mixture was charged with N$_2$ gas for 5 minutes. PdCl$_2$(dppf)-DCM (0.4 g, 0.49 mmol) was added thereto, and the mixture was stirred for 3 hours under reflux. The mixture was filtered through Celite and purified by column chromatography to obtain the title compound (1.91 g, 77%).

$^1$H NMR (CDCl$_3$) δ 7.77 (1H, s), 7.62 (1H, dd), 7.00 (1H, d), 5.73 (1H, s), 1.36 (12H, s)

Step B: 4-[2-chloro-4-(4,4,5,5-tetramethyl-1,3,2-dioxaborolan-2-yl)phenoxy]butyric acid ethyl ester 2-Chloro-4-(4,4,5,5-tetramethyl-1,3,2-dioxaborolan-2-yl)phenol obtained from Step A (0.43 g, 1.7 mmol), 4-bromo-butyric acid ethyl ester (0.25 mL, 1.7 mmol) and Cs$_2$CO$_3$ (0.66 g, 2 mmol) were dissolved in 5 mL of DMF. The reaction mixture was stirred for 16 hours at room temperature. The mixture was concentrated and purified by column chromatography to obtain the title compound (0.47 g, 75%).

$^1$H NMR (CDCl$_3$) δ 7.79 (1H, d), 7.63 (1H, dd), 6.89 (1H, d), 4.15 (2H, t), 4.10 (2H, q), 2.56 (2H, t), 2.16 (2H, m), 1.33 (12H, s), 1.25 (3H, t)

Preparation Example 4

4-[2-fluoro-4-(4,4,5,5-tetramethyl-1,3,2-dioxaborolan-2-yl)phenoxy]butyric acid ethyl ester Step A: 2-fluoro-4-(4,4,5,5-tetramethyl-1,3,2-dioxaborolan-2-yl)phenol 4-Bromo-2-fluorophenol (1.9 g, 9.9 mmol), bis(pinacolato)diboron (2.9 g, 11.4 mmol), potassium acetate (3.90 g, 39.7 mmol) and DPPF (0.27 g, 0.49 mmol) were dissolved in 32 mL of 1,4-dioxane. The mixture was charged with N$_2$ gas for 5 minutes. PdCl$_2$(dppf)-DCM (0.4 g, 0.49 mmol) was added thereto, and the mixture was stirred for 4 hours under reflux. The mixture was filtered through Celite and then purified by column chromatography to obtain the title compound (2.2 g, 93%).

$^1$H NMR (CDCl$_3$) δ 7.49 (2H, m), 6.98 (1H, t), 5.31 (1H, brs), 1.33 (12H, s)

Step B: 4-[2-fluoro-4-(4,4,5,5-tetramethyl-1,3,2-dioxaborolan-2-yl)phenoxy]butyric acid ethyl ester 2-Fluoro-4-(4,4,5,5-tetramethyl-1,3,2-dioxaborolan-2-yl)phenol obtained from Step A (0.56 g, 2.3 mmol), 4-bromo-butyric acid ethyl ester (0.34 mL, 2.3 mmol) and Cs$_2$CO$_3$ (0.92 g, 2.8 mmol) were dissolved in 8 mL of DMF. The reaction mixture was stirred for 16 hours at room temperature. The mixture was concentrated and purified by column chromatography to obtain the title compound (0.52 g, 63%).

$^1$H NMR (CDCl$_3$) δ 7.49 (2H, m), 6.93 (1H, t), 4.15 (2H, t), 4.10 (2H, q), 2.53 (2H, t), 2.15 (2H, m), 1.33 (12H, s), 1.25 (3H, t)

Preparation Example 5

2-chloro-6-cyclopentylsulfanyl-pyridine 2,6-Dichloropyridine (3.08 g, 20.7 mmol) and Cs$_2$CO$_3$ (6.8 g, 20.7 mmol) were dissolved in 40 mL of DMF. Cyclopentylthiol (2.17 mL, 20.7 mmol) was added thereto and the mixture was stirred for 16 hours at 80° C. Solids were filtered and the filtrate was concentrated to obtain the title compound (4.24 g, 95%).

$^1$H NMR (CDCl$_3$) δ 7.40 (1H, t), 7.06 (1H, d), 6.97 (1H, d), 4.01 (1H, m), 2.22 (2H, m), 1.76 (2H, m), 1.64 (4H, m)

Preparation Example 6

4-[2-methoxy-4-(4,4,5,5-tetramethyl-1,3,2-dioxaborolan-2-yl)phenoxy]butyric acid ethyl ester 4-Bromo-2-methoxy-phenol (0.41 g, 2.02 mmol) and 4-bromo-butyric acid ethyl ester (0.39 g, 2.02 mmol) were reacted in the same manner as in Step B of Preparation Example 4 to obtain 4-(4-bromo-2-methoxy-phenoxy)-butyric acid ethyl ester (0.55 g, 86%).

4-(4-Bromo-2-methoxy-phenoxy)-butyric acid ethyl ester (130 mg, 0.41 mmol) and bis(pinacolato)diboron (125 mg, 0.49 mmol) were reacted in the same manner as in Step A of Preparation Example 4 to obtain the title compound (80 mg, 54%).

$^1$H NMR (CDCl$_3$) δ 7.39 (1H, d), 7.28 (1H, s), 6.88 (1H, d), 4.14 (2H, q), 4.09 (2H, t), 3.89 (3H, s), 2.52 (2H, t), 2.14 (2H, m), 1.33 (12H, s), 1.26 (3H, t)

Preparation Example 7

4-[4-(2-chloro-4-pyridyl)-2,6-difluoro-phenoxy]butyric acid ethyl ester 2 mL of THF and 0.5 mL of water were added to 4-[2,6-Difluoro-4-(4,4,5,5-tetramethyl-1,3,2-dioxaborolan-2-yl)phenoxy]butyric acid ethyl ester obtained from Preparation Example 2 (0.1 g, 0.27 mmol), 2-chloro-4-iodopyridine (0.078 g, 0.32 mmol) and K$_2$CO$_3$ (0.112 g, 0.81 mmol). The mixture was charged with N$_2$ gas for 5 minutes. PdCl$_2$(dppf)-DCM (0.011 g, 0.013 mmol) was added thereto, and the mixture was stirred for 16 hours at 80° C. Water was added thereto and the reaction mixture was extracted with EtOAc. The extract was dried with MgSO$_4$ and purified by column chromatography to obtain the title compound (0.084 g, 87%).

$^1$H NMR (CDCl$_3$) δ 8.44 (1H, d), 7.45 (1H, d), 7.33 (1H, dd), 7.17 (2H, m), 4.26 (2H, t), 4.17 (2H, q), 2.58 (2H, t), 2.11 (2H, m), 1.27 (3H, t)

Preparation Example 8

2-chloro-6-(cyclopentoxy)pyridine

6-Chloro-2-pyridinol (1.95 g, 15 mmol) and K$_2$CO$_3$ (4.16 g, 30 mmol) were dissolved in 50 mL of DMF. Cyclopentyl bromide (1.94 mL, 18 mmol) was added thereto and the mixture was stirred for 24 hours at 80° C. Solids were removed and the filtrate was concentrated to obtain the title compound (2.92 g, 98%).

$^1$H NMR (CDCl$_3$) δ 7.47 (1H, t), 6.84 (1H, d), 6.51 (1H, d), 5.38 (1H, m), 1.97 (2H, m), 1.79 (4H, m), 1.62 (2H, m)

Preparation Example 9

1-bromo-3-(cyclopentoxy)benzene 44 mL of CH$_3$CN was added to 3-Bromophenol (2.31 g, 13.3 mmol) and K$_2$CO$_3$ (1.84 g, 13.3 mmol), and the mixture was stirred for 1 hour under reflux. Bromocyclopentane (1.43 mL, 13.3 mmol) was added thereto, and the reaction mixture was stirred for 16 hours under reflux. The mixture was filtered through Celite and then purified by column chromatography to obtain the title compound (1.5 g, 46%).

$^1$H NMR (CDCl$_3$) δ 7.11 (1H, t), 7.02 (2H, m), 6.80 (1H, dd), 4.72 (1H, m), 1.94-1.73 (6H, m), 1.62 (2H, m),

Preparation Example 10

2-chloro-6-pyrrolidine-1-yl-pyridine 2,6-Dichloropyridine (2.08 g, 14 mmol) and pyrrolidine (1.0 g, 14 mmol), Cs$_2$CO$_3$ (4.58 g, 14 mmol) were dissolved in 28 mL of DMF and the mixture was stirred for 16 hours at 80° C. The mixture was filtered through Celite, concentrated under reduced pressure and diluted with water. The mixture was extracted with EtOAc and the extract was dried with MgSO$_4$ to obtain the title compound (2.31 g, 90%).

$^1$H NMR (CDCl$_3$) δ 7.32 (1H, t), 6.49 (1H, d), 6.20 (1H, d), 3.43 (4H, m), 1.99 (4H, m)

Preparation Example 11

4-[2,6-dimethyl-4-(4,4,5,5-tetramethyl-1,3,2-dioxaborolan-2-yl)phenoxy]butyric acid ethyl ester 4-Bromo-2,6-dimethyl-phenol (1.0 g, 4.97 mmol) and 4-bromo-butyric acid ethyl ester (0.97 g, 4.97 mmol) were reacted in the same manner as in Step B of Preparation Example 4 to obtain 4-(4-bromo-2,6-dimethyl-phenoxy)-butyric acid ethyl ester (1.4 g, 89%).

4-(4-Bromo-2,6-dimethyl-phenoxy)-butyric acid ethyl ester (200 mg, 0.63 mmol) and bis(pinacolato)diboron (193 mg, 0.76 mmol) were reacted in the same manner as in Step A of Preparation Example 4 to obtain the title compound (60 mg, 26%).

$^1$H NMR (CDCl$_3$) δ 7.47 (2H, s), 4.16 (2H, q), 3.80 (2H, t), 2.60 (2H, t), 2.25 (6H, s), 2.14 (2H, m), 1.32 (12H, s), 1.27 (3H, t)

Preparation Example 12

4-(4-bromo-2,3-difluoro-phenoxy)butyric acid ethyl ester

4-Bromo-2,3-difluorophenol (0.45 g, 2 mmol) was dissolved in 10 mL of DMF and the solution was cooled to 0° C. NaH (60% in mineral oil, 0.11 g, 2.6 mmol) was added thereto and the mixture was stirred for 30 minutes. 4-Bromo-butyric acid ethyl ester (0.37 mL, 2.4 mmol) was added thereto, and the reaction mixture was stirred for 16 hours at room temperature. The mixture was concentrated under reduced pressure, added with aqueous solution of ammonium chloride and extracted with EtOAc. Separated organic layer was dried with MgSO$_4$ and purified by column chromatography to obtain the title compound (0.533 g, 76%).

$^1$H NMR (CDCl$_3$) δ 7.19 (1H, m), 6.66 (1H, m), 4.16 (2H, q), 4.09 (2H, t), 2.52 (2H, t), 2.14 (2H, m), 1.26 (3H, t)

Preparation Example 13

4-[2,3-difluoro-4-(3-hydroxyphenyl)phenoxy]butyric acid ethyl ester 4-(4-Bromo-2,3-difluoro-phenoxy)butyric acid ethyl ester obtained from Preparation Example 12 (0.108 g, 0.33 mmol) and 3-hydroxyphenyl boronic acid (0.059 g, 0.43 mmol) were dissolved in 1.7 mL of 1,4-dioxane and 2M Na$_2$CO$_3$ aqueous solution (0.5 mL, 1 mmol). The mixture was charged for 5 minutes with N$_2$ gas. Pd(PPh$_3$)$_4$ (0.019 g, 0.016 mmol) was added thereto, and the reaction mixture was stirred for 1 hour under reflux. The organic layer was extracted with EtOAc and purified by column chromatography to obtain title compound (0.089 g, 79%).

¹H NMR (CDCl₃) δ 7.29 (1H, t), 7.06 (2H, m), 6.98 (1H, d), 6.84 (1H, dd), 6.78 (1H, m), 5.15 (1H, brs), 4.16 (4H, m), 2.56 (2H, t), 2.17 (2H, m), 1.27 (3H, t)

Preparation Example 14

2-chloro-6-(1-piperidyl)pyridine 2,6-Dichloropyridine (2.0 g, 13.5 mmol), piperidine (1.33 mL, 13.5 mmol) and Cs₂CO₃ (4.4 g, 13.5 mmol) were dissolved in 27 mL of DMF, and the mixture was stirred for 16 hours at 80° C. The mixture was filtered through Celite, concentrated under reduced pressure and diluted with water. The mixture was extracted with EtOAc and the extract was purified by column chromatography to obtain the title compound (1.91 g, 72%).
¹H NMR (CDCl₃) δ 7.34 (1H, t), 6.52 (1H, d), 6.47 (1H, d), 3.52 (4H, m), 1.64 (6H, m)

Preparation Example 15

6-chloro-N-phenyl-pyridine-2-amine 2,6-Dichloropyridine (2.0 g, 13.5 mmol), aniline (1.23 mL, 13.5 mmol), BINAP (0.33 g, 0.53 mmol) and sodium tert-butoxide (1.82 g, 18.9 mmol) were dissolved in 27 mL of toluene. The mixture was charged with N₂ gas for 5 minutes. Pd₂(dba)₃ (0.25 g, 0.27 mmol) was added thereto, and the mixture was stirred for 3 hours at 80° C. The mixture was filtered through Celite and then purified by column chromatography to obtain the title compound (1.32 g, 48%).
¹H NMR (CDCl₃) δ 7.43 (1H, t), 7.35 (2H, t), 7.27 (2H, m), 7.10 (1H, t), 6.75 (1H, d), 6.73 (1H, d), 6.57 (1H, brs)

Preparation Example 16

6-chloro-N-cyclopentyl-pyridine-2-amine 2,6-Dichloropyridine (2 g, 13.5 mmol) was dissolved in 14 mL of pyridine, and cyclopentylamine (4 mL, 40.5 mmol) was added thereto. The reaction mixture was stirred for 24 hours under reflux. The mixture was concentrated under reduced pressure and then purified by column chromatography to obtain the title compound (1.2 g, 44%).
¹H NMR (CDCl₃) δ 7.34 (1H, t), 6.54 (1H, d), 6.25 (1H, d), 4.69 (1H, brs), 3.91 (1H, m), 2.01 (2H, m), 1.72 (2H, m), 1.63 (2H, m), 1.47 (2H, m)

Preparation Example 17

2-tert-butylsulfanyl-6-chloro-pyridine 2,6-Dichloropyridine (2.0 g, 13.5 mmol) and Cs₂CO₃ (8.8 g, 27 mmol) were dissolved in 27 mL of DMF. 2-Methyl-2-propanethiol (1.68 mL, 14.8 mmol) was added thereto, and the mixture was stirred for 16 hours at 80° C. Solids were removed and the filtrate was concentrated under reduced pressure to obtain the title compound (2.4 g, 88%).
¹H NMR (CDCl₃) δ 7.42 (1H, t), 7.15 (1H, d), 7.04 (1H, d), 1.56 (9H, s)

Preparation Example 18

2-chloro-6-(cyclopropylmethylsulfanyl)pyridine

Step A: 6-chloropyridine-2-thiol 2-tert-butylsulfanyl-6-chloro-pyridine obtained from Preparation Example 17 (1.98 g, 9.8 mmol) was dissolved in 50 mL of acetyl chloride. 0.05 mL (0.098 mmol) of Br2 dissolved in respective 2.5 ml of acetyl chloride and acetic acid was slowly added thereto. The mixture was stirred for 4 hours at room temperature, concentrated under reduced pressure and purified by column chromatography to obtain the title compound (0.787 g, 55%).
¹H NMR (CDCl₃) δ 7.57 (2H, m), 7.15 (1H, m)

Step B:
2-chloro-6-(cyclopropylmethylsulfanyl)pyridine

6-Chloropyridine-2-thiol obtained from Step A (0.2 g, 1.3 mmol) was dissolved in 4.6 mL of DMF. Cs₂CO₃ (0.9 g, 2.6 mmol) and (bromomethyl)cyclopropane (0.16 mL, 1.6 mmol) were added thereto, and the reaction mixture was stirred for 16 hours at room temperature and for further 30 minutes at 70° C. The mixture was concentrated under reduced pressure and purified by column chromatography to obtain the title compound (0.206 g, 75%).
¹H NMR (CDCl₃) δ 7.40 (1H, t), 7.08 (1H, d), 6.98 (1H, d), 3.12 (2H, d), 1.15 (1H, m), 0.59 (2H, m), 0.33 (2H, m)

Preparation Example 19

2-chloro-6-cyclobutylsulfanyl-pyridine

6-Chloropyridine-2-thiol obtained from Step A of Preparation Example 18 (0.2 g, 1.3 mmol) was dissolved in 4.6 mL of DMF. Cs₂CO₃ (0.9 g, 2.6 mmol) and bromocyclobutane (0.16 mL, 1.6 mmol) were added thereto, and the reaction mixture was stirred for 16 hours at room temperature and for further 4 hours at 70° C. The mixture was concentrated under reduced pressure and purified by column chromatography to obtain the title compound (0.16 g, 58%).
¹H NMR (CDCl₃) δ 7.40 (1H, t), 6.98 (2H, m), 4.30 (1H, m), 2.56 (2H, m), 2.08 (4H, m)

Preparation Example 20

2-chloro-6-propylsulfanyl-pyridine

6-Chloropyridine-2-thiol obtained from Step A of Preparation Example 18 (0.2 g, 1.3 mmol) was dissolved in 4.6 mL of DMF. Cs₂CO₃ (0.9 g, 2.6 mmol) and iodopropane (0.16 mL, 1.6 mmol) were added thereto, and the reaction mixture was stirred for 16 hours at room temperature and for further 30 minutes at 70° C. The mixture was concentrated under reduced pressure and purified by column chromatography to obtain the title compound (0.18 g, 70%).
¹H NMR (CDCl₃) δ 7.40 (1H, t), 7.07 (1H, d), 6.97 (1H, d), 3.14 (2H, t), 1.74 (2H, m), 1.04 (3H, t)

Preparation Example 21

2-chloro-6-isopropoxy-pyridine

Isopropanol (0.97 g, 16.1 mmol) was dissolved in 45 mL of THF and the solution was cooled to 0° C. NaH (55% in mineral oil, 0.7 g, 16 mmol) was added thereto, and the mixture was stirred for 1 hour at room temperature. 2,6-Dichloropyridine (2.0 g, 13.5 mmol) was added thereto, and the reaction mixture was stirred for 16 hours under reflux. The mixture was cooled at room temperature, added with water (20 mL) and then extracted with EtOAc. The separated organic layer was dried with MgSO₄ and purified by column chromatography to obtain the title compound (1.917 g, 82%).

¹H NMR (CDCl₃) δ 7.48 (1H, t), 6.83 (1H, d), 6.58 (1H, d), 5.29 (1H, m), 1.34 (6H, d)

Preparation Example 22

2-chloro-6-propoxy-pyridine 30 mL of DMF was added to 6-chloro-2-pyridol (2.0 g, 15 mmol), 1-iodopropane (2.75 g, 16 mmol) and K₂CO₃ (4.27 g, 30 mmol) and the reaction mixture was stirred for 16 hours at 80° C. The mixture was concentrated under reduced pressure, added with water and then extracted with EtOAc. The separated organic layer was dried with MgSO₄ and purified by column chromatography to obtain the title compound (1.146 g, 43%).
¹H NMR (CDCl₃) δ 7.50 (1H, t), 6.87 (1H, d), 6.63 (1H, d), 4.24 (2H, t), 1.80 (2H, m), 1.02 (3H, t)

Preparation Example 23

2-chloro-6-(cyclopropylmethoxy)-pyridine 15 mL of DMF was added to 6-chloro-2-pyridol (1.0 g, 7.7 mmol), K₂CO₃ (2.13 g, 15.4 mmol) and (bromomethyl)cyclopropane (1.1 g, 8.1 mmol) and the reaction mixture was stirred for 16 hours at 80° C. The mixture was concentrated under reduced pressure and purified by column chromatography to obtain the title compound (0.65 g, 45%).
¹H NMR (CDCl₃) δ 7.50 (1H, t), 6.87 (1H, d), 6.67 (1H, d), 4.12 (2H, d), 1.26 (1H, m), 0.62 (2H, m), 0.36 (2H, m)

Preparation Example 24

2-chloro-6-(cyclobutoxy)-pyridine 5 mL of DMF was added to 6-chloro-2-pyridol (0.2 g, 1.5 mmol), bromocyclobutane (0.26 g, 1.8 mmol) and K₂CO₃ (0.43 g. 3 mmol) and the reaction mixture was stirred for 16 hours at 80° C. The mixture was concentrated under reduced pressure and purified by column chromatography to obtain the title compound (0.28 g, 98%).
¹H NMR (CDCl₃) δ 7.49 (1H, t), 6.86 (1H, d), 6.59 (1H, d), 5.16 (1H, m), 2.46 (2H, m), 2.13 (2H, m), 1.83 (1H, m), 1.66 (1H, m)

Preparation Example 25

4-[2-methyl-4-(4,4,5,5-tetramethyl-1,3,2-dioxaborolan-2-yl)phenoxy]butyric acid ethyl ester Step A: 4-bromo-2-methyl-phenol 48% HBr aqueous solution (4.8 mL) dissolved in 4.8 mL of DMSO was added slowly to o-cresol (1.04 g, 9.6 mmol) dissolved in 9.6 mL of acetic acid. The mixture was stirred for 16 hours at room temperature and then NaHCO₃ aqueous solution was slowly added. The mixture was extracted with Et₂O and the extract was dried with MgSO₄ to obtain the title compound (1.82 g, 99%).
¹H NMR (DMSO-d₆) δ 9.62 (1H, brs), 7.22 (1H, d), 7.12 (1H, dd), 6.72 (1H, d), 2.09 (3H, s)

Step B: 2-methyl-4-(4,4,5,5-tetramethyl-1,3,2-dioxaborolan-2-yl)phenol 4.6 mL of 1,4-dioxane was added to 4-bromo-2-methyl-phenol obtained from step A (0.26 g, 1.4 mmol), bis(pinacolato)diboron (0.39 g, 1.5 mmol) and potassium acetate (0.41 g, 4.1 mmol). The mixture was charged with N₂ gas for 5 minutes. PdCl₂ (dppf)-DCM (0.057 g, 0.07 mmol) was added thereto, and the mixture was stirred for 16 hours under reflux. Solids were removed and the mixture was purified by column chromatography to obtain the title compound (0.228 g, 70%).
¹H NMR (DMSO-d₆) δ 9.70 (1H, brs), 7.37 (1H, d), 7.32 (1H, dd), 6.75 (1H, d), 2.09 (3H, s), 1.25 (12H, s)

Step C: 4-[2-methyl-4-(4,4,5,5-tetramethyl-1,3,2-dioxaborolan-2-yl)phenoxy]butyric acid ethyl ester 2-Methyl-4-(4,4,5,5-tetramethyl-1,3,2-dioxaborolan-2-yl)phenol obtained from step B (0.228 g, 0.97 mmol) was dissolved in 3.2 mL of DMF. Cs₂CO₃ (0.8 g, 2.43 mmol) and 4-bromo-butyric acid ethyl ester (0.15 mL, 1.06 mmol) were added thereto, and the mixture was stirred for 16 hours at room temperature. Solids were removed and the mixture was purified by column chromatography to obtain the title compound (0.268 g, 79%).
¹H NMR (CDCl₃) δ 7.60 (1H, dd), 7.58 (1H, d), 6.79 (1H, d), 4.13 (2H, q), 4.03 (2H, t), 2.53 (2H, t), 2.20 (3H, s), 2.15 (2H, m), 1.33 (12H, s), 1.25 (3H, t)

Preparation Example 26

4-[4-(4,4,5,5-tetramethyl-1,3,2-dioxaborolan-2-yl)-2-(trifluoromethyl)phenoxy]butyric acid ethyl ester Step A: 4-bromo-2-(trifluoromethyl)phenol 2-Hydroxybenzotrifluoride (1.0 g, 6.2 mmol) was dissolved in 20 mL of chloroform. Br₂ (0.98 g, 6.2 mmol) was slowly added thereto and the mixture was stirred for 16 hours at room temperature. Sodium thiosulfate aqueous solution was added thereto and the mixture was extracted with DCM. Separated organic layer was dried with MgSO₄ to obtain the title compound (0.97 g, 65%).
¹H NMR (DMSO-d₆) δ 10.93 (1H, brs), 7.63 (2H, m), 6.99 (1H, dd)

Step B: 4-(4,4,5,5-tetramethyl-1,3,2-dioxaborolan-2-yl)-2-(trifluoromethyl)phenol 13 mL of 1,4-Dioxane was added to 4-bromo-2-(trifluoromethyl)phenol obtained from Step A (0.97 g, 4 mmol), bis(pinacolato)diboron (1.13 g, 4.4 mmol), potassium acetate (1.18 g, 12 mmol) and DPPF (0.11 g, 0.2 mmol). The mixture was charged with N₂ gas for 5 minutes. PdCl₂ (dppf)-DCM (0.164 g, 0.2 mmol) was added thereto and the mixture was stirred for 1 hour under reflux. The mixture was filtered through Celite to remove solids, and then purified by column chromatography to obtain the title compound (0.76 g, 65%).
¹H NMR (DMSO-d₆) δ 11.02 (1H, brs), 7.72 (2H, m), 7.02 (1H, dd), 1.27 (12H, s)

Step C: 4-[4-(4,4,5,5-tetramethyl-1,3,2-dioxaborolan-2-yl)-2-(trifluoromethyl)phenoxy]butyric acid ethyl ester 4-(4,4,5,5-tetramethyl-1,3,2-dioxaborolan-2-yl)-2-(trifluoromethyl)phenol obtained from Step B (0.36 g, 1.26 mmol) was dissolved in 4.2 mL of DMF. Cs₂CO₃ (0.81 g, 2.52 mmol) and 4-bromo-butyric acid ethyl ester (0.2 mL, 1.38 mmol) were added thereto and the mixture was stirred for 16 hours at room temperature. Solids were removed and the mixture was purified by column chromatography to obtain the title compound (0.374 g, 74%).

$^1$H NMR (CDCl$_3$) δ 7.99 (1H, d), 7.90 (1H, dd), 6.95 (1H, dd), 4.13 (4H, m), 2.54 (2H, t), 2.14 (2H, m), 1.33 (12H, s), 1.25 (3H, t)

Preparation Example 27

4-[2,6-difluoro-4-(4,4,5,5-tetramethyl-1,3,2-dioxaborolan-2-yl)phenoxy]pentanoic acid methyl ester Step A: 4-hydroxypentanoic acid r-Valerolactone (0.97 g, 9.68 mmol) was dissolved in 10 mL of 1,4-dioxane. 1N NaOH aqueous solution (10.6 mL, 10.6 mmol) was added thereto and the mixture was stirred for 1 hour. Using 1N HCl aqueous solution, pH of the reaction mixture was adjusted to 5 and the mixture was extracted with EtOAc. The organic layer was dried with MgSO$_4$ to obtain the title compound (0.88 g, 74%).

$^1$H NMR (CDCl$_3$) δ 3.89 (1H, m), 2.51 (2H, t), 1.82 (1H, m), 1.75 (1H, m), 1.24 (3H, d)

Step B: 4-hydroxypentanoic acid methyl ester

4-Hydroxypentanoic acid obtained from Step A (0.62 g, 5.25 mmol) was dissolved in 17 mL of THF, and diazomethane (0.25M in Et$_2$O, 31 mL, 7.88 mmol) was slowly added thereto. The mixture was stirred for 1 hour at room temperature, and then concentrated under reduced pressure. The concentrate was purified by column chromatography to obtain the title compound (0.42 g, 60%).

$^1$H NMR (CDCl$_3$) δ 3.84 (1H, m), 3.68 (3H, s), 2.46 (2H, t), 1.82 (1H, m), 1.74 (1H, m), 1.21 (3H, d)

Step C: 4-[2,6-difluoro-4-(4,4,5,5-tetramethyl-1,3,2-dioxaborolan-2-yl)phenoxy]pentanoic acid methyl ester 4-Hydroxypentanoic acid methyl ester obtained from Step B (0.05 g, 0.39 mmol), 2,6-difluoro-4-(4,4,5,5-tetramethyl-1,3,2-dioxaborolan-2-yl)phenol obtained from Step B of Preparation Example 2 (0.1 g, 0.39 mmol) and triphenylphosphine (0.1 g, 0.39 mmol) were dissolved in 4 mL of THF, and the mixture was slowly cooled to 0° C. Diisopropyl azodicarboxylate (0.077 mL, 0.39 mmol) was slowly added thereto and the reaction mixture was stirred for 18 hours at room temperature. The mixture was concentrated under reduced pressure and purified by column chromatography to obtain title compound (0.1 g, 70%).

$^1$H NMR (CDCl$_3$) δ 7.31 (2H, m), 4.38 (1H, m), 3.68 (3H, s), 2.59 (2H, t), 2.00 (2H, m), 1.32 (12H, s), 1.25 (3H, d)

Preparation Example 28

4-[[5-(4,4,5,5-tetramethyl-1,3,2-dioxaborolan-2-yl)-2-pyridyl]oxy]pentanoic acid methyl ester Step A: 4-[(5-bromo-2-pyridyl)oxy]pentanoic acid methyl ester 5-Bromo-2(1H)-pyridone (0.05 g, 0.29 mmol), 4-hydroxypentanoic acid methyl ester (0.047 g, 0.29 mmol) and triphenylphosphine (0.075 g, 0.29 mmol) were dissolved in 3 mL of THF. Diisopropyl azodicarboxylate (0.056 mL, 0.29 mmol) was added thereto, and the reaction mixture was stirred for 16 hours at room temperature. The mixture was concentrated under reduced pressure and purified by column chromatography to obtain the title compound (0.051 g, 62%).

$^1$H NMR (CDCl$_3$) δ 8.15 (1H, m), 7.60 (1H, m), 6.58 (1H, d), 5.18 (1H, m), 3.65 (3H, s), 2.41 (2H, m), 2.00 (2H, m), 1.31 (3H, d)

Step B: methyl 4-[[5-(4,4,5,5-tetramethyl-1,3,2-dioxaborolan-2-yl)-2-pyridyl]oxy]pentanoic acid methyl ester 4-[(5-Bromo-2-pyridyl)oxy]pentanoic acid methyl ester obtained from Step A (0.05 g, 0.17 mmol), bis(pinacolato)diboron (0.048 g, 0.19 mmol) and potassium acetate (0.067 g, 0.68 mmol) were dissolved in 1 mL of 1,4-dioxane, and the mixture was charged with N$_2$ gas for 5 minutes. PdCl$_2$(dppf)-DCM (0.007 g, 0.009 mmol) was added thereto, and the reaction mixture was stirred for 2 hours at 80° C. The mixture was filtered through Celite and purified by column chromatography to obtain the title compound (0.038 g, 65%).

$^1$H NMR (CDCl$_3$) δ 8.05 (1H, m), 7.89 (1H, m), 6.64 (1H, d), 5.30 (1H, m), 3.65 (3H, s), 2.44 (2H, m), 2.01 (2H, m), 1.34 (3H, d), 1.26 (12H, s)

Preparation Example 29

2-(4-bromo-phenylsulfanyl)-propionic acid methyl ester

4-Bromo-benzenethiol (0.5 g, 2.64 mmol), NaH (60% in mineral oil, 0.11 g, 2.64 mmol) and methyl 2-bromopropionate (0.32 mL, 2.91 mmol) were reacted in the same manner as in Preparation Example 12 to obtain the title compound (0.58 g, 80%).

$^1$H-NMR (CDCl$_3$) δ 7.43 (2H, d), 7.30 (2H, d), 3.76 (1H, q), 3.66 (3H, s), 1.47 (3H, d).

Preparation Example 30

2-[1-[[2,6-difluoro-4-(4,4,5,5-tetramethyl-1,3,2-dioxaborolan-2-yl)phenoxy]methyl]cyclopropyl]acetonitrile Step A: [1-(hydroxymethyl)cyclopropyl]methanol LAH (0.28 g, 7.52 mmol) was dissolved in 10 mL of THF, and the solution was cooled to −18° C. Diethyl 1,1-cyclopropanedicarboxylate (1.0 g, 5.37 mmol) in 7 mL of THF was slowly added thereto, and the reaction mixture was stirred for 16 hours at room temperature. 0.3 mL of water and the 0.3 mL of 4M NaOH aqueous solution were added thereto. The mixture was filtered with Celite and purified by column chromatography to obtain the title compound (0.2 g, 35%).

$^1$H NMR (CDCl$_3$) δ 3.62 (4H, s), 2.35 (2H, brs), 0.53 (4H, s)

Step B: [1-[(4-bromo-2,6-difluoro-phenoxy)methyl]cyclopropyl]methanol

[1-(Hydroxymethyl)cyclopropyl]methanol obtained from Step A (0.2 g, 1.96 mmol), 4-bromo-2,6-difluoro-phenol (0.314 g, 1.5 mmol) and triphenylphosphine (0.393 g, 1.5 mmol) were dissolved in 24 mL of THF. Diisopropyl azocarboxylate (0.3 mL, 1.5 mmol) was added thereto, and the reaction mixture was stirred for 16 hours at room temperature. The mixture was concentrated under reduced pressure and purified by column chromatography to obtain the title compound (0.307 g, 70%).

$^1$H NMR (CDCl$_3$) δ 7.08 (2H, m), 4.08 (2H, s), 3.68 (2H, d), 1.84 (1H, t, OH), 0.62 (4H, m)

Step C: [1-[(4-bromo-2,6-difluoro-phenoxy)methyl]cyclopropyl]methyl methanesulfonate

[1-[(4-Bromo-2,6-difluoro-phenoxy)methyl]cyclopropyl]methanol obtained from Step B (0.3 g, 1 mmol) was dissolved in 5 mL of DCM, and the solution was cooled to 0° C. Methanesulfonyl chloride (0.09 mL, 1.12 mmol) and TEA (0.21 mL, 1.5 mmol) were sequentially added thereto, and the mixture was stirred at 0° C. for 40 minutes. 5 mL of Water was added thereto, and the mixture was extracted with DCM to obtain the title compound (0.4 g, 99%).

$^1$H NMR (CDCl$_3$) δ 7.09 (2H, m), 4.29 (2H, s), 4.01 (2H, s), 3.05 (3H, s), 0.77 (2H, m), 0.73 (2H, m)

Step D: 2-[1-[(4-bromo-2,6-difluoro-phenoxy)methyl]cyclopropyl]acetonitrile

[1-[(4-Bromo-2,6-difluoro-phenoxy)methyl]cyclopropyl]methyl methane sulfonate obtained from Step C (0.4 g, 1 mmol) was dissolved in 5 mL of DMF. Sodium cyanide (0.054 g, 1.1 mmol) was added thereto, and the reaction mixture was stirred at 60° C. for 16 hours. The mixture was concentrated under reduced pressure. Water was added thereto and the mixture was extracted with EtOAc. The extract was purified by column chromatography to obtain the title compound (0.205 g, 63%).

$^1$H NMR (CDCl$_3$) δ 7.09 (2H, m), 3.98 (2H, s), 2.72 (2H, s), 0.75 (2H, m), 0.70 (2H, m)

Step E: 2-[1-[[2,6-difluoro-4-(4,4,5,5-tetramethyl-1,3,2-dioxaborolan-2-yl)phenoxy]methyl]cyclopropyl]acetonitrile 2-[1-[(4-Bromo-2,6-difluoro-phenoxy)methyl]cyclopropyl]acetonitrile obtained from Step D (0.2 g, 0.67 mmol), bis(pinacolato)diboron (0.172 g, 0.67 mmol), potassium acetate (0.266 g, 2.71 mmol) and DPPF (0.019 g, 0.033 mmol) were dissolved in 4 mL of 1,4-dioxane. The mixture was charged for 5 minutes with N$_2$ gas. PdCl$_2$ (dppf)-DCM (0.027 g, 0.033 mmol) was added thereto, and the mixture was stirred at 80° C. for 2 hours. The mixture was filtered through Celite and purified by column chromatography to obtain the title compound (0.185 g, 79%).

$^1$H NMR (CDCl$_3$) δ 7.32 (2H, m), 4.04 (2H, s), 2.75 (2H, s), 1.33 (12H, s), 0.73 (2H, m), 0.68 (2H, m)

Preparation Example 31

4-[[6-(3-hydroxyphenyl)-3-pyridyl]oxy]butyric acid ethyl ester

Step A: 4-[(6-bromo-3-pyridyl)oxy]butyric acid ethyl ester

2-Bromo-5-hydroxypyridine (1.07 g, 6.18 mmol) was dissolved in 20 mL of DMF. K$_2$CO$_3$ (1.7 g, 12.4 mmol) and 4-bromo-butyric acid ethyl ester (1.2 g, 6.18 mmol) were added thereto, and the reaction mixture was stirred for 16 hours at room temperature. The mixture was concentrated under reduced pressure. Water was added thereto and the mixture was extracted with EtOAc to obtain the title compound (1.67 g, 94%).

$^1$H NMR (CDCl$_3$) δ 8.04 (1H, m), 7.36 (1H, d), 7.09 (1H, m), 4.15 (2H, q), 4.04 (2H, t), 2.51 (2H, t), 2.13 (2H, m), 1.26 (3H, t)

Step B: 4-[[6-(3-hydroxyphenyl)-3-pyridyl]oxy]butyric acid ethyl ester

4-[(6-Bromo-3-pyridyl)oxy]butyric acid ethyl ester obtained from Step A (0.3 g, 1 mmol) and 3-hydroxyphenylboronic acid (0.172 g, 1.25 mmol) were dissolved in 3 mL of 1,2-dimethoxyethane and Na$_2$CO$_3$ (2M aqueous solution, 1.6 mL, 3.2 mmol). The mixture was charged with N$_2$ gas for 5 minutes. PdCl$_2$(PPh$_3$)$_2$ (0.036 g, 0.052 mmol) was added thereto, and the reaction mixture was stirred at 80° C. for 3 hours. Water was added thereto and the mixture was extracted with EtOAc. The organic layer was dried with MgSO$_4$ and purified by column chromatography to obtain the title compound (0.129 g, 41%).

$^1$H NMR (CDCl$_3$) δ 8.34 (1H, m), 7.62 (1H, d), 7.48 (1H, m), 7.41 (1H, m), 7.29 (1H, t), 7.25 (1H, m), 6.85 (1H, m), 5.75 (1H, brs), 4.16 (2H, q), 4.10 (2H, t), 2.54 (2H, t), 2.16 (2H, m), 1.26 (3H, t)

Preparation Example 32

2'-phenoxy-biphenyl-4-ol

2-Phenoxyphenylboronic acid (0.033 g, 0.15 mmol) and 4-iodophenol (0.034 g, 0.15 mmol) were dissolved in 3 mL of H$_2$O, and the mixture was charged with N$_2$ gas for 5 minutes. Pd/C (catalytic amount) and K$_2$CO$_3$ (0.064 g, 0.46 mmol) were added thereto, and the reaction mixture was stirred for 16 hours at room temperature. 1N HCl was added thereto and the mixture was extracted with EtOAc. The separated organic layer was dried with MgSO$_4$ and purified by column chromatography (eluent, EtOAc/Hex=1/4) to obtain the title compound (0.022 g, 55%).

$^1$H-NMR (CDCl$_3$) δ 7.46 (3H, m), 7.25 (3H, m), 7.20 (1H, m), 7.00 (2H, 6.90 (2H, m), 6.89 (2H, m), 4.65 (1H, s)

Preparation Example 33

4-(2-isopropylsulfanyl-pyridine-3-yl)-phenol

Step A: 3-chloro-2-isopropylsulfanyl-pyridine

To Isopropyl thiol (0.102 g, 1.351 mmol) dissolved in dry DMF (2 ml), NaH (60%) (0.07 g, 1.75 mmol) was added slowly dropwise at 0° C. The mixture was stirred for 30 minutes, added to the flask charged with 2,3-dichloropyridine (0.53 g, 3.58 mmol), and stirred at room temperature for 1 hour. After NH$_4$Cl aqueous solution was added thereto, organic layer was separated by extracting with EtOAc. The organic layer was dried with anhydrous MgSO$_4$ and purified by column chromatography (eluent, EtOAc/Hex=1/4) to obtain the title compound (0.062 g, 24%).

$^1$H-NMR (CDCl$_3$) δ 8.35 (1H, m), 7.52 (1H, m), 6.94 (1H, m), 4.05 (1H, m), 1.43 (6H, d)

Step B: 2-Isopropylsulfanyl-3-(4-methoxy-phenyl)-pyridine

3-Chloro-2-isopropylsulfanyl-pyridine obtained from Step A (0.02 g, 0.10 mmol) and (4-methoxy-phenyl)-boronic acid (0.024 g, 0.15 mmol) were dissolved in DMF. The mixture was charged for 5 minutes with N$_2$ gas. Pd$_2$(dba)$_3$ (catalytic amount) and Sphos (catalytic amount) were added thereto, and the reaction mixture was stirred at 80° C. for 16 hours. After NaCl aqueous solution was added thereto, the mixture was extracted with EtOAc. The separated organic layer was dried with MgSO$_4$ and purified by column chromatography (eluent, EtOAc/Hex=1/4) to obtain the title compound (0.01 g, 37%).

$^1$H-NMR (CDCl$_3$) δ 8.41 (1H, m), 7.35 (3H, m), 7.02 (1H, m), 6.95 (2H, m), 4.06 (1H, m), 3.84 (3H, s), 1.35 (6H, d)

Step C:
4-(2-isopropylsulfanyl-pyridine-3-yl)-phenol

2-Isopropylsulfanyl-3-(4-methoxy-phenyl)-pyridine obtained from Step B (0.02 g, 0.07 mmol) was dissolved in DCM (3 mL), and the solution was cooled to −78° C. BBr$_3$ (1.0 M in DCM, 0.116 mL, 0.11 mmol) was slowly added thereto, and the mixture was stirred for 3 hours at room temperature. Upon completion of the reaction, the mixture was cooled to −20° C. Methanol was added to the residue to dilute. The mixture was extracted with DCM. The organic layer was dried with MgSO$_4$ and concentrated under reduced pressure. The obtained residue was purified by column chromatography (eluent, EtOAc/Hex=1/3) to obtain the title compound (15 mg, 75%).

$^1$H-NMR (CDCl$_3$) δ 8.41 (1H, m), 7.34 (1H, m), 7.26 (2H, m), 7.02 (1H, m), 6.89 (2H, m), 4.79 (1H, s), 4.05 (1H, m), 1.35 (6H, d)

Preparation Example 34

3,5-difluoro-2'-phenoxy-biphenyl-4-ol

Step A:
3,5-difluoro-4-methoxy-2'-phenoxy-biphenyl

2-Phenoxyphenylboronic acid (0.045 g, 0.21 mmol) and 5-bromo-1,3-difluoro-2-methoxy-benzene (0.031 g, 0.14 mmol) were dissolved in isopropyl alcohol/water (1/1). Pd/C (catalytic amount) and Na$_3$PO$_4$ 12H$_2$O (0.186 g, 0.49 mmol) were added thereto, and the mixture was stirred at 80° C. for 1 hour. The mixture was filtered through Celite, and extracted with EtOAc to separate organic layer. The organic layer was dried with MgSO$_4$ and purified by column chromatography (eluent, EtOAc/Hex=1/20) to obtain the title compound (0.026 g, 40%).

$^1$H-NMR (CDCl$_3$) δ 7.40 (1H, m), 7.30 (3H, m), 7.20 (1H, m), 7.11 (2H, m), 7.05 (1H, m), 6.97 (1H, m), 6.91 (2H, m), 4.00 (3H, s)

Step B: 3,5-difluoro-2'-phenoxy-biphenyl-4-ol 3,5-Difluoro-4-methoxy-2'-phenoxy-biphenyl obtained from Step A (0.026 g, 0.083 mmol) was reacted in the same manner as in step C of Preparation Example 33 to obtain the title compound (0.018 g, 72%).

$^1$H-NMR (CDCl$_3$) δ 7.40 (1H, m), 7.30 (3H, m), 7.20 (1H, m), 7.11 (2H, m), 7.05 (1H, m), 6.96 (1H, m), 6.91 (2H, m), 5.08 (1H, s)

Preparation Example 35

4-(2-cyclopentylsulfanyl-pyridine-3-yl)-phenol

Step A: 3-chloro-2-cyclopentylsulfanyl-pyridine

Cyclopentyl thiol (0.477 g 4.67 mmol) was dissolved in dry DMF (2 ml) and the solution was cooled to 0° C. NaH (60%)(0.24 g, 6.03 mmol) was added slowly dropwise thereto and the mixture was stirred for 30 minutes. The mixture was added to the flask charged with 2,3-dichloro-pyridine (0.69 g, 4.67 mmol) and stirred for 1 hour at room temperature. To the reaction mixture, NH$_4$Cl aqueous solution was added and the mixture was extracted with EtOAc to separate organic layer. The organic layer was dried with anhydrous MgSO$_4$ and purified by column chromatography (eluent, EtOAc/Hex=1/4) to obtain the title compound (0.61 g, 61%).

$^1$H-NMR (CDCl$_3$) δ 8.33 (1H, m), 7.51 (1H, m), 6.92 (1H, m), 4.09 (1H, m), 2.23 (2H, m), 1.79 (2H, m), 1.66 (4H, m)

Step B: 2-cyclopentylsulfanyl-3-(4-methoxy-phenyl)-pyridine

3-Chloro-2-cyclopentylsulfanyl-pyridine obtained from Step A (0.057 g, 0.266 mmol) was reacted in the same manner as in Step B of Preparation Example 33 to obtain the title compound (0.046 g, 61%).

$^1$H-NMR (CDCl$_3$) δ 8.41 (1H, m), 7.36 (3H, m), 7.01 (1H, m), 6.96 (2H, m), 4.08 (1H, m), 3.85 (3H, s), 2.19 (2H, m), 1.70 (2H, m), 1.66 (4H, m)

Step C:
4-(2-cyclopentylsulfanyl-pyridine-3-yl)-phenol

2-Cyclopentylsulfanyl-3-(4-methoxy-phenyl)-pyridine obtained from Step B (0.046 g, 0.161 mmol) was reacted in the same manner as in Step C of Preparation Example 33 to obtain the title compound (0.024 g, 55%).

$^1$H-NMR (CDCl$_3$) δ 8.40 (1H, m), 7.33 (3H, m), 7.01 (1H, m), 6.98 (2H, m), 4.87 (1H, s), 4.09 (1H, m), 2.18 (2H, m), 1.70 (2H, m), 1.66 (4H, m)

Preparation Example 36

3-iodo-2-phenoxy-pyridine

2-Fluoro-3-iodo-pyridine (0.054 g, 0.24 mmol) and Cs$_2$CO$_3$ (0.158 g, 0.266 mmol) and phenol (0.025 g, 0.266 mmol) were dissolved in 2 mL of DMF. The reaction mixture was stirred at 80° C. for 16 hours. NaCl aqueous solution was added thereto and the mixture was extracted with EtOAc to separate organic layer. The organic layer was dried with anhydrous MgSO$_4$ and purified by column chromatography (eluent, EtOAc/Hex=1/7) to obtain the title compound (0.058 g, 71%).

$^1$H-NMR (CDCl$_3$) δ 8.15 (1H, m), 8.08 (1H, m), 7.40 (2H, m), 7.26 (1H, m), 7.15 (2H, m), 6.75 (1H, m)

Preparation Example 37

3-iodo-2-isopropoxy-pyridine

Isopropyl alcohol (0.043 g, 717 mmol) was dissolved in dry DMF (3 ml), and at 0° C. NaH (60%)(0.03 g, 0.71 mmol) was added slowly dropwise thereto. The mixture was stirred for 30 minutes. The reaction mixture was added to the flask charged with 2-fluoro-3-iodo-pyridine (0.10 g, 0.44 mmol), and stirred for 1 hour at room temperature. NH$_4$Cl aqueous solution was added thereto, and the mixture was extracted with EtOAc to separate organic layer. The organic layer was dried with anhydrous MgSO$_4$ and purified by column chromatography (eluent, EtOAc/Hex=1/4) to obtain the title compound (0.029 g, 24%).

¹H-NMR (CDCl₃) δ 8.08 (1H, m), 8.00 (1H, m), 6.59 (1H, m), 5.27 (1H, m), 1.38 (6H, d)

Preparation Example 38

2-cyclopentoxy-3-iodo-pyridine

Cyclopentanol and 2-fluoro-3-iodo-pyridine (0.10 g, 0.44 mmol) were reacted in the same manner as in Preparation Example 37 to obtain the title compound (0.091 g, 70%).
¹H-NMR (CDCl₃) δ 8.09 (1H, m), 7.99 (1H, m), 6.59 (1H, m), 5.43 (1H, m), 2.00 (2H, m), 1.94 (4H, m), 1.66 (2H, m)

Preparation Example 39

2-cyclopentylsulfanyl-3-iodo-pyridine

2-Fluoro-3-iodo-pyridine (0.065 g, 0.29 mmol), Cs₂CO₃ (0.19 g, 0.58 mmol) and cyclopentylthiol (0.03 g, 0.291 mmol) were dissolved in 2 mL of DMF. The reaction mixture was stirred at 80° C. for 2 hours. NaCl aqueous solution was added thereto and the mixture was extracted with EtOAc to separate organic layer. The organic layer was dried with MgSO₄ and purified by column chromatography (eluent, EtOAc/Hex=1/4) to obtain the title compound (0.053 g, 65%).
¹H-NMR (CDCl₃) δ 8.38 (1H, m), 7.89 (1H, m), 6.68 (1H, m), 4.00 (1H, m), 2.22 (2H, m), 1.80 (2H, m), 1.66 (4H, m)

Preparation Example 40

2-cyclopropylmethoxy-3-iodo-pyridine

Cyclopropyl-methanol (0.089 g, 1.23 mmol) was dissolved in dry DMF (2 ml), and at 0° C. NaH (60%)(0.054 g, 1.35 mmol) was added slowly dropwise thereto. The mixture was stirred for 30 minutes, slowly added to the flask charged with 2-fluoro-3-iodo-pyridine (0.137 g, 0.617 mmol) and then stirred for 1 hour at room temperature. NH₄Cl aqueous solution was added thereto and the mixture was extracted with EtOAc to separate organic layer. The organic layer was dried with anhydrous MgSO₄ and purified by column chromatography (eluent, EtOAc/Hex=1/5) to obtain the title compound (0.141 g, 83%).
¹H-NMR (CDCl₃) δ 8.07 (1H, m), 8.00 (1H, m), 6.61 (1H, m), 4.20 (2H, d), 1.32 (1H, m), 0.60 (2H, m), 0.39 (2H, m)

Preparation Example 41

2-cyclopropylmethylsulfanyl-3-(3,5-difluoro-4-methoxy-phenyl)-pyridine

Step A:
3-iodo-2-(4-methoxy-benzylsulfanyl)-pyridine

2-Fluoro-3-iodo-pyridine (0.42 g, 1.8 mmol) and (4-methoxyphenyl)methanethiol (0.43 g, 2.8 mmol) were reacted in the same manner as in Preparation Example 12 to obtain the title compound (0.56 g, 84%).
¹H-NMR (CDCl₃) δ 8.43 (1H, m), 7.93 (1H, m), 7.32 (2H, d), 6.85 (2H, d), 6.74 (1H, m), 4.35 (2H, s), 3.79 (3H, s)

Step B: 3-(3,5-difluoro-4-methoxy-phenyl)-2-(4-methoxy-benzylsulfanyl)-pyridine

3-Iodo-2-(4-methoxy-benzylsulfanyl)-pyridine obtained from Step A (0.1 g, 0.28 mmol) and 2-(3,5-difluoro-4-methoxy-phenyl)-4,4,5,5-tetramethyl-[1,3,2]dioxaborolane obtained from Preparation Example 238 (0.11 g, 0.42 mmol) were reacted in the same manner as in Step A of Example 28 to obtain the title compound (0.08 g, 77%).
¹H-NMR (CDCl₃) δ 8.47 (1H, m), 7.36 (1H, m), 7.30 (2H, d), 7.07 (1H, m), 6.96 (2H, m), 6.81 (2H, d), 4.38 (2H, s), 4.03 (3H, s), 3.78 (3H, s)

Step C:
3-(3,5-difluoro-4-methoxy-phenyl)-pyridine-2-thiol 3-(3,5-Difluoro-4-methoxy-phenyl)-2-(4-methoxy-benzylsulfanyl)-pyridine obtained from Step B (0.033 g, 0.097 mmol) was dissolved in TFA (2 ml). Anisole (0.5 ml) and triflic acid (0.2 mL) were slowly added thereto, and the mixture was stirred at 70° C. for 1 hour. At 0° C., sodium bicarbonate aqueous solution was added slowly thereto and the mixture was extracted with EtOAc. The organic layer was dried with MgSO₄, evaporated under reduced pressure and recrystallized with Et₂O to obtain the title compound (0.033 g, 61%).
¹H-NMR (DMSO-d₆) δ 7.72 (1H, m), 7.57 (1H, m), 7.42 (2H, m), 6.84 (1H, m), 3.96 (3H, s)

Step D: 2-cyclopropylmethylsulfanyl-3-(3,5-difluoro-4-methoxy-phenyl)-pyridine 3-(3,5-Difluoro-4-methoxy-phenyl)-pyridine-2-thiol obtained from Step C (0.033 g, 0.13 mmol) was dissolved in dry DMF (1.5 ml), and at 0° C. NaH (60%)(0.01 g, 0.195 mmol) was added slowly dropwise thereto. The mixture was stirred for 30 minutes. Bromomethyl cyclopropane (0.021 g, 0.156 mmol) was added slowly at 0° C. thereto, and the reaction mixture was stirred for 2 hours at room temperature. NH₄Cl aqueous solution was added thereto, and the mixture was extracted with EtOAc to separate organic layer. The organic layer was dried with MgSO₄, purified with column chromatography (eluent, EtOAc/Hex=1/5) to obtain the title compound (0.032 g, 82%).
¹H-NMR (CDCl₃) δ 8.42 (1H, m), 7.33 (1H, m), 7.00 (3H, m), 4.06 (3H, s), 3.12 (2H, d), 1.12 (1H, m), 0.57 (2H, m), 0.29 (2H, m)

Preparation Example 42

2-cyclobutylsulfanyl-3-(4-methoxy-phenyl)-pyridine

Step A: 2-(4-methoxy-benzylsulfanyl)-3-(4-methoxy-phenyl)-pyridine

3-Iodo-2-(4-methoxy-benzylsulfanyl)-pyridine obtained from Step A of Preparation Example 41 (0.1 g, 0.28 mmol) and (4-methoxyphenyl)boronic acid (0.085 g, 0.56 mmol) were reacted in the same manner as in Step A of Example 28 to obtain the title compound (0.075 g, 79%).
¹H-NMR (CDCl₃) δ 8.44 (1H, m), 7.36 (1H, m), 7.33 (4H, m), 7.05 (1H, m), 6.93 (2H, d), 6.80 (2H, d), 4.36 (2H, s), 3.83 (3H, s), 3.76 (3H, s)

Step B: 3-(4-methoxy-phenyl)-pyridine-2-thiol 2-(4-methoxy-benzylsulfanyl)-3-(4-methoxy-phenyl)-pyridine obtained from Step A (0.212 g, 0.628 mmol) was reacted in the same manner as in Step C of Preparation Example 41 to obtain the title compound (0.109 g, 80%).

$^1$H-NMR (DMSO-d$_6$) δ 7.65 (1H, m), 7.55 (2H, d), 7.48 (1H, m), 6.93 (2H, d), 6.82 (1H, m), 3.78 (3H, s)

Step C:
2-cyclobutylsulfanyl-3-(4-methoxy-phenyl)-pyridine 3-(4-Methoxy-phenyl)-pyridine-2-thiol obtained from Step B (0.212 g, 0.628 mmol), NaH (0.012 g, 0.294 mmol) and bromo-cyclobutane (0.024 g, 0.176 mmol) were reacted in the same manner as in Step D of Preparation Example 41 to obtain the title compound (0.0094 g, 24%).
$^1$H-NMR (CDCl$_3$) δ 8.37 (1H, m), 7.34 (3H, m), 7.02 (3H, m), 4.42 (1H, m), 3.86 (3H, s), 2.49 (2H, m), 2.03 (4H, m)

Preparation Example 43

2-cyclopropylmethylsulfanyl-3-(4-methoxy-phenyl)-pyridine 2-(4-Methoxy-benzylsulfanyl)-3-(4-methoxy-phenyl)-pyridine obtained from Step A of Preparation Example 42 (0.04 g, 0.184 mmol) was reacted in the same manner as in Steps C and D of Preparation Example 41 to obtain the title compound (0.02 g, 44%).
$^1$H-NMR (CDCl$_3$) δ 8.40 (1H, m), 7.37 (3H, m), 7.02 (3H, m), 4.09 (2H, m), 3.86 (3H, s), 1.09 (1H, m), 0.54 (2H, m), 0.27 (2H, m)

Preparation Example 44

2-cyclobutylsulfanyl-3-iodo-pyridine

Step A: cyclobutanethiol

Magnesium (0.99 g, 40.74 mmol) was dissolved in THF (20 mL). At 50° C., cyclobutyl bromide (5.0 g, 37.03 mmol) in THF (5 mL) was slowly added thereto and the mixture was stirred for 2 hours under reflux. At 0° C., sulfur (1.06 g, 33.33 mmol) was added slowly and the mixture was stirred at 50° C. for 2 hours. At 0° C., LAH (0.843 g, 22.22 mmol) was slowly added thereto and the mixture was stirred for 30 minutes under reflux. At 0° C., ammonium chloride aqueous solution (20 mL) and 1N HCl (20 mL) was used to terminate the reaction. The mixture was extracted with Et$_2$O (30 ml*3) to separate organic layers. The organic layers were dried with MgSO$_4$ and used for the next reaction.

Step B: 2-cyclobutylsulfanyl-3-iodo-pyridine

Cyclobutanethiol obtained from Step A (0.069 g, 0.782 mmol) and 2-fluoro-3-iodo-pyridine (0.1 g, 0.43 mmol) were dissolved in DMF (3 mL). Cs$_2$CO$_3$ (0.26 g, 0.86 mmol) was added thereto, and the reaction mixture was stirred with heating at 80° C. NaCl aqueous solution was added thereto and the mixture was extracted with EtOAc. The organic layer was dried with MgSO$_4$ and purified by column chromatography (eluent, EtOAc/Hex=1/4) to obtain the title compound (0.115 g, 91%).
$^1$H-NMR (CDCl$_3$) δ 8.36 (1H, m), 7.90 (1H, m), 6.69 (1H, m), 4.33 (1H, m), 2.54 (2H, m), 2.14 (2H, m), 2.05 (2H, m)

Preparation Example 45

3-(4-methoxy-phenyl)-2-propylsulfanyl-pyridine 3-(4-Methoxy-phenyl)-pyridine-2-thiol obtained from Step B of Preparation Example 42 (0.053 g, 0.243 mmol), NaH (0.02 g, 0.487 mmol) and 1-iodo-propane (0.049 g, 0.292 mmol) were reacted in the same manner as in Step D of Preparation Example 41 to obtain the title compound (0.023 g, 36%).
$^1$H-NMR (CDCl$_3$) δ 8.40 (1H, m), 7.36 (3H, m), 7.03 (1H, m), 6.98 (2H, m), 3.86 (3H, s), 3.13 (2H, m), 1.68 (2H, m), 1.01 (3H, m)

Preparation Example 46

1-bromo-2-isopropoxy-benzene

2-Bromo-phenol (0.373 g, 2.15 mmol) and 2-bromo-propane (0.291 g, 2.371 mmol) were reacted in the same manner as in Step B of Preparation Example 44 to obtain the title compound (0.257 g, 55%).
$^1$H-NMR (CDCl$_3$) δ 7.52 (1H, m), 7.25 (1H, m), 6.91 (1H, m), 6.80 (1H, m), 4.54 (1H, m), 1.38 (6H, d)

Preparation Example 47

1-bromo-2-cyclobutoxy-benzene

2-Bromo-phenol (0.235 g, 1.35 mmol) and bromo-cyclobutane (0.201 g, 1.49 mmol) were reacted in the same manner as in step B of Preparation Example 44 to obtain the title compound (0.061 g, 19%).
$^1$H-NMR (CDCl$_3$) δ 7.53 (1H, m), 7.19 (1H, m), 6.76 (1H, m), 6.80 (1H, m), 4.68 (1H, m), 2.46 (2H, m), 2.27 (2H, m), 1.88 (1H, m), 1.68 (1H, m)

Preparation Example 48

1-bromo-2-cyclopropylmethoxy-benzene

2-Bromo-phenol (0.235 g, 1.35 mmol) and bromomethyl-cyclopropane (0.201 g, 1.49 mmol) were reacted in the same manner as in Step B of Preparation Example 44 to obtain the title compound (0.267 g, 86%).
$^1$H-NMR (CDCl$_3$) δ 7.54 (1H, m), 7.22 (1H, m), 6.90 (1H, m), 6.83 (1H, m), 3.89 (2H, d), 1.31 (1H, m), 0.63 (2H, m), 0.40 (2H, m)

Preparation Example 49

1-bromo-2-cyclopentoxy-benzene

2-Bromo-phenol (0.366 g, 2.11 mmol) and bromo-cyclopentane (0.341 g, 2.32 mmol) were reacted in the same manner as in Step B of Preparation Example 44 to obtain the title compound (0.369 g, 72%).
$^1$H-NMR (CDCl$_3$) δ 7.51 (1H, m), 7.25 (1H, m), 6.88 (1H, m), 6.78 (1H, m), 4.80 (1H, m), 1.88 (6H, m), 1.65 (2H, m)

Preparation Example 50

4-bromo-2-methyl-butyric acid ethyl ester

Step A: (E)-4-benzyloxy-2-methyl-2-butenoic acid ethyl ester

Benzyloxy-acetaldehyde (0.95 g, 6.35 mmol) was dissolved in benzene (21 mL), and at room temperature, (1-ethoxycarbonylethylidene)triphenylphosporane (2.76 g, 7.63 mmol) was added thereto. The mixture was stirred at 70° C. for 16 hours. After completion of the reaction, the mixture was concentrated under reduced pressure and purified by column chromatography (eluent, EtOAc/Hex=1/4) to obtain the title compound (1.31 g, 94%).

$^1$H-NMR (CDCl$_3$) δ 7.35 (5H, m), 6.86 (1H, m), 4.54 (2H, s), 4.19 (4H, m), 1.81 (3H, m), 1.28 (3H, m)

Step B: 4-hydroxy-2-methyl-butyric acid ethyl ester (E)-4-benzyloxy-2-methyl-2-butenoic acid ethyl ester obtained from Step A (1.31 g, 5.97 mmol) was dissolved in EtOAc/MeOH (8/2)(20 mL), and 10% Pd/C (0.13 g) was added thereto. The mixture was stirred for 12 hours under H$_2$ atmosphere at room temperature. After completion of the reaction, the mixture was filtered by Celite, concentrated under reduced pressure and purified by column chromatography (eluent, EtOAc/Hex=1/2) to obtain the title compound (0.726 g, 98%).

$^1$H-NMR (CDCl$_3$) δ 4.13 (2H, m), 3.68 (2H, m), 2.62 (1H, m), 1.19 (1H, m), 1.70 (1H, m), 1.56 (1H, m), 1.24 (3H, m), 1.18 (3H, d)

Step C: 4-bromo-2-methyl-butyric acid ethyl ester

NBS (2.14 g, 12.05 mmol) was dissolved in DCM (10 ml), and triphenylphosphine (2.94 g, 11.22 mmol) was added thereto. The mixture was stirred for 10 minutes. Pyridine (0.38 g, 4.80 mmol) and then 4-hydroxy-2-methyl-butyric acid ethyl ester (0.586 g, 4.00 mmol) obtained from Step B were added thereto. The mixture was stirred for 16 hours. After completion of the reaction, the mixture was concentrated under reduced pressure and purified by column chromatography (eluent, EtOAc/Hex=1/4) to obtain a small amount of title compound (0.061 g, 7.3%).

$^1$H-NMR (CDCl$_3$) δ 4.13 (2H, m), 3.41 (2H, m), 2.67 (1H, m), 2.27 (1H, m), 1.91 (1H, m), 1.26 (3H, m), 1.19 (3H, d)

Preparation Example 51

4-(2-cyclobutylsulfanyl-pyridin-3-yl)-2,6-difluoro-phenol

2-Cyclobutylsulfanyl-3-iodo-pyridine (0.193 g, 0.66 mmol) obtained in Preparation Example 44 and 2,6-difluoro-4-(4,4,5,5-tetramethyl-1,3,2-dioxaborolan-2-yl)phenol (0.254 g, 0.992 mmol) obtained in step B of Preparation Example 2 were reacted in the same manner as in Step A of Example 50 to obtain the title compound (0.078 g, 40%).

$^1$H-NMR (CDCl$_3$) δ 8.39 (1H, m), 7.30 (1H, m), 6.98 (3H, m), 5.15 (1H, s), 4.40 (1H, m), 2.49 (2H, m), 2.02 (4H, m)

Preparation Example 52

2-[2,6-difluoro-4-(4,4,5,5-tetramethyl-[1,3,2]dioxaborolan-2-yl)-phenoxymethyl]-cyclopropanecarboxylic acid ethyl ester Step A: (E/Z)-4-benzyloxy-but-2-enoic acid ethyl ester Benzyloxy-acetaldehyde (0.95 g, 6.35 mmol) and ethyl 2-(triphenylphosphoranylidene)acetate (1.36 g, 3.92 mmol) were reacted in the same manner as in Step A of Preparation Example 50 to obtain the title compound (E/Z mixture) (0.043 g, 40%).

$^1$H-NMR (CDCl$_3$) δ 7.34 (5H, m), 6.96 (0.62H, m), 6.42 (0.38H, m), 6.13 (0.62H, m), 5.82 (0.38H, m), 4.56 (2H, s), 4.19 (4H, m), 1.27 (3H, m)

Step B: 2-benzyloxymethyl-cyclopropanecarboxylic acid ethyl ester

After (E/Z)-4-benzyloxy-but-2-enoic acid ethyl ester (0.36 g, 1.63 mmol) obtained in Step A was dissolved in THF (5 mL), diazomethane (30 mL, 8.23 mmol, 0.25M Et$_2$O) was added thereto. After the reactant was cooled to 0-5° C., palladium(II) acetate (0.022 g, 0.098 mmol) was added slowly thereto, and the mixture was agitated at room temperature for 1 hours. After the termination of the reaction, the reactant was added with water and then extracted. The organic layer was concentrated under reduced pressure and the residue was purified by column chromatography (eluent: EtOAc/Hex=1/4) to obtain the title compound (0.119 g, 31%).

$^1$H-NMR (CDCl$_3$) δ 7.32 (5H, m), 4.51 (2H, s), 4.10 (2H, m), 3.41 (2H, m), 1.70 (1H, m), 1.55 (1H, m), 1.24 (4H, m), 0.85 (1H, m)

Step C: 2-hydroxymethyl-cyclopropanecarboxylic acid ethyl ester

2-Benzyloxymethyl-cyclopropanecarboxylic acid ethyl ester (0.119 g, 0.50 mmol) obtained in Step B was reacted in the same manner as in Step B of Preparation Example 50 to obtain the title compound (0.067 g, 91%).

$^1$H-NMR (CDCl$_3$) δ 4.13 (2H, s), 3.60 (1H, m), 3.50 (1H, m), 1.70 (1H, m), 1.55 (2H, m), 1.20 (4H, m), 0.85 (1H, m)

Step D: 2-[2,6-difluoro-4-(4,4,5,5-tetramethyl-[1,3,2]dioxaborolan-2-yl)-phenoxymethyl]-cyclopropanecarboxylic acid ethyl ester After 2-hydroxymethyl-cyclopropanecarboxylic acid ethyl ester (0.067 g, 0.46 mmol) obtained in Step C, 2,6-difluoro-4-(4,4,5,5-tetramethyl-1,3,2-dioxaborolan-2-yl) phenol (0.118 g, 0.46 mmol) obtained in Step B of Preparation Example 2 and triphenylphosphine (0.121 g, 0.46 mmol) were dissolved in THF (5 mL), diisopropyl azocarboxylate was added thereto, and the mixture was agitated at room temperature for 16 hours. The reactant was concentrated under reduced pressure and purified by column chromatography to obtain the title compound (0.084 g, 47%).

$^1$H-NMR (CDCl$_3$) δ 7.28 (2H, m), 4.11 (3H, m), 4.00 (1H, m), 1.85 (1H, m), 1.60 (1H, m), 1.29 (12H, s), 1.25 (4H, m), 0.85 (1H, m)

Preparation Example 53

4-[2,5-difluoro-4-(4,4,5,5-tetramethyl-[1,3,2]dioxaborolan-2-yl)-phenoxy]-butyric acid ethyl ester Step A: 4-bromo-2,5-difluoro-phenol 2,5-Difluoro-phenol (0.70 g, 2.4 mmol) was dissolved in chloroform (18 mL), and bromine (0.431 g, 5.4 mmol) dissolved in chloroform (2 mL) was added thereto dropwise at 0° C. The mixture was reacted for 16 hours, and the reaction was terminated by adding NaS$_2$O$_3$ aqueous solution. The reactant was diluted with water, and extracted with EtOAc. The organic layer was separated and dried with MgSO$_4$ and next step was progressed.

$^1$H-NMR (CDCl$_3$) δ 7.25 (1H, m), 6.83 (1H, m), 5.23 (1H, s)

Step B: 4-(4-bromo-2,5-difluoro-phenoxy)-butyric acid ethyl ester

4-Bromo-2,5-difluoro-phenol (0.865 g, 4.13 mmol) obtained in step A was reacted in the same manner as in Step A of Example 38 to obtain the title compound (1.07 g, 79%).

$^1$H-NMR (CDCl$_3$) δ 7.24 (1H, m), 6.78 (1H, m), 4.15 (2H, q), 4.05 (2H, t), 2.53 (2H, t), 2.13 (2H, m), 1.25 (3H, t)

Step C: 4-[2,5-difluoro-4-(4,4,5,5-tetramethyl-[1,3,2]dioxaborolan-2-yl)-phenoxy]-butyric acid ethyl ester 4-(4-Bromo-2,5-difluoro-phenoxy)-butyric acid ethyl ester (1.07 g, 3.31 mmol) obtained in step B, bis(pinacolato)diboron (0.88 g, 3.47 mmol), potassium acetate (1.30 g, 13.24 mmol) and DPPF (0.092 g, 0.16 mmol) were dissolved in 1,4-dioxane (20 mL), the mixture was charged with N$_2$ gas for 5 minutes, then PdCl$_2$(dppf)-DCM (0.135 g, 0.16 mmol) was added thereto. The reactant was agitated at 80° C. for 16 hours, and filtered by using celite, and purified by column chromatography to obtain the title compound (0.727 g, 59%).

$^1$H-NMR (CDCl$_3$) δ 7.37 (1H, m), 6.16 (1H, m), 4.13 (2H, q), 4.06 (2H, t), 2.52 (2H, t), 2.14 (2H, m), 1.30 (12H, s), 1.25 (3H, t)

Preparation Example 54

4-[3,5-difluoro-4-(4,4,5,5-tetramethyl-1,3,2-dioxaborolan-2-yl)phenoxy]butyric acid ethyl ester 4-Bromo-3,5-difluoro-phenol (1.1 g, 5.26 mmol) and 4-bromo-butyric acid ethyl ester (1.03 g, 5.26 mmol) were reacted in the same manner as in step B of Preparation Example 4 to obtain 4-(4-bromo-3,5-difluoro-phenoxy)-butyric acid ethyl ester (0.90 g, 54%).

Then, 4-(4-bromo-3,5-difluoro-phenoxy)-butyric acid ethyl ester (0.37 g, 1.15 mmol) and bis(pinacolato)diboron (0.35 g, 1.37 mmol) were reacted in the same manner as in step A of Preparation Example 4 to obtain the title compound (0.10 g, 24%).

$^1$H-NMR (CDCl$_3$) δ 6.38 (2H, m), 4.15 (2H, q), 3.98 (2H, t), 2.49 (2H, t), 2.11 (2H, m), 1.35 (12H, s), 1.26 (3H, t)

Preparation Example 55

4-(2-cyclopentyloxy-pyridin-3-yl)-2,6-difluoro-phenol

2-Cyclopentoxy-3-iodo-pyridine (0.52 g, 1.8 mmol) obtained in Preparation Example 38 and 2,6-difluoro-4-(4,4,5,5-tetramethyl-1,3,2-dioxaborolan-2-yl)phenol (0.46 g, 1.8 mmol) obtained in step B of Preparation Example 2 were reacted in the same manner as in Preparation Example 13 to obtain the title compound (0.35 g, 67%).

$^1$H-NMR (CDCl$_3$) δ 8.14 (1H, m), 7.56 (1H, m), 7.17 (2H, m), 6.93 (1H, m), 5.96 (1H, bs), 5.51 (1H, m), 1.94 (2H, m), 1.82 (2H, m), 1.74 (2H, m), 1.63 (2H, m)

Preparation Example 56

4-[2,6-difluoro-4-(2-fluoro-3-pyridyl)phenoxy]butyric acid

Ethyl 4-[2,6-difluoro-4-(2-fluoro-3-pyridyl)phenoxy]butanoate (1.7 g, 5.01 mmol) obtained in Preparation Example 109 was reacted in the same manner as in step B of Example 1 to obtain the title compound (1.5 g, 96%).

$^1$H-NMR (CDCl$_3$) δ 8.22 (1H, m), 7.82 (1H, m), 7.29 (1H, m), 7.15 (2H, m), 4.27 (2H, t), 2.68 (2H, t), 2.14 (2H, m)

Preparation Example 57

4-[2,6-difluoro-4-(6-formyl-pyridin-2-yl)-phenoxy]-butyric acid ethyl ester 6-Bromo-pyridine-2-carbaldehyde (0.50 g, 2.7 mmol) and 4-[2,6-difluoro-4-(4,4,5,5-tetramethyl-1,3,2-dioxaborolan-2-yl)phenoxy]butyric acid ethyl ester (1.0 g, 2.7 mmol) obtained in Preparation Example 2 were reacted in the same manner as in Preparation Example 13 to obtain the title compound (0.40 g, 43%).

$^1$H-NMR (CDCl$_3$) δ 10.1 (1H, s), 7.93 (2H, m), 7.86 (1H, d), 7.69 (2H, m), 4.27 (2H, t), 4.16 (2H, q), 2.62 (2H, t), 2.13 (2H, m), 1.28 (3H, t)

Preparation Example 58

3-iodo-2-(tetrahydro-pyran-4-yloxy)-pyridine

Tetrahydro-pyran-4-ol (0.45 g, 4.44 mmol) and 2-fluoro-3-iodo-pyridine (0.66 g, 2.96 mmol) were reacted in the same manner as in Preparation Example 37 to obtain the title compound (0.80 g, 89%).

$^1$H-NMR (CDCl$_3$) δ 8.07 (1H, d), 8.01 (1H, d), 6.63 (1H, m), 5.30 (1H, m), 4.01 (2H, m), 3.68 (2H, m), 2.04 (2H, m), 1.85 (2H, m)

Preparation Example 59

3-iodo-2-(tetrahydro-furan-3-yloxy)-pyridine

Tetrahydro-furan-3-ol (0.39 g, 4.44 mmol) and 2-fluoro-3-iodo-pyridine (0.66 g, 2.96 mmol) were reacted in the same manner as in Preparation Example 37 to obtain the title compound (0.68 g, 80%).

$^1$H-NMR (CDCl$_3$) δ 8.08 (1H, m), 8.03 (1H, m), 6.65 (1H, m), 5.53 (1H, m), 4.12 (1H, m), 4.06 (1H, m), 3.94 (2H, m), 2.23 (2H, m)

Preparation Example 60

1-cyclobutoxy-3-iodo-benzene

After 3-iodophenol (0.5 g, 2.27 mmol) was dissolved in CH$_3$CN (5 mL), Cs$_2$CO$_3$ (2.22 g, 6.81 mmol) and bromo-cyclobutane (0.21 mL, 2.27 mmol) were added thereto. The mixture was agitated at 80-85° C. for 10 hours, and the reactant was cooled and filtered by using celite. The residue was concentrated under reduced pressure and purified by column chromatography (eluent: EtOAc/Hex=1/10) to obtain the title compound (0.45 g, 72%).

$^1$H NMR (400 MHz, CDCl$_3$) δ 7.25-7.20 (m, 1H), 7.17-7.13 (m, 1H), 6.92 (t, 1H), 6.77-6.72 (m, 1H), 4.59-4.50 (m, 1H), 2.44-2.33 (m, 2H), 2.19-2.05 (m, 2H), 1.88-1.77 (m, 1H), 1.70-1.57 (m, 1H)

Preparation Example 61

2-cyclobutylmethoxy-3-iodo-pyridine

Cyclobutyl-methanol (0.37 g, 4.31 mmol) and 2-fluoro-3-iodo-pyridine (0.60 g, 2.69 mmol) were reacted in the same manner as in Preparation Example 37 to obtain the title compound (0.75 g, 96%).

$^{1}$H-NMR (CDCl$_3$) δ 8.08 (1H, m), 8.02 (1H, m), 6.63 (1H, m), 4.29 (2H, d), 2.79 (1H, m), 2.12 (2H, m), 1.96 (4H, m)

Preparation Example 62

2-cyclopropoxy-3-iodo-pyridine

Cyclopropanol (0.20 g, 3.43 mmol) and 2-fluoro-3-iodo-pyridine (0.51 g, 2.29 mmol) were reacted in the same manner as in Preparation Example 37 to obtain the title compound (0.30 g, 50%).
$^{1}$H-NMR (CDCl$_3$) δ 8.16 (1H, d), 8.01 (1H, d), 6.68 (1H, m), 4.30 (1H, m), 0.82 (4H, m)

Preparation Example 63

2,6-difluoro-4-(2-isopropylsulfanyl-pyridin-3-yl)-phenol

Step A: 3-(3,5-difluoro-4-methoxy-phenyl)-2-isopropylsulfanyl-pyridine

3-Chloro-2-isopropylsulfanyl-pyridine (0.04 g, 0.213 mmol) obtained in step A of Preparation Example 33 and 2-(3,5-difluoro-4-methoxy-phenyl)-4,4,5,5-tetramethyl-[1,3,2]dioxaborolane (0.086 g, 0.139 mmol) obtained in Preparation Example 238 were reacted in the same manner as in step B of Preparation Example 33 to obtain the title compound (0.015 g, 24%).
$^{1}$H-NMR (CDCl$_3$) δ 8.44 (1H, m), 7.33 (1H, m), 7.00 (3H, m), 4.05 (4H, m), 1.37 (6H, d)

Step B: 2,6-difluoro-4-(2-isopropylsulfanyl-pyridin-3-yl)-phenol 3-(3,5-Difluoro-4-methoxy-phenyl)-2-isopropylsulfanyl-pyridine (0.015 g, 0.05 mmol) obtained in step A was reacted in the same manner as in step C of Preparation Example 33 to obtain the title compound (0.012 g, 85%).
$^{1}$H-NMR (CDCl$_3$) δ 8.44 (1H, m), 7.33 (1H, m), 7.00 (3H, m), 5.25 (1H, s), 4.06 (1H, m), 1.37 (6H, d)

Preparation Example 64

N-cyclopentyl-3-iodo-pyridin-2-amine

After 2-fluoro-3-iodo-pyridine (0.3 g, 1.34 mmol), cyclopentylamine (0.34 g, 4 mmol) and diisopropyl ethylamine (0.46 mL, 2.68 mmol) were dissolved in CH$_3$CN (3.3 mL), the mixture was agitated at 110° C. for 2 hours by using microwave. The reactant was concentrated under reduced pressure and purified by column chromatography to obtain the title compound (0.155 g, 40%).
$^{1}$H-NMR (CDCl$_3$) δ 8.07 (1H, d), 7.80 (1H, d), 6.28 (1H, m), 4.88 (1H, brs), 4.30 (1H, m), 2.10 (2H, m), 1.75 (2H, m), 1.65 (2H, m), 1.48 (2H, m)

Preparation Example 65

6-Chloro-N-(cyclopropylmethyl)pyridin-2-amine 2,6-Dichloropyridine (0.15 g, 10 mmol), cyclopropyl methaneamine (1.3 mL, 15 mmol), (2-biphenyl)di-tert-butylphosphine (0.15 g, 0.5 mmol) and sodium tert-butoxide (1.44 g, 15 mmol) were dissolved in toluene (50 mL), palladium(II) acetate (0.11 g, 0.05 mmol) was added slowly thereto, and the mixture was agitated at 80° C. for 6 hours. The reactant was concentrated under reduced pressure and purified by column chromatography to obtain the title compound (0.21 g, 8.8%).
$^{1}$H-NMR (CDCl$_3$) δ 7.33 (1H, t), 6.56 (1H, d), 6.24 (1H, d), 3.10 (2H, m), 1.06 (1H, m), 0.54 (2H, m), 0.25 (2H, m)

Preparation Example 66

3-iodo-N-isopropyl-pyridin-2-amine

2-Fluoro-3-iodo-pyridine (0.15 g, 0.67 mmol) and propane-2-amine (0.17 mL, 2 mmol) were reacted in the same manner as in Preparation Example 64 to obtain the title compound (0.047 g, 27%).
$^{1}$H-NMR (CDCl$_3$) δ 8.06 (1H, m), 7.80 (1H, d), 6.28 (1H, m), 4.73 (1H, brs), 4.20 (1H, m), 1.25 (6H, d)

Preparation Example 67

N-cyclopropyl-3-iodo-pyridin-2-amine

2-Fluoro-3-iodo-pyridine (0.15 g, 0.67 mmol) and cyclopropaneamine (0.14 mL, 2 mmol) were reacted in the same manner as in Preparation Example 64 to obtain the title compound (0.013 g, 8%).
$^{1}$H-NMR (CDCl$_3$) δ 8.17 (1H, m), 7.82 (1H, m), 6.37 (1H, m), 5.17 (1H, brs), 2.78 (1H, m), 0.86 (2H, m), 0.56 (2H, m)

Preparation Example 68

Tert-butyl N-(6-bromo-2-pyridyl)carbamate

6-Bromo-pyridin-2-ylamine (0.717 g, 4.14 mmol), TEA (0.75 mL, 5.39 mmol) and dimethyl aminopyridine (0.1 g, 0.83 mmol) were dissolved in DCM (6 mL), tert-butoxycarbonyl tert-butyl carbonate (1.08 g, 4.96 mmol) dissolved in DCM (1.4 mL) was added slowly thereto at room temperature. The mixture was agitated at room temperature for 3 hours, and concentrated under reduced pressure, and purified by column chromatography to obtain the title compound (0.648 g, 57%).
$^{1}$H-NMR (CDCl$_3$) δ 7.88 (1H, d), 7.50 (1H, t), 7.20 (1H, brs), 7.12 (1H, d), 1.51 (9H, s)

Preparation Example 69

Tert-butyl N-(6-bromo-2-pyridyl)-N-isopropyl-carbamate

After tert-butyl N-(6-bromo-2-pyridyl)carbamate (0.2 g, 0.73 mmol) obtained in Preparation Example 68 was dissolved in DMF (2.5 mL), NaH (60% in mineral oil, 0.048 g, 1.1 mmol) was added slowly thereto, and the mixture was agitated at room temperature for 30 minutes. 2-Bromopropane (0.14 mL, 1.46 mmol) was added thereto, and the mixture was agitated at room temperature for 16 hours. The reactant was concentrated under reduced pressure, and added with ammonium chloride aqueous solution and then extracted with EtOAc. The organic layer was separated and dried with MgSO$_4$, and was purified by column chromatography to obtain the title compound (0.06 g, 26%).
$^{1}$H-NMR (CDCl$_3$) δ 7.84 (1H, t), 7.27 (1H, d), 7.21 (1H, d), 4.55 (1H, m), 1.44 (9H, s), 1.30 (6H, d)

Preparation Example 70

N-cyclopentyl-2-iodo-aniline

After 2-iodoaniline (0.39 g, 1.78 mmol) dissolved in dichloroethane (6 mL), cyclopentanone (0.15 g, 1.78 mmol)

and acetic acid (0.11 mL, 1.96 mmol) were added thereto, and the mixture was agitated at room temperature for 16 hours. Sodium triacetoxyborohydride (0.56 g, 2.67 mmol) was added thereto, and the mixture was agitated for 5 hours. The reactant was diluted with water and extracted with DCM. The organic layer was separated and dried with MgSO$_4$, and was purified by column chromatography to obtain the title compound (0.12 g, 23%).

$^1$H-NMR (CDCl$_3$) δ 7.64 (1H, d), 7.18 (1H, t), 6.60 (1H, d), 6.40 (1H, t), 4.14 (1H, brs), 3.80 (1H, m), 2.02 (2H, m), 1.76 (2H, m), 1.63 (2H, m), 1.53 (2H, m)

Preparation Example 71

3-bromo-N-cyclopentyl-aniline

3-Bromoaniline (0.306 g, 1.78 mmol) and cyclopentanone (0.15 g, 1.78 mmol) were reacted in the same manner as in Preparation Example 70 to obtain the title compound (0.347 g, 81%).

$^1$H-NMR (CDCl$_3$) δ 6.98 (1H, t), 6.77 (1H, d), 6.72 (1H, m), 6.49 (1H, m), 3.77 (2H, m), 2.02 (2H, m) 1.72 (2H, m), 1.62 (2H, m), 1.45 (2H, m)

Preparation Example 72

2-iodo-N-propyl-aniline

2-Iodoaniline (0.5 g, 2.3 mmol) and propanal (0.22 mL, 3.0 mmol) were reacted in the same manner as in Preparation Example 70 to obtain the title compound (0.39 g, 60%).

$^1$H-NMR (CDCl$_3$) δ 7.65 (1H, d), 7.20 (1H, t), 6.56 (1H, d), 6.42 (1H, t), 4.15 (1H, brs), 3.12 (2H, q), 1.70 (2H, m), 1.03 (3H, t)

Preparation Example 73

N-(cyclopropylmethyl)-2-iodo-aniline

2-Iodoaniline (0.5 g, 2.3 mmol) and cyclopropanecarbaldehyde (0.2 mL, 2.76 mmol) were reacted in the same manner as in Preparation Example 70 to obtain the title compound (0.5 g, 80%).

$^1$H-NMR (CDCl$_3$) δ 7.66 (1H, d), 7.20 (1H, t), 6.54 (1H, d), 6.43 (1H, t), 4.27 (1H, brs), 3.00 (2H, m), 1.15 (1H, m), 0.60 (2H, m), 0.28 (2H, m)

Preparation Example 74

2-iodo-N-isopropyl-aniline

2-Iodoaniline (0.5 g, 2.3 mmol) and acetone (0.25 mL, 3.42 mmol) were reacted in the same manner as in Preparation Example 70 to obtain the title compound (0.4 g, 66%).

$^1$H-NMR (CDCl$_3$) δ 7.69 (1H, d), 7.23 (1H, t), 6.60 (1H, d), 6.45 (1H, t), 4.03 (1H, brs), 3.70 (1H, m), 1.31 (6H, d)

Preparation Example 75

2-bromo-N-cyclobutyl-aniline

After 1,2-dibromobenzene (0.3 g, 1.27 mmol), cyclobutylamine (0.22 mL, 2.54 mmol), Cs$_2$CO$_3$ (0.83 g, 2.54 mmol) and 4,5-bis(diphenylphosphino)-9,9-dimethylxanthene (0.073 mg, 0.13 mmol) were dissolved in 1,4-dioxane (12 mL), Pd$_2$(dba)$_3$ (0.03 g, 0.03 mmol) was added thereto and the mixture was agitated under reflux for 16 hours. The reactant was filtered by using celite and was purified by column chromatography to obtain the title compound (0.136 g, 47%).

$^1$H-NMR (CDCl$_3$) δ 7.39 (1H, d), 7.15 (1H, t), 6.54 (2H, m), 4.42 (1H, brs), 3.92 (1H, m), 2.45 (2H, m), 1.87 (4H, m)

Preparation Example 76

3-bromo-N-(cyclopropylmethyl)aniline

3-Bromoaniline (0.5 g, 2.9 mmol) and cyclopropanecabaldehyde (0.26 mL, 3.48 mmol) were reacted in the same manner as in Preparation Example 70 to obtain the title compound (0.413 g, 62%).

$^1$H-NMR (CDCl$_3$) δ 6.99 (1H, t), 6.79 (1H, d), 6.73 (1H, m), 6.51 (1H, m), 3.86 (1H, brs), 2.93 (2H, d), 1.07 (1H, m), 0.56 (2H, m), 0.24 (2H, m)

Preparation Example 77

3-bromo-N-isopropyl-aniline

3-Bromoaniline (0.5 g, 2.9 mmol) and acetone (0.43 mL, 5.8 mmol) were reacted in the same manner as in Preparation Example 70 to obtain the title compound (0.6 g, 96%).

$^1$H-NMR (CDCl$_3$) δ 7.00 (1H, t), 6.77 (1H, d), 6.70 (1H, m), 6.46 (1H, m), 3.60 (1H, m), 3.51 (1H, brs), 1.20 (6H, d)

Preparation Example 78

1-(3-bromophenyl)pyrrolidine

After 1,3-dibromobenzene (1.0 g, 4.24 mmol), pyrrolidine (0.43 mL, 5.0 mmol), sodium tert-butoxide (1.14 g, 11.87 mmol) and BINAP (0.2 g, 0.32 mmol) were dissolved in toluene (17 mL), Pd$_2$(dba)$_3$ (0.097 g, 0.1 mmol) was added thereto and the mixture was agitated under reflux for 4 hours. The reactant was filtered by using celite and was purified by column chromatography to obtain the title compound (0.52 g, 54%).

$^1$H-NMR (CDCl$_3$) δ 7.05 (1H, t), 6.75 (1H, d), 6.67 (1H, m), 6.45 (1H, m), 3.26 (4H, m), 2.00 (4H, m)

Preparation Example 79

3-bromo-N-propyl-aniline

3-Bromoaniline (1.45 g, 8.42 mmol) and propanal (0.49 g, 8.42 mmol) were reacted in the same manner as in Preparation Example 70 to obtain the title compound (0.22 g, 12%).

$^1$H-NMR (CDCl$_3$) δ 6.99 (1H, t), 6.78 (1H, d), 6.72 (1H, m), 6.50 (1H, m), 3.70 (1H, brs), 3.05 (2H, t), 1.66 (2H, m), 1.00 (3H, t)

Preparation Example 80

3-bromo-N-cyclobutyl-aniline 1,3-Dibromobenzene (0.45 mL, 3.7 mmol) and cyclobutylamine (0.53 g, 7.45 mmol) were reacted in the same manner as in Preparation Example 75 to obtain the title compound (0.028 g, 3%).

$^1$H-NMR (CDCl$_3$) δ 7.00 (1H, t), 6.79 (1H, d), 6.66 (1H, m), 6.45 (1H, m), 3.87 (2H, m), 2.42 (2H, m), 1.81 (4H, m)

Preparation Example 81

2-bromo-4-chloro-N-cyclopentyl-aniline

2-Bromo-4-chloroaniline (0.508 g, 2.46 mmol) and cyclopentanone (0.207 g, 2.46 mmol) were reacted in the same manner as in Preparation Example 70 to obtain the title compound (0.083 g, 12%).
$^1$H-NMR (CDCl$_3$) δ 7.39 (1H, m), 7.12 (1H, m), 6.57 (1H, m), 4.25 (1H, brs), 3.76 (1H, m), 2.03 (2H, m), 1.76 (2H, m), 1.63 (2H, m), 1.50 (2H, m)

Preparation Example 82

N-cyclopentyl-4-fluoro-2-iodo-aniline

4-Fluoro-2-iodo-aniline (2.0 g, 18 mmol) and cyclopentanone (0.195 g, 2.32 mmol) were reacted in the same manner as in Preparation Example 70 to obtain the title compound (0.19 g, 27%).
$^1$H-NMR (CDCl$_3$) δ 7.40 (1H, m), 6.95 (1H, m), 6.52 (1H, m), 3.93 (1H, brs), 3.75 (1H, m), 2.03 (2H, m), 1.76 (2H, m), 1.64 (2H, m), 1.51 (2H, m)

Preparation Example 83

Cyclopenten-1-yl trifluoromethanesulfonate

Cyclopentanone (0.3 g, 3.6 mmol) was dissolved in THF (10 mL), and the mixture was cooled to −78° C. Lithium bis(trimethylsilyl)amide (1.0M in THF, 3.3 mL, 3.3 mmol) was added slowly thereto, and the mixture was agitated for 50 minutes. N-phenyl-bis(trifluoromethanesulfonimide) (1.17 g, 3.27 mmol) was added slowly thereto, and the mixture was agitated for 16 hours. The reactant was added with ammonium chloride aqueous solution and then extracted with Et$_2$O. The organic layer was separated and dried with MgSO$_4$, and was purified by column chromatography, and was concentrated under reduced pressure at 20° C. to obtain the title compound (0.196 g, 27%).
$^1$H-NMR (CDCl$_3$) δ 5.63 (1H, m), 2.57 (2H, m), 2.42 (2H, m), 2.03 (2H, m)

Preparation Example 84

1-(cyclopenten-1-yl)-3-nitro-benzene

After cyclopenten-1-yl trifluoromethanesulfonate (0.525 g, 2.43 mmol) obtained in Preparation Example 83 and (3-nitrophenyl)boronic acid (0.81 g, 4.86 mmol) were added with 1N NaOH aqueous solution (7.29 mL, 7.29 mmol) and 1,4-dioxane (24 mL), the mixture was charged with N$_2$ gas for 5 minutes, then PdCl$_2$(dppf)-DCM (0.10 g, 0.12 mmol) and DPPF (0.067 g, 0.12 mmol) were added thereto, and the mixture was agitated under reflux for 16 hours. The reactant was added with water and then extracted with EtOAc, and dried with MgSO$_4$. The residue was purified by column chromatography to obtain the title compound (0.055 g, 12%).
$^1$H-NMR (CDCl$_3$) δ 8.24 (1H, m), 8.04 (1H, m), 7.72 (1H, d), 7.48 (1H, t), 6.35 (1H, m), 2.74 (2H, m), 2.58 (2H, m), 2.07 (2H, m)

Preparation Example 85

3-cyclopentylaniline 1-(Cyclopenten-1-yl)-3-nitro-benzene (0.073 g, 0.39 mmol) obtained in Preparation Example 84 was reacted in the same manner as in step B of Preparation Example 50 to obtain the title compound (0.06 g, 95%).
$^1$H-NMR (CDCl$_3$) δ 7.05 (1H, t), 6.66 (1H, d), 6.58 (1H, m), 6.52 (1H, m), 3.59 (2H, brs), 2.90 (1H, m), 2.02 (2H, m), 1.78 (2H, m), 1.66 (2H, m), 1.55 (2H, m)

Preparation Example 86

1-cyclopentyl-3-iodo-benzene

After 3-cyclopentylaniline (0.06 g, 0.37 mmol) obtained in Preparation Example 85 was dissolved in 6M HCl aqueous solution (1.9 mL), sodium nitrite (0.5M aqueous solution, 1.2 mL, 0.6 mmol) was added slowly thereto at 0° C. The mixture was agitated at 0° C. for 10 minutes, and added slowly with potassium iodide (1.0M aqueous solution, 0.9 mL, 0.9 mmol), and then the mixture was agitated for 40 minutes. After sodium bicarbonate aqueous solution was added thereto to adjust the pH of the solution to 10, the reactant was extracted with EtOAc, and the organic layer was dried with MgSO$_4$ to obtain the title compound (0.07 g, 70%).
$^1$H-NMR (CDCl$_3$) δ 7.58 (1H, m), 7.50 (1H, d), 7.19 (1H, d), 7.00 (1H, t), 2.92 (1H, m), 2.04 (2H, m), 1.80 (2H, m), 1.68 (2H, m), 1.58 (2H, m)

Preparation Example 87

1-bromo-3-(cyclopentylmethyl)benzene

Cyclopentyl magnesium bromide (2.0M in Et$_2$O, 2.4 mL, 4.8 mmol) was added with catalytic copper(I) iodide at 0° C., and the mixture was agitated for 30 minutes. 1-Bromo-3-(bromomethyl)benzene (1.0 g, 4 mmol) dissolved in THF (10 mL) was added slowly thereto, and the mixture was agitated for 16 hours. The reactant was added with potassium dihydrogen phosphate aqueous solution and extracted with EtOAc. The organic layer was dried with MgSO$_4$ and was purified by column chromatography to obtain the title compound (0.116 g, 12%).
$^1$H-NMR (CDCl$_3$) δ 7.33 (1H, m), 7.32 (1H, m), 7.12 (1H, t), 7.09 (1H, m), 2.57 (2H, d), 2.06 (1H, m), 1.70 (2H, m), 1.64 (2H, m), 1.53 (2H, m), 1.17 (2H, m)

Preparation Example 88

1-bromo-2-(cyclopentylmethyl)benzene

1-Bromo-2-(bromomethyl)benzene (1.0 g, 4 mmol) was reacted in the same manner as in Preparation Example 87 to obtain the title compound (0.24 g, 25%).
$^1$H-NMR (CDCl$_3$) δ 7.51 (1H, d), 7.20 (2H, m), 7.03 (1H, m), 2.74 (2H, d), 2.20 (1H, m), 1.68 (4H, m), 1.26 (4H, m)

Preparation Example 89

2-bromo-6-(bromomethyl)pyridine

After (6-bromo-2-pyridyl)methanol (0.768 g, 4.08 mmol) and triphenylphosphine (1.12 g, 4.28 mmol) were dissolved in DCM (7 mL), carbon tetrabromide (1.48 g, 4.45 mmol) was added thereto at 0° C., and then the mixture was agitated for 2 hours. The reactant was concentrated under reduced pressure and the residue was purified by column chromatography to obtain the title compound (0.527 g, 51%).

$^1$H-NMR (CDCl$_3$) δ 7.55 (1H, t), 7.42 (2H, m), 4.49 (2H, s)

Preparation Example 90

2-bromo-6-(diethoxyphosphorylmethyl)pyridine

After 2-bromo-6-(bromomethyl)pyridine (0.527 g, 2.1 mmol) obtained in Preparation Example 89 and triethylphosphite (0.36 mL, 2.1 mmol) were dissolved in toluene (4 mL), the mixture was agitated under reflux for 5 days, and then concentrated under reduced pressure to obtain the title compound (0.718 g, 99%).
$^1$H-NMR (CDCl$_3$) δ 7.50 (1H, t), 7.37 (2H, m), 4.10 (4H, m), 3.38 (2H, d), 1.29 (6H, t)

Preparation Example 91

2-bromo-6-(cyclopentylidenemethyl)pyridine

After 2-bromo-6-(diethoxyphosphorylmethyl)pyridine (0.24 g, 0.7 mmol) obtained in Preparation Example 90 and cyclopentanone (0.058 mg, 0.7 mmol) were dissolved in THF (3.5 mL), lithium bis(trimethylsilyl)amide (1.0M in THF, 0.84 mL, 0.84 mmol) was added slowly thereto, and the mixture was agitated for 4 hours. The reactant was added with water and then extracted with EtOAc. The organic layer was separated and dried with MgSO$_4$, and was purified by column chromatography to obtain the title compound (0.115 g, 68%).
$^1$H-NMR (CDCl$_3$) δ 7.43 (1H, t), 7.19 (1H, d), 7.12 (1H, d), 6.40 (1H, m), 2.73 (2H, m), 2.52 (2H, m), 1.80 (2H, m), 1.68 (2H, m)

Preparation Example 92

1-bromo-2-(cyclobutylmethyl)benzene

1-Bromo-2-(bromomethyl)benzene (0.4 g, 1.6 mmol) and cyclobutyl magnesium bromide (1.0M in THF) were reacted in the same manner as in Preparation Example 87 to obtain the title compound (0.06 g, 17%).
$^1$H-NMR (CDCl$_3$) δ 7.50 (1H, d), 7.20 (1H, t), 7.16 (1H, m), 7.03 (1H, m), 2.83 (2H, d), 2.67 (1H, m), 2.05 (2H, m), 1.85 (2H, m), 1.75 (2H, m)

Preparation Example 93

1-bromo-3-(cyclobutylmethyl)benzene

1-Bromo-3-(bromomethyl)benzene (0.4 g, 1.6 mmol) and cyclobutyl magnesium bromide (1.0M in THF) were reacted in the same manner as in Preparation Example 87 to obtain the title compound (0.03 g, 8%).
$^1$H-NMR (CDCl$_3$) δ 7.28 (2H, m), 7.12 (1H, t), 7.05 (1H, m), 2.66 (2H, d), 2.55 (1H, m), 2.03 (2H, m), 1.83 (2H, m), 1.71 (2H, m)

Preparation Example 94

2-bromo-6-(cyclobutylidenemethyl)pyridine

2-Bromo-6-(diethoxyphosphorylmethyl)pyridine (0.225 g, 0.73 mmol) obtained in Preparation Example 90 and cyclobutanone (0.051 g, 0.73 mmol) were reacted in the same manner as in Preparation Example 91 to obtain the title compound (0.1 g, 61%).

$^1$H-NMR (CDCl$_3$) δ 7.42 (1H, t), 7.19 (1H, d), 7.04 (1H, d), 6.18 (1H, m), 3.13 (2H, m), 2.92 (2H, m), 2.13 (2H, m)

Preparation Example 95

1-(cyclopenten-1-yl)-2-nitro-benzene

Cyclopenten-1-yl trifluoromethanesulfonate (0.196 g, 0.9 mmol) obtained in Preparation Example 83 and (2-nitrophenyl)boronic acid (0.226 g, 1.36 mmol) were reacted in the same manner as in Preparation Example 13 to obtain the title compound (0.085 g, 50%).
$^1$H-NMR (CDCl$_3$) δ 7.74 (1H, d), 7.54 (1H, t), 7.35 (2H, m), 5.84 (1H, m), 2.58 (2H, m), 2.50 (2H, m), 2.02 (2H, m)

Preparation Example 96

2-cyclopentylaniline 1-(Cyclopenten-1-yl)-2-nitro-benzene (0.085 g, 0.45 mmol) obtained in Preparation Example 95 was reacted in the same manner as in Preparation Example 85 to obtain the title compound (0.061 g, 84%).
$^1$H-NMR (CDCl$_3$) δ 7.13 (1H, d), 7.01 (1H, t), 6.75 (1H, t), 6.68 (1H, d), 3.66 (2H, brs), 2.98 (1H, m), 2.04 (2H, m), 1.80 (2H, m), 1.69 (4H, m)

Preparation Example 97

1-cyclopentyl-2-iodo-benzene

2-Cyclopentylaniline (0.061 g, 0.38 mmol) obtained in Preparation Example 96 was reacted in the same manner as in Preparation Example 85 to obtain the title compound (0.067 g, 65%).
$^1$H-NMR (CDCl$_3$) δ 7.91 (1H, m), 7.27 (2H, m), 6.87 (1H, m), 3.24 (1H, m), 2.12 (2H, m), 1.82 (2H, m), 1.72 (2H, m), 1.53 (2H, m)

Preparation Example 98

2-bromo-6-cyclopentyl-pyridine

After 2,6-dibromopyridine (0.41 g, 1.73 mmol), copper(I) iodide (0.078 g, 0.41 mmol) and PdCl$_2$(dppf)-DCM (0.167 g, 0.20 mmol) were dissolved in THF (3.5 mL), the mixture was charged with N$_2$ gas for 5 minutes. The reactant was added slowly with cyclopentyl zinc bromide (0.5M in THF, 4.1 mL, 2.05 mmol), and the mixture was agitated at room temperature for 16 hours. The reactant was added with Hex and purified by column chromatography to obtain the title compound (0.175 g, 44%).
$^1$H-NMR (CDCl$_3$) δ 7.42 (1H, t), 7.27 (1H, d), 7.12 (1H, d), 3.14 (1H, m), 2.07 (2H, m), 1.79 (6H, m)

Preparation Example 99

3-benzyloxy-2-methyl-pyridine

After 2-methylpyridin-3-ol (1.25 g, 11 mmol) was added with CH$_3$CN (32 mL) and tetrabutylammonium hydroxide (40 wt % aqueous solution, 2.97 g, 11 mmol), the mixture was agitated at room temperature for 30 minutes. The reactant was concentrated under reduced pressure, and added with bromomethylbenzene (1.37 mL, 11 mmol) and CH$_3$CN (63 mL), and the mixture was agitated under reflux for 4 hours. The reactant was concentrated under reduced pressure and purified by column chromatography to obtain the title compound (1.94 g, 88%).

$^1$H-NMR (CDCl$_3$) δ 8.08 (1H, m), 7.41 (4H, m), 7.35 (1H, m), 7.11 (1H, d), 7.07 (1H, m), 5.09 (2H, s), 2.53 (3H, s)

Preparation Example 100

3-benzyloxypyridine-2-carbaldehyde

After 3-benzyloxy-2-methyl-pyridine (0.36 g, 1.8 mmol) obtained in Preparation Example 99 was dissolved in 1,4-dioxane (30 mL), selenium dioxide (0.4 g, 3.6 mmol) was added thereto, and the mixture was agitated under reflux for 4 days. The reactant was added with sodium bicarbonate aqueous solution and then extracted with EtOAc. The organic layer was dried with MgSO$_4$, and was purified by column chromatography to obtain the title compound (0.29 g, 75%).

$^1$H-NMR (CDCl$_3$) δ 10.44 (1H, s), 8.41 (1H, m), 7.40 (7H, m), 5.26 (2H, s)

Preparation Example 101

3-benzyloxy-2-(2-methylprop-1-enyl)pyridine

Isopropyltriphenylphosphonium iodide (0.7 g, 1.6 mmol) was added with THF (10 mL), and cooled to 0° C. After lithium bis(trimethylsilyl)amide (1.0M in THF, 1.6 mL, 1.6 mmol) was added slowly thereto, the mixture was agitated for 10 minutes, and 3-benzyloxypyridine-2-carbaldehyde (0.29 g, 1.35 mmol) obtained in Preparation Example 100 dissolved in THF (5 mL) was added slowly thereto. The mixture was agitated at room temperature for 2 hours, and added with ammonium chloride aqueous solution, and then extracted with EtOAc. The organic layer was dried with MgSO$_4$, and was purified by column chromatography to obtain the title compound (0.03 g, 9%).

$^1$H-NMR (CDCl$_3$) δ 8.19 (1H, m), 7.37 (5H, m), 7.14 (1H, d), 7.02 (1H, m), 6.57 (1H, s), 5.09 (2H, s), 2.08 (3H, s), 1.97 (3H, s)

Preparation Example 102

2-isobutylpyridin-3-ol

3-Benzyloxy-2-(2-methylprop-1-enyl)pyridine (0.03 g, 0.12 mmol) obtained in Preparation Example 101 was reacted in the same manner as in step B of Preparation Example 50 to obtain the title compound (0.023 g, 99%).

$^1$H-NMR (CDCl$_3$) δ 8.00 (1H, m), 7.95 (1H, m), 7.34 (1H, m), 2.90 (2H, d), 2.54 (1H, m), 0.94 (6H, d)

Preparation Example 103

(2-isobutyl-3-pyridyl) trifluoromethane sulfonate

2-Isobutylpyridin-3-ol (0.023 g, 0.15 mmol) obtained in Preparation Example 102 was added with DCM (0.8 mL), TEA (0.023 mL, 0.17 mmol) and N-phenyl-bis(trifluoromethanesulfonimide) (0.06 g, 0.17 mmol), and the mixture was agitated at room temperature for 16 hours. The reactant was added with water, and extracted with DCM, and then was purified by column chromatography to obtain the title compound (0.017 g, 40%).

$^1$H-NMR (CDCl$_3$) δ 8.57 (1H, m), 7.58 (1H, m), 7.25 (1H, m), 2.79 (2H, d), 2.22 (1H, m), 0.95 (6H, d)

Preparation Example 104

3-benzyloxy-2-bromo-pyridine

2-Bromo-3-pyridol (10 g, 57 mmol) and bromomethylbenzene (7.2 mL, 60 mmol) were reacted in the same manner as in Preparation Example 8 to obtain the title compound (15 g, 99%).

$^1$H-NMR (CDCl$_3$) δ 8.00 (1H, m), 7.44 (2H, m), 7.40 (2H, m), 7.32 (1H, m), 7.18 (2H, m), 5.19 (2H, s)

Preparation Example 105

3-benzyloxy-2-cyclopentyl-pyridine

3-Benzyloxy-2-bromo-pyridine (1.32 g, 5 mmol) obtained in Preparation Example 104 was added with toluene (10 mL), palladium(II) acetate (0.17 g, 0.75 mmol), and SPhos (0.62 g, 1.5 mmol), and then cooled to 0° C. The reactant was added slowly with cyclopentyl zinc bromide (0.5M in THF, 15 mL, 7.5 mmol), and agitated at room temperature for 4 hours. The reactant was then added with ammonium chloride aqueous solution, and extracted with EtOAc. The organic layer was dried with MgSO$_4$, and was purified by column chromatography to obtain the title compound (0.832 g, 65%).

$^1$H-NMR (CDCl$_3$) δ 8.15 (1H, m), 7.42 (4H, m), 7.40 (1H, m), 7.12 (1H, m), 7.05 (1H, m), 5.08 (2H, s), 3.64 (1H, m), 1.99 (2H, m), 1.85 (4H, m), 1.67 (2H, m)

Preparation Example 106

(2-cyclopentyl-3-pyridyl)trifluoromethane sulfonate

3-Benzyloxy-2-cyclopentyl-pyridine (0.5 g, 2 mmol) obtained in Preparation Example 105 was reacted in the same manner as in step B of Preparation Example 50 and Preparation Example 103 in turn to obtain the title compound (0.376 g, 66%).

$^1$H-NMR (CDCl$_3$) δ 8.58 (1H, m), 7.54 (1H, m), 7.22 (1H, m), 3.49 (1H, m), 2.05 (2H, m), 1.89 (4H, m), 1.72 (2H, m)

Preparation Example 107

3-benzyloxy-2-(cyclopentylidenemethyl)pyridine

3-Benzyloxypyridine-2-carbaldehyde (0.3 g, 1.4 mmol) obtained in Preparation Example 100 and cyclopentyltriphenylphosphonium bromide (0.87 g, 2.11 mmol) were reacted in the same manner as in Preparation Example 101 to obtain the title compound (0.096 g, 26%).

$^1$H-NMR (CDCl$_3$) δ 8.19 (1H, m), 7.42 (4H, m), 7.32 (1H, m), 7.10 (1H, m), 6.99 (1H, m), 6.83 (1H, m), 5.09 (2H, s), 2.84 (2H, m), 2.54 (2H, m), 1.76 (2H, m), 1.68 (2H, m)

Preparation Example 108

[2-(cyclopentylmethyl)-3-pyridyl]trifluoromethanesulfonate

3-Benzyloxy-2-(cyclopentylidenemethyl)pyridine (0.096 g, 0.36 mmol) obtained in Preparation Example 107 was reacted in the same manner as in step B of Preparation Example 50 and Preparation Example 103 in turn to obtain the title compound (0.04 g, 36%).

¹H-NMR (CDCl₃) δ 8.56 (1H, m), 7.58 (1H, m), 7.25 (1H, m), 2.92 (2H, d), 2.37 (1H, m), 1.72 (4H, m), 1.56 (2H, m), 1.26 (2H, m)

Preparation Example 109

Ethyl 4-[2,6-difluoro-4-(2-fluoro-3-pyridyl)phenoxy]butanoate

2-Fluoro-3-iodo-pyridine (0.394 g, 1.77 mmol) and 4-[2,6-difluoro-4-(4,4,5,5-tetramethyl-1,3,2-dioxaborolan-2-yl)phenoxy]butyric acid ethyl ester (0.72 g, 1.94 mmol) obtained in Preparation Example 2 were reacted in the same manner as in Preparation Example 13 to obtain the title compound (0.55 g, 92%).
¹H-NMR (CDCl₃) δ 8.22 (1H, m), 7.83 (1H, m), 7.30 (1H, m), 7.15 (2H, m), 4.25 (2H, t), 4.15 (2H, q), 2.59 (2H, t), 2.10 (2H, m), 1.27 (3H, t)

Preparation Example 110

4-(3-iodo-2-pyridyl)morpholine

2-Fluoro-3-iodo-pyridine (0.3 g, 1.34 mmol) and morpholine (0.35 g, 4 mmol) were reacted in the same manner as in Preparation Example 64 to obtain the title compound (0.12 g, 28%).
¹H-NMR (CDCl₃) δ 8.27 (1H, m), 8.07 (1H, m), 6.68 (1H, m), 3.88 (4H, m), 3.28 (4H, m)

Preparation Example 111

3-iodo-N-(tetrahydropyran-4-ylmethyl)pyridin-2-amine

2-Fluoro-3-iodo-pyridine (0.3 g, 1.34 mmol) and 4-aminomethyltetrahydropyran (0.46 g, 4 mmol) were reacted in the same manner as in Preparation Example 64 to obtain the title compound (0.24 g, 56%).
¹H-NMR (CDCl₃) δ 8.06 (1H, m), 7.81 (1H, m), 6.32 (1H, m), 5.00 (1H, brs), 4.00 (2H, m), 3.41 (2H, m), 3.36 (2H, m), 1.90 (1H, m), 1.70 (2H, m), 1.38 (2H, m)

Preparation Example 112

Methyl (2R)-2-(4-bromo-2,6-difluoro-phenoxy)propanoate

4-Bromo-2,6-difluoro-phenol (2.57 g, 12.3 mmol) obtained in step A of Preparation Example 2 and (S)-methyl lactate (1.28 g, 12.3 mmol) were reacted in the same manner as in step C of Preparation Example 27 to obtain the title compound (3.28 g, 90%).
¹H-NMR (CDCl₃) δ 7.08 (2H, m), 4.79 (1H, m), 3.77 (3H, s), 1.62 (3H, d)

Preparation Example 113

(2R)-2-(4-bromo-2,6-difluoro-phenoxy)propane-1-ol

Methyl (2R)-2-(4-bromo-2,6-difluoro-phenoxy)propanoate (3.28 g, 11.1 mmol) obtained in Preparation Example 112 was reacted in the same manner as in step A of Preparation Example 30 to obtain the title compound (2.80 g, 94%).

¹H NMR (CDCl₃) δ 7.10 (2H, m), 4.33 (1H, m), 3.75 (1H, m), 3.70 (1H, m), 2.08 (1H, brs), 1.31 (3H, d)

Preparation Example 114

(2R)-2-(4-bromo-2,6-difluoro-phenoxy)propanal

DCM (75 mL) was added with oxalyl chloride (1.08 mL, 12.6 mmol), and cooled to −78° C. DMSO (1.93 mL, 27.3 mmol) dissolved in DCM (37 mL) was added slowly thereto, and the mixture was agitated for 2 hours. The mixture was added slowly with (2R)-2-(4-bromo-2,6-difluoro-phenoxy)propane-1-ol (2.80 g, 10.48 mmol) obtained in Preparation Example 113 dissolved in DCM (37 mL) and TEA (7.0 mL, 50 mmol) in turn. The mixture was agitated at room temperature for 1 hour, and added with 1N HCl aqueous solution, and then extracted with DCM. The organic layer was dried with MgSO₄, and was purified by column chromatography to obtain the title compound (2.28 g, 58%).
¹H NMR (CDCl₃) δ 9.85 (1H, s), 7.13 (2H, m), 4.51 (1H, m), 1.48 (3H, d)

Preparation Example 115

Methyl (Z,4R)-4-(4-bromo-2,6-difluoro-phenoxy)pent-2-enoate

Bis(2,2,2-trifluoroethyl)(methoxycarbonylmethyl)phosphonate (1.2 g, 3.77 mmol) was dissolved in THF (30 mL), cooled to 0° C., and was added with sodium iodide (0.67 g, 4.52 mmol) and 1,8-diazabicyclo[5.4.0]undec-7-ene (0.62 mL, 4.15 mmol) in turn. The mixture was cooled to −78° C. in 10 minutes later, was added slowly with (2R)-2-(4-bromo-2,6-difluoro-phenoxy)propanal (1.0 g, 3.77 mmol) obtained in Preparation Example 114 dissolved in THF (8 mL). The reactant was agitated at 0° C. for 1 hour, added with ammonium chloride aqueous solution, and then extracted with EtOAc. The organic layer was dried with MgSO₄, and was purified by column chromatography to obtain the title compound (0.7 g, 58%).
¹H NMR (CDCl₃) δ 7.05 (2H, m), 6.37 (1H, m), 5.81 (2H, m), 3.68 (3H, s), 1.51 (3H, d)

Preparation Example 116

Methyl (4R)-4-(4-bromo-2,6-difluoro-phenoxy)pentanoate

Methyl (Z,4R)-4-(4-bromo-2,6-difluoro-phenoxy)pent-2-enoate (0.66 g, 2 mmol) obtained in Preparation Example 115 was reacted in the same manner as in step B of Preparation Example 50 to obtain the title compound (0.45 g, 70%).
1H NMR (CDCl₃) δ 7.08 (2H, m), 4.28 (1H, m), 3.69 (3H, s), 2.58 (2H, t), 2.00 (2H, m), 1.27 (3H, d)

Preparation Example 117

Methyl (4R)-4-[2,6-difluoro-4-(4,4,5,5-tetramethyl-1,3,2-dioxaborolan-2-yl)phenoxy]pentanoate Methyl (4R)-4-(4-bromo-2,6-difluoro-phenoxy)pentanoate (0.45 g, 1.4 mmol) obtained in Preparation Example 116 was reacted in the same manner as in step A of Preparation Example 1 to obtain the title compound (0.062 g, 13%).

1H NMR (CDCl$_3$) δ 7.31 (2H, m), 4.38 (1H, m), 3.68 (3H, s), 2.59 (2H, t), 2.00 (2H, m), 1.32 (12H, s), 1.25 (3H, d)

Preparation Example 118

Methyl (2S)-2-(4-bromo-2,6-difluoro-phenoxy)propanoate

4-Bromo-2,6-difluoro-phenol (1.0 g, 4.7 mmol) obtained in step A of Preparation Example 2 and (R)-methyl lactate (0.49 g, 4.7 mmol) were reacted in the same manner as in step C of Preparation Example 27 to obtain the title compound (1.17 g, 83%).
$^1$H-NMR (CDCl$_3$) δ 7.08 (2H, m), 4.79 (1H, m), 3.77 (3H, s), 1.62 (3H, d)

Preparation Example 119

(2S)-2-(4-bromo-2,6-difluoro-phenoxy)propane-1-ol

Methyl (2S)-2-(4-bromo-2,6-difluoro-phenoxy)propanoate (1.17 g, 4.0 mmol) obtained in Preparation Example 118 was reacted in the same manner as in step A of Preparation Example 30 to obtain the title compound (0.9 g, 85%).
1H NMR (CDCl$_3$) δ 7.10 (2H, m), 4.33 (1H, m), 3.75 (1H, m), 3.70 (1H, m), 2.08 (1H, brs), 1.31 (3H, d)

Preparation Example 120

(2S)-2-(4-bromo-2,6-difluoro-phenoxy)propanal (2S)-2-(4-bromo-2,6-difluoro-phenoxy)propane-1-ol (0.9 g, 3.3 mmol) obtained in Preparation Example 119 was reacted in the same manner as in Preparation Example 114 to obtain the title compound (0.61 g, 68%).
1H NMR (CDCl$_3$) δ 9.85 (1H, s), 7.13 (2H, m), 4.51 (1H, m), 1.48 (3H, d)

Preparation Example 121

Ethyl (E,4S)-4-(4-bromo-2,6-difluoro-phenoxy)pent-2-enoate (2S)-2-(4-bromo-2,6-difluoro-phenoxy)propanal (0.61 g, 2.3 mmol) obtained in Preparation Example 120 and ethyl (triphenylphosphoranylidene)acetate (0.8 g, 2.3 mmol) were reacted in the same manner as in step A of Preparation Example 50 to obtain the title compound (0.69 g, 90%, E/Z=2/1).
1H NMR (CDCl$_3$) δ (Z-isomer) 7.05 (2H, m), 6.34 (1H, m), 5.81 (2H, m), 4.14 (2H, q), 1.51 (3H, d), 1.26 (3H, t)
(E-isomer) δ 7.08 (2H, m), 6.93 (1H, m), 6.03 (1H, d), 4.83 (1H, m), 4.20 (2H, q), 1.48 (3H, d), 1.29 (3H, t)

Preparation Example 122

Ethyl (4S)-4-(4-bromo-2,6-difluoro-phenoxy)pentanoate

Ethyl (E,4S)-4-(4-bromo-2,6-difluoro-phenoxy)pent-2-enoate (0.49 g, 1.4 mmol) obtained in Preparation Example 121 was reacted in the same manner as in step B of Preparation Example 50 to obtain the title compound (0.326 g, 71%).
1H NMR (CDCl$_3$) δ 7.08 (2H, m), 4.29 (1H, m), 4.14 (2H, q), 2.58 (2H, t), 2.00 (2H, m), 1.27 (6H, m)

Preparation Example 123

Ethyl (4S)-4-[2,6-difluoro-4-(4,4,5,5-tetramethyl-1,3,2-dioxaborolan-2-yl)phenoxy]pentanoate Ethyl (4S)-4-(4-bromo-2,6-difluoro-phenoxy)pentanoate (0.326 g, 1 mmol) obtained in Preparation Example 122 was reacted in the same manner as in step A of Preparation Example 1 to obtain the title compound (0.237 g, 62%).
1H NMR (CDCl$_3$) δ 7.31 (2H, m), 4.37 (1H, m), 4.13 (2H, q), 2.58 (2H, t), 2.00 (2H, m), 1.33 (12H, s), 1.27 (6H, m)

Preparation Example 124

1-(6-chloro-2-pyridyl)-N,N-dimethyl-pyrrolidine-3-amine 2,6-Dichloropyridine (1 g, 6.75 mmol) and N,N-dimethylpyrrolidine-3-amine (0.77 g, 6.75 mmol) were reacted in the same manner as in Preparation Example 5 to obtain the title compound (1.42 g, 90%).
1H NMR (CDCl$_3$) δ7.35 (1H, t), 6.52 (1H, m), 6.20 (1H, m), 3.75 (1H, m), 3.63 (1H, m), 3.39 (1H, m), 3.22 (1H, m), 2.78 (1H, m), 2.31 (6H, s), 2.23 (1H, m), 1.93 (1H, m)

Preparation Example 125

2-chloro-6-isopropylsulfanyl-pyridine 2,6-Dichloropyridine (3.0 g, 20.3 mmol) and propane-2-thiol (1.88 mL, 20.3 mmol) were reacted in the same manner as in Preparation Example 37 to obtain the title compound (3.63 g, 95%).
$^1$H-NMR (CDCl$_3$) δ 7.40 (1H, t), 7.05 (1H, t), 6.98 (1H, t), 4.00 (1H, m), 1.40 (6H, d)

Preparation Example 126

2-chloro-6-phenoxy-pyridine 2,6-Dichloropyridine (2.0 g, 13.5 mmol) and phenol (1.4 mL, 14.9 mmol) were reacted in the same manner as in Preparation Example 37 to obtain the title compound (3.5 g, 84%).
$^1$H-NMR (CDCl$_3$) δ 7.62 (1H, t), 7.41 (2H, m), 7.21 (1H, t), 7.14 (2H, d), 6.74 (2H, d)

Preparation Example 127

2-bromo-5-methoxy-phenol

After 3-methoxy-phenol (1 g, 8.05 mmol) was dissolved in CS$_2$ (4 mL), Br$_2$ (0.4 mL) was added thereto, and the mixture was agitated at room temperature for 2 hours. The reactant was added with Na$_2$S$_2$O$_3$ aqueous solution and then extracted with EtOAc. The organic layer was separated and dried with MgSO$_4$, and was concentrated under reduced pressure to obtain the title compound (1.05 g, 64%).
$^1$H-NMR (CDCl$_3$) δ 7.31 (1H, d), 6.59 (1H, m), 6.40 (1H, m), 5.45 (1H, s), 3.79 (3H, s).

Preparation Example 128

1-bromo-2-cyclopentyloxy-4-methoxy-benzene

2-Bromo-5-methoxy-phenol (0.2 g, 0.98 mmol) obtained in Preparation Example 127, bromo-cyclopentane (0.16 mL)

and Cs$_2$CO$_3$ (0.96 g) were reacted in the same manner as in step B of Preparation Example 44 to obtain the title compound (0.26 g, 96%).

$^1$H-NMR (CDCl$_3$) δ 7.38 (1H, d), 6.47 (1H, m), 6.36 (1H, m), 4.75 (1H, m), 3.79 (3H, s), 1.88 (6H, m), 1.61 (2H, m).

Preparation Example 129

2-bromo-1-cyclopentyloxy-4-fluoro-benzene

2-Bromo-4-fluoro-phenol (0.3 g, 1.57 mmol), bromo-cyclopentane (0.25 mL) and Cs$_2$CO$_3$ (1.53 g) were reacted in the same manner as in step B of Preparation Example 44 to obtain the title compound (0.38 g, 93%).

$^1$H-NMR (CDCl$_3$) δ 7.27 (1H, m), 6.94 (1H, m), 6.82 (1H, m), 4.73 (1H, m), 1.86 (6H, m), 1.62 (2H, m).

Preparation Example 130

3-bromo-5-methyl-pyridin-2-ol

5-Methyl-pyridin-2-ol (1 g, 9.16 mmol) and Br$_2$ (0.47 mL) were reacted in the same manner as in Preparation Example 127 to obtain the title compound (1.7 g, 98%).

$^1$H-NMR (CDCl$_3$) δ 7.73 (1H, s), 7.22 (1H, s), 2.10 (3H, s).

Preparation Example 131

3-bromo-2-cyclopentyloxy-5-methyl-pyridine

3-Bromo-5-methyl-pyridin-2-ol (0.5 g, 2.66 mmol) obtained in Preparation Example 130, bromo-cyclopentane (0.43 mL) and Cs$_2$CO$_3$ (2.6 g) were reacted in the same manner as in step B of Preparation Example 44 to obtain the title compound (0.25 g, 37%).

$^1$H-NMR (CDCl$_3$) δ 7.86 (1H, s), 7.60 (1H, s), 5.38 (1H, m), 2.21 (3H, s), 1.93 (2H, m), 1.82 (4H, m), 1.61 (2H, m).

Preparation Example 132

1-bromo-2-isopropoxy-4-methoxy-benzene

2-Bromo-5-methoxy-phenol (0.2 g, 0.98 mmol) obtained in Preparation Example 127, 2-bromo-propane (0.14 mL) and Cs$_2$CO$_3$ (0.96 g) were reacted in the same manner as in step B of Preparation Example 44 to obtain the title compound (0.23 g, 94%).

$^1$H-NMR (CDCl$_3$) δ 7.39 (1H, d), 6.48 (1H, m), 6.39 (1H, m), 4.51 (1H, m), 3.77 (3H, s), 1.37 (6H, d).

Preparation Example 133

3-bromo-2-isopropoxy-5-methyl-pyridine

3-Bromo-5-methyl-pyridin-2-ol (0.3 g, 2.66 mmol) obtained in Preparation Example 130, 2-bromo-propane (0.22 mL) and Cs$_2$CO$_3$ (1.56 g) were reacted in the same manner as in step B of Preparation Example 44 to obtain the title compound (0.09 g, 25%).

$^1$H-NMR (CDCl$_3$) δ 7.85 (1H, s), 7.62 (1H, s), 5.26 (1H, m), 2.21 (3H, s), 1.35 (6H, d).

Preparation Example 134

2-bromo-4-fluoro-1-isopropoxy-benzene

2-Bromo-4-fluoro-phenol (0.3 g, 1.57 mmol), 2-bromo-propane (0.22 mL) and Cs$_2$CO$_3$ (1.53 g) were reacted in the same manner as in step B of Preparation Example 44 to obtain the title compound (0.33 g, 89%).

$^1$H-NMR (CDCl$_3$) δ 7.28 (1H, m), 6.94 (1H, m), 6.88 (1H, m), 4.44 (1H, m), 1.32 (6H, d).

Preparation Example 135

3-bromo-6-methyl-pyridin-2-ol

6-Methyl-pyridin-2-ol (0.3 g, 2.7 mmol) and Br$_2$ (0.14 mL) were reacted in the same manner as in Preparation Example 127 to obtain the title compound (0.09 g, 18%).

$^1$H-NMR (CDCl$_3$) δ 7.48 (1H, d), 6.32 (1H, d), 2.43 (3H, s).

Preparation Example 136

3-bromo-2-cyclopentyloxy-6-methyl-pyridine

3-Bromo-6-methyl-pyridin-2-ol (0.09 g, 0.50 mmol) obtained in Preparation Example 135, bromo-cyclopentane (0.08 mL) and Cs$_2$CO$_3$ (0.49 g) were reacted in the same manner as in step B of Preparation Example 44 to obtain the title compound (0.12 g, 93%).

$^1$H-NMR (CDCl$_3$) δ 7.60 (1H, d), 6.40 (1H, d), 5.30 (1H, m), 2.53 (3H, s), 1.94 (2H, m), 1.78 (4H, m), 1.61 (2H, m).

Preparation Example 137

2-bromo-6-fluoro-4-methyl-phenol

2-Fluoro-4-methyl-phenol (0.4 g, 3.17 mmol) and Br$_2$ (0.16 mL) were reacted in the same manner as in Preparation Example 127 to obtain the title compound (0.37 g, 56%).

$^1$H-NMR (CDCl$_3$) δ 7.07 (1H, s), 6.87 (1H, m), 5.32 (1H, s), 2.26 (3H, s).

Preparation Example 138

1-bromo-3-fluoro-2-isopropoxy-5-methyl-benzene

2-Bromo-6-fluoro-4-methyl-phenol (0.10 g, 0.49 mmol) obtained in Preparation Example 137, 2-bromo-propane (0.07 mL) and Cs$_2$CO$_3$ (0.48 g) were reacted in the same manner as in step B of Preparation Example 44 to obtain the title compound (0.11 g, 88%).

$^1$H-NMR (CDCl$_3$) δ 7.12 (1H, s), 6.84 (1H, m), 4.45 (1H, m), 2.26 (3H, s), 1.34 (6H, d).

Preparation Example 139

1-bromo-3-fluoro-5-methyl-2-propoxy-benzene

2-Bromo-6-fluoro-4-methyl-phenol (0.10 g, 0.49 mmol) obtained in Preparation Example 137, 1-bromo-propane (0.07 mL) and Cs$_2$CO$_3$ (0.48 g) were reacted in the same manner as in step B of Preparation Example 44 to obtain the title compound (0.10 g, 85%).

$^1$H-NMR (CDCl$_3$) δ 7.11 (1H, s), 6.83 (1H, m), 3.99 (2H, t), 2.26 (3H, s), 1.80 (2H, m), 1.05 (3H, t).

Preparation Example 140

1-bromo-2,4-dipropoxy-benzene

4-Bromo-benzene-1,3-diol (0.1 g, 0.53 mmol), 1-bromo-propane (0.10 mL) and Cs$_2$CO$_3$ (0.52 g) were reacted in the same manner as in step B of Preparation Example 44 to obtain the title compound (0.13 g, 93%).

¹H-NMR (CDCl₃) δ 7.37 (1H, d), 6.46 (1H, m), 6.36 (1H, m), 3.94 (2H, t), 3.86 (2H, t), 1.84 (2H, m), 1.78 (2H, m), 1.06 (3H, t), 1.02 (3H, t).

Preparation Example 141

2-bromo-3-fluoro-4-methyl-phenol

3-Fluoro-4-methyl-phenol (0.3 g, 2.38 mmol) and Br₂ (0.12 mL) were reacted in the same manner as in Preparation Example 127 to obtain the title compound (0.37 g, 75%).

¹H-NMR (CDCl₃) δ 7.03 (1H, m), 6.83 (1H, m), 5.35 (1H, s), 2.26 (3H, s).

Preparation Example 142

2-bromo-1-cyclopentyloxy-3-fluoro-4-methyl-benzene

2-Bromo-3-fluoro-4-methyl-phenol (0.10 g, 0.49 mmol) obtained in Preparation Example 141, bromo-cyclopentane (0.08 mL) and Cs₂CO₃ (0.48 g) were reacted in the same manner as in step B of Preparation Example 44 to obtain the title compound (0.09 g, 67%).

¹H-NMR (CDCl₃) δ 7.11 (1H, m), 6.84 (1H, m), 4.66 (1H, m), 2.29 (3H, s), 1.90 (4H, m), 1.75 (2H, m), 1.60 (2H, m).

Preparation Example 143

2-bromo-6-fluoro-phenol

2-Fluoro-phenol (0.32 g, 2.85 mmol) and Br₂ (0.14 mL) were reacted in the same manner as in Preparation Example 127 to obtain the title compound (0.53 g, 97%).

¹H-NMR (CDCl₃) δ 7.25 (1H, m), 7.14 (1H, d), 6.88 (1H, t), 5.20 (1H, s).

Preparation Example 144

1-bromo-2-cyclopentyloxy-3-fluoro-benzene

2-Bromo-6-fluoro-phenol (0.10 g, 0.52 mmol) obtained in Preparation Example 143, bromo-cyclopentane (0.08 mL) and Cs₂CO₃ (0.51 g) were reacted in the same manner as in step B of Preparation Example 44 to obtain the title compound (0.13 g, 96%).

¹H-NMR (CDCl₃) δ 7.23 (1H, m), 7.15 (1H, m), 6.83 (1H, t), 4.75 (1H, m), 1.89-1.78 (6H, m), 1.63 (2H, m).

Preparation Example 145

1-bromo-2-cyclopentyloxy-3-fluoro-5-methyl-benzene

2-Bromo-6-fluoro-4-methyl-phenol (0.10 g, 0.49 mmol) obtained in Preparation Example 137, bromo-cyclopentane (0.08 mL) and Cs₂CO₃ (0.48 g) were reacted in the same manner as in step B of Preparation Example 44 to obtain the title compound (0.12 g, 87%).

¹H-NMR (CDCl₃) δ 7.13 (1H, s), 6.84 (1H, d), 4.87 (1H, m), 2.27 (3H, s), 1.94 (4H, m), 1.75 (2H, m), 1.60 (2H, m).

Preparation Example 146

Ethyl 6-[2,6-difluoro-4-(4,4,5,5-tetramethyl-1,3,2-dioxaborolan-2-yl)phenoxy]hexanoate 2,6-Difluoro-4-(4,4,5,5-tetramethyl-1,3,2-dioxaborolan-2-yl)phenol (1.11 g, 4.34 mmol) obtained in step B of Preparation Example 2, ethyl 6-bromohexanoate (0.97 g, 4.34 mmol), and Cs₂CO₃ (2.83 g, 8.68 mmol) were added with CH₃CN (15 mL), and the mixture was agitated under reflux for 2 hours. The residue was separated and concentrated under reduced pressure to obtain the title compound (1.4 g, 80%).

¹H-NMR (CDCl₃) δ 7.31 (2H, m), 4.17 (2H, m), 4.14 (2H, q), 2.32 (2H, t), 1.77 (2H, m), 1.68 (2H, m), 1.51 (2H, m), 1.32 (12H, s), 1.24 (3H, t)

Preparation Example 147

5-[2-fluoro-4-(4,4,5,5-tetramethyl-[1,3,2]dioxaborolan-2-yl)-phenoxy]-pentanoic acid ethyl ester 2-Fluoro-4-(4,4,5,5-tetramethyl-1,3,2-dioxaborolan-2-yl)phenol (0.50 g, 2.10 mmol) obtained in step A of Preparation Example 4, ethyl 5-bromopentanoate (0.53 g, 2.52 mmol) and Cs₂CO₃ (1.37 g, 4.20 mmol) were added with CH₃CN (7 mL), and the mixture was agitated under reflux for 2 hours. The residue was separated and concentrated under reduced pressure to obtain the title compound (0.40 g, 52%).

¹H-NMR (CDCl₃) δ 7.50 (2H, t), 6.92 (1H, t), 4.13 (2H, q), 4.06 (2H, t), 2.39 (2H, t), 1.92-1.77 (4H, m), 1.32 (12H, s), 1.24 (3H, t)

Preparation Example 148

4-(4-bromo-phenylsulfanyl)-butyric acid ethyl ester

4-Bromo-benzenethiol (0.5 g, 2.64 mmol), NaH (60% in mineral oil, 0.11 g, 2.64 mmol) and 4-bromo-butyric acid ethyl ester (0.42 mL, 2.91 mmol) were reacted in the same manner as in Preparation Example 12 to obtain the title compound (0.80 g, 99%).

¹H-NMR (CDCl₃) δ 7.38 (2H, d), 7.19 (2H, d), 4.13 (2H, q), 2.93 (2H, t), 2.43 (2H, t), 1.93 (2H, m), 1.24 (3H, t).

Preparation Example 149

4-(3'-hydroxy-biphenyl-4-ylsulfanyl)-butyric acid ethyl ester 4-(4-Bromo-phenylsulfanyl)-butyric acid ethyl ester (0.92 g, 3.04 mmol) obtained in Preparation Example 148, 3-hydroxyphenylboronic acid (0.42 g, 3.04 mmol), 2M Na₂CO₃ solution (3 mL) and Pd(PPh₃)₄ (0.18 g, 0.15 mmol) were reacted in the same manner as in Preparation Example 13 to obtain the title compound (0.27 g, 28%).

¹H-NMR (CDCl₃) δ 7.48 (2H, d), 7.38 (2H, d), 7.28 (1H, t), 7.13 (1H, m), 7.02 (1H, m), 6.81 (1H, m), 5.00 (1H, s), 4.13 (2H, q), 2.99 (2H, t), 2.49 (2H, t), 2.00 (2H, m), 1.25 (3H, t).

Preparation Example 150

[1-(1-methoxycarbonylmethyl-cyclopropylmethyld-isulfanylmethyl)-cyclopropyl]-acetic acid methyl ester After (1-mercaptomethyl-cyclopropyl)-acetic acid methyl ester (1 g, 6.2 mmol) was dissolved in methanol (20 mL), 12 (0.79 g, 3.1 mmol) was added thereto, and the mixture was agitated at room temperature for 1 hour. The reactant was added with water and then extracted with EtOAc. The organic layer was separated and dried with MgSO$_4$, and was purified by column chromatography to obtain the title compound (0.80 g, 40%).

$^1$H-NMR (CDCl$_3$) δ 3.68 (6H, s), 2.89 (4H, s), 2.44 (4H, s), 0.62 (4H, m), 0.56 (4H, m).

Preparation Example 151

[1-(4-bromo-2,6-difluoro-phenylsulfanyl methyl)-cyclopropyl]aetic acid methyl ester

[1-(1-Methoxycarbonylmethyl-cyclopropylmethyldisulfanylmethyl)-cyclopropyl]-acetic acid methyl ester (0.40 g, 1.25 mmol) obtained in Preparation Example 150 and 4-bromo-2,6-difluoro-phenylamine (0.2 g, 0.96 mmol) was charged with N$_2$ gas at 75° C. Isopentyl nitrite (0.33 mL, 2.50 mmol) was added slowly thereto dropwise, and the mixture was agitated at 75° C. for 1 hour. The reactant was concentrated under reduced pressure and purified by column chromatography to obtain the title compound (0.10 g, 29%).

$^1$H-NMR (CDCl$_3$) δ 7.10 (2H, d), 3.66 (3H, s), 2.99 (2H, s), 2.55 (2H, s), 0.45 (2H, m), 0.36 (2H, m).

Preparation Example 152

[1-(3,5-difluoro-3'-hydroxy-biphenyl-4-ylsulfanylmethyl)-cyclopropyl]-acetic acid methyl ester

[1-(4-Bromo-2,6-difluoro-phenylsulfanylmethyl)-cyclopropyl]-acetic acid methyl ester (0.10 g, 0.28 mmol) obtained in Preparation Example 151, 3-hydroxyphenylboronic acid (0.04 g, 0.28 mmol), 2M Na$_2$CO$_3$ aqueous solution (0.3 mL) and Pd(PPh$_3$)$_4$ (0.02 g, 0.01 mmol) were reacted in the same manner as in Preparation Example 13 to obtain the title compound (0.02 g, 19%).

$^1$H-NMR (CDCl$_3$) δ 7.32 (1H, t), 7.12 (3H, m), 7.03 (1H, s), 6.89 (1H, m), 5.51 (1H, s), 3.65 (3H, s), 3.00 (2H, s), 2.57 (2H, s), 0.45-0.39 (4H, m).

Preparation Example 153

Methoxycarbonylmethyldisulfanyl-acetic acid methyl ester

Mercapto-acetic acid methyl ester (1 g, 9.4 mmol) and I$_2$ (1.19 g, 4.7 mmol) were reacted in the same manner as in Preparation Example 150 to obtain the title compound (0.50 g, 25%).

$^1$H-NMR (CDCl$_3$) δ 3.75 (6H, s), 3.58 (4H, s).

Preparation Example 154

(4-bromo-2,6-difluoro-phenylsulfanyl)-acetic acid methyl ester

Methoxycarbonylmethyldisulfanyl-acetic acid methyl ester (0.9 g, 4.28 mmol) obtained in Preparation Example 153, 4-bromo-2,6-difluoro-phenylamine (0.5 g, 2.40 mmol) and isopentyl nitrite (0.84 mL, 6.25 mmol) were reacted in the same manner as in Preparation Example 151 to obtain the title compound (0.30 g, 42%).

$^1$H-NMR (CDCl$_3$) δ 7.13 (2H, d), 3.67 (3H, s), 3.52 (2H, s).

Preparation Example 155

(3,5-difluoro-3'-hydroxy-biphenyl-4-ylsulfanyl)-acetic acid methyl ester (4-Bromo-2,6-difluoro-phenylsulfanyl)-acetic acid methyl ester (0.12 g, 0.40 mmol) obtained in Preparation Example 154, 3-hydroxyphenylboronic acid (0.06 g, 0.40 mmol), 2M Na$_2$CO$_3$ aqueous solution (0.4 mL) and Pd(PPh$_3$)$_4$ (0.02 g, 0.02 mmol) were reacted in the same manner as in Preparation Example 13 to obtain the title compound (0.04 g, 30%).

$^1$H-NMR (CDCl$_3$) δ 7.31 (1H, t), 7.15 (2H, d), 7.11 (1H, m), 7.00 (1H, s), 6.88 (1H, m), 4.84 (1H, s), 3.69 (3H, s), 3.58 (2H, s).

Preparation Example 156

(3'-cyclopentyloxy-3,5-difluoro-biphenyl-4-ylsulfanyl)-acetic acid methyl ester (3,5-Difluoro-3'-hydroxy-biphenyl-4-ylsulfanyl)-acetic acid methyl ester (0.037 g, 0.12 mmol) obtained in Preparation Example 155, bromo-cyclopentane (0.02 mL) and Cs$_2$CO$_3$ (0.12 g, 0.36 mmol) were reacted in the same manner as in step B of Preparation Example 44 to obtain the title compound (0.035 g, 77%).

$^1$H-NMR (CDCl$_3$) δ 7.33 (1H, t), 7.16 (2H, d), 7.07 (1H, m), 7.02 (1H, s), 6.90 (1H, m), 4.80 (1H, m), 3.69 (3H, s), 3.57 (2H, s), 1.92-1.80 (6H, m), 1.63 (2H, m).

Preparation Example 157

2-(3'-cyclopentyloxy-3,5-difluoro-biphenyl-4-ylsulfanyl)-ethanol

After (3'-cyclopentyloxy-3,5-difluoro-biphenyl-4-ylsulfanyl)-acetic acid methyl ester (0.034 g, 0.09 mmol) obtained in Preparation Example 156 was dissolved in THF (1 mL), LiBH$_4$ (0.09 g, 0.18 mmol) was added thereto at 0° C., and the mixture was agitated at room temperature for 2 hours. The reactant was added with water and then extracted with EtOAc. The organic layer was separated and dried with MgSO$_4$, and was purified by column chromatography to obtain the title compound (0.027 g, 87%).

$^1$H-NMR (CDCl$_3$) δ 7.33 (1H, t), 7.16 (2H, d), 7.07 (1H, m), 7.02 (1H, s), 6.91 (1H, m), 4.81 (1H, m), 3.65 (2H, q), 3.04 (2H, t), 2.24 (1H, t), 1.92-1.80 (6H, m), 1.63 (2H, m).

Preparation Example 158

4-(2-chloro-ethylsulfanyl)-3'-cyclopentyloxy-3,5-difluoro-biphenyl

After 2-(3'-cyclopentyloxy-3,5-difluoro-biphenyl-4-ylsulfanyl)-ethanol (0.027 g, 0.08 mmol) obtained in Preparation Example 157 was dissolved in CH$_3$CN (1 mL), SOCl$_2$ (0.01 mL, 0.15 mmol) was added thereto at 0° C., the mixture was agitated at room temperature for 1 hour. The reactant was concentrated under reduced pressure to obtain the title compound (0.028 g, 98%).

$^1$H-NMR (CDCl$_3$) δ 7.34 (1H, t), 7.17 (2H, d), 7.08 (1H, m), 7.03 (1H, s), 6.91 (1H, m), 4.81 (1H, m), 3.62 (2H, t), 3.17 (2H, t), 1.93-1.81 (6H, m), 1.64 (2H, m).

Preparation Example 159

4-[4-(4,4,5,5-tetramethyl-[1,3,2]dioxaborolan-2-yl)-phenylsulfanyl]-butyric acid ethyl ester 4-(4-Bromo-phenylsulfanyl)-butyric acid ethyl ester (0.83 g, 2.7 mmol) obtained in Preparation Example 148, bis(pinacolato)diboron (0.76 g, 3.0 mmol), potassium acetate (0.67 g, 6.8 mmol) and dichloro[1,1'-bis(diphenylphosphino)ferrocene]palladium(II) (0.20 g, 0.27 mmol) were reacted in the same manner as in step A of Preparation Example 1 to obtain the title compound (0.73 g, 75%).

$^1$H-NMR (CDCl$_3$) δ 7.70 (2H, d), 7.27 (2H, d), 4.11 (2H, q), 2.99 (2H, t), 2.44 (2H, t), 1.96 (2H, m), 1.32 (12H, s), 1.24 (3H, t).

Preparation Example 160

4-(4-methoxy-benzylsulfanyl)-butyric acid ethyl ester (4-Methoxy-phenyl)-methanethiol (0.5 g, 3.24 mmol), NaH (60% in mineral oil, 0.13 g, 3.24 mmol) and 4-bromo-butyric acid ethyl ester (0.51 mL, 3.57 mmol) were reacted in the same manner as in Preparation Example 12 to obtain the title compound (0.70 g, 80%).

$^1$H-NMR (CDCl$_3$) δ 7.22 (2H, d), 6.83 (2H, d), 4.12 (2H, q), 3.79 (3H, s), 3.65 (2H, s), 2.43 (2H, t), 2.38 (2H, t), 1.87 (2H, m), 1.24 (3H, t).

Preparation Example 161

4-mercapto-butyric acid ethyl ester

After 4-(4-methoxy-benzylsulfanyl)-butyric acid ethyl ester (0.7 g, 2.61 mmol) obtained in Preparation Example 160 was dissolved in TFA (5 mL), anisole (1.5 mL) and trifluoromethanesulfonic acid (0.5 mL) were added thereto, and the mixture was agitated at room temperature for 1 hour. The reactant was added with NaHCO$_3$ aqueous solution and then extracted with EtOAc. The organic layer was separated and dried with MgSO$_4$, and was purified by column chromatography to obtain the title compound (0.37 g, 95%).

$^1$H-NMR (CDCl$_3$) δ 4.13 (2H, q), 3.11 (2H, t), 2.41 (2H, t), 1.99 (2H, m), 1.26 (3H, t).

Preparation Example 162

3',4',5'-trifluoro-biphenyl-3-ol

5-Bromo-1,2,3-trifluoro-benzene (0.20 g, 0.95 mmol), 3-hydroxyphenylboronic acid (0.13 g, 0.95 mmol), 2M Na$_2$CO$_3$ aqueous solution (0.9 mL) and Pd(PPh$_3$)$_4$ (0.055 g, 0.05 mmol) were reacted in the same manner as in Preparation Example 13 to obtain the title compound (0.18 g, 83%).

$^1$H-NMR (CDCl$_3$) δ 7.30 (1H, t), 7.17 (2H, m), 7.06 (1H, m), 6.95 (1H, s), 6.85 (1H, m), 4.91 (1H, s).

Preparation Example 163

3'-cyclobutoxy-3,4,5-trifluoro-biphenyl

3',4',5'-Trifluoro-biphenyl-3-ol (0.05 g, 0.22 mmol) obtained in Preparation Example 162, bromo-cyclobutane (0.03 mL) and Cs$_2$CO$_3$ (0.22 g) were reacted in the same manner as in step B of Preparation Example 44 to obtain the title compound (0.04 g, 64%).

$^1$H-NMR (CDCl$_3$) δ 7.32 (1H, t), 7.15 (2H, m), 7.04 (1H, m), 6.92 (1H, s), 6.82 (1H, m), 4.68 (1H, m), 2.46 (2H, m), 2.20 (2H, m), 1.88 (1H, m), 1.71 (1H, m).

Preparation Example 164

3,4,5-trifluoro-3'-isopropoxy-biphenyl

3',4',5'-Trifluoro-biphenyl-3-ol (0.05 g, 0.22 mmol) obtained in Preparation Example 162, 2-bromo-propane (0.03 mL) and Cs$_2$CO$_3$ (0.22 g) were reacted in the same manner as in step B of Preparation Example 44 to obtain the title compound (0.06 g, 100%).

$^1$H-NMR (CDCl$_3$) δ 7.32 (1H, t), 7.18 (2H, m), 7.03 (1H, m), 6.99 (1H, s), 6.89 (1H, m), 4.60 (1H, m), 1.35 (6H, d).

Preparation Example 165

4,4,5,5-tetramethyl-2-(3,4,5-trifluoro-phenyl)-[1,3,2]dioxaborolane

5-Bromo-1,2,3-trifluoro-benzene (0.50 g, 2.37 mmol), bis(pinacolato)diboron (0.66 g, 2.61 mmol), potassium acetate (0.58 g, 5.92 mmol) and transdichlorobis(triphenylphosphine)palladium(II) (0.17 g, 0.24 mmol) were reacted in the same manner as in step A of Preparation Example 1 to obtain the title compound (0.24 g, 39%).

$^1$H-NMR (CDCl$_3$) δ 7.36 (2H, m), 1.35 (12H, s).

Preparation Example 166

2-propoxy-6-(3,4,5-trifluoro-phenyl)-pyridine 4,4,5,5-Tetramethyl-2-(3,4,5-trifluoro-phenyl)-[1,3,2]dioxaborolane (0.03 g, 0.12 mmol) obtained in Preparation Example 165, 2-bromo-6-propoxy-pyridine (0.027, 0.13 mmol) obtained in Preparation Example 227, 2M Na$_2$CO$_3$ aqueous solution (0.2 mL) and Pd(PPh$_3$)$_4$ (0.007 g, 0.006 mmol) were reacted in the same manner as in Preparation Example 13 to obtain the title compound (0.023 g, 74%).

$^1$H-NMR (CDCl$_3$) δ 7.64 (3H, m), 7.23 (1H, d), 6.71 (1H, d), 4.35 (2H, t), 1.84 (2H, m), 1.05 (3H, t).

Preparation Example 167

2-isopropoxy-6-(3,4,5-trifluoro-phenyl)-pyridine 4,4,5,5-Tetramethyl-2-(3,4,5-trifluoro-phenyl)-[1,3,2]dioxaborolane (0.054 g, 0.21 mmol) obtained in Preparation Example 165, 2-bromo-6-isopropoxy-pyridine (0.050 g, 0.23 mmol) obtained in Preparation Example 228, 2M Na$_2$CO$_3$ aqueous solution (0.3 mL) and Pd(PPh$_3$)$_4$ (0.012 g, 0.01 mmol) were reacted in the same manner as in Preparation Example 13 to obtain the title compound (0.02 g, 32%).

$^1$H-NMR (CDCl$_3$) δ 7.63 (3H, m), 7.22 (1H, d), 6.67 (1H, d), 5.44 (1H, m), 1.40 (6H, d).

Preparation Example 168

4-bromo-2,6-difluoro-benzenethiol

Step A: 4-bromo-2,6-difluoro-benzenesulfonyl chloride

After CuCl$_2$ (0.77 g, 5.77 mmol) was dissolved in water (200 mL), SOCl$_2$ (29 mL, 0.40 mol) was added thereto at 0°

C., and the mixture was agitated at room temperature for 18 hours. Then, 4-bromo-2,6-difluoroaniline (20 g, 0.096 mol) was dissolved in HCl (240 mL) and water (900 mL), and a solution of $NaNO_2$ (7 g, 0.10 mol) dissolved in water (200 mL) was added thereto at 0° C. The mixture was added with a prepared thionyl chloride solution, and reacted for 1 hour to obtain the solid state title compound (24 g, 85%).

Step B: 4-bromo-2,6-difluoro-benzenethiol

After 4-bromo-2,6-difluoro-benzenesulfonyl chloride (24 g, 0.08 mol) obtained in step A was dissolved in THF (270 mL), $PPh_3$ (75 g, 0.28 mol) was added thereto. Then, the mixture was agitated at room temperature for 15 minute, added with water, and was agitated at room temperature for 18 hours. The reactant was added with water and then extracted with EtOAc. The organic layer was separated and dried with $MgSO_4$, and was purified by column chromatography to obtain the title compound (15 g, 83%).
$^1$H-NMR ($CDCl_3$) δ 7.10 (2H, d), 3.58 (1H, s).

Preparation Example 169

4-(4-bromo-2,6-difluoro-phenylsulfanyl)-butyric acid ethyl ester

4-Bromo-2,6-difluoro-benzenethiol (15 g, 0.066 mol) obtained in Preparation Example 168, NaH (60% in mineral oil, 2.6 g, 0.066 mol) and 4-bromo-butyric acid ethyl ester (10 mL, 0.073 mol) were reacted in the same manner as in Preparation Example 12 to obtain the title compound (18.56 g, 82%).
$^1$H-NMR ($CDCl_3$) δ 7.11 (2H, d), 4.11 (2H, q), 2.90 (2H, t), 2.43 (2H, t), 1.82 (2H, m), 1.24 (3H, t).

Preparation Example 170

4-[2,6-difluoro-4-(4,4,5,5-tetramethyl-[1,3,2]dioxaborolan-2-yl)-phenylsulfanyl]-butyric acid ethyl ester 4-(4-Bromo-2,6-difluoro-phenylsulfanyl)-butyric acid ethyl ester (11.6 g, 0.034 mol) obtained in Preparation Example 169, bis(pinacolato)diboron (9.5 g, 0.038 mol), potassium acetate (8.4 g, 0.085 mol) and dichloro[1,1'-bis(diphenylphosphino)ferrocene]palladium(II) (2.5 g, 0.003 mol) were reacted in the same manner as in step A of Preparation Example 1 to obtain the title compound (10.6 g, 80%).
$^1$H-NMR ($CDCl_3$) δ 7.30 (2H, d), 4.09 (2H, q), 2.94 (2H, t), 2.43 (2H, t), 1.83 (2H, m), 1.33 (12H, s), 1.22 (3H, t).

Preparation Example 171

2-propoxy-3-(3,4,5-trifluoro-phenyl)-pyridine 4,4,5,5-Tetramethyl-2-(3,4,5-trifluoro-phenyl)-[1,3,2]dioxaborolane (0.05 g, 0.19 mmol) obtained in Preparation Example 165, 3-iodo-2-propoxy-pyridine (0.056 g, 0.21 mmol) obtained in Preparation Example 202, 2M $Na_2CO_3$ aqueous solution (0.3 mL) and $Pd(PPh_3)_4$ (0.011 g, 0.01 mmol) were reacted in the same manner as in Preparation Example 13 to obtain the title compound (0.02 g, 43%).
$^1$H-NMR ($CDCl_3$) δ 8.15 (1H, m), 7.55 (1H, m), 7.21 (2H, m), 6.95 (1H, m), 4.31 (2H, t), 1.77 (2H, m), 1.00 (3H, t).

Preparation Example 172

2-isopropylsulfanyl-6-(3,4,5-trifluoro-phenyl)-pyridine 4,4,5,5-Tetramethyl-2-(3,4,5-trifluoro-phenyl)-[1,3,2]dioxaborolane (0.050 g, 0.19 mmol) obtained in Preparation Example 165, 2-bromo-6-isopropylsulfanyl-pyridine (0.049 g, 0.21 mmol) obtained in Preparation Example 201, 2M $Na_2CO_3$ aqueous solution (0.3 mL) and $Pd(PPh_3)_4$ (0.011 g, 0.01 mmol) were reacted in the same manner as in Preparation Example 13 to obtain the title compound (0.035 g, 64%).
$^1$H-NMR ($CDCl_3$) δ 7.67 (2H, m), 7.53 (1H, t), 7.32 (1H, d), 7.12 (1H, d), 4.11 (1H, m), 1.46 (6H, d).

Preparation Example 173

2-propylsulfanyl-6-(3,4,5-trifluoro-phenyl)-pyridine 4,4,5,5-Tetramethyl-2-(3,4,5-trifluoro-phenyl)-[1,3,2]dioxaborolane (0.050 g, 0.19 mmol) obtained in Preparation Example 165, 2-bromo-6-propylsulfanyl-pyridine (0.049 g, 0.21 mmol) obtained in Preparation Example 229, 2M $Na_2CO_3$ aqueous solution (0.3 mL) and $Pd(PPh_3)_4$ (0.011 g, 0.01 mmol) were reacted in the same manner as in Preparation Example 13 to obtain the title compound (0.03 g, 57%).
$^1$H-NMR ($CDCl_3$) δ 7.66 (2H, m), 7.53 (1H, t), 7.32 (1H, d), 7.14 (1H, d), 3.22 (2H, t), 1.80 (2H, m), 1.09 (3H, t).

Preparation Example 174

2-cyclobutylsulfanyl-3-(3,4,5-trifluoro-phenyl)-pyridine 4,4,5,5-Tetramethyl-2-(3,4,5-trifluoro-phenyl)-[1,3,2]dioxaborolane (0.050 g, 0.19 mmol) obtained in Preparation Example 165, 2-cyclobutylsulfanyl-3-iodo-pyridine (0.062 g, 0.21 mmol) obtained in Preparation Example 44, 2M $Na_2CO_3$ aqueous solution (0.3 mL) and $Pd(PPh_3)_4$ (0.011 g, 0.01 mmol) were reacted in the same manner as in Preparation Example 13 to obtain the title compound (0.056 g, 98%).
$^1$H-NMR ($CDCl_3$) δ 8.43 (1H, m), 7.33 (1H, m), 7.04 (3H, m), 4.43 (1H, m), 2.52 (2H, m), 2.05 (4H, m).

Preparation Example 175

2-cyclobutoxy-3-(3,4,5-trifluoro-phenyl)-pyridine 4,4,5,5-Tetramethyl-2-(3,4,5-trifluoro-phenyl)-[1,3,2]dioxaborolane (0.050 g, 0.19 mmol) obtained in Preparation Example 165, 2-cyclobutoxy-3-iodo-pyridine (0.059 g, 0.21 mmol) obtained in Preparation Example 200, 2M $Na_2CO_3$ aqueous solution (0.3 mL) and $Pd(PPh_3)_4$ (0.011 g, 0.01 mmol) were reacted in the same manner as in Preparation Example 13 to obtain the title compound (0.01 g, 18%).
$^1$H-NMR ($CDCl_3$) δ 8.14 (1H, m), 7.55 (1H, m), 7.25 (2H, m), 6.93 (1H, m), 5.28 (1H, m), 2.46 (2H, m), 2.12 (2H, m), 1.82 (1H, m), 1.68 (1H, m).

Preparation Example 176

2-cyclopentylsulfanyl-3-(3,4,5-trifluoro-phenyl)-pyridine 4,4,5,5-Tetramethyl-2-(3,4,5-trifluoro-phenyl)-[1,3,2]dioxaborolane (0.050 g, 0.19 mmol) obtained in Preparation Example 165, 2-cyclopentylsulfanyl-3-iodo-pyridine (0.065 g, 0.21 mmol) obtained in Preparation Example 39, 2M Na$_2$CO$_3$ aqueous solution (0.3 mL) and Pd(PPh$_3$)$_4$ (0.011 g, 0.01 mmol) were reacted in the same manner as in Preparation Example 13 to obtain the title compound (0.02 g, 33%).

$^1$H-NMR (CDCl$_3$) δ 8.44 (1H, m), 7.31 (1H, m), 7.05 (3H, m), 4.10 (1H, m), 2.19 (2H, m), 1.72-1.52 (6H, m).

Preparation Example 177

4-bromo-2-fluoro-benzenesulfonyl chloride

4-Bromo-2-fluoro-aniline (1 g, 5.26 mmol) was reacted in the same manner as in step A of Preparation Example 168 to obtain the title compound (0.49 g, 34%).

$^1$H-NMR (CDCl$_3$) δ 7.85 (1H, m), 7.55 (2H, m).

Preparation Example 178

4-bromo-2-fluoro-benzenethiol

4-Bromo-2-fluoro-benzenesulfonyl chloride (0.49 g, 1.79 mmol) obtained in Preparation Example 177 was reacted in the same manner as in step B of Preparation Example 168 to obtain the title compound (0.37 g, 99%).

$^1$H-NMR (CDCl$_3$) δ 7.23 (1H, m), 7.16 (2H, m), 3.57 (1H, s).

Preparation Example 179

4-(4-bromo-2-fluoro-phenylsulfanyl)-butyric acid ethyl ester

4-Bromo-2-fluoro-benzenethiol (0.37 g, 1.81 mmol) obtained in Preparation Example 178, NaH (60% in mineral oil, 0.07 g, 1.81 mmol) and 4-bromo-butyric acid ethyl ester (0.28 mL, 1.99 mmol) were reacted in the same manner as in Preparation Example 12 to obtain the title compound (0.43 g, 75%).

$^1$H-NMR (CDCl$_3$) δ 7.23 (3H, m), 4.12 (2H, q), 2.92 (2H, t), 2.44 (2H, t), 1.90 (2H, m), 1.25 (3H, t).

Preparation Example 180

4-[2-fluoro-4-(4,4,5,5-tetramethyl-[1,3,2]dioxaborolan-2-yl)-phenylsulfanyl]-butyric acid ethyl ester 4-(4-Bromo-2-fluoro-phenylsulfanyl)-butyric acid ethyl ester (0.43 g, 1.36 mmol) obtained in Preparation Example 179, bis(pinacolato)diboron (0.34 g, 1.50 mmol), potassium acetate (0.33 g, 3.4 mmol) and dichloro[1,1'-bis(diphenylphosphino)ferrocene]palladium(II) (0.10 g, 0.14 mmol) were reacted in the same manner as in step A of Preparation Example 1 to obtain the title compound (0.27 g, 53%).

$^1$H-NMR (CDCl$_3$) δ 7.50 (1H, d), 7.43 (1H, d), 7.32 (1H, t), 4.11 (2H, q), 2.98 (2H, t), 2.45 (2H, t), 1.93 (2H, m), 1.33 (12H, s), 1.24 (3H, t).

Preparation Example 181

2-cyclobutoxy-6-(3,4,5-trifluoro-phenyl)-pyridine 4,4,5,5-Tetramethyl-2-(3,4,5-trifluoro-phenyl)-[1,3,2]dioxaborolane (0.050 g, 0.19 mmol) obtained in Preparation Example 165, 2-bromo-6-(cyclobutoxy)-pyridine (0.044 g, 0.19 mmol) obtained in Preparation Example 230, 2M Na$_2$CO$_3$ aqueous solution (0.3 mL) and Pd(PPh$_3$)$_4$ (0.011 g, 0.01 mmol) were reacted in the same manner as in Preparation Example 13 to obtain the title compound (0.03 g, 49%).

$^1$H-NMR (CDCl$_3$) δ 7.64 (3H, m), 7.22 (1H, d), 6.67 (1H, d), 5.25 (1H, m), 2.52 (2H, m), 2.19 (2H, m), 1.87 (1H, m), 1.76 (1H, m).

Preparation Example 182

2-cyclopentyloxy-6-(3,4,5-trifluoro-phenyl)-pyridine 4,4,5,5-Tetramethyl-2-(3,4,5-trifluoro-phenyl)-[1,3,2]dioxaborolane (0.050 g, 0.19 mmol) obtained in Preparation Example 165, 2-bromo-6-(cyclopentoxy)pyridine (0.047 g, 0.19 mmol) obtained in Preparation Example 231, 2M Na$_2$CO$_3$ aqueous solution (0.3 mL) and Pd(PPh$_3$)$_4$ (0.011 g, 0.01 mmol) were reacted in the same manner as in Preparation Example 13 to obtain the title compound (0.035 g, 62%).

$^1$H-NMR (CDCl$_3$) δ 7.67-7.59 (3H, m), 7.19 (1H, d), 6.67 (1H, d), 5.49 (1H, m), 2.03 (2H, m), 1.85 (4H, m), 1.65 (2H, m).

Preparation Example 183

2-cyclopropylmethoxy-6-(3,4,5-trifluoro-phenyl)-pyridine 4,4,5,5-Tetramethyl-2-(3,4,5-trifluoro-phenyl)-[1,3,2]dioxaborolane (0.04 g, 0.15 mmol) obtained in Preparation Example 165, 2-bromo-6-(cyclopropylmethoxy)-pyridine (0.035 g, 0.15 mmol) obtained in Preparation Example 232, 2M Na$_2$CO$_3$ aqueous solution (0.2 mL) and Pd(PPh$_3$)$_4$ (0.01 g, 0.01 mmol) were reacted in the same manner as in Preparation Example 13 to obtain the title compound (0.034 g, 80%).

$^1$H-NMR (CDCl$_3$) δ 7.64 (3H, m), 7.24 (1H, d), 6.74 (1H, d), 4.23 (2H, d), 1.33 (1H, m), 0.64 (2H, m), 0.39 (2H, m).

Preparation Example 184

2-cyclobutylsulfanyl-6-(3,4,5-trifluoro-phenyl)-pyridine 4,4,5,5-Tetramethyl-2-(3,4,5-trifluoro-phenyl)-[1,3,2]dioxaborolane (0.050 g, 0.19 mmol) obtained in Preparation Example 165, 2-bromo-6-cyclobutylsulfanyl-pyridine (0.047 g, 0.19 mmol) obtained in Preparation Example 233, 2M Na$_2$CO$_3$ aqueous solution (0.3 mL) and Pd(PPh$_3$)$_4$ (0.011 g, 0.01 mmol) were reacted in the same manner as in Preparation Example 13 to obtain the title compound (0.03 g, 52%).

$^1$H-NMR (CDCl$_3$) δ 7.66 (2H, m), 7.53 (1H, t), 7.29 (1H, d), 7.06 (1H, d), 4.41 (1H, m), 2.60 (2H, m), 2.20-2.10 (4H, m).

Preparation Example 185

2-cyclopentylsulfanyl-6-(3,4,5-trifluoro-phenyl)-pyridine 4,4,5,5-Tetramethyl-2-(3,4,5-trifluoro-phenyl)-[1,3,2]dioxaborolane (0.050 g, 0.19 mmol) obtained in Preparation Example 165, 2-bromo-6-cyclopentylsulfanyl-pyridine (0.050 g, 0.19 mmol) obtained in Preparation Example 234, 2M Na$_2$CO$_3$ aqueous solution (0.3 mL) and Pd(PPh$_3$)$_4$ (0.011 g, 0.01 mmol) were reacted in the same manner as in Preparation Example 13 to obtain the title compound (0.042 g, 71%).

$^1$H-NMR (CDCl$_3$) δ 7.66 (2H, m), 7.52 (1H, t), 7.27 (1H, d), 7.11 (1H, d), 4.13 (1H, m), 2.22 (2H, m), 1.80-1.63 (6H, m).

Preparation Example 186

4-(2'-hydroxy-5'-methyl-biphenyl-4-ylsulfanyl)-butyric acid ethyl ester

4-[4-(4,4,5,5-Tetramethyl-[1,3,2]dioxaborolan-2-yl)-phenylsulfanyl]-butyric acid ethyl ester (0.1 g, 0.28 mmol) obtained in Preparation Example 159 and 2-bromo-4-methyl-phenol (0.038 ml, 0.31 mmol) were reacted in the same manner as in Preparation Example 13 to obtain the title compound (0.02 g, 21%).

$^1$H-NMR (CDCl$_3$) δ 7.47 (2H, d), 7.39 (2H, d), 7.02 (2H, m), 6.86 (1H, d), 5.00 (1H, s), 4.12 (2H, q), 3.00 (2H, t), 2.47 (2H, t), 2.30 (3H, s), 1.99 (2H, m), 1.25 (3H, t).

Preparation Example 187

4-(2'-cyclopentyloxy-5'-methyl-biphenyl-4-ylsulfanyl)-butyric acid ethyl ester 4-(2'-Hydroxy-5'-methyl-biphenyl-4-ylsulfanyl)-butyric acid ethyl ester (0.02 g, 0.06 mmol) obtained in Preparation Example 186, bromo-cyclopentane (0.01 mL) and Cs$_2$CO$_3$ (0.06 g, 0.18 mmol) were reacted in the same manner as in step B of Preparation Example 44 to obtain the title compound (0.02 g, 83%).

$^1$H-NMR (CDCl$_3$) δ 7.45 (2H, d), 7.32 (2H, d), 7.10 (1H, s), 7.04 (1H, m), 6.85 (1H, d), 4.67 (1H, m), 4.12 (2H, q), 3.00 (2H, t), 2.48 (2H, t), 2.31 (3H, s), 1.98 (2H, m), 1.78 (4H, m), 1.64-1.53 (4H, m), 1.25 (3H, t).

Preparation Example 188

2-[4-(4,4,5,5-tetramethyl-[1,3,2]dioxaborolan-2-yl)-phenylsulfanyl]-propionic acid methyl ester Step A: 2-(4-bromo-phenylsulfanyl)-propionic acid methyl ester 4-Bromo-benzenethiol (0.5 g, 2.64 mmol), NaH (60% in mineral oil, 0.11 g, 2.64 mmol) and methyl 2-bromopropionate (0.32 mL, 2.91 mmol) were reacted in the same manner as in Preparation Example 12 to obtain the title compound (0.58 g, 80%).

$^1$H-NMR (CDCl$_3$) δ 7.43 (2H, d), 7.30 (2H, d), 3.76 (1H, q), 3.66 (3H, s), 1.47 (3H, d).

Step B: 2-[4-(4,4,5,5-tetramethyl-[1,3,2]dioxaborolan-2-yl)-phenylsulfanyl]-propionic acid methyl ester 2-(4-Bromo-phenylsulfanyl)-propionic acid methyl ester (0.62 g, 2.2 mmol) obtained in step A, bis(pinacolato)diboron (0.63 g, 2.4 mmol), potassium acetate (0.55 g, 5.6 mmol) and dichloro[1,1'-bis(diphenylphosphino)ferrocene]palladium(II) (0.16 g, 0.22 mmol) were reacted in the same manner as in step A of Preparation Example 1 to obtain the title compound (0.30 g, 42%).

$^1$H-NMR (CDCl$_3$) δ 7.72 (2H, d), 7.40 (2H, d), 3.88 (1H, q), 3.67 (3H, s), 1.51 (3H, d), 1.33 (12H, s).

Preparation Example 189

2-[4-(2-cyclopentyloxy-pyridin-3-yl)-phenylsulfanyl]-propionic acid methyl ester 2-[4-(4,4,5,5-Tetramethyl-[1,3,2]dioxaborolan-2-yl)-phenylsulfanyl]-propionic acid methyl ester (0.15 g, 0.46 mmol) obtained in Preparation Example 188 and 2-cyclopentoxy-3-iodo-pyridine (0.16 g, 0.56 mmol) obtained in Preparation Example 38 were reacted in the same manner as in Preparation Example 13 to obtain the title compound (0.045 g, 27%).

$^1$H-NMR (CDCl$_3$) δ 8.13 (1H, m), 7.59 (1H, m), 7.50 (2H, d), 7.46 (2H, d), 6.91 (1H, m), 5.50 (1H, m), 3.88 (1H, m), 3.68 (3H, s), 1.93 (2H, m), 1.82-1.58 (6H, m), 1.53 (3H, d)

Preparation Example 190

(E)-4-[4-(2-cyclopentyloxy-pyridin-3-yl)-phenylsulfanyl]-pent-2-enoic acid ethyl ester After 2-[4-(2-cyclopentyloxy-pyridin-3-yl)-phenylsulfanyl]-propionic acid methyl ester (0.07 g, 0.19 mmol) obtained in Preparation Example 189 was dissolved in DCM (1 mL), DIBAL-H (1.5M toluene, 0.15 mL, 0.21 mol) was added thereto at −78° C. Then, a solution prepared by dissolving NaH (60% in mineral oil, 0.009 g, 0.23 mmol) and triethyl phosphonoacetate (0.053 g, 0.23 mmol) in DCM (1 mL) with stirring for 30 minutes was added thereto, and the mixture was agitated at room temperature for 18 hours. The reactant was added with potassium sodium tartrate aqueous solution and then extracted with DCM. The organic layer was separated and dried with MgSO$_4$, and was purified by column chromatography to obtain the title compound (0.023 g, 29%).

$^1$H-NMR (CDCl$_3$) δ 8.13 (1H, m), 7.59 (1H, m), 7.49 (2H, d), 7.40 (2H, d), 6.90 (2H, m), 5.64 (1H, d), 5.50 (1H, m), 4.16 (2H, m), 3.85 (1H, m), 1.93 (2H, m), 1.82-1.58 (6H, m), 1.46 (3H, d), 1.24 (3H, t).

Preparation Example 191

4-[4-(2-cyclopentyloxy-pyridin-3-yl)-phenylsulfanyl]-pentanoic acid ethyl ester

After (E)-4-[4-(2-cyclopentyloxy-pyridin-3-yl)-phenylsulfanyl]-pent-2-enoic acid ethyl ester (0.023 g, 0.06 mmol) obtained in Preparation Example 190 was dissolved in ethanol (0.8 mL) and THF (0.3 mL), cobalt(II) chloride 6 hydrate (0.016 g, 0.07 mmol) was added thereto. Then, NaBH$_4$ (0.005 g, 0.14 mol) was added thereto at 0° C., the mixture was agitated at room temperature for 4 hours. The reactant was added with water and then extracted with Et$_2$O. The organic layer was separated and dried with MgSO$_4$, and was purified by column chromatography to obtain the title compound (0.01 g, 43%).

$^1$H-NMR (CDCl$_3$) δ 8.13 (1H, m), 7.59 (1H, m), 7.49 (2H, d), 7.40 (2H, d), 6.91 (1H, m), 5.51 (1H, m), 4.14 (2H, q), 3.30 (1H, m), 2.53 (2H, m), 1.93 (4H, m), 1.81-1.60 (6H, m), 1.35 (3H, d), 1.24 (3H, t).

Preparation Example 192

2-[4-(2-isopropoxy-pyridin-3-yl)-phenylsulfanyl]-propionic acid methyl ester 2-[4-(4,4,5,5-Tetramethyl-[1,3,2]dioxaborolan-2-yl)-phenylsulfanyl]-propionic acid methyl ester (0.15 g, 0.46 mmol) obtained in Preparation Example 188 and 3-iodo-2-isopropoxy-pyridine (0.15 g, 0.56 mmol) obtained in Preparation Example 37 were reacted in the same manner as in Preparation Example 13 to obtain the title compound (0.043 g, 27%).

$^1$H-NMR (CDCl$_3$) δ 8.12 (1H, m), 7.57 (1H, m), 7.53 (2H, d), 7.47 (2H, d), 6.91 (1H, m), 5.39 (1H, m), 3.83 (1H, m), 3.69 (3H, s), 1.55 (3H, d), 1.33 (6H, d)

Preparation Example 193

(E)-4-[4-(2-isopropoxy-pyridin-3-yl)-phenylsulfanyl]-pent-2-enoic acid ehtyl ester 2-[4-(2-Isopropoxy-pyridin-3-yl)-phenylsulfanyl]-propionic acid methyl ester (0.054 g, 0.16 mmol) obtained in Preparation Example 192, DIBAL-H (1.5M toluene, 0.12 mL, 0.18 mol), NaH (60% in mineral oil, 0.008 g, 0.19 mmol) and triethyl phosphonoacetate (0.044 g, 0.19 mmol) were reacted in the same manner as in Preparation Example 190 to obtain the title compound (0.025 g, 41%).

$^1$H-NMR (CDCl$_3$) δ 8.12 (1H, m), 7.59 (1H, m), 7.52 (2H, d), 7.42 (2H, d), 6.92 (2H, m), 5.67 (1H, d), 5.39 (1H, m), 4.18 (2H, q), 3.85 (1H, m), 1.46 (3H, d), 1.34 (6H, d), 1.25 (3H, t).

Preparation Example 194

2-(4-bromo-2,6-difluoro-phenylsulfanyl)-propionic acid methyl ester

4-Bromo-2,6-difluoro-benzenethiol (0.45 g, 2.0 mmol) obtained in Preparation Example 168, NaH (60% in mineral oil, 0.08 g, 2.0 mmol) and methyl 2-bromopropionate (0.24 mL, 2.2 mmol) were reacted in the same manner as in Preparation Example 12 to obtain the title compound (0.52 g, 83%).

$^1$H-NMR (CDCl$_3$) δ 7.14 (2H, d), 3.72 (1H, q), 3.69 (3H, s), 1.45 (3H, d).

Preparation Example 195

2-[2,6-difluoro-4-(4,4,5,5-tetramethyl-[1,3,2]dioxaborolan-2-yl)-phenylsulfanyl]-propionic acid methyl ester 2-(4-Bromo-2,6-difluoro-phenylsulfanyl)-propionic acid methyl ester (0.52 g, 1.67 mmol) obtained in Preparation Example 194, bis(pinacolato)diboron (0.47 g, 1.84 mmol), potassium acetate (0.41 g, 4.18 mmol) and dichloro[1,1'-bis(diphenylphosphino)ferrocene]palladium(II) (0.12 g, 0.17 mmol) were reacted in the same manner as in step A of Preparation Example 1 to obtain the title compound (0.27 g, 45%).

$^1$H-NMR (CDCl$_3$) δ 7.32 (2H, d), 3.80 (1H, q), 3.64 (3H, s), 1.46 (3H, d), 1.33 (12H, s).

Preparation Example 196

2-[4-(2-cyclopentyloxy-pyridin-3-yl)-2,6-difluoro-phenylsulfanyl]-propionic acid methyl ester 2-[2,6-Difluoro-4-(4,4,5,5-tetramethyl-[1,3,2]dioxaborolan-2-yl)-phenylsulfanyl]-propionic acid methyl ester (0.1 g, 0.28 mmol) obtained in Preparation Example 195 and 2-cyclopentoxy-3-iodo-pyridine (0.12 g, 0.42 mmol) obtained in Preparation Example 38 were reacted in the same manner as in Preparation Example 13 to obtain the title compound (0.052 g, 47%).

$^1$H-NMR (CDCl$_3$) δ 8.18 (1H, m), 7.62 (1H, m), 7.22 (2H, d), 6.95 (1H, m), 5.54 (1H, m), 3.80 (1H, m), 3.66 (3H, s), 1.95 (2H, m), 1.82-1.63 (6H, m), 1.48 (3H, d).

Preparation Example 197

(E)-4-[4-(2-cyclopentyloxy-pyridin-3-yl)-2,6-difluoro-phenylsulfanyl]-pent-2-enoic acid ethyl ester 2-[4-(2-Cyclopentyloxy-pyridin-3-yl)-2,6-difluoro-phenylsulfanyl]-propionic acid methyl ester (0.052 g, 0.13 mmol) obtained in Preparation Example 196, DIBAL-H (1.5M toluene, 0.10 mL, 0.14 mol), NaH (60% in mineral oil, 0.006 g, 0.16 mmol) and triethyl phosphonoacetate (0.035 g, 0.16 mmol) were reacted in the same manner as in Preparation Example 190 to obtain the title compound (0.041 g, 71%).

$^1$H-NMR (CDCl$_3$) δ 8.18 (1H, m), 7.61 (1H, m), 7.19 (2H, d), 6.95 (1H, m), 6.85 (1H, m), 5.60 (1H, d), 5.52 (1H, m), 4.14 (2H, m), 3.95 (1H, m), 1.95 (2H, m), 1.81-1.64 (6H, m), 1.48 (3H, d), 1.24 (3H, t).

Preparation Example 198

2-[4-(2-cyclopentylsulfanyl-pyridin-3-yl)-2,6-difluoro-phenylsulfanyl]-propionic acid methyl ester 2-[2,6-Difluoro-4-(4,4,5,5-tetramethyl-[1,3,2]dioxaborolan-2-yl)-phenylsulfanyl]-propionic acid methyl ester (0.1 g, 0.28 mmol) obtained in Preparation Example 195 and 2-cyclopentylsulfanyl-3-iodo-pyridine (0.13 g, 0.42 mmol) obtained in Preparation Example 39 were reacted in the same manner as in Preparation Example 13 to obtain the title compound (0.064 g, 56%).

$^1$H-NMR (CDCl$_3$) δ 8.46 (1H, m), 7.36 (1H, m), 7.07 (3H, m), 4.10 (1H, m), 3.83 (1H, m), 3.69 (3H, s), 2.19 (2H, m), 1.72-1.55 (6H, m), 1.54 (3H, d).

Preparation Example 199

(E)-4-[4-(2-cyclopentylsulfanyl-pyridin-3-yl)-2,6-difluoro-phenylsulfanyl]-pent-2-enoic acid ethyl ester 2-[4-(2-Cyclopentylsulfanyl-pyridin-3-yl)-2,6-difluoro-phenylsulfanyl]-propionic acid methyl ester (0.064 g, 0.15 mmol) obtained in Preparation Example 196, DIBAL-H (1.5M toluene, 0.11 ml, 0.17 mol), NaH (60% in mineral oil, 0.008 g, 0.19 mmol) and triethyl phosphonoacetate (0.042 g, 0.19 mmol) were reacted in the same manner as in Preparation Example 190 to obtain the title compound (0.039 g, 55%).

¹H-NMR (CDCl₃) δ 8.45 (1H, m), 7.33 (1H, m), 7.04 (3H, m), 6.81 (1H, m), 5.60 (1H, d), 4.15 (3H, m), 3.95 (1H, m), 2.19 (2H, m), 1.72-1.51 (6H, m), 1.47 (3H, d), 1.25 (3H, t).

Preparation Example 200

2-cyclobutoxy-3-iodo-pyridine

Cyclobutanol (0.064 g, 1.34 mmol) and 2-fluoro-3-iodo-pyridine (0.2 g, 0.89 mmol) were reacted in the same manner as in Preparation Example 37 to obtain the title compound (0.16 g, 66%).
¹H-NMR (CDCl₃) δ 8.07 (1H, m), 8.00 (1H, m), 6.61 (1H, m), 5.18 (1H, m), 2.47 (2H, m), 2.20 (2H, m), 1.84 (1H, m), 1.67 (1H, m)

Preparation Example 201

2-bromo-6-isopropylsulfanyl-pyridine

After 2,6-dibromopyridine (0.2 g, 0.84 mmol) and Cs₂CO₃ (0.41 g, 1.27 mmol) were dissolved in DMF (4 mL), propane-2-thiol (0.08 mL, 0.84 mmol) was added thereto, and the mixture was agitated at room temperature for 8 hours. The reactant was added with water and then extracted with EtOAc. The organic layer was separated and dried with MgSO₄, and was purified by column chromatography to obtain the title compound (0.17 g, 89%).
1H NMR (CDCl₃) δ 7.28 (1H, t), 7.11 (1H, d), 7.08 (1H, d), 3.98 (1H, m), 1.41 (6H, d).

Preparation Example 202

3-iodo-2-propoxy-pyridine

Propanol (0.1 mL, 1.34 mmol) and 2-fluoro-3-iodo-pyridine (0.2 g, 0.89 mmol) were reacted in the same manner as in Preparation Example 37 to obtain the title compound (0.11 g, 46%).
¹H-NMR (CDCl₃) δ 8.08 (1H, m), 8.00 (1H, m), 6.61 (1H, m), 4.28 (2H, t), 1.82 (2H, m), 1.04 (3H, t)

Preparation Example 203

3-iodo-2-propylsulfanyl-pyridine

After 2-fluoro-3-iodo-pyridine (2.08 g, 9.3 mmol) and propane-1-thiol (0.89 mL, 9.8 mmol) were added with CH₃CN (31 mL) and Cs₂CO₃ (3.33 g, 10.2 mmol), the mixture was agitated under reflux for 5 hours. The reactant was cooled to room temperature and separated, and the residue was purified by column chromatography to obtain the title compound (1.58 g, 60%).
¹H-NMR (CDCl₃) δ 8.40 (1H, m), 7.92 (1H, m), 6.71 (1H, m), 3.13 (2H, t), 1.75 (2H, m), 1.06 (3H, t)

Preparation Example 204

3-iodo-2-pyrrolidine-1-yl-pyridine

After 2-fluoro-3-iodo-pyridine (0.3 g, 1.34 mmol) was dissolved in DMF (5 mL), TEA (0.19 mL, 1.34 mmol) and pyrrolidine (0.17 mL, 2.02 mmol) were added thereto, and the mixture was agitated at 60° C. for 4 hours. The reactant was added with water and then extracted with EtOAc. The organic layer was separated and dried with MgSO₄, and was purified by column chromatography to obtain the title compound (0.36 g, 98%).
1H NMR (CDCl₃) δ 8.11 (1H, m), 7.97 (1H, m), 6.39 (1H, m), 3.65 (4H, m), 1.92 (4H, m).

Preparation Example 205

3-[(3-iodo-2-pyridyl)oxy]-5-methyl-isoxazole

2-Fluoro-3-iodo-pyridine (0.3 g, 1.34 mmol) and 5-methylisoxazole-3-ol (0.147 g, 1.47 mmol) were reacted in the same manner as in Preparation Example 37 at 80° C. to obtain the title compound (0.15 g, 37%).
¹H-NMR (CDCl₃) δ 8.17 (2H, m), 6.87 (1H, m), 6.03 (1H, s), 2.44 (3H, s)

Preparation Example 206

2-[(3-iodo-2-pyridyl)oxy]-N,N-dimethyl-ethanamine

2-Fluoro-3-iodo-pyridine (0.3 g, 1.34 mmol) and 2-(dimethylamino)ethanol (0.131 g, 1.47 mmol) were reacted in the same manner as in Preparation Example 37 at 80° C. to obtain the title compound (0.29 g, 75%).
¹H-NMR (CDCl₃) δ 8.09 (1H, m), 8.02 (1H, m), 6.64 (1H, m), 4.46 (2H, t), 2.79 (2H, t), 2.38 (6H, s)

Preparation Example 207

2-[2-(aziridine-1-yl)ethoxy]-3-iodo-pyridine

2-Fluoro-3-iodo-pyridine (0.3 g, 1.34 mmol) and 2-(aziridine-1-yl)ethanol (0.117 g, 1.34 mmol) were reacted in the same manner as in Preparation Example 37 at 80° C. to obtain the title compound (0.19 g, 49%).
¹H-NMR (CDCl₃) δ 8.09 (1H, m), 8.02 (1H, m), 6.64 (1H, m), 4.52 (2H, t), 2.65 (2H, t), 1.82 (2H, m), 1.35 (2H, m)

Preparation Example 208

2-(3-furylmethoxy)-3-iodo-pyridine

2-Fluoro-3-iodo-pyridine (0.3 g, 1.34 mmol) and 3-furylmethanol (0.132 g, 1.34 mmol) were reacted in the same manner as in Preparation Example 37 at 80° C. to obtain the title compound (0.36 g, 89%).
¹H-NMR (CDCl₃) δ 8.12 (1H, m), 8.04 (1H, m), 7.56 (1H, s), 7.41 (1H, s), 6.65 (1H, m), 6.53 (1H, m), 5.30 (2H, s)

Preparation Example 209

2-(2-furylmethoxy)-3-iodo-pyridine

2-Fluoro-3-iodo-pyridine (0.3 g, 1.34 mmol) and 2-furylmethanol (0.132 g, 1.34 mmol) were reacted in the same manner as in Preparation Example 37 at 80° C. to obtain the title compound (0.334 g, 83%).
¹H-NMR (CDCl₃) δ 8.12 (1H, m), 8.03 (1H, m), 7.44 (1H, m), 6.67 (1H, m), 6.47 (1H, m), 6.37 (1H, m), 5.38 (2H, s)

Preparation Example 210

3-iodo-2-[(3-methyloxetane-3-yl)methoxy]pyridine

2-Fluoro-3-iodo-pyridine (0.3 g, 1.34 mmol) and (3-methyloxetane-3-yl)methanol (0.137 g, 1.34 mmol) were reacted in the same manner as in Preparation Example 37 at 80° C. to obtain the title compound (0.30 g, 74%).

¹H-NMR (CDCl₃) δ 8.11 (1H, m), 8.04 (1H, m), 6.67 (1H, m), 4.68 (2H, d), 4.46 (2H, d), 4.40 (2H, s), 1.48 (3H, s)

Preparation Example 211

3-iodo-2-(tetrahydrofuran-3-ylmethoxy)pyridine

2-Fluoro-3-iodo-pyridine (0.3 g, 1.34 mmol) and tetrahydrofuran-3-ylmethanol (0.137 g, 1.34 mmol) were reacted in the same manner as in Preparation Example 37 at 80° C. to obtain the title compound (0.30 g, 74%).

¹H-NMR (CDCl₃) δ 8.08 (1H, m), 8.02 (1H, m), 6.65 (1H, m), 4.34 (1H, m), 4.24 (1H, m), 3.94 (2H, m), 3.80 (1H, m), 3.73 (1H, m), 2.78 (1H, m), 2.11 (1H, m), 1.80 (1H, m)

Preparation Example 212

3-iodo-2-(tetrahydrofuran-2-ylmethoxy)pyridine

2-Fluoro-3-iodo-pyridine (0.3 g, 1.34 mmol) and tetrahydrofuran-2-ylmethanol (0.137 g, 1.34 mmol) were reacted in the same manner as in Preparation Example 37 at 80° C. to obtain the title compound (0.31 g, 76%).

¹H-NMR (CDCl₃) δ 8.08 (1H, m), 8.01 (1H, m), 6.63 (1H, m), 4.34 (3H, m), 3.99 (1H, m), 3.86 (1H, m), 2.08 (2H, m), 1.92 (2H, m)

Preparation Example 213

2-[3-(tert-butyl-dimethyl-silanyloxy)-cyclopentyloxy]-3-iodo-pyridine 3-(tert-butyl-dimethyl-silanyloxy)-cyclopentanol (0.44 g, 2.02 mmol) and 2-fluoro-3-iodo-pyridine (0.30 g, 1.35 mmol) were reacted in the same manner as in Preparation Example 37 to obtain the title compound (0.39 g, 69%).

¹H-NMR (CDCl₃) δ 8.08 (1H, m), 7.99 (1H, m), 6.60 (1H, m), 5.49 (1H, m), 4.49 (1H, m), 2.23 (1H, m), 2.04 (3H, m), 1.80 (1H, m), 1.62 (1H, m), 0.88 (9H, s), 0.06 (6H, s)

Preparation Example 214

2-[4-(2-fluoro-pyridin-3-yl)-phenylsulfanyl]-propionic acid methyl ester

2-[4-(4,4,5,5-Tetramethyl-[1,3,2]dioxaborolan-2-yl)-phenylsulfanyl]-propionic acid methyl ester (0.52 g, 1.62 mmol) obtained in Preparation Example 188 and 2-fluoro-3-iodo-pyridine (0.54 g, 2.43 mmol) were reacted in the same manner as in Preparation Example 13 to obtain the title compound (0.27 g, 57%).

¹H-NMR (CDCl₃) δ 8.20 (1H, m), 7.87 (1H, m), 7.55 (4H, m), 7.30 (1H, m), 3.88 (1H, m), 3.71 (3H, s), 1.53 (3H, d).

Preparation Example 215

(E)-4-[4-(2-fluoro-pyridin-3-yl)-phenylsulfanyl]-pent-2-enoic acid ethyl ester

2-[4-(2-Fluoro-pyridin-3-yl)-phenylsulfanyl]-propionic acid methyl ester (0.27 g, 0.92 mmol) obtained in Preparation Example 214 was reacted in the same manner as in Preparation Example 190 to obtain the title compound (0.17 g, 54%).

¹H-NMR (CDCl₃) δ 8.20 (1H, m), 7.85 (1H, m), 7.52 (4H, m), 7.27 (1H, m), 6.88 (1H, q), 5.65 (1H, d), 4.16 (2H, q), 3.86 (1H, m), 1.46 (3H, d), 1.25 (3H, t).

Preparation Example 216

4-[4-(2-fluoro-pyridin-3-yl)-phenylsulfanyl]-pentanoic acid ethyl ester

After (E)-4-[4-(2-fluoro-pyridin-3-yl)-phenylsulfanyl]-pent-2-enoic acid ethyl ester (0.17 g, 0.5 mmol) obtained in Preparation Example 215 was dissolved in 1,2-dimethoxyethane (5 mL), p-toluenesulfonhydrazide (0.65 g, 3.51 mmol) was added thereto, and the mixture was agitated under reflux for 5 minutes. Then, a 1.4M NaOAc aqueous solution (3.6 mL) was added thereto, and the mixture was agitated under reflux for 18 hours. The reactant was diluted with water and then extracted with DCM. The organic layer was separated and dried with MgSO₄, and was purified by column chromatography to obtain the title compound (0.1 g, 59%).

¹H-NMR (CDCl₃) δ 8.20 (1H, m), 7.87 (1H, m), 7.53-7.44 (4H, m), 7.28 (1H, m), 4.14 (2H, q), 3.35 (1H, m), 2.54 (2H, t), 1.94 (2H, m), 1.32 (3H, d), 1.26 (3H, t).

Preparation Example 217

4-[4-(2-cyclopentylsulfanyl-pyridin-3-yl)-phenylsulfanyl]-pentanoic acid ethyl ester 4-[4-(2-Fluoro-pyridin-3-yl)-phenylsulfanyl]-pentanoic acid ethyl ester (0.03 g, 0.09 mmol) obtained in Preparation Example 216, cyclopentyl thiol (0.01 mL, 0.09 mmol) and Cs₂CO₃ (0.044 g, 0.13 mmol) were reacted in the same manner as in step B of Preparation Example 44 to obtain the title compound (0.004 g, 10%).

¹H-NMR (CDCl₃) δ 8.40 (1H, m), 7.41 (2H, d), 7.35 (3H, m), 7.02 (1H, m), 4.13 (2H, q), 3.30 (1H, m), 2.52 (2H, m), 2.17 (2H, m), 1.92 (2H, m), 1.71-1.48 (6H, m), 1.34 (3H, d), 1.26 (3H, t).

Preparation Example 218

2-[2,6-difluoro-4-(2-isopropoxy-pyridin-3-yl)-phenylsulfanyl]-propionic acid methyl ester 2-[4-(4,4,5,5-Tetramethyl-[1,3,2]dioxaborolan-2-yl)-phenylsulfanyl]-propionic acid methyl ester (0.07 g, 0.19 mmol) obtained in Preparation Example 188 and 3-iodo-2-isopropoxy-pyridine (0.077 g, 0.29 mmol) obtained in Preparation Example 37 were reacted in the same manner as in Preparation Example 13 to obtain the title compound (0.05 g, 71%).

¹H-NMR (CDCl₃) δ 8.15 (1H, m), 7.60 (1H, m), 7.21 (2H, d), 6.93 (1H, m), 5.42 (1H, m), 3.77 (1H, m), 3.67 (3H, s), 1.50 (3H, d), 1.35 (6H, d).

Preparation Example 219

4-[2,6-difluoro-4-(2-isopropoxy-pyridin-3-yl)-phenylsulfanyl]-pentanoic acid ethyl ester 2-[2,6-Difluoro-4-(2-isopropoxy-pyridin-3-yl)-phenylsulfanyl]-propionic acid methyl ester (0.05 g, 0.14 mmol) obtained in Preparation Example 218 was reacted in the same manner as in Preparation Example 190 and Preparation Example 191 in turn to obtain the title compound (0.015 g, 26%).

$^1$H-NMR (CDCl$_3$) δ 8.21 (1H, m), 7.65 (1H, m), 7.24 (2H, d), 6.97 (1H, m), 5.46 (1H, m), 4.17 (2H, q), 3.36 (1H, m), 2.60 (2H, m), 1.93 (2H, m), 1.40 (6H, d), 1.34 (3H, d), 1.27 (3H, t).

Preparation Example 220

3-iodo-2-(2,2,2-trifluoro-ethoxy)-pyridine 2,2,2-Trifluoroethanol (0.098 mL, 1.34 mmol) and 2-fluoro-3-iodo-pyridine (0.2 g, 0.89 mmol) were reacted in the same manner as in Preparation Example 37 to obtain the title compound (0.22 g, 81%).

$^1$H-NMR (CDCl$_3$) δ 8.08 (2H, m), 6.74 (1H, m), 4.78 (2H, m).

Preparation Example 221

5-(4-bromo-2,6-difluoro-phenylsulfanyl)-pentanoic acid ethyl ester

4-Bromo-2,6-difluoro-benzenethiol (0.5 g, 2.22 mmol) obtained in Preparation Example 168, NaH (60% in mineral oil, 0.1 g, 2.44 mmol) and ethyl 5-bromopentanoate (0.387 mL, 2.44 mmol) were reacted in the same manner as in Preparation Example 12 to obtain the title compound (0.7 g, 89%).

$^1$H-NMR (CDCl$_3$) δ 7.10 (2H, d), 4.10 (2H, q), 2.84 (2H, t), 2.27 (2H, t), 1.72 (2H, m), 1.56 (2H, m), 1.23 (3H, t).

Preparation Example 222

5-[2,6-difluoro-4-(4,4,5,5-tetramethyl-[1,3,2]dioxaborolan-2-yl)-phenylsulfanyl]-pentanoic acid ethyl ester 5-(4-Bromo-2,6-difluoro-phenylsulfanyl)-pentanoic acid ethyl ester (0.7 g, 1.99 mmol) obtained in Preparation Example 221, bis(pinacolato)diboron (0.56 g, 2.19 mmol), potassium acetate (0.49 g, 4.99 mmol) and dichloro[1,1'-bis(diphenylphosphino)ferrocene]palladium(II) (0.15 g, 0.20 mmol) were reacted in the same manner as in step A of Preparation Example 1 to obtain the title compound (0.42 g, 53%).

$^1$H-NMR (CDCl$_3$) δ 7.30 (2H, d), 4.08 (2H, q), 2.90 (2H, t), 2.26 (2H, t), 1.72 (2H, m), 1.54 (2H, m), 1.32 (12H, s), 1.23 (3H, t).

Preparation Example 223

5-(4-bromo-phenylsulfanyl)-pentanoic acid ethyl ester

4-Bromo-benzenethiol (0.5 g, 2.64 mmol), NaH (60% in mineral oil, 0.12 g, 2.91 mmol) and ethyl 5-bromopentanoate (0.46 mL, 2.91 mmol) were reacted in the same manner as in Preparation Example 12 to obtain the title compound (0.78 g, 93%).

$^1$H-NMR (CDCl$_3$) δ 7.38 (2H, d), 7.16 (2H, d), 4.11 (2H, q), 2.88 (2H, t), 2.30 (2H, t), 1.75 (2H, m), 1.65 (2H, m), 1.23 (3H, t).

Preparation Example 224

5-[4-(4,4,5,5-tetramethyl-[1,3,2]dioxaborolan-2-yl)-phenylsulfanyl]-pentanoic acid ethyl ester 5-(4-Bromo-phenylsulfanyl)-pentanoic acid ethyl ester (0.78 g, 2.46 mmol) obtained in Preparation Example 223, bis(pinacolato)diboron (0.69 g, 2.70 mmol), potassium acetate (0.6 g, 6.15 mmol) and dichloro[1,1'-bis(diphenylphosphino)ferrocene]palladium(II) (0.18 g, 0.25 mmol) were reacted in the same manner as in step A of Preparation Example 1 to obtain the title compound (0.73 g, 81%).

$^1$H-NMR (CDCl$_3$) δ 7.68 (2H, d), 7.25 (2H, d), 4.10 (2H, q), 2.94 (2H, t), 2.30 (2H, t), 1.75 (2H, m), 1.68 (2H, m), 1.32 (12H, s), 1.22 (3H, t).

Preparation Example 225

Ethyl 5-[2,6-difluoro-4-(4,4,5,5-tetramethyl-1,3,2-dioxaborolan-2-yl)phenoxy]pentanoate After 2,6-difluoro-4-(4,4,5,5-tetramethyl-1,3,2-dioxaborolan-2-yl)phenol (2.23 g, 8.7 mmol) obtained in step B of Preparation Example 2, ethyl 5-bromopentanoate (1.82 g, 8.7 mmol) and Cs$_2$CO$_3$ (5.67 g, 17.4 mmol) were added with CH$_3$CN (29 mL), the mixture was agitated under reflux for 2 hours. The reactant was separated and the residue was purified by column chromatography to obtain the title compound (2.40 g, 72%).

$^1$H-NMR (CDCl$_3$) δ 7.30 (2H, m), 4.18 (2H, t), 4.13 (2H, q), 2.37 (2H, t), 1.81 (4H, m), 1.32 (12H, s), 1.25 (3H, t)

Preparation Example 226

3-iodo-2-isopropylsulfanyl-pyridine

2-Fluoro-3-iodo-pyridine (0.3 g, 1.34 mmol), Cs$_2$CO$_3$ (0.66 g, 1.34 mmol) and propane-2-thiol (0.125 mL, 1.34 mmol) were reacted in the same manner as in Preparation Example 201 to obtain the title compound (0.21 g, 56%).

$^1$H-NMR (CDCl$_3$) δ 8.40 (1H, m), 7.92 (1H, m), 6.69 (1H, m), 3.95 (1H, m), 1.39 (6H, d)

Preparation Example 227

2-bromo-6-propoxy-pyridine

Propanol (0.07 mL, 0.92 mmol) and 2,6-dibromopyridine (0.2 g, 0.84 mmol) were reacted in the same manner as in Preparation Example 37 to obtain the title compound (0.067 g, 36%).

$^1$H-NMR (CDCl$_3$) δ 7.39 (1H, t), 7.03 (1H, d), 6.65 (1H, d), 4.23 (2H, t), 1.76 (2H, m), 1.00 (3H, t)

Preparation Example 228

2-bromo-6-isopropoxy-pyridine

Propane-2-ol (0.065 mL, 0.84 mmol) and 2,6-dibromopyridine (0.2 g, 0.84 mmol) were reacted in the same manner as in Preparation Example 37 to obtain the title compound (0.027 g, 14%).

¹H-NMR (CDCl₃) δ 7.37 (1H, t), 7.00 (1H, d), 6.60 (1H, d), 5.27 (1H, m), 1.33 (6H, d)

Preparation Example 229

2-bromo-6-propylsulfanyl-pyridine 2,6-Dibromopyridine (0.2 g, 0.84 mmol), Cs₂CO₃ (0.412 g, 1.27 mmol) and propanethiol (0.076 mL, 0.84 mmol) were reacted in the same manner as in Preparation Example 201 to obtain the title compound (0.184 g, 93%).
¹H-NMR (CDCl₃) δ 7.27 (1H, t), 7.11 (2H, m), 3.13 (2H, t), 1.74 (2H, m), 1.04 (3H, t)

Preparation Example 230

2-bromo-6-(cyclobutoxy)-pyridine

Cyclobutanol (0.06 mL, 0.84 mmol) and 2,6-dibromopyridine (0.2 g, 0.84 mmol) were reacted in the same manner as in Preparation Example 37 to obtain the title compound (0.06 g, 31%).
¹H-NMR (CDCl₃) δ 7.39 (1H, t), 7.01 (1H, d), 6.61 (1H, d), 5.14 (1H, m), 2.45 (2H, m), 2.11 (2H, m), 1.82 (1H, m), 1.65 (1H, m)

Preparation Example 231

2-bromo-6-(cyclopentoxy)pyridine

Cyclopentanol (0.077 mL, 0.84 mmol) and 2,6-dibromopyridine (0.2 g, 0.84 mmol) were reacted in the same manner as in Preparation Example 37 to obtain the title compound (0.09 g, 44%).
¹H-NMR (CDCl₃) δ 7.36 (1H, t), 7.00 (1H, d), 6.60 (1H, d), 5.36 (1H, m), 1.98 (2H, m), 1.77 (4H, m), 1.61 (2H, m)

Preparation Example 232

2-bromo-6-(cyclopropylmethoxy)-pyridine

Cyclopropylmethanol (0.068 mL, 0.84 mmol) and 2,6-dibromopyridine (0.2 g, 0.84 mmol) were reacted in the same manner as in Preparation Example 37 to obtain the title compound (0.1 g, 53%).
¹H-NMR (CDCl₃) δ 7.39 (1H, t), 7.03 (1H, d), 6.70 (1H, d), 4.12 (2H, d), 1.24 (1H, m), 0.59 (2H, m), 0.35 (2H, m)

Preparation Example 233

2-bromo-6-cyclobutylsulfanyl-pyridine

Cyclobutylthiol (0.074 g, 0.84 mmol) and 2,6-dibromopyridine (0.2 g, 0.84 mmol) were reacted in the same manner as in Preparation Example 37 to obtain the title compound (0.047 g, 22%).
¹H-NMR (CDCl₃) δ 7.27 (1H, t), 7.11 (1H, d), 7.00 (1H, d), 4.28 (1H, m), 2.53 (2H, m), 2.08 (4H, m)

Preparation Example 234

2-bromo-6-cyclopentylsulfanyl-pyridine

Cyclopentanethiol (0.09 mL, 0.84 mmol) and 2,6-dibromopyridine (0.2 g, 0.84 mmol) were reacted in the same manner as in Preparation Example 37 to obtain the title compound (0.2 g, 92%).
¹H-NMR (CDCl₃) δ 7.27 (1H, t), 7.12 (1H, d), 7.08 (1H, d), 3.98 (1H, m), 2.21 (2H, m), 1.76 (2H, m), 1.63 (4H, m)

Preparation Example 235

Cyclopropylmethyl-(3-iodo-pyridin-2-yl)-amine

After 2-fluoro-3-iodo-pyridin (0.3 g, 1.34 mmol) was dissolved in DMF (4 mL), cyclopropanemethylamine (0.173 mL, 2.02 mmol) and triethylamine (0.186 mL, 1.34 mmol) were added thereto, and the mixture was agitated at 110° C. for 18 hours. The reactant was concentrated under reduced pressure and purified by column chromatography to obtain the title compound (0.09 g, 24%).
¹H-NMR (CDCl₃) δ 8.05 (1H, d), 7.80 (1H, d), 6.29 (1H, m), 5.01 (1H, brs), 3.26 (2H, t), 1.12 (1H, m), 0.54 (2H, m), 0.27 (2H, m)

Preparation Example 236

6-(4-bromo-2,6-difluoro-phenylsulfanyl)-hexanoic acid ethyl ester

4-Bromo-2,6-difluoro-benzenethiol (0.455 g, 2.02 mmol) obtained in Preparation Example 168, NaH (60% in mineral oil, 0.09 g, 2.22 mmol) and 6-bromo-hexanoic acid ethyl ester (0.496 g, 2.22 mmol) were reacted in the same manner as in Preparation Example 12 to obtain the title compound (0.7 g, 94%).
¹H-NMR (CDCl₃) δ 7.10 (2H, d), 4.11 (2H, q), 2.83 (2H, t), 2.26 (2H, t), 1.60 (2H, m), 1.54 (2H, m), 1.42 (2H, m), 1.23 (3H, t).

Preparation Example 237

6-[2,6-difluoro-4-(4,4,5,5-tetramethyl-[1,3,2]dioxaborolan-2-yl)-phenylsulfanyl]-hexanoic acid ethyl ester 6-(4-Bromo-2,6-difluoro-phenylsulfanyl)-hexanoic acid ethyl ester (0.7 g, 1.91 mmol) obtained in Preparation Example 236, bis(pinacolato)diboron (0.53 g, 2.10 mmol), potassium acetate (0.467 g, 4.76 mmol) and dichloro[1,1'-bis(diphenylphosphino)ferrocene]palladium(II) (0.14 g, 0.19 mmol) were reacted in the same manner as in step A of Preparation Example 1 to obtain the title compound (0.4 g, 50%).
¹H-NMR (CDCl₃) δ 7.28 (2H, d), 4.12 (2H, q), 2.90 (2H, t), 2.28 (2H, t), 1.64-1.55 (4H, m), 1.45 (2H, m), 1.34 (12H, s), 1.24 (3H, t).

Preparation Example 238

2-(3,5-difluoro-4-methoxy-phenyl)-4,4,5,5-tetramethyl-1,3,2-dioxaborolane

5-Bromo-1,3-difluoro-2-methoxy-benzene (1.04 g, 4.66 mmol) was reacted in the same manner as in step B of Preparation Example 2 to obtain the title compound (0.85 g, 68%).
¹H-NMR (CDCl₃) δ 7.32 (2H, m), 4.03 (3H, s), 1.33 (12H, s)

Preparation Example 239

2-cyclopropylsulfanyl-3-iodo-pyridine

2-Fluoro-3-iodo-pyridine (0.1 g, 0.34 mmol), Cs₂CO₃ (0.335 g, 1.03 mmol) and cyclopropane thiol (0.02 mL, 0.51 mmol) were reacted in the same manner as in Preparation Example 39 to obtain the title compound (0.06 g, 63%).

$^1$H-NMR (CDCl$_3$) δ 8.47 (1H, m), 7.90 (1H, m), 6.74 (1H, m), 2.38 (1H, m), 1.10 (2H, m), 0.68 (2H, m)

Preparation Example 240

2-ethylsulfanyl-3-iodo-pyridine

2-Fluoro-3-iodo-pyridine (0.475 g, 2.13 mmol), Cs$_2$CO$_3$ (3.47 g, 10.65 mmol) and ethane thiol (0.239 mL, 3.19 mmol) were reacted in the same manner as in Preparation Example 39 to obtain the title compound (0.512 g, 90%).

$^1$H-NMR (CDCl$_3$) δ 8.40 (1H, m), 7.92 (1H, m), 6.72 (1H, m), 3.16 (2H, q), 1.39 (3H, t)

Preparation Example 241

2-butylsulfanyl-3-iodo-pyridine 2-fluoro-3-iodo-pyridine (0.262 g, 1.17 mmol), Cs$_2$CO$_3$ (1.91 g, 5.87 mmol) and butane thiol (0.189 mL, 1.76 mmol) were reacted in the same manner as in Preparation Example 39 to obtain the title compound (0.228 g, 66%).

$^1$H-NMR (CDCl$_3$) δ 8.40 (1H, m), 7.92 (1H, m), 6.71 (1H, m), 3.15 (2H, t), 1.73 (2H, m), 1.50 (2H, m), 0.95 (3H, t)

Example 1

4-[4-(6-phenoxy-2-pyridyl)phenoxy]butyric acid

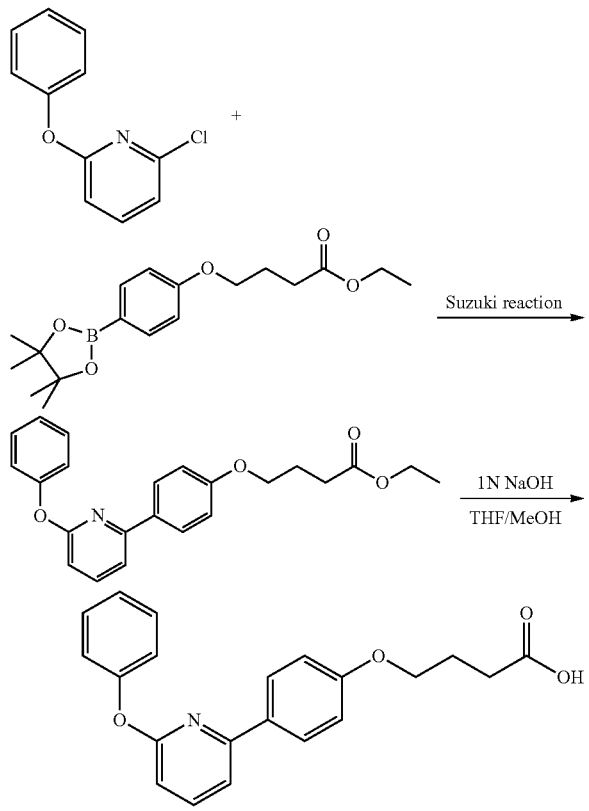

Step A: 4-[4-(6-phenoxy-2-pyridyl)phenoxy]butyric acid ethyl ester

4-[4-(4,4,5,5-Tetramethyl-1,3,2-dioxaborolan-2-yl)phenoxy]butyric acid ethyl ester (0.04 g, 0.12 mmol) obtained in Step B of Preparation Example 1 and 2-chloro-6-phenoxy-pyridine (0.025 g, 0.12 mmol) obtained in Preparation Example 126 were dissolved in 0.2 mL of 2M sodium carbonate aqueous solution and 0.6 mL of 1,4-dioxane, and N$_2$ gas was charged thereto for 5 minutes. Pd(PPh$_3$)$_4$ (0.014 g, 0.012 mmol) was added thereto and the resultant was agitated under reflux for 1 hour. After finishing the reaction, the reaction solution was added with water and extracted with EtOAc to separate the organic layer. The organic layer was dried with MgSO$_4$ and purified by column chromatography to obtain the title compound (0.034 g, 75%).

1H NMR (CDCl$_3$) δ 7.86 (2H, d), 7.68 (1H, t), 7.39 (3H, m), 7.21 (3H, m), 6.90 (2H, d), 6.70 (1H, d), 4.14 (2H, q), 4.04 (2H, t), 2.52 (2H, t), 2.12 (2H, m), 1.26 (3H, t)

Step B: 4-[4-(6-phenoxy-2-pyridyl)phenoxy]butyric acid

4-[4-(6-Phenoxy-2-pyridyl)phenoxy]butyric acid ethyl ester (0.034 g, 0.09 mmol) obtained in Step A was dissolved in each 0.3 mL of THF, MeOH and 1N NaOH aqueous solution, and the resultant was agitated at room temperature for 4 hours. After finishing the reaction, the organic solvent was removed, and the pH was adjusted to 3 by the use of 1N HCl aqueous solution. The precipitate was dried to obtain the title compound (0.019 g, 60%).

1H NMR (CDCl$_3$) δ 7.86 (2H, d), 7.68 (1H, t), 7.39 (3H, m), 7.21 (3H, m), 6.90 (2H, d), 6.70 (1H, d), 4.05 (2H, t), 2.60 (2H, t), 2.14 (2H, m)

Example 2

4-[2,6-difluoro-4-(6-isopropylsulfanyl-2-pyridyl)phenoxy]butyric acid

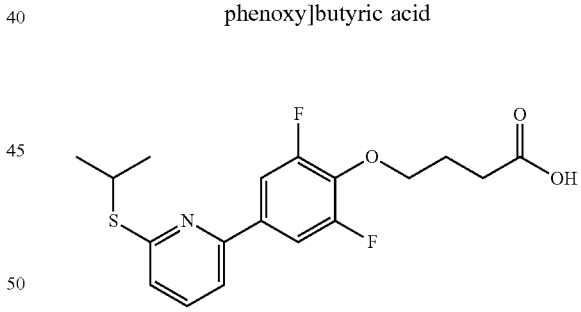

Step A: 4-[2,6-difluoro-4-(6-isopropylsulfanyl-2-pyridyl)phenoxy]butyric acid ethyl ester 4-[2,6-Difluoro-4-(4,4,5,5-tetramethyl-1,3,2-dioxaborolan-2-yl)phenoxy]butyric acid ethyl ester (0.06 g, 0.16 mmol) obtained in Step C of Preparation Example 2 and 2-chloro-6-isopropylsulfanyl-pyridine (0.037 g, 0.2 mmol) obtained in Preparation Example 125 were dissolved in 0.24 mL of 2M Na$_2$CO$_3$ aqueous solution and 1.6 mL of 1,4-dioxane, and N$_2$ gas was charged thereto for 5 minutes. Pd(PPh$_3$)$_4$ (0.018 g, 0.015 mmol) was added thereto and the resultant was agitated under reflux for 16 hours. After finishing the reaction, the resultant was diluted with water, and the organic layer was separated by the extraction with EtOAc. The organic layer was dried with MgSO₄ and purified by column chromatography to obtain the title compound (0.05 g, 78%).

1H NMR (CDCl₃) δ 7.58 (2H, m), 7.52 (1H, t), 7.31 (1H, d), 7.08 (1H, d), 4.23 (2H, m), 4.16 (2H, q), 4.15 (1H, m), 2.58 (2H, t), 2.11 (2H, m), 1.47 (6H, d), 1.27 (3H, t)

Step B: 4-[2,6-difluoro-4-(6-isopropylsulfanyl-2-pyridyl)phenoxy]butyric acid

4-[2,6-Difluoro-4-(6-isopropylsulfanyl-2-pyridyl)phenoxy]butyric acid ethyl ester (50 mg, 0.12 mmol) obtained in Step A was dissolved in each 0.4 mL of 1N NaOH, THF and EtOH, and the resultant was agitated at room temperature for 2 hours. After finishing the reaction, the organic solvent was removed, and the pH was adjusted to 3 by the use of 1N HCl. The organic layer was separated and purified by column chromatography to obtain the title compound (0.04 g, 85%).

1H NMR (CDCl₃) δ 7.60 (2H, m), 7.52 (1H, t), 7.31 (1H, d), 7.09 (1H, d), 4.25 (2H, m), 4.13 (1H, m), 2.67 (2H, t), 2.12 (2H, m), 1.47 (6H, d)

Example 3

4-[2,6-difluoro-4-(6-phenoxy-2-pyridyl)phenoxy]butyric acid

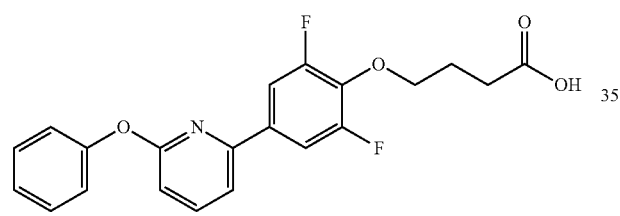

Step A: 4-[2,6-difluoro-4-(6-phenoxy-2-pyridyl)phenoxy]butyric acid ethyl ester

4-[2,6-Difluoro-4-(4,4,5,5-tetramethyl-1,3,2-dioxaborolan-2-yl)phenoxy]butyric acid ethyl ester (0.032 g, 0.086 mmol) obtained in Step C of Preparation Example 2 and 2-chloro-6-phenoxy-pyridine (0.018 g, 0.087 mmol) obtained in Preparation Example 126 were used to react in the same manner as in Step A of Example 1 to obtain the title compound (0.026 g, 72%).

1H NMR (CDCl₃) δ 7.73 (1H, t), 7.44 (4H, m), 7.36 (1H, d), 7.24 (1H, t), 7.20 (2H, m), 6.81 (1H, d), 4.19 (2H, t), 4.13 (2H, q), 2.56 (2H, t), 2.08 (2H, m), 1.26 (3H, t)

Step B: 4-[2,6-difluoro-4-(6-phenoxy-2-pyridyl)phenoxy]butyric acid

4-[2,6-Difluoro-4-(6-phenoxy-2-pyridyl)phenoxy]butyric acid ethyl ester (0.025 g, 0.06 mmol) obtained in Step A was used to react in the same manner as in Step B of Example 1 to obtain the title compound (0.018 g, 77%).

1H NMR (CDCl₃) δ 7.72 (1H, t), 7.44 (4H, m), 7.36 (1H, d), 7.24 (1H, t), 7.20 (2H, m), 6.81 (1H, d), 4.21 (2H, t), 2.64 (2H, t), 2.10 (2H, m)

Example 4

4-[2-chloro-4-(6-isopropylsulfanyl-2-pyridyl)phenoxy]butyric acid

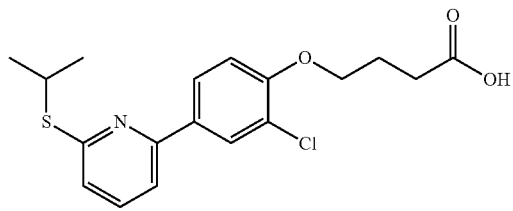 [SMILES: CC(C)Sc1cccc(-c2ccc(OCCCC(=O)O)c(Cl)c2)n1]

4-[2-Chloro-4-(4,4,5,5-tetramethyl-1,3,2-dioxaborolan-2-yl)phenoxy]butyric acid ethyl ester (0.052 g, 0.14 mmol) obtained in Step B of Preparation Example 3 and 2-chloro-6-isopropylsulfanyl-pyridine (0.026 g, 0.14 mmol) obtained in Preparation Example 125 were used to react sequentially in the same manner as in Steps A and B of Example 1 to obtain the title compound (0.012 g, 23%).

1H NMR (CDCl₃) δ 8.05 (1H, d), 7.88 (1H, dd), 7.48 (1H, t), 7.32 (1H, d), 7.06 (1H, d), 6.98 (1H, d), 4.16 (2H, t), 4.12 (1H, m), 2.67 (2H, t), 2.20 (2H, m), 1.46 (6H, d)

Example 5

4-[2-fluoro-4-(6-isopropylsulfanyl-2-pyridyl)phenoxy]butyric acid

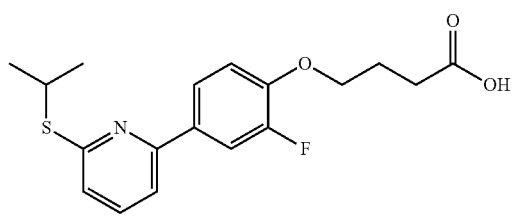 [SMILES: CC(C)Sc1cccc(-c2ccc(OCCCC(=O)O)c(F)c2)n1]

4-[2-Fluoro-4-(4,4,5,5-tetramethyl-1,3,2-dioxaborolan-2-yl)phenoxy]butyric acid ethyl ester (0.053 g, 0.15 mmol) obtained in Step B of Preparation Example 4 and 2-chloro-6-isopropylsulfanyl-pyridine (0.028 g, 0.15 mmol) obtained in Preparation Example 125 were used to react sequentially in the same manner as in Steps A and B of Example 1 to obtain the title compound (0.007 g, 13%).

1H NMR (CDCl₃) δ 7.82 (1H, dd), 7.73 (1H, dd), 7.50 (1H, t), 7.33 (1H, d), 7.04 (2H, m), 4.17 (2H, t), 4.11 (1H, m), 2.64 (2H, t), 2.19 (2H, m), 1.47 (6H, d)

Example 6

4-[4-(6-cyclopentylsulfanyl-2-pyridyl)-2,6-difluorophenoxy]butyric acid

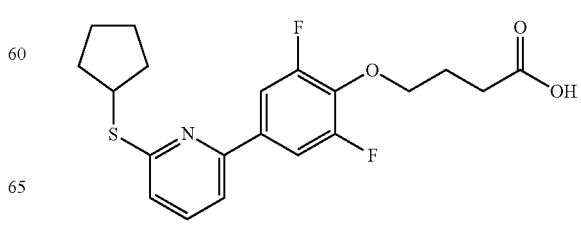

2-Chloro-6-cyclopentylsulfanyl-pyridine (0.044 g, 0.2 mmol) obtained in Preparation Example 5 and 4-[2,6-difluoro-4-(4,4,5,5-tetramethyl-1,3,2-dioxaborolan-2-yl)phenoxy]butyric acid ethyl ester (0.068 g, 0.18 mmol) obtained in Step C of Preparation Example 2 were used to react sequentially in the same manner as in Steps A and B of Example 1 to obtain the title compound (0.008 g, 10%).

1H NMR (CDCl$_3$) δ 7.60 (2H, m), 7.50 (1H, t), 7.30 (1H, d), 7.10 (1H, d), 4.26 (2H, t), 4.16 (1H, m), 2.67 (2H, t), 2.24 (2H, m), 2.12 (2H, m), 1.80 (2H, m), 1.70 (4H, m)

Example 7

4-[4-(2-cyclobutylsulfanyl-pyridin-3-yl)-2-methoxyphenoxy]-butyric acid

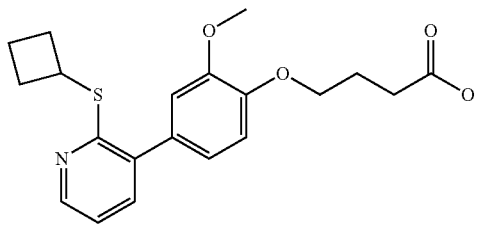 [SMILES: COc1cc(-c2cccnc2SC2CCC2)ccc1OCCCC(=O)O]

2-Cyclobutylsulfanyl-3-iodo-pyridine (0.060 g, 0.21 mmol) obtained in Preparation Example 44 and 4-[2-methoxy-4-(4,4,5,5-tetramethyl-1,3,2-dioxaborolan-2-yl)phenoxy]butyric acid ethyl ester (0.075 g, 0.21 mmol) obtained in Preparation Example 6 were reacted in the same manner as in Example 1 to obtain the title compound (0.050 g, 60%).

1H NMR (CDCl$_3$) δ 8.38 (1H, m), 7.38 (1H, m), 7.02 (1H, m), 6.94 (3H, m), 4.27 (1H, m), 4.14 (2H, t), 3.88 (3H, s), 2.66 (2H, t), 2.49 (2H, m), 2.21 (2H, m), 2.00 (4H, m)

Example 8

4-[2,6-difluoro-4-(2-isopropylsulfanyl-4-pyridyl)phenoxy]butyric acid

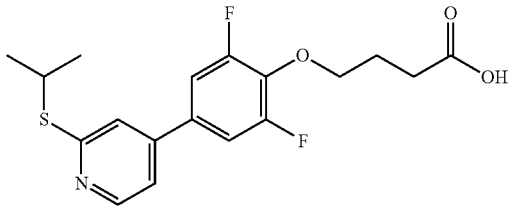 [SMILES: CC(C)Sc1cc(-c2cc(F)c(OCCCC(=O)O)c(F)c2)ccn1]

Step A: 4-[2,6-difluoro-4-(2-isopropylsulfanyl-4-pyridyl)phenoxy]butyric acid ethyl ester 0.7 mL of DMF was added to 4-[4-(2-chloro-4-pyridyl)-2,6-difluoro-phenoxy]butyric acid ethyl ester (0.025 g, 0.07 mmol) obtained in Preparation Example 7, Cs$_2$CO$_3$ (0.046 g, 0.14 mmol) and 2-propanethiol (0.013 mL, 0.14 mmol), and the resultant was agitated at 80° C. for 4 hours. The reaction solution was concentrated under reduced pressure and purified by column chromatography to obtain the title compound (0.007 g, 25%).

1H NMR (CDCl$_3$) δ 8.43 (1H, d), 7.46 (1H, d), 7.34 (1H, dd), 7.32 (1H, m), 7.18 (1H, m), 4.20 (2H, t), 4.17 (3H, m), 2.63 (2H, t), 2.13 (2H, m), 1.34 (6H, d), 1.28 (3H, t)

Step B: 4-[2,6-difluoro-4-(2-isopropylsulfanyl-4-pyridyl)phenoxy]butyric acid

4-[2,6-Difluoro-4-(2-isopropylsulfanyl-4-pyridyl)phenoxy]butyric acid ethyl ester (0.007 g, 0.018 mmol) obtained in Step A was used to react in the same manner as in Step B of Example 1 to obtain the title compound (0.004 g, 55%).

1H NMR (CDCl$_3$) δ 8.43 (1H, d), 7.46 (1H, d), 7.35 (1H, m), 7.32 (1H, m), 7.20 (1H, dd), 4.21 (2H, t), 3.55 (1H, m), 2.73 (2H, t), 2.15 (2H, m), 1.35 (6H, d)

Example 9

4-[4-[6-(cyclopentoxy)-2-pyridyl]-2,6-difluoro-phenoxy]butyric acid

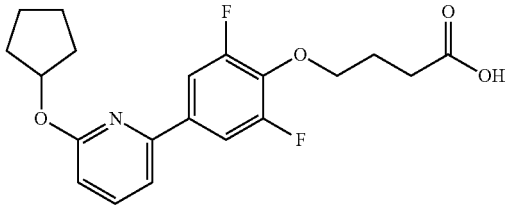 [SMILES: O=C(O)CCCOc1c(F)cc(-c2cccc(OC3CCCC3)n2)cc1F]

Step A: 4-[4-[6-(cyclopentoxy)-2-pyridyl]-2,6-difluoro-phenoxy]butyric acid ethyl ester 2-Chloro-6-(cyclopentoxy)pyridine (0.055 g, 0.27 mmol) obtained in Preparation Example 8 and 4-[2,6-difluoro-4-(4,4,5,5-tetramethyl-1,3,2-dioxaborolan-2-yl)phenoxy]butyric acid ethyl ester (0.068 g, 0.18 mmol) obtained in Step C of Preparation Example 2 were reacted in the same manner as in Step A of Example 1 to obtain the title compound (0.051 g, 68%).

1H NMR (CDCl$_3$) δ 7.58 (3H, m), 7.18 (1H, d), 6.63 (1H, d), 5.50 (1H, m), 4.22 (2H, t), 4.16 (2H, m), 2.58 (2H, t), 2.12 (2H, m), 2.06 (2H, m), 1.82 (4H, m), 1.65 (2H, m), 1.27 (3H, t)

Step B: 4-[4-[6-(cyclopentoxy)-2-pyridyl]-2,6-difluoro-phenoxy]butyric acid

4-[4-[6-(Cyclopentoxy)-2-pyridyl]-2,6-difluoro-phenoxy]butyric acid ethyl ester (0.05 g, 0.12 mmol) obtained in Step A was used to react in the same manner as in Step B of Example 1 to obtain the title compound (0.023 g, 50%).

1H NMR (CDCl$_3$) δ 7.59 (3H, m), 7.18 (1H, d), 6.63 (1H, d), 5.50 (1H, m), 4.24 (2H, t), 2.67 (2H, t), 2.14 (2H, m), 2.04 (2H, m), 1.82 (4H, m), 1.65 (2H, m)

Example 10

4-[4-(2-cyclobutylsulfanyl-pyridin-3-yl)-2,6-dimethyl-phenoxy]-butyric acid

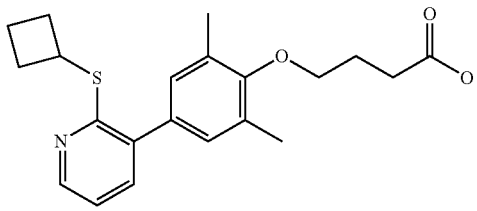 [SMILES: Cc1cc(-c2cccnc2SC2CCC2)cc(C)c1OCCCC(=O)O]

2-Cyclobutylsulfanyl-3-iodo-pyridine (0.048 g, 0.16 mmol) obtained in Preparation Example 44 and 4-[2,6-dimethyl-4-(4,4,5,5-tetramethyl-1,3,2-dioxaborolan-2-yl)phenoxy]butyric acid ethyl ester (0.060 g, 0.16 mmol) obtained in Preparation Example 11 were reacted in the same manner as in Example 1 to obtain the title compound (0.040 g, 61%).

1H NMR (CDCl$_3$) δ 8.37 (1H, m), 7.33 (1H, m), 7.05 (2H, s), 6.99 (1H, m), 4.42 (1H, m), 3.89 (2H, t), 2.71 (2H, t), 2.49 (2H, m), 2.30 (6H, s), 2.18 (2H, m), 2.07 (4H, m)

Example 11

4-[4-[3-(cyclopentoxy)phenyl]-2,6-difluoro-phenoxy]butyric acid

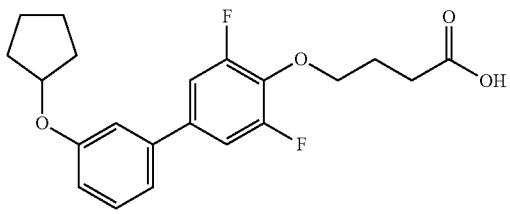 [SMILES: O=C(O)CCCOc1c(F)cc(-c2cccc(OC3CCCC3)c2)cc1F]

1-Bromo-3-(cyclopentoxy)benzene (0.04 g, 0.16 mmol) obtained in Preparation Example 9 and 4-[2,6-difluoro-4-(4,4,5,5-tetramethyl-1,3,2-dioxaborolan-2-yl)phenoxy]butyric acid ethyl ester (0.05 g, 0.13 mmol) obtained in Step C of Preparation Example 2 were used to react sequentially in the same manner as in Steps A and B of Example 1 to obtain the title compound (0.01 g, 20%).

1H NMR (CDCl$_3$) δ 7.30 (1H, t), 7.11 (2H, m), 7.04 (1H, d), 7.00 (1H, m), 6.87 (1H, dd), 4.81 (1H, m), 4.22 (2H, t), 2.65 (2H, t), 2.12 (2H, m), 1.95 (2H, m), 1.88 (2H, m), 1.82 (2H, m), 1.64 (2H, m)

Example 12

4-[2,6-difluoro-4-(6-pyrrolidin-1-yl-2-pyridyl)phenoxy]butyric acid

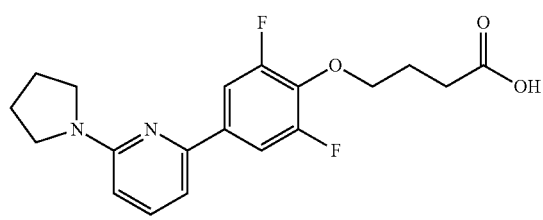 [SMILES: O=C(O)CCCOc1c(F)cc(-c2cccc(N3CCCC3)n2)cc1F]

2-Chloro-6-pyrrolidin-1-yl-pyridine (0.028 g, 0.15 mmol) obtained in Preparation Example 10 and 4-[2,6-difluoro-4-(4,4,5,5-tetramethyl-1,3,2-dioxaborolan-2-yl)phenoxy]butyric acid ethyl ester (0.051 g, 0.13 mmol) obtained in Step C of Preparation Example 2 were used to react sequentially in the same manner as in Steps A and B of Example 1 to obtain the title compound (0.006 g, 13%).

1H NMR (CDCl$_3$) δ 7.62 (2H, m), 7.46 (1H, t), 6.90 (1H, d), 6.32 (1H, d), 4.20 (2H, t), 3.53 (4H, t), 2.65 (2H, t), 2.12 (2H, t), 2.01 (4H, m)

Example 13

4-[4-(2-sec-butylsulfanyl-pyridin-3-yl)-2,6-difluoro-phenoxy]-butyric acid

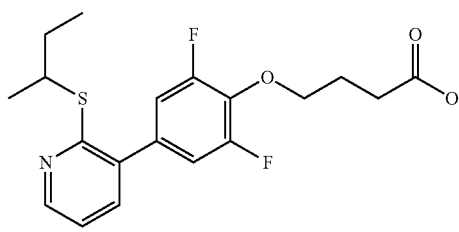 [SMILES: CCC(C)Sc1ncccc1-c1cc(F)c(OCCCC(=O)O)c(F)c1]

Butain-2-thiol (27 mg, 0.29 mmol) and 4-[2,6-difluoro-4-(2-fluoro-3-pyridyl)phenoxy]butyric acid ethyl ester (100 mg, 0.29 mmol) obtained in Preparation Example 109 were used to react sequentially in the same manner as in Preparation Example 5 and Step B of Example 1 to obtain the title compound (65 mg, 54%).

1H NMR (CDCl$_3$) δ 8.43 (1H, m), 7.32 (1H, m), 7.01 (3H, m), 4.26 (2H, t), 3.96 (1H, m), 2.69 (2H, t), 2.14 (2H, m), 1.73 (2H, m), 1.33 (3H, d), 1.00 (3H, t)

Example 14

4-[4-[3-(cyclopentoxy)phenyl]-2,3-difluoro-phenoxy]butyric acid

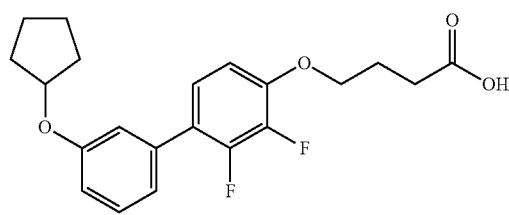 [SMILES: O=C(O)CCCOc1ccc(-c2cccc(OC3CCCC3)c2)c(F)c1F]

Step A: 4-[4-[3-(cyclopentoxy)phenyl]-2,3-difluoro-phenoxy]butyric acid ethyl ester 1.5 mL of acetonitrile was added to 4-[2,3-difluoro-4-(3-hydroxyphenyl)phenoxy]butyric acid ethyl ester (0.089 g, 0.26 mmol) obtained in Preparation Example 13, cyclopentyl bromide (0.034 g, 0.31 mmol) and K$_2$CO$_3$ (0.036 g, 0.26 mmol), and the resultant was agitated under reflux for 16 hours. After finishing the reaction, the reaction solution was concentrated under reduced pressure and purified by column chromatography to obtain the title compound (0.042 g, 39%).

1H NMR (CDCl$_3$) δ 7.31 (1H, t), 7.10 (1H, m), 7.04 (1H, dd), 7.00 (1H, d), 6.88 (1H, dd), 6.78 (1H, m), 4.79 (1H, m), 4.15 (4H, m), 2.55 (2H, t), 2.16 (2H, m), 1.92 (4H, m), 1.80 (2H, m), 1.62 (2H, m), 1.27 (3H, t)

Step B: 4-[4-[3-(cyclopentoxy)phenyl]-2,3-difluoro-phenoxy]butyric acid

4-[4-[3-(Cyclopentoxy)phenyl]-2,3-difluoro-phenoxy] butyric acid ethyl ester (0.041 g, 0.1 mmol) obtained in Step A was dissolved each 0.5 mL of EtOH and NaOH (1M aqueous solution), and the resultant was agitated at room temperature for 1 hour. After finishing the reaction, EtOAc was added thereto, and the aqueous layer was adjusted to pH 4 by the use of 1N HCl aqueous solution. The organic layer was separated and purified by column chromatography to obtain the title compound (0.036 g, 96%).

1H NMR (CDCl$_3$) δ 7.31 (1H, t), 7.09 (1H, m), 7.04 (1H, dd), 7.00 (1H, d), 6.88 (1H, dd), 6.78 (1H, dd), 4.79 (1H, m), 4.15 (2H, t), 2.63 (2H, t), 2.18 (2H, m), 1.90 (4H, m), 1.81 (2H, m), 1.62 (2H, m)

Example 15

4-[2,6-difluoro-4-[6-(1-piperidyl)-2-pyridyl]phenoxy]butyric acid

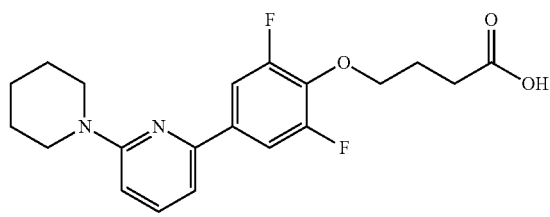 [SMILES: O=C(O)CCCOc1c(F)cc(-c2cccc(N3CCCCC3)n2)cc1F]

2-Chloro-6-(1-piperidyl)pyridine (0.09 g, 0.45 mmol) obtained in Preparation Example 14 and 4-[2,6-difluoro-4-(4,4,5,5-tetramethyl-1,3,2-dioxaborolan-2-yl)phenoxy]butyric acid ethyl ester (0.154 g, 0.41 mmol) obtained in Step C of Preparation Example 2 were used to react sequentially in the same manner as in Steps A and B of Example 1 to obtain the title compound (0.06 g, 39%).

1H NMR (CDCl$_3$) δ 7.56 (2H, m), 7.49 (1H, t), 6.92 (1H, d), 6.60 (1H, d), 4.22 (2H, t), 3.61 (4H, brs), 2.64 (2H, t), 2.10 (2H, m), 1.67 (6H, brs)

Example 16

4-[4-(6-anilino-2-pyridyl)-2,6-difluoro-phenoxy]butyric acid

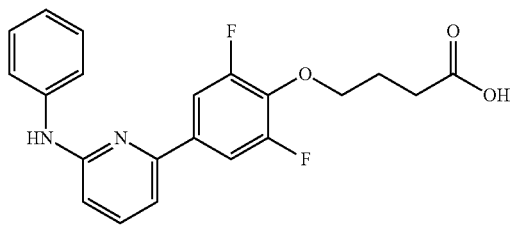 [SMILES: O=C(O)CCCOc1c(F)cc(-c2cccc(Nc3ccccc3)n2)cc1F]

6-Chloro-N-phenyl-pyridin-2-amine (0.09 g, 0.44 mmol) obtained in Preparation Example 15 and 4-[2,6-difluoro-4-(4,4,5,5-tetramethyl-1,3,2-dioxaborolan-2-yl)phenoxy]butyric acid ethyl ester (0.148 g, 0.4 mmol) obtained in Step C of Preparation Example 2 were used to react sequentially in the same manner as in Steps A and B of Example 1 to obtain the title compound (0.037 g, 24%).

1H NMR (CDCl$_3$) δ 7.54 (3H, m), 7.37 (4H, m), 7.08 (2H, m), 6.83 (1H, brs), 6.82 (1H, d), 4.24 (2H, t), 2.66 (2H, t), 2.11 (2H, m)

Example 17

4-[2,6-difluoro-4-[6-(N-methylanilino)-2-pyridyl] phenoxy]butyric acid

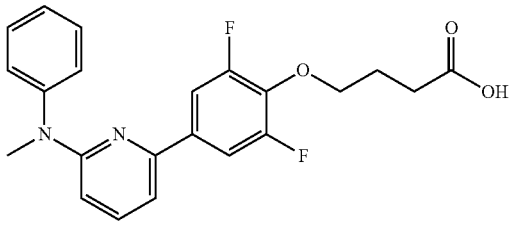 [SMILES: CN(c1ccccc1)c1cccc(-c2cc(F)c(OCCCC(=O)O)c(F)c2)n1]

Step A: 4-[2,6-difluoro-4-[6-(N-methylanilino)-2-pyridyl]phenoxy]butyric acid methyl ester 4-[4-(6-Anilino-2-pyridyl)-2,6-difluoro-phenoxy]butyric acid (0.033 g, 0.085 mmol) obtained in Example 16 was dissolved in 1 mL of DMF, and potassium tert-butoxide (0.036 g, 0.34 mmol) and iodomethane (0.02 mL, 0.34 mmol) were added thereto. The resultant was agitated at room temperature for 16 hours. After finishing the reaction, the reaction solution was concentrated under reduced pressure and purified by column chromatography to obtain the title compound (0.02 g, 57%).

1H NMR (CDCl$_3$) δ 7.63 (2H, m), 7.42 (2H, m), 7.36 (1H, t), 7.30 (2H, m), 7.24 (1H, m), 6.98 (1H, d), 6.48 (1H, d), 4.22 (2H, t), 3.70 (3H, s), 3.57 (3H, s), 2.62 (2H, t), 2.11 (2H, m)

Step B: 4-[2,6-difluoro-4-[6-(N-methylanilino)-2-pyridyl]phenoxy]butyric acid 4-[2,6-Difluoro-4-[6-(N-methylanilino)-2-pyridyl]phenoxy]butyric acid methyl ester (0.02 g, 0.048 mmol) obtained in Step A was used to react in the same manner as in Step B of Example 1 to obtain the title compound (0.013 g, 66%).

1H NMR (CDCl$_3$) δ 7.62 (2H, m), 7.42 (2H, m), 7.36 (1H, m), 7.30 (2H, m), 7.24 (1H, m), 6.98 (1H, d), 6.48 (1H, d), 4.21 (2H, t), 3.58 (3H, s), 2.67 (2H, t), 2.12 (2H, m)

Example 18

4-[4-[6-(cyclopentylamino)-2-pyridyl]-2,6-difluoro-phenoxy]butyric acid

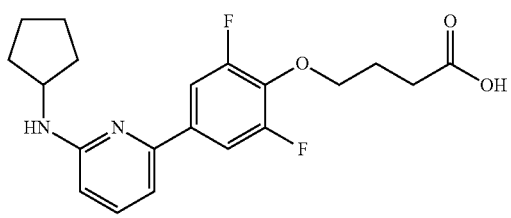

Step A: 4-[4-[6-(cyclopentylamino)-2-pyridyl]-2,6-difluoro-phenoxy]butyric acid ethyl ester 6-Chloro-N-cyclopentyl-pyridin-2-amine (0.05 g, 0.25 mmol) obtained in Preparation Example 16 and 4-[2,6-difluoro-4-(4,4,5,5-tetramethyl-1,3,2-dioxaborolan-2-yl)phenoxy]butyric acid ethyl ester (0.06 g, 0.16 mmol) obtained in Step C of Preparation Example 2 were used to react in the same manner as in Step A of Example 1 to obtain the title compound (0.03 g, 48%).

1H NMR (CDCl$_3$) δ 7.50 (2H, m), 7.46 (1H, t), 6.90 (1H, d), 6.35 (1H, d), 4.65 (1H, d), 4.20 (2H, t), 4.15 (2H, q), 4.05 (1H, m), 2.58 (2H, t), 2.08 (4H, m), 1.76 (2H, m), 1.66 (2H, m), 1.52 (2H, m), 1.26 (3H, t)

Step B: 4-[4-[6-(cyclopentylamino)-2-pyridyl]-2,6-difluoro-phenoxy]butyric acid

4-[4-[6-(Cyclopentylamino)-2-pyridyl]-2,6-difluoro-phenoxy]butyric acid ethyl ester (0.03 g, 0.07 mmol) obtained in Step A was used to react in the same manner as in Step B of Example 1 to obtain the title compound (0.026 g, 93%).

1H NMR (CDCl$_3$) δ 7.47 (3H, m), 6.87 (1H, d), 6.36 (1H, d), 4.22 (2H, t), 4.02 (1H, m), 2.64 (2H, t), 2.10 (4H, m), 1.78 (2H, m), 1.65 (2H, m), 1.52 (2H, m)

Example 19

4-[4-[6-(cyclopropylmethylsulfanyl)-2-pyridyl]-2,6-difluoro-phenoxy]butyric acid

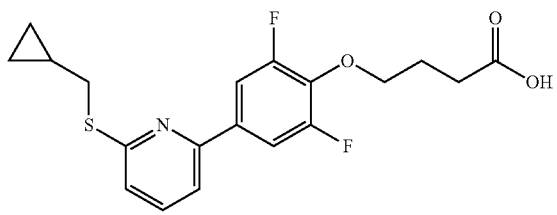 [SMILES: O=C(O)CCCOc1c(F)cc(-c2cccc(SCC3CC3)n2)cc1F]

2-Chloro-6-(cyclopropylmethylsulfanyl)pyridine (0.033 g, 0.16 mmol) obtained in Step B of Preparation Example 18 and 4-[2,6-difluoro-4-(4,4,5,5-tetramethyl-1,3,2-dioxaborolan-2-yl)phenoxy]butyric acid ethyl ester (0.05 g, 0.135 mmol) obtained in Step C of Preparation Example 2 were used to react sequentially in the same manner as in Steps A and B of Example 1 to obtain the title compound (0.03 g, 58%).

1H NMR (CDCl$_3$) δ 7.58 (2H, m), 7.52 (1H, t), 7.30 (1H, d), 7.14 (1H, d), 4.25 (2H, t), 3.22 (2H, d), 2.67 (2H, t), 2.12 (2H, m), 1.21 (1H, m), 0.62 (2H, m), 0.36 (2H, m)

Example 20

4-[4-(6-cyclobutylsulfanyl-2-pyridyl)-2,6-difluoro-phenoxy]butyric acid

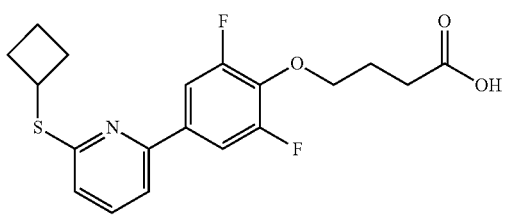 [SMILES: O=C(O)CCCOc1c(F)cc(-c2cccc(SC3CCC3)n2)cc1F]

2-Chloro-6-cyclobutylsulfanyl-pyridine (0.033 g, 0.165 mmol) obtained in Preparation Example 19 and 4-[2,6-difluoro-4-(4,4,5,5-tetramethyl-1,3,2-dioxaborolan-2-yl)phenoxy]butyric acid ethyl ester (0.05 g, 0.135 mmol) obtained in Step C of Preparation Example 2 were used to react sequentially in the same manner as in Steps A and B of Example 1 to obtain the title compound (0.035 g, 68%).

1H NMR (CDCl$_3$) δ 7.58 (2H, m), 7.52 (1H, t), 7.30 (1H, d), 7.04 (1H, d), 4.42 (1H, m), 4.25 (2H, t), 2.68 (2H, t), 2.60 (2H, m), 2.12 (6H, m)

Example 21

4-[2,6-difluoro-4-(6-propylsulfanyl-2-pyridyl)phenoxy]butyric acid

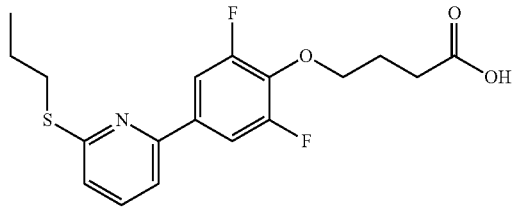

2-Chloro-6-propylsulfanyl-pyridine (0.03 g, 0.16 mmol) obtained in Preparation Example 20 and 4-[2,6-difluoro-4-(4,4,5,5-tetramethyl-1,3,2-dioxaborolan-2-yl)phenoxy]butyric acid ethyl ester (0.05 g, 0.135 mmol) obtained in Step C of Preparation Example 2 were used to react sequentially in the same manner as in Steps A and B of Example 1 to obtain the title compound (0.037 g, 75%).

1H NMR (CDCl$_3$) δ 7.58 (2H, m), 7.52 (1H, t), 7.30 (1H, d), 7.12 (1H, d), 4.25 (2H, t), 3.23 (2H, t), 2.67 (2H, t), 2.12 (2H, m), 1.81 (2H, m), 1.08 (3H, t)

Example 22

4-[2,6-difluoro-4-(6-isopropoxy-2-pyridyl)phenoxy]butyric acid

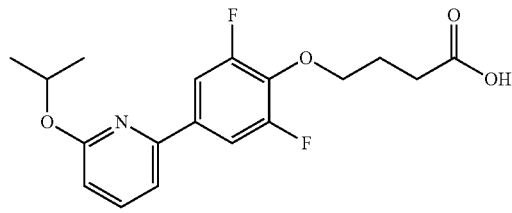 [SMILES: CC(C)Oc1cccc(-c2cc(F)c(OCCCC(=O)O)c(F)c2)n1]

Step A: 4-[2,6-difluoro-4-(6-isopropoxy-2-pyridyl)phenoxy]butyric acid ethyl ester 2-Chloro-6-isopropoxy-pyridine (0.03 g, 0.17 mmol) obtained in Preparation Example 21 and 4-[2,6-difluoro-4-(4,4,5,5-tetramethyl-1,3,2-dioxaborolan-2-yl)phenoxy]butyric acid ethyl ester (0.05 g, 0.135 mmol) obtained in Step C of Preparation Example 2 were used to react in the same manner as in Step A of Example 1 to obtain the title compound (0.038 g, 74%).

1H NMR (CDCl$_3$) δ 7.57 (3H, m), 7.19 (1H, d), 6.63 (1H, d), 5.44 (1H, m), 4.22 (2H, t), 4.16 (2H, q), 2.59 (2H, t), 2.10 (2H, m), 1.40 (6H, d), 1.27 (3H, t)

Step B: 4-[2,6-difluoro-4-(6-isopropoxy-2-pyridyl)phenoxy]butyric acid

4-[2,6-difluoro-4-(6-isopropoxy-2-pyridyl)phenoxy]butyric acid ethyl ester (0.037 g, 0.1 mmol) obtained in Step A was used to react in the same manner as in Step B of Example 1 to obtain the title compound (0.03 g, 88%).

1H NMR (CDCl$_3$) δ 7.61 (1H, t), 7.56 (2H, m), 7.19 (1H, d), 6.63 (1H, d), 5.44 (1H, m), 4.24 (2H, t), 2.67 (2H, t), 2.11 (2H, m), 1.40 (6H, d)

Example 23

4-[2,6-difluoro-4-(6-propoxy-2-pyridyl)phenoxy]butyric acid

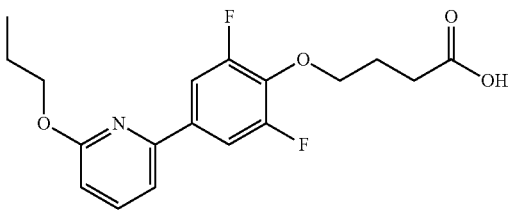 [SMILES: CCCOc1cccc(-c2cc(F)c(OCCCC(=O)O)c(F)c2)n1]

Step A: 4-[2,6-difluoro-4-(6-propoxy-2-pyridyl)phenoxy]butyric acid ethyl ester 2-Chloro-6-propoxy-pyridine (0.03 g, 0.17 mmol) obtained in Preparation Example 22 and 4-[2,6-difluoro-4-(4,4,5,5-tetramethyl-1,3,2-dioxaborolan-2-yl)phenoxy]butyric acid ethyl ester (0.05 g, 0.135 mmol) obtained in Step C of Preparation Example 2 were used to react in the same manner as in Step A of Example 1 to obtain the title compound (0.026 g, 40%).

1H NMR (CDCl$_3$) δ 7.62 (1H, t), 7.58 (2H, m), 7.21 (1H, d), 6.69 (1H, d), 4.35 (2H, t), 4.22 (2H, t), 4.16 (2H, q), 2.59 (2H, t), 2.10 (2H, m), 1.84 (2H, m), 1.27 (3H, t), 1.06 (3H, t)

Step B: 4-[2,6-difluoro-4-(6-propoxy-2-pyridyl)phenoxy]butyric acid

4-[2,6-Difluoro-4-(6-propoxy-2-pyridyl)phenoxy]butyric acid ethyl ester (0.026 g, 0.068 mmol) obtained in Step A was used to react in the same manner as in Step B of Example 1 to obtain the title compound (0.018 g, 81%).

1H NMR (CDCl$_3$) δ 7.60 (1H, t), 7.58 (2H, m), 7.21 (1H, d), 6.68 (1H, d), 4.35 (2H, t), 4.24 (2H, t), 2.67 (2H, t), 2.11 (2H, m), 1.83 (2H, m), 1.06 (3H, t)

Example 24

4-[4-[6-(cyclopropylmethoxy)-2-pyridyl]-2,6-difluoro-phenoxy]butyric acid

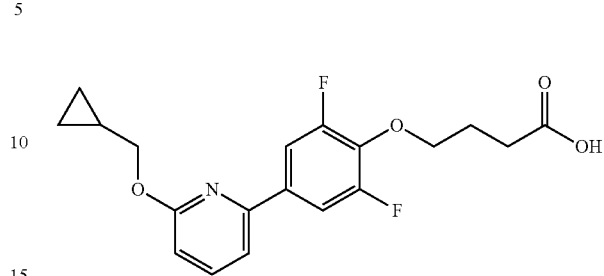

Step A: 4-[4-[6-(cyclopropylmethoxy)-2-pyridyl]-2,6-difluoro-phenoxy]butyric acid ethyl ester 2-Chloro-6-(cyclopropylmethoxy)-pyridine (0.033 g, 0.18 mmol) obtained in Preparation Example 23 and 4-[2,6-difluoro-4-(4,4,5,5-tetramethyl-1,3,2-dioxaborolan-2-yl)phenoxy]butyric acid ethyl ester (0.05 g, 0.135 mmol) obtained in Step C of Preparation Example 2 were used to react in the same manner as in Step A of Example 1 to obtain the title compound (0.050 g, 95%).

1H NMR (CDCl$_3$) δ 7.61 (1H, t), 7.57 (2H, m), 7.21 (1H, d), 6.72 (1H, d), 4.22 (4H, m), 4.16 (2H, q), 2.58 (2H, t), 2.10 (2H, m), 1.33 (1H, m), 1.26 (3H, t), 0.64 (2H, m), 0.39 (2H, m)

Step B: 4-[4-[6-(cyclopropylmethoxy)-2-pyridyl]-2,6-difluoro-phenoxy]butyric acid 4-[4-[6-(Cyclopropylmethoxy)-2-pyridyl]-2,6-difluoro-phenoxy]butyric acid ethyl ester (0.05 g, 0.127 mmol) obtained in Step A was used to react in the same manner as in Step B of Example 1 to obtain the title compound (0.034 g, 73%).

1H NMR (CDCl$_3$) δ 7.62 (1H, t), 7.57 (2H, m), 7.21 (1H, d), 6.73 (1H, d), 4.23 (4H, m), 2.67 (2H, t), 2.11 (2H, m), 1.33 (1H, m), 0.64 (2H, m), 0.39 (2H, m)

Example 25

4-[4-[6-(cyclobutoxy)-2-pyridyl]-2,6-difluoro-phenoxy]butyric acid

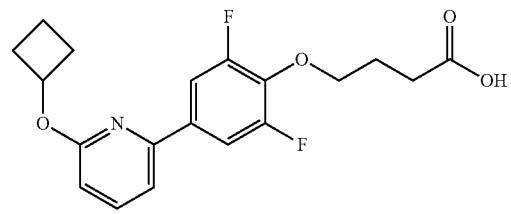 [SMILES: O=C(O)CCCOc1c(F)cc(-c2cccc(OC3CCC3)n2)cc1F]

Step A: 4-[4-[6-(cyclobutoxy)-2-pyridyl]-2,6-difluoro-phenoxy]butyric acid ethyl ester 2-Chloro-6-(cyclobutoxy)-pyridine (0.033 g, 0.18 mmol) obtained in Preparation Example 24 and 4-[2,6-difluoro-4-(4,4,5,5-tetramethyl-1,3,2-dioxaborolan-2-yl)phenoxy]butyric acid ethyl ester (0.05 g, 0.135 mmol) obtained in Step C of Preparation Example 2 were used to react in the same manner as in Step A of Example 1 to obtain the title compound (0.042 g, 80%).

1H NMR (CDCl$_3$) δ 7.61 (1H, t), 7.56 (2H, m), 7.21 (1H, d), 6.65 (1H, d), 5.26 (1H, m), 4.22 (2H, t), 4.15 (2H, q), 2.60 (2H, t), 2.52 (2H, m), 2.19 (2H, m), 2.10 (2H, m), 1.87 (1H, m), 1.76 (1H, m), 1.27 (3H, t)

Step B: 4-[4-[6-(cyclobutoxy)-2-pyridyl]-2,6-difluoro-phenoxy]butyric acid

4-[4-[6-(Cyclobutoxy)-2-pyridyl]-2,6-difluoro-phenoxy]butyric acid ethyl ester (0.042 g, 0.1 mmol) obtained in Step A was used to react in the same manner as in Step B of Example 1 to obtain the title compound (0.024 g, 61%).

1H NMR (CDCl$_3$) δ 7.61 (1H, t), 7.56 (2H, m), 7.21 (1H, d), 6.65 (1H, d), 5.25 (1H, m), 4.24 (2H, t), 2.67 (2H, t), 2.52 (2H, m), 2.19 (2H, m), 2.11 (2H, m), 1.87 (1H, m), 1.76 (1H, m)

Example 26

4-[4-[6-(cyclobutoxy)-2-pyridyl]-2-methyl-phenoxy]butyric acid

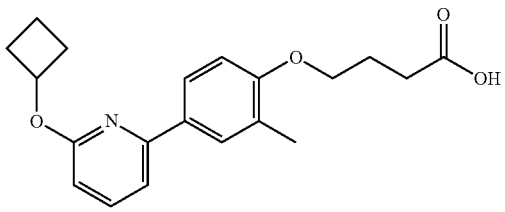 [SMILES: Cc1cc(-c2cccc(OC3CCC3)n2)ccc1OCCCC(=O)O]

Step A: 4-[4-[6-(cyclobutoxy)-2-pyridyl]-2-methyl-phenoxy]butyric acid ethyl ester 2-Chloro-6-(cyclobutoxy)-pyridine (0.041 g, 0.22 mmol) obtained in Preparation Example 24 and 4-[2-methyl-4-(4,4,5,5-tetramethyl-1,3,2-dioxaborolan-2-yl)phenoxy]butyric acid ethyl ester (0.059 g, 0.17 mmol) obtained in Step C of Preparation Example 25 were used to react in the same manner as in Step A of Example 1 to obtain the title compound (0.031 g, 49%).

1H NMR (CDCl$_3$) δ 7.80 (2H, m), 7.57 (1H, t), 7.25 (1H, d), 6.86 (1H, d), 6.56 (1H, d), 5.56 (1H, m), 4.15 (2H, q), 4.06 (2H, t), 2.56 (2H, t), 2.54 (2H, m), 2.28 (3H, s), 2.18 (2H, m), 2.16 (2H, m), 1.87 (1H, m), 1.74 (1H, m), 1.27 (3H, t)

Step B: 4-[4-[6-(cyclobutoxy)-2-pyridyl]-2-methyl-phenoxy]butyric acid

4-[4-[6-(Cyclobutoxy)-2-pyridyl]-2-methyl-phenoxy]butyric acid ethyl ester (0.031 g, 0.08 mmol) obtained in Step A was used to react in the same manner as in Step B of Example 1 to obtain the title compound (0.013 g, 45%).

1H NMR (CDCl$_3$) δ 7.80 (2H, m), 7.56 (1H, t), 7.24 (1H, d), 6.87 (1H, d), 6.56 (1H, d), 5.25 (1H, m), 4.08 (2H, t), 2.63 (2H, t), 2.52 (2H, m), 2.28 (3H, s), 2.18 (4H, m), 1.87 (1H, m), 1.72 (1H, m)

Example 27

4-[4-[6-(cyclobutoxy)-2-pyridyl]-2-(trifluoromethyl)phenoxy]butyric acid

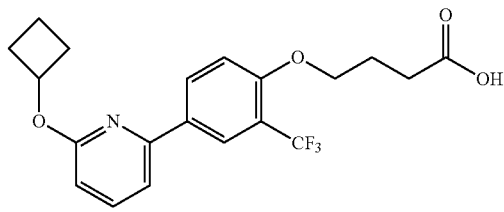 [SMILES: O=C(O)CCCOc1ccc(-c2cccc(OC3CCC3)n2)cc1C(F)(F)F]

Step A: 4-[4-[6-(cyclobutoxy)-2-pyridyl]-2-(trifluoromethyl)phenoxy]butyric acid ethyl ester 2-Chloro-6-(cyclobutoxy)-pyridine (0.035 g, 0.19 mmol) obtained in Preparation Example 24 and 4-[4-(4,4,5,5-tetramethyl-1,3,2-dioxaborolan-2-yl)-2-(trifluoromethyl)phenoxy]butyric acid ethyl ester (0.061 g, 0.15 mmol) obtained in Step C of Preparation Example 26 were used to react in the same manner as in Step A of Example 1 to obtain the title compound (0.041 g, 63%).

1H NMR (CDCl$_3$) δ 8.24 (1H, d), 8.13 (1H, dd), 7.61 (1H, t), 7.25 (1H, m), 7.05 (1H, dd), 6.62 (1H, d), 5.25 (1H, m), 4.15 (4H, m), 2.57 (4H, m), 2.17 (4H, m), 1.87 (1H, m), 1.74 (1H, m), 1.26 (3H, t)

Step B: 4-[4-[6-(cyclobutoxy)-2-pyridyl]-2-(trifluoromethyl)phenoxy]butyric acid 4-[4-[6-(Cyclobutoxy)-2-pyridyl]-2-(trifluoromethyl)phenoxy]butyric acid ethyl ester (0.04 g, 0.09 mmol) obtained in Step A was used to react in the same manner as in Step B of Example 1 to obtain the title compound (0.03 g, 84%).

1H NMR (CDCl$_3$) δ 8.24 (1H, d), 8.12 (1H, dd), 7.60 (1H, t), 7.26 (1H, d), 7.04 (1H, m), 6.62 (1H, d), 5.25 (1H, m), 4.17 (2H, t), 2.65 (2H, m), 2.52 (2H, m), 2.20 (4H, m), 1.87 (1H, m), 1.73 (1H, m)

Example 28

4-[4-(2-cyclobutylsulfanyl-3-pyridyl)-2,6-difluoro-phenoxy]pentanoic acid

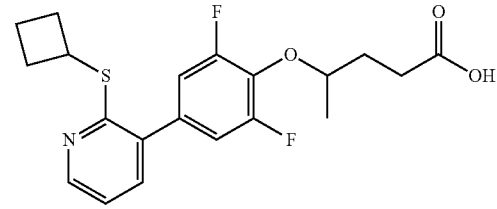 [SMILES: CC(CCC(=O)O)Oc1c(F)cc(-c2cccnc2SC2CCC2)cc1F]

Step A: 4-[4-(2-cyclobutylsulfanyl-3-pyridyl)-2,6-difluoro-phenoxy]pentanoic acid methyl ester 4-[2,6-Difluoro-4-(4,4,5,5-tetramethyl-1,3,2-dioxaborolan-2-yl)phenoxy]pentanoic acid methyl ester (0.053 g, 0.14 mmol) obtained in Step C of Preparation Example 27 and 2-cyclobutylsulfanyl-3-iodo-pyridine (0.045 g, 0.15 mmol) obtained in Step B of Preparation Example 44 were dissolved in 0.7 mL of 1,2-dimethoxyethane and Na$_2$CO$_3$ (2M aqueous solution, 0.21 mL, 0.43 mmol), and N$_2$ gas was charged thereto for 5 minutes. PdCl$_2$(PPh$_3$)$_2$ (0.005 g, 0.007 mmol) was added thereto, and the resultant was agitated at 80° C. for 3 hours. After finishing the reaction, the reaction solution was added with 3 mL of water and extracted with EtOAc. The organic layer was dried with MgSO$_4$ and purified by column chromatography to obtain the title compound (0.046 g, 79%).

1H NMR (CDCl$_3$) δ 8.41 (1H, m), 7.33 (1H, m), 7.01 (3H, m), 4.41 (2H, m), 3.69 (3H, s), 2.63 (2H, t), 2.51 (2H, m), 2.05 (6H, m), 1.33 (3H, d)

Step B: 4-[4-(2-cyclobutylsulfanyl-3-pyridyl)-2,6-difluoro-phenoxy]pentanoic acid 4-[4-(2-Cyclobutylsulfanyl-3-pyridyl)-2,6-difluoro-phenoxy]pentanoic acid methyl ester (0.069 g, 0.17 mmol) obtained in Step A was used to react in the same manner as in Step B of Example 1 to obtain the title compound (0.045 g, 67%).

1H NMR (CDCl$_3$) δ 8.41 (1H, m), 7.33 (1H, m), 7.00 (3H, m), 4.41 (2H, m), 2.71 (2H, t), 2.52 (2H, m), 2.05 (6H, m), 1.35 (3H, d)

Example 29

4-[4-[6-(cyclobutoxy)-2-pyridyl]-2,6-difluoro-phenoxy]pentanoic acid

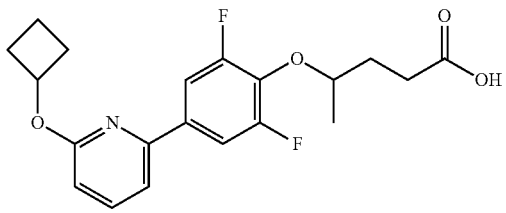 [SMILES: CC(CCC(=O)O)Oc1c(F)cc(-c2cccc(OC3CCC3)n2)cc1F]

Step A: 4-[4-[6-(cyclobutoxy)-2-pyridyl]-2,6-difluoro-phenoxy]pentanoic acid methyl ester 4-[2,6-Difluoro-4-(4,4,5,5-tetramethyl-1,3,2-dioxaborolan-2-yl)phenoxy]pentanoic acid methyl ester (0.04 g, 0.11 mmol) obtained in Step C of Preparation Example 27 and 2-chloro-6-(cyclobutoxy)-pyridine (0.02 g, 0.11 mmol) obtained in Preparation Example 24 were dissolved in 1 mL of 1,2-dimethoxyethane and Na$_2$CO$_3$ (2M aqueous solution, 0.16 mL, 0.32 mmol), and N$_2$ gas was charged thereto for 5 minutes. Pd(PPh$_3$)$_4$ (0.011 g, 0.01 mmol) was added thereto, and the resultant was agitated at 80° C. for 2 hours. After finishing the reaction, the reaction solution was added with 3 mL of water and extracted with EtOAc. The organic layer was dried with MgSO$_4$ and purified by column chromatography to obtain the title compound (0.028 g, 66%).

1H NMR (CDCl$_3$) δ 7.58 (3H, m), 7.22 (1H, d), 6.66 (1H, d), 5.26 (1H, m), 4.38 (1H, m), 3.70 (3H, s), 2.64 (2H, t), 2.53 (2H, m), 2.19 (2H, m), 2.03 (2H, m), 1.89 (1H, m), 1.74 (1H, m), 1.31 (3H, d)

Step B: 4-[4-[6-(cyclobutoxy)-2-pyridyl]-2,6-difluoro-phenoxy]pentanoic acid

4-[4-[6-(Cyclobutoxy)-2-pyridyl]-2,6-difluoro-phenoxy] pentanoic acid methyl ester (0.027 g, 0.07 mmol) obtained in Step A was used to react in the same manner as in Step B of Example 1 to obtain the title compound (0.02 g, 76%).

1H NMR (CDCl$_3$) δ 7.60 (3H, m), 7.21 (1H, d), 6.65 (1H, d), 5.26 (1H, m), 4.40 (1H, m), 2.70 (2H, t), 2.53 (2H, m), 2.20 (2H, m), 2.05 (2H, m), 1.86 (1H, m), 1.76 (1H, m), 1.32 (3H, d)

Example 30

4-[[5-(2-cyclobutylsulfanyl-3-pyridyl)-2-pyridyl]oxy]pentanoic acid

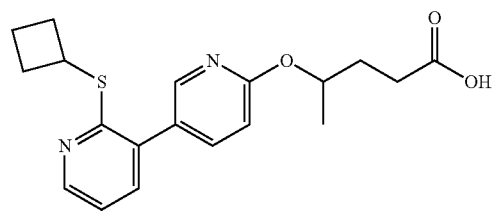 [SMILES: CC(CCC(=O)O)Oc1ccc(-c2cccnc2SC2CCC2)cn1]

Step A: 4-[[5-(2-cyclobutylsulfanyl-3-pyridyl)-2-pyridyl]oxy]pentanoic acid methyl ester 0.6 mL of 1,2-dimethoxyethane was added to 4-[[5-(4,4,5,5-tetramethyl-1,3,2-dioxaborolan-2-yl)-2-pyridyl]oxy] pentanoic acid methyl ester (0.038 g, 0.11 mmol) obtained in Step B of Preparation Example 28, 2-cyclobutylsulfanyl-3-iodo-pyridine (0.033 g, 0.11 mmol) obtained in Step B of Preparation Example 44 and Na$_2$CO$_3$ (2M aqueous solution, 0.17 mL, 0.34 mmol), and N$_2$ gas was charged thereto for 5 minutes. PdCl$_2$(PPh$_3$)$_2$ (0.004 g, 0.005 mmol) was added thereto, and the resultant was agitated at 80° C. for 16 hours. The reactant was added with water and extracted with EtOAc. The organic layer was dried with MgSO$_4$ and purified by column chromatography to obtain the title compound (0.006 g, 14%).

1H NMR (CDCl$_3$) δ 8.40 (1H, m), 8.12 (1H, m), 7.66 (1H, m), 7.35 (1H, m), 7.05 (1H, m), 6.73 (1H, d), 5.29 (1H, m), 4.43 (1H, m), 3.67 (3H, s), 2.50 (4H, m), 2.04 (6H, m), 1.37 (3H, d)

Step B: 4-[[5-(2-cyclobutylsulfanyl-3-pyridyl)-2-pyridyl]oxy]pentanoic acid

4-[[5-(2-Cyclobutylsulfanyl-3-pyridyl)-2-pyridyl]oxy] pentanoic acid methyl ester (0.006 g, 0.016 mmol) obtained in Step A was used to react in the same manner as in Step B of Example 1 to obtain the title compound (0.005 g, 90%).

1H NMR (MeOH-d$_4$) δ 8.56 (1H, m), 8.33 (1H, m), 8.17 (1H, m), 7.98 (1H, m), 7.55 (1H, m), 7.33 (1H, m), 5.23 (1H, m), 4.36 (1H, m), 2.53 (2H, m), 2.46 (2H, m), 2.05 (6H, m), 1.42 (3H, d)

Example 31

4-{2,6-difluoro-4-[2-(3-methyl-butylsulfanyl)-pyridin-3-yl]-phenoxy}-butyric acid

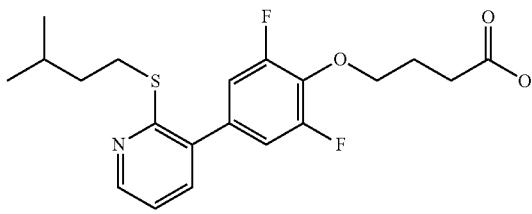 [SMILES: CC(C)CCSc1ncccc1-c1cc(F)c(OCCCC(=O)O)c(F)c1]

3-Methyl-butane-1-thiol (31 mg, 0.29 mmol) and 4-[2,6-difluoro-4-(2-fluoro-3-pyridyl)phenoxy]butyric acid ethyl ester (100 mg, 0.29 mmol) obtained in Preparation Example 109 were used to react sequentially in the same manner as in Preparation Example 5 and Step B of Example 1 to obtain the title compound (75 mg, 60%).

1H NMR (CDCl$_3$) δ 8.43 (1H, m), 7.33 (1H, m), 7.03 (3H, m), 4.26 (2H, t), 3.18 (2H, t), 2.69 (2H, t), 2.14 (2H, m), 1.70 (1H, m), 1.56 (2H, m), 0.93 (6H, d)

Example 32

4-{2,6-difluoro-4-[2-(2-fluoro-ethoxy)-pyridin-3-yl]-phenoxy}-butyric acid

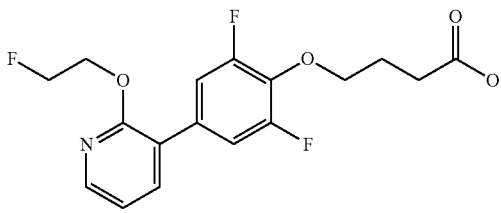 [SMILES: O=C(O)CCCOc1c(F)cc(-c2cccnc2OCCF)cc1F]

2-Fluoro-ethanol (29 mg, 0.45 mmol) and 4-[2,6-difluoro-4-(2-fluoro-3-pyridyl)phenoxy]butyric acid (70 mg, 0.22 mmol) obtained in Preparation Example 56 were used to react in the same manner as in Preparation Example 37 to obtain the title compound (5 mg, 6%).

$^1$H-NMR (CDCl$_3$) δ 8.14 (1H, m), 7.61 (1H, m), 7.18 (2H, m), 6.99 (1H, m), 4.80 (1H, m), 4.69 (1H, m), 4.67 (1H, m), 4.62 (1H, m), 4.25 (2H, t), 2.69 (2H, t), 2.13 (2H, m)

Example 33

2-[1-[[4-(2-cyclobutylsulfanyl-3-pyridyl)-2,6-difluoro-phenoxy]methyl]cyclopropyl]acetic acid

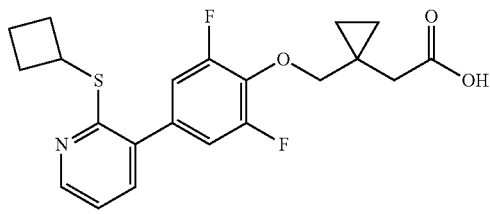 [SMILES: O=C(O)CC1(COc2c(F)cc(-c3cccnc3SC3CCC3)cc2F)CC1]

Step A: 2-[1-[[4-(2-cyclobutylsulfanyl-3-pyridyl)-2,6-difluoro-phenoxy]methyl]cyclopropyl]acetonitrile 2-Cyclobutylsulfanyl-3-iodo-pyridine (0.064 g, 0.22 mmol) obtained in Step B of Preparation Example 44 and 2-[1-[[2,6-difluoro-4-(4,4,5,5-tetramethyl-1,3,2-dioxaborolan-2-yl)phenoxy]methyl]cyclopropyl]acetonitrile (0.092 g, 0.26 mmol) obtained in Step E of Preparation Example 30 were dissolved in 2 mL of 1,2-dimethoxyethane and Na$_2$CO$_3$ (2M aqueous solution, 0.33 mL, 0.66 mmol), and N$_2$ gas was charged thereto for 5 minutes. PdCl$_2$(PPh$_3$)$_2$ (0.008 g, 0.011 mmol) was added thereto, and the resultant was agitated at 80° C. for 2 hours. The reactant was added with water and extracted with EtOAc. The organic layer was dried with MgSO$_4$ and purified by column chromatography to obtain the title compound (0.043 g, 50%).

1H NMR (CDCl$_3$) δ 8.41 (1H, m), 7.33 (1H, m), 7.00 (3H, m), 4.42 (1H, m), 4.06 (2H, s), 2.77 (2H, s), 2.51 (2H, m), 2.04 (4H, m), 0.77 (4H, m)

Step B: 2-[1-[[4-(2-cyclobutylsulfanyl-3-pyridyl)-2,6-difluoro-phenoxy]methyl]cyclopropyl]acetic acid 2-[1-[[4-(2-Cyclobutylsulfanyl-3-pyridyl)-2,6-difluoro-phenoxy]methyl]cyclopropyl]acetonitrile (0.042 g, 0.108 mmol) obtained in Step A was dissolved in 1 mL of ethanol, and NaOH (6M aqueous solution, 0.11 mL, 6.6 mmol) was added thereto. The resultant was agitated at 100° C. for 16 hours. The pH was adjusted to 3 by the use of HCl aqueous solution, and the reactant was then extracted with EtOAc. The organic layer was dried with MgSO$_4$ and purified by column chromatography to obtain the title compound (0.008 g, 18%).

1H NMR (CDCl$_3$) δ 8.41 (1H, m), 7.32 (1H, m), 6.98 (3H, m), 4.41 (1H, m), 4.11 (2H, s), 2.66 (2H, s), 2.52 (2H, m), 2.04 (4H, m), 0.66 (4H, m)

Example 34

2-[1-[[4-[3-(cyclobutoxy)phenyl]-2,6-difluoro-phenoxy]methyl]cyclopropyl]acetic acid

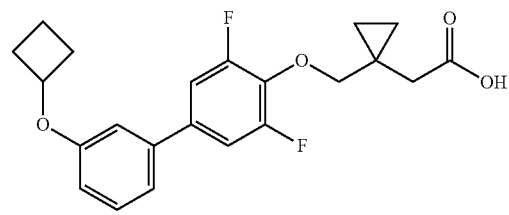 [SMILES: O=C(O)CC1(COc2c(F)cc(-c3cccc(OC4CCC4)c3)cc2F)CC1]

Step A: 2-[1-[[4-[3-(cyclobutoxy)phenyl]-2,6-difluoro-phenoxy]methyl]cyclopropyl]acetonitrile 1-Cyclobutoxy-3-iodo-benzene (0.06 g, 0.22 mmol) obtained in Preparation Example 60 and 2-[1-[[2,6-difluoro-4-(4,4,5,5-tetramethyl-1,3,2-dioxaborolan-2-yl)phenoxy]methyl]cyclopropyl]acetonitrile (0.092 g, 0.26 mmol) obtained in Step E of Preparation Example 30 were dissolved in 2 mL of 1,2-dimethoxyethane and Na$_2$CO$_3$ (2M aqueous solution, 0.33 mL, 0.66 mmol), and N$_2$ gas was charged thereto for 5 minutes. Pd(PPh$_3$)$_4$ (0.025 g, 0.022 mmol) was added thereto, and the resultant was agitated at 80° C. for 3 hours. The reactant was added with water and extracted with EtOAc. The organic layer was dried with MgSO₄ and purified by column chromatography to obtain the title compound (0.067 g, 83%).

1H NMR (CDCl₃) δ 7.31 (1H, t), 7.12 (2H, m), 7.06 (1H, d), 6.94 (1H, m), 6.81 (1H, m), 4.69 (1H, m), 4.03 (2H, s), 2.77 (2H, s), 2.47 (2H, m), 2.20 (2H, m), 1.88 (1H, m), 1.72 (1H, m), 0.74 (4H, m)

Step B: 2-[1-[[4-[3-(cyclobutoxy)phenyl]-2,6-difluoro-phenoxy]methyl]cyclopropyl]acetic acid 2-[1-[[4-[3-(cyclobutoxy)phenyl]-2,6-difluoro-phenoxy]methyl]cyclopropyl]acetonitrile (0.067 g, 0.18 mmol) obtained in Step A was dissolved in 2 mL of EtOH, and NaOH (6M aqueous solution, 0.18 mL, 1.08 mmol) was added thereto. The resultant was agitated at 100° C. for 16 hours. The pH was adjusted to 3 by the use of HCl aqueous solution, and the reactant was then extracted with EtOAc. The organic layer was dried with MgSO₄ and purified by column chromatography to obtain the title compound (0.04 g, 55%).

1H NMR (CDCl₃) δ 7.29 (1H, t), 7.08 (3H, m), 6.93 (1H, m), 6.80 (1H, m), 4.69 (1H, m), 4.11 (2H, s), 2.65 (2H, s), 2.48 (2H, m), 2.19 (2H, m), 1.88 (1H, m), 1.72 (1H, m), 0.66 (4H, m)

Example 35

4-[[6-[3-(cyclobutoxy)phenyl]-3-pyridyl]oxy]butyric acid

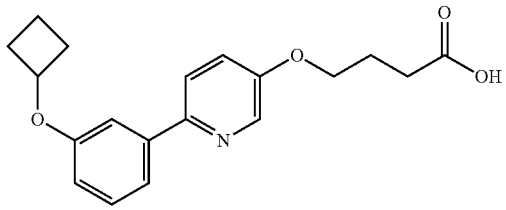 [SMILES: O=C(O)CCCOc1ccc(-c2cccc(OC3CCC3)c2)nc1]

Step A: 4-[[6-[3-(cyclobutoxy)phenyl]-3-pyridyl]oxy]butyric acid ethyl ester

4-[[6-(3-Hydroxyphenyl)-3-pyridyl]oxy]butyric acid ethyl ester (0.061 g, 0.2 mmol) obtained in Step B of Preparation Example 31 was dissolved in 2 mL of DMF and cooled to 0° C. NaH (60% in mineral oil, 0.012 g, 0.3 mmol) was added thereto, and the resultant was agitated at 0° C. for 1 hour. Bromocyclobutane (0.027 g, 0.2 mmol) was added thereto, and the resultant was agitated at 70° C. for 6 hours. After the reaction solution was concentrated under reduced pressure, it was added with water and extracted with EtOAc. The organic layer was dried with MgSO₄ and purified by column chromatography to obtain the title compound (0.014 g, 19%).

1H NMR (CDCl₃) δ 8.35 (1H, m), 7.62 (1H, d), 7.45 (1H, m), 7.41 (1H, m), 7.32 (1H, t), 7.24 (1H, m), 6.83 (1H, m), 4.75 (1H, m), 4.16 (2H, q), 4.10 (2H, t), 2.54 (2H, t), 2.50 (2H, m), 2.17 (4H, m), 1.86 (1H, m), 1.72 (1H, m), 1.27 (3H, t)

Step B: 4-[[6-[3-(cyclobutoxy)phenyl]-3-pyridyl]oxy]butyric acid

4-[[6-[3-(Cyclobutoxy)phenyl]-3-pyridyl]oxy]butyric acid ethyl ester (0.014 g, 0.039 mmol) obtained in Step A was used to react in the same manner as in Step B of Example 1 to obtain the title compound (0.013 g, 99%).

1H NMR (CDCl₃) δ 8.39 (1H, m), 7.62 (1H, d), 7.44 (1H, d), 7.37 (1H, m), 7.32 (1H, t), 7.27 (1H, m), 6.83 (1H, m), 4.74 (1H, m), 4.13 (2H, t), 2.61 (2H, t), 2.48 (2H, m), 2.18 (4H, m), 1.87 (1H, m), 1.70 (1H, m)

Example 36

4-[[6-[3-(cyclopentoxy)phenyl]-3-pyridyl]oxy]butyric acid

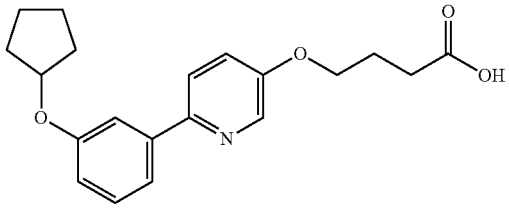 [SMILES: O=C(O)CCCOc1ccc(-c2cccc(OC3CCCC3)c2)nc1]

Step A: 4-[[6-[3-(cyclopentoxy)phenyl]-3-pyridyl]oxy]butyric acid ethyl ester

4-[[6-(3-Hydroxyphenyl)-3-pyridyl]oxy]butyric acid ethyl ester (0.068 g, 0.22 mmol) obtained in Step B of Preparation Example 31 was dissolved in 2 mL of DMF and cooled to 0° C. NaH (60% in mineral oil, 0.013 g, 0.33 mmol) was added thereto, and the resultant was agitated at 0° C. for 1 hour. Bromocyclopentane (0.033 g, 0.2 mmol) was added thereto, and the resultant was agitated at 70° C. for 16 hours. After the reaction solution was concentrated under reduced pressure, it was added with water and extracted with EtOAc. The organic layer was dried with MgSO₄ and purified by column chromatography to obtain the title compound (0.028 g, 34%).

1H NMR (CDCl₃) δ 8.35 (1H, m), 7.63 (1H, d), 7.45 (2H, m), 7.32 (1H, t), 7.25 (1H, m), 6.88 (1H, m), 4.87 (1H, m), 4.16 (2H, q), 4.10 (2H, t), 2.54 (2H, t), 2.15 (2H, m), 1.92 (4H, m), 1.82 (2H, m), 1.62 (2H, m), 1.27 (3H, t)

Step B: 4-[[6-[3-(cyclopentoxy)phenyl]-3-pyridyl]oxy]butyric acid

4-[[6-[3-(Cyclopentoxy)phenyl]-3-pyridyl]oxy]butyric acid ethyl ester (0.028 g, 0.075 mmol) obtained in Step A was used to react in the same manner as in Step B of Example 1 to obtain the title compound (0.02 g, 77%).

1H NMR (CDCl₃+Methanol-d₄) δ 8.68 (1H, m), 7.92 (1H, m), 7.83 (1H, m), 7.48 (3H, m), 7.06 (1H, m), 4.99 (1H, m), 4.29 (2H, t), 2.53 (2H, t), 2.19 (2H, m), 2.00 (2H, m), 1.87 (2H, m), 1.80 (2H, m), 1.64 (2H, m)

Example 37

4-(2'-phenoxy-biphenyl-4-yloxy)-butyric acid

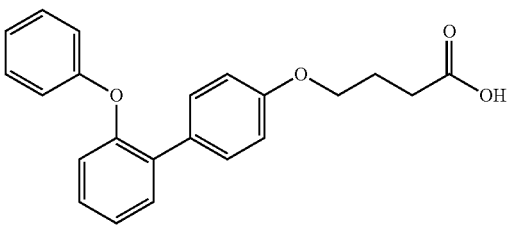 [SMILES: O=C(O)CCCOc1ccc(-c2ccccc2Oc2ccccc2)cc1]

Step A: 4-(2'-phenoxy-biphenyl-4-yloxy)-butyric acid ethyl ester

2'-Phenoxy-biphenyl-4-ol (0.022 g, 0.083 mmol), Cs₂CO₃ (0.055 g, 0.16 mmol) and 4-bromobutyric acid ethyl ester (0.027 g, 0.10 mmol) were dissolved in 2 mL of DMF, and the resultant was agitated at room temperature for 2 hours. Solid was filtered and purified by column chromatography (eluent: EtOAc/Hex=1/4) to obtain the title compound (0.026 g, 86%).

$^1$H-NMR (CDCl₃) δ 7.46 (3H, m), 7.26 (2H, m), 7.19 (1H, m), 7.00 (3H, m), 6.89 (2H, m), 6.84 (2H, m), 4.15 (2H, q), 4.00 (2H, t), 2.50 (2H, t), 2.10 (2H, m), 1.25 (3H, t)

Step B: 4-(2'-phenoxy-biphenyl-4-yloxy)-butyric acid 4-(2'-Phenoxy-biphenyl-4-yloxy)-butyric acid ethyl ester (26 mg, 0.071 mmol) obtained in Step A was dissolved in each 1 mL of 1N NaOH, TFH and MeOH, and the resultant was agitated at room temperature for 3 hours. After removing organic solvent, the pH was adjusted to 3 by the use of 1N HCl, and the resultant was extracted with EtOAc. The organic layer was dried with anhydrous MgSO₄ and purified by column chromatography (eluent: EtOAc/Hex=1/2) to obtain the title compound (0.018 g, 75%).

1H-NMR (MeOD) δ 7.46 (3H, m), 7.31 (1H, m), 7.25 (3H, m), 7.01 (2H, m), 6.89 (2H, d), 6.82 (2H, d), 4.02 (2H, t), 2.48 (2H, t), 2.04 (2H, m)

Example 38

4-[4-(2-isopropylsulfanyl-pyridin-3-yl)-phenoxy]-butyric acid

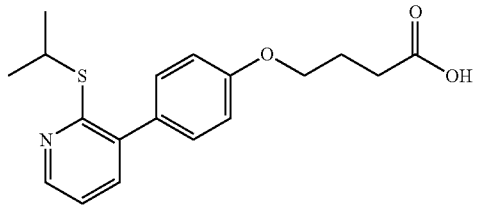 [SMILES: CC(C)Sc1ncccc1-c1ccc(OCCCC(=O)O)cc1]

Step A: 4-[4-(2-isopropylsulfanyl-pyridin-3-yl)-phenoxy]-butyric acid ethyl ester 4-(2-Isopropylsulfanyl-pyridin-3-yl)-phenol (0.015 g, 0.061 mmol) obtained in Preparation Example 33, cesium carbonate (0.04 g, 0.12 mmol) and 4-bromobutyric acid ethyl ester (0.014 g, 0.07 mmol) were dissolved in 2 mL of DMF, and the resultant was agitated at room temperature for 24 hours. The reaction solution was added with NaCl aqueous solution and extracted with EtOAc to separate the organic layer. The organic layer was dried with anhydrous MgSO₄ and purified by column chromatography (eluent: EtOAc/Hex=1/4) to obtain the title compound (0.01 g, 45%).

$^1$H-NMR (CDCl₃) δ 8.41 (1H, m), 7.32 (3H, m), 7.02 (1H, m), 6.94 (2H, m), 4.16 (2H, q), 4.04 (3H, m), 2.53 (2H, t), 2.13 (2H, m), 1.35 (6H, d), 1.27 (3H, t)

Step B: 4-[4-(2-isopropylsulfanyl-pyridin-3-yl)-phenoxy]-butyric acid

4-[4-(2-Isopropylsulfanyl-pyridin-3-yl)-phenoxy]-butyric acid ethyl ester (0.01 g, 0.02 mmol) obtained in Step A was used to react in the same manner as in Step B of Example 37 to obtain the title compound (0.006 g, 65%).

$^1$H-NMR (CDCl₃) δ 8.41 (1H, m), 7.32 (3H, m), 7.02 (1H, m), 6.95 (2H, m), 4.06 (3H, m), 2.62 (2H, t), 2.15 (2H, m), 1.35 (6H, d)

Example 39

4-(3,5-difluoro-2'-phenoxy-biphenyl-4-yloxy)-butyric acid

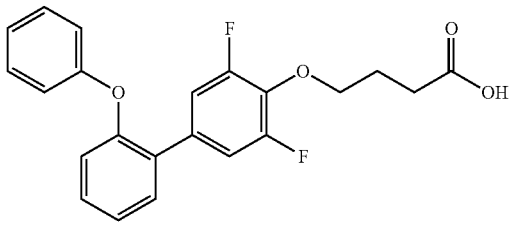

Step A: 4-(3,5-difluoro-2'-phenoxy-biphenyl-4-yloxy)-butyric acid ethyl ester 3,5-Difluoro-2'-phenoxy-biphenyl-4-ol (0.017 g, 0.056 mmol) obtained in Preparation Example 34 and 4-bromobutyric acid ethyl ester (0.013 g, 0.068 mmol) were used to react in the same manner as in Step A of Example 37 to obtain the title compound (0.023 g, 95%).

$^1$H-NMR (CDCl₃) δ 7.40 (1H, m), 7.30 (3H, m), 7.20 (1H, m), 7.11 (2H, m), 7.05 (1H, m), 6.97 (1H, m), 6.91 (2H, m), 4.15 (4H, m), 2.56 (2H, t), 2.07 (2H, m), 1.27 (3H, t)

Step B: 4-(3,5-difluoro-2'-phenoxy-biphenyl-4-yloxy)-butyric acid 4-(3,5-Difluoro-2'-phenoxy-biphenyl-4-yloxy)-butyric acid ethyl ester (0.022 g, 0.053 mmol) obtained in Step A was used to react in the same manner as in Step B of Example 37 to obtain the title compound (0.014 g, 69%).

$^1$H-NMR (CDCl₃) δ 7.40 (1H, m), 7.30 (3H, m), 7.20 (1H, m), 7.11 (2H, m), 7.05 (1H, m), 6.97 (1H, m), 6.91 (2H, d), 4.19 (2H, t), 2.64 (2H, t), 2.08 (2H, m)

Example 40

4-[4-(2-cyclopentylsulfanyl-pyridin-3-yl)-phenoxy]-butyric acid

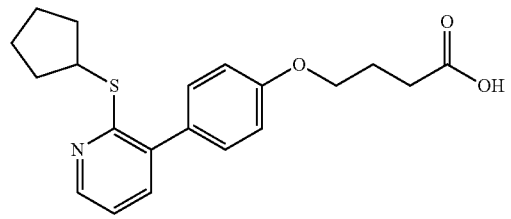 [SMILES: O=C(O)CCCOc1ccc(-c2cccnc2SC2CCCC2)cc1]

Step A: 4-[4-(2-cyclopentylsulfanyl-pyridin-3-yl)-phenoxy]-butyric acid ethyl ester 4-(2-Cyclopentylsulfanyl-pyridin-3-yl)-phenol (0.024 g, 0.088 mmol) obtained in Preparation Example 35 was to react in the same manner as in Step A of Example 38 to obtain the title compound (0.03 g, 88%).

¹H-NMR (CDCl₃) δ 8.38 (1H, m), 7.32 (3H, m), 7.01 (1H, m), 6.94 (2H, m), 4.14 (2H, q), 4.05 (3H, m), 2.52 (2H, t), 2.13 (4H, m), 1.60 (2H, m), 1.66 (4H, m), 1.26 (3H, t)

Step B: 4-[4-(2-cyclopentylsulfanyl-pyridin-3-yl)-phenoxy]-butyric acid

4-[4-(2-Cyclopentylsulfanyl-pyridin-3-yl)-phenoxy]-butyric acid ethyl ester (0.03 g, 0.077 mmol) obtained in Step A was used to react in the same manner as in Step B of Example 37 to obtain the title compound (0.017 g, 63%).

¹H-NMR (CDCl₃) δ 8.40 (1H, m), 7.32 (3H, m), 7.01 (1H, m), 6.95 (2H, m), 4.07 (3H, m), 2.62 (2H, t), 2.15 (4H, m), 1.69 (2H, m), 1.58 (4H, m)

Example 41

4-[2,6-difluoro-4-(2-isopropylsulfanyl-pyridin-3-yl)-phenoxy]-butyric acid

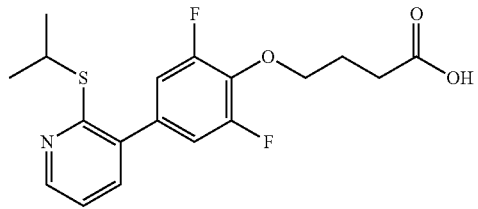 [SMILES: CC(C)Sc1ncccc1-c1cc(F)c(OCCCC(=O)O)c(F)c1]

2,6-Difluoro-4-(2-isopropylsulfanyl-pyridin-3-yl)-phenol (0.015 g, 0.053 mmol) obtained in Preparation Example 63 was used to react in the same manner as in Steps A and B of Example 38 to obtain the title compound (0.005 g, 27%).

¹H-NMR (CDCl₃) δ 8.44 (1H, m), 7.32 (1H, m), 7.03 (1H, m), 6.99 (2H, m), 4.25 (2H, t), 4.06 (1H, m), 2.67 (2H, t), 2.13 (2H, m), 1.37 (6H, d)

Example 42

4-[2,6-difluoro-4-(2-phenoxy-pyridin-3-yl)-phenoxy]-butyric acid

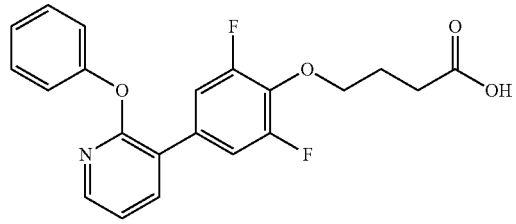 [SMILES: O=C(O)CCCOc1c(F)cc(-c2cccnc2Oc2ccccc2)cc1F]

3-Iodo-2-phenoxy-pyridine (0.043 g, 0.144 mmol) obtained in Preparation Example 36 and 4-[2,6-difluoro-4-(4,4,5,5-tetramethyl-1,3,2-dioxaborolan-2-yl)phenoxy]butyric acid ethyl ester (0.048 g, 0.131 mmol) obtained in Preparation Example 2 were used to react sequentially in the same manner as in Step B of Preparation Example 33 and Step B of Example 1 to obtain the title compound (0.004 g, 7%).

¹H-NMR (CDCl₃) δ 8.42 (1H, m), 7.12 (1H, m), 7.40 (2H, m), 7.22 (3H, m), 7.11 (3H, m), 4.23 (2H, t), 2.65 (2H, t), 2.11 (2H, m)

Example 43

4-[2,6-difluoro-4-(2-isopropoxy-pyridin-3-yl)-phenoxy]-butyric acid

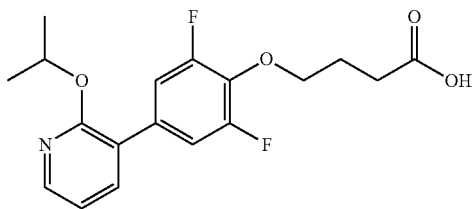 [SMILES: CC(C)Oc1ncccc1-c1cc(F)c(OCCCC(=O)O)c(F)c1]

3-Iodo-2-isopropoxy-pyridine (0.029 g, 0.11 mmol) obtained in Preparation Example 37 and 4-[2,6-difluoro-4-(4,4,5,5-tetramethyl-1,3,2-dioxaborolan-2-yl)phenoxy]butyric acid ethyl ester (0.034 g, 0.091 mmol) obtained in Preparation Example 2 were used to react in the same manner as in Steps A and B of Example 1 to obtain the title compound (0.011 g, 21%).

¹H-NMR (CDCl₃) δ 8.14 (1H, m), 7.55 (1H, m), 7.15 (2H, m), 6.91 (1H, m), 5.41 (1H, m), 4.24 (2H, t), 2.67 (2H, t), 2.13 (2H, m), 1.37 (6H, d)

Example 44

4-[4-(2-cyclopentyloxy-pyridin-3-yl)-2,6-difluoro-phenoxy]-butyric acid

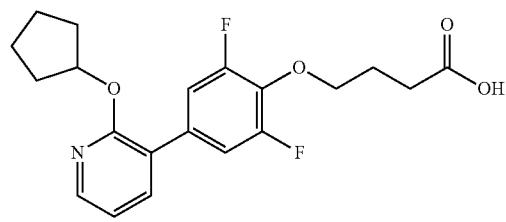 [SMILES: O=C(O)CCCOc1c(F)cc(-c2cccnc2OC2CCCC2)cc1F]

2-Cyclopentoxy-3-iodo-pyridine (0.042 g, 0.14 mmol) obtained in Preparation Example 38 and 4-[2,6-difluoro-4-(4,4,5,5-tetramethyl-1,3,2-dioxaborolan-2-yl)phenoxy]butyric acid ethyl ester (0.045 g, 0.121 mmol) obtained in Preparation Example 2 were used to react in the same manner as in Steps A and B of Example 1 to obtain the title compound (0.021 g, 41%).

¹H-NMR (CDCl₃) δ 8.14 (1H, m), 7.55 (1H, m), 7.15 (2H, m), 6.91 (1H, m), 5.52 (1H, m), 4.24 (2H, t), 2.67 (2H, t), 2.13 (2H, m), 1.95 (2H, m), 1.78 (4H, m), 1.65 (2H, m)

Example 45

4-[4-(2-cyclopentylsulfanyl-pyridin-3-yl)-2,6-difluoro-phenoxy]-butyric acid

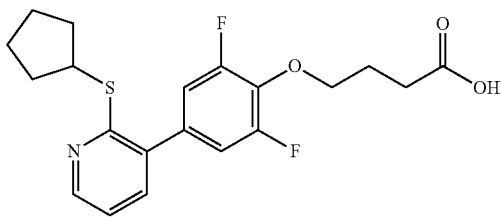 [SMILES: O=C(O)CCCOc1c(F)cc(-c2cccnc2SC2CCCC2)cc1F]

2-Cyclopentylsulfanyl-3-iodo-pyridine (0.026 g, 0.09 mmol) obtained in Preparation Example 39 and 4-[2,6-difluoro-4-(4,4,5,5-tetramethyl-1,3,2-dioxaborolan-2-yl)phenoxy]butyric acid ethyl ester (0.031 g, 0.083 mmol) obtained in Preparation Example 2 were used to react in the same manner as in Steps A and B of Example 1 to obtain the title compound (0.009 g, 25%).

$^1$H-NMR (CDCl$_3$) δ 8.42 (1H, m), 7.30 (1H, m), 7.02 (3H, m), 4.25 (2H, t), 4.07 (1H, m), 2.67 (2H, t), 2.15 (4H, m), 1.69 (2H, m), 1.58 (4H, m)

Example 46

4-[4-(2-cyclopropylmethoxy-pyridin-3-yl)-2,6-difluoro-phenoxy]-butyric acid

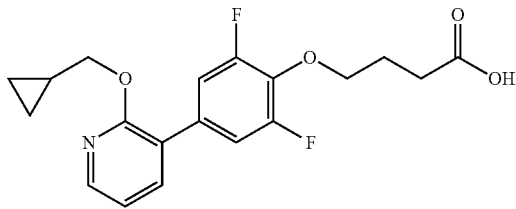 [SMILES: O=C(O)CCCOc1c(F)cc(-c2cccnc2OCC2CC2)cc1F]

2-Cyclopropylmethoxy-3-iodo-pyridine (0.05 g, 0.181 mmol) obtained in Preparation Example 40 and 4-[2,6-difluoro-4-(4,4,5,5-tetramethyl-1,3,2-dioxaborolan-2-yl)phenoxy]butyric acid ethyl ester (0.061 g, 0.165 mmol) obtained in Step C of Preparation Example 2 were used to react sequentially in the same manner as in Steps A and B of Example 1 to obtain the title compound (0.022 g, 34%).

$^1$H-NMR (CDCl$_3$) δ 8.12 (1H, m), 7.57 (1H, m), 7.20 (2H, m), 6.94 (1H, m), 4.23 (4H, m), 2.67 (2H, t), 2.12 (2H, m), 1.42 (1H, m), 0.59 (2H, m), 0.34 (2H, m)

Example 47

4-[4-(2-cyclopropylmethylsulfanyl-pyridin-3-yl)-2,6-difluoro-phenoxy]-butyric acid

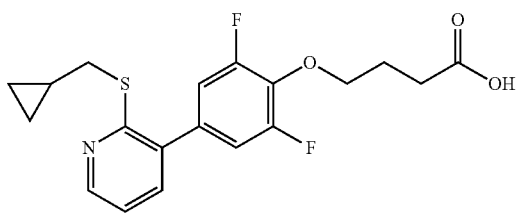 [SMILES: O=C(O)CCCOc1c(F)cc(-c2cccnc2SCC2CC2)cc1F]

2-Cyclopropylmethylsulfanyl-3-(3,5-difluoro-4-methoxy-phenyl)-pyridine (0.033 g, 0.107 mmol) obtained in Preparation Example 41 was used to react sequentially in the same manner as in Step C of Preparation Example 33, Step A of Example 38 and Step B of Example 37 to obtain the title compound (0.0088 g, 13%).

$^1$H-NMR (CDCl$_3$) δ 8.40 (1H, m), 7.31 (1H, m), 7.02 (3H, m), 4.26 (2H, m), 3.11 (2H, m), 2.69 (2H, m), 2.15 (2H, m), 1.15 (1H, m), 0.57 (2H, m), 0.34 (2H, m)

Example 48

4-[4-(2-cyclobutylsulfanyl-pyridin-3-yl)-phenoxy]-butyric acid

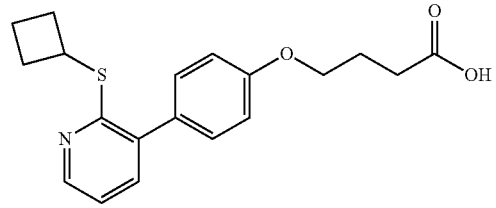 [SMILES: O=C(O)CCCOc1ccc(-c2cccnc2SC2CCC2)cc1]

2-Cyclobutylsulfanyl-3-(4-methoxy-phenyl)-pyridine (0.009 g, 0.034 mmol) obtained in Preparation Example 42 was used to react sequentially in the same manner as in Step C of Preparation Example 33, Step A of Example 38 and Step B of Example 37 to obtain the title compound (0.0034 g, 28%).

$^1$H-NMR (CDCl$_3$) δ 8.38 (1H, m), 7.34 (3H, m), 7.02 (3H, m), 4.42 (1H, m), 4.08 (2H, m), 2.62 (2H, m), 2.49 (2H, m), 2.16 (2H, m), 2.01 (4H, m)

Example 49

4-[4-(2-cyclopropylmethylsulfanyl-pyridin-3-yl)-phenoxy]-butyric acid

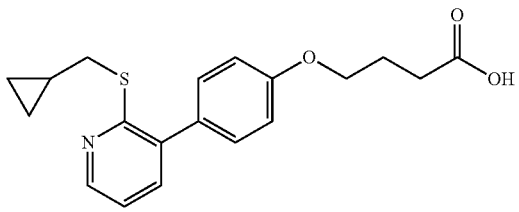

2-Cyclopropylmethylsulfanyl-3-(4-methoxy-phenyl)-pyridine (0.02 g, 0.073 mmol) obtained in Preparation Example 43 was used to react sequentially in the same manner as in Step C of Preparation Example 33, Step A of Example 38 and Step B of Example 37 to obtain the title compound (0.0031 g, 12%).

$^1$H-NMR (CDCl$_3$) δ 8.40 (1H, m), 7.37 (3H, m), 7.02 (3H, m), 4.09 (2H, m), 3.09 (2H, m), 2.63 (2H, m), 2.13 (2H, m), 1.09 (1H, m), 0.54 (2H, m), 0.27 (2H, m)

Example 50

4-[4-(2-cyclobutylsulfanyl-pyridin-3-yl)-2,6-difluoro-phenoxy]-butyric acid

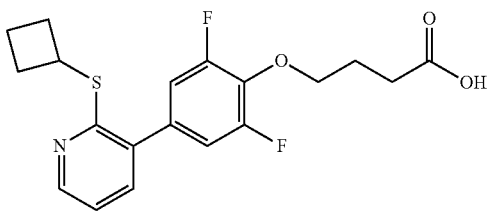 [SMILES: O=C(O)CCCOc1c(F)cc(-c2cccnc2SC2CCC2)cc1F]

Step A: 4-[4-(2-cyclobutylsulfanyl-pyridin-3-yl)-2,6-difluoro-phenoxy]-butyric acid ethyl ester 2-Cyclobutylsulfanyl-3-iodo-pyridine (0.15 g, 0.394 mmol) obtained in Preparation Example 44 and ethyl 4-[2,6-difluoro-4-(4,4,5,5-tetramethyl-1,3,2-dioxaborolan-2-yl)phenoxy]butyric acid ethyl ester (0.12 g, 0.329 mmol) obtained in Preparation Example 2 were dissolved in 1 mL of 2M $Na_2CO_3$ aqueous solution and 2 mL of 1,2-dimethoxyethane, and $N_2$ gas was charged thereto for 5 minutes. $PdCl_2(PPh_3)_2$ (0.012 g, 0.016 mmol) was added thereto and the resultant was agitated under reflux for 5 hours. After finishing the reaction, the resultant was diluted with water and extracted with EtOAc. The organic layer was dried with $MgSO_4$ and purified by column chromatography (eluent: EtOAc/Hex=1/4) to obtain the title compound (0.084 g, 62%).

$^1$H-NMR ($CDCl_3$) δ 8.41 (1H, m), 7.32 (1H, m), 7.01 (3H, m), 4.42 (1H, m), 4.24 (2H, m), 4.16 (2H, q), 2.59 (2H, m), 2.69 (2H, m), 2.13 (3H, m), 2.06 (3H, m), 1.28 (3H, t)

Step B: 4-[4-(2-cyclobutylsulfanyl-pyridin-3-yl)-2,6-difluoro-phenoxy]-butyric acid 4-[4-(2-Cyclobutylsulfanyl-pyridin-3-yl)-2,6-difluoro-phenoxy]-butyric acid ethyl ester (0.068 g, 0.166 mmol) obtained Step A was reacted in the same manner as in Step B of Example 37 to obtain the title compound (0.031 g, 50%).

$^1$H-NMR ($CDCl_3$) δ 8.41 (1H, m), 7.32 (1H, m), 7.01 (3H, m), 4.41 (1H, m), 4.26 (2H, m), 2.69 (2H, m), 2.51 (2H, m), 2.15 (3H, m), 2.06 (3H, m)

Example 51

4-[4-(2-propylsulfanyl-pyridin-3-yl)-phenoxy]-butyric acid

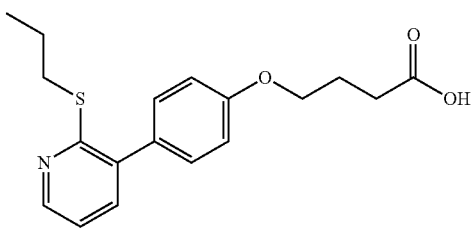 [SMILES: CCCSc1ncccc1-c1ccc(OCCCC(=O)O)cc1]

3-(4-Methoxy-phenyl)-2-propylsulfanyl-pyridine (0.023 g, 0.088 mmol) obtained in Preparation Example 45 was used to react sequentially in the same manner as in Step C of Preparation Example 33, Step A of Example 38 and Step B of Example 37 to obtain the title compound (0.005 g, 18%).

$^1$H-NMR ($CDCl_3$) δ 8.40 (1H, m), 7.34 (3H, m), 7.02 (1H, m), 6.95 (2H, m), 4.08 (2H, m), 3.12 (2H, m), 2.62 (2H, m), 2.16 (2H, m), 1.70 (2H, m), 1.00 (3H, t)

Example 52

4-(3,5-difluoro-2'-isopropoxy-biphenyl-4-yloxy)-butyric acid

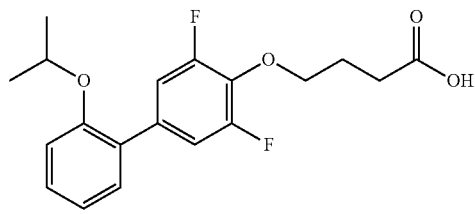 [SMILES: CC(C)Oc1ccccc1-c1cc(F)c(OCCCC(=O)O)c(F)c1]

1-Bromo-2-isopropoxy-benzene (0.051 g, 0.237 mmol) obtained in Preparation Example 46 and 4-[2,6-difluoro-4-(4,4,5,5-tetramethyl-1,3,2-dioxaborolan-2-yl)phenoxy]butyric acid ethyl ester (0.067 g, 0.182 mmol) obtained in Preparation Example 2 were used to react sequentially in the same manner as in Step A of Example 50 and Step B of Example 37 to obtain the title compound (0.022 g, 35%).

$^1$H-NMR ($CDCl_3$) δ 7.28 (2H, m), 7.14 (2H, m), 6.98 (2H, m), 4.49 (1H, m), 4.23 (2H, t), 2.69 (2H, m), 2.12 (2H, m), 1.29 (6H, d)

Example 53

4-(2'-cyclobutoxy-3,5-difluoro-biphenyl-4-yloxy)-butyric acid

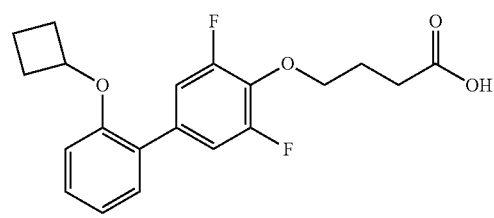 [SMILES: O=C(O)CCCOc1c(F)cc(-c2ccccc2OC2CCC2)cc1F]

1-Bromo-2-cyclobutoxy-benzene (0.023 g, 0.101 mmol) obtained in Preparation Example 47 and 4-[2,6-difluoro-4-(4,4,5,5-tetramethyl-1,3,2-dioxaborolan-2-yl)phenoxy]butyric acid ethyl ester (0.029 g, 0.0779 mmol) obtained in Preparation Example 2 were used to react sequentially in the same manner as in Step A of Example 50 and Step B of Example 37 to obtain the title compound (0.01 g, 35%).

$^1$H-NMR ($CDCl_3$) δ 7.28 (2H, m), 7.15 (2H, m), 6.99 (1H, m), 6.80 (1H, m), 4.65 (1H, m), 4.23 (2H, m), 2.68 (2H, m), 2.44 (2H, m), 2.17 (4H, m), 1.85 (1H, m), 1.70 (1H, m)

Example 54

4-(2'-cyclopropylmethoxy-3,5-difluoro-biphenyl-4-yloxy)-butyric acid

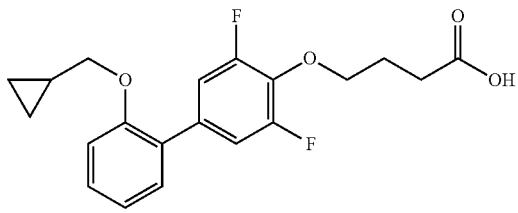 [SMILES: O=C(O)CCCOc1c(F)cc(-c2ccccc2OCC2CC2)cc1F]

1-Bromo-2-cyclopropylmethoxy-benzene (0.054 g, 0.23 mmol) obtained in Preparation Example 48 and 4-[2,6-difluoro-4-(4,4,5,5-tetramethyl-1,3,2-dioxaborolan-2-yl)phenoxy]butyric acid ethyl ester (0.067 g, 0.182 mmol) obtained in Preparation Example 2 was used to react sequentially in the same manner as in Step A of Example 50 and Step B of Example 37 to obtain the title compound (0.021 g, 32%).

$^1$H-NMR (CDCl$_3$) δ 7.29 (2H, m), 7.16 (2H, m), 6.99 (1H, m), 6.94 (1H, m), 4.23 (2H, m), 3.83 (2H, m), 2.69 (2H, m), 2.13 (2H, m), 1.22 (1H, m), 0.61 (2H, m), 0.31 (2H, m)

Example 55

4-(2'-cyclopentyloxy-3,5-difluoro-biphenyl-4-yloxy)-butyric acid

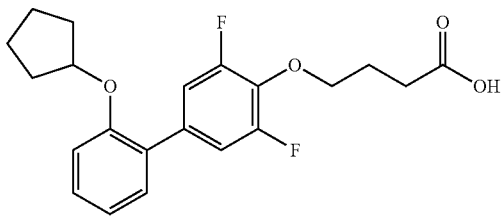 [SMILES: O=C(O)CCCOc1c(F)cc(-c2ccccc2OC2CCCC2)cc1F]

1-Bromo-2-cyclopentoxy-benzene (0.079 g, 0.33 mmol) obtained in Preparation Example 49 and 4-[2,6-difluoro-4-(4,4,5,5-tetramethyl-1,3,2-dioxaborolan-2-yl)phenoxy]butyric acid ethyl ester (0.093 g, 0.25 mmol) obtained in Preparation Example 2 were used to react sequentially in the same manner as in Step A of Example 50 and Step B of Example 37 to obtain the title compound (0.047 g, 50%).

$^1$H-NMR (CDCl$_3$) δ 7.28 (2H, m), 7.13 (2H, m), 6.96 (2H, m), 4.77 (1H, m), 4.23 (2H, m), 2.68 (2H, t), 2.12 (2H, m), 1.86 (4H, m), 1.64 (2H, m), 1.55 (2H, m)

Example 56

4-(2'-cyclopentyloxy-biphenyl-4-yloxy)-butyric acid

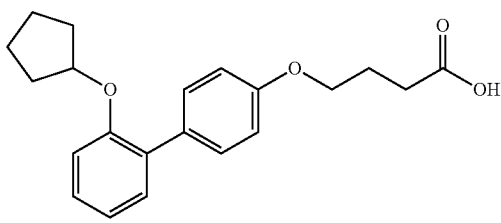 [SMILES: O=C(O)CCCOc1ccc(-c2ccccc2OC2CCCC2)cc1]

1-Bromo-2-cyclopentoxy-benzene (0.063 g, 0.26 mmol) obtained in Preparation Example 49 and 4-[4-(4,4,5,5-tetramethyl-1,3,2-dioxaborolan-2-yl)phenoxy]butyric acid ethyl ester (0.067 g, 0.20 mmol) obtained in Preparation Example 1 were used to react sequentially in the same manner as in Step A of Example 50 and Step B of Example 37 to obtain the title compound (0.027 g, 39%).

$^1$H-NMR (CDCl$_3$) δ 7.46 (2H, m), 7.28 (2H, m), 6.97 (2H, m), 6.89 (2H, m), 4.74 (1H, m), 4.07 (2H, m), 2.62 (2H, t), 2.15 (2H, m), 1.82 (4H, m), 1.64 (2H, m), 1.55 (2H, m)

Example 57

4-(2'-isopropoxy-biphenyl-4-yloxy)-butyric acid

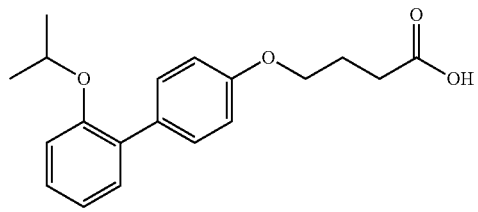 [SMILES: CC(C)Oc1ccccc1-c1ccc(OCCCC(=O)O)cc1]

1-Bromo-2-isopropoxy-benzene (0.058 g, 0.26 mmol) obtained in Preparation Example 46 and 4-[4-(4,4,5,5-tetramethyl-1,3,2-dioxaborolan-2-yl)phenoxy]butyric acid ethyl ester (0.069 g, 0.20 mmol) obtained in Preparation Example 1 were used to react sequentially in the same manner as in Step A of Example 50 and Step B of Example 37 to obtain the title compound (0.026 g, 40%).

$^1$H-NMR (CDCl$_3$) δ 7.48 (2H, m), 7.28 (2H, m), 6.96 (2H, m), 6.90 (2H, m), 4.41 (1H, m), 4.06 (2H, m), 2.61 (2H, t), 2.14 (2H, m), 1.24 (6H, d)

Example 58

4-(2'-cyclopropylmethoxy-biphenyl-4-yloxy)-butyric acid

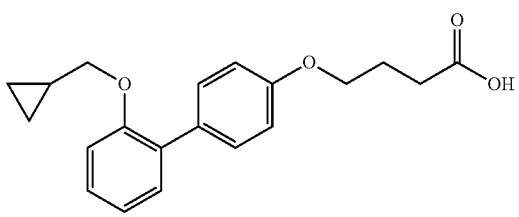 [SMILES: O=C(O)CCCOc1ccc(-c2ccccc2OCC2CC2)cc1]

1-Bromo-2-cyclopropylmethoxy-benzene (0.059 g, 0.26 mmol) obtained in Preparation Example 48 and 4-[4-(4,4,5,5-tetramethyl-1,3,2-dioxaborolan-2-yl)phenoxy]butyric acid ethyl ester (0.066 g, 0.19 mmol) obtained in Preparation Example 1 were used to react sequentially in the same manner as in Step A of Example 50 and Step B of Example 37 to obtain the title compound (0.024 g, 36%).

$^1$H-NMR (CDCl$_3$) δ 7.51 (2H, m), 7.29 (2H, m), 6.99 (2H, m), 6.92 (2H, m), 4.06 (2H, m), 3.79 (2H, d), 2.61 (2H, t), 2.14 (2H, m), 1.19 (1H, m), 0.55 (2H, m), 0.26 (2H, m)

Example 59

4-[4-(2-cyclobutylsulfanyl-pyridin-3-yl)-2,6-difluoro-phenoxy]-2-methyl-butyric acid

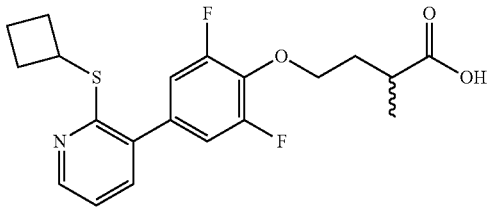 [SMILES: CC(CCOc1c(F)cc(-c2cccnc2SC2CCC2)cc1F)C(=O)O]

4-(2-Cyclobutylsulfanyl-pyridin-3-yl)-2,6-difluoro-phenol (0.078 g, 0.26 mmol) obtained in Preparation Example 51 and 4-bromo-2-methyl-butyric acid ethyl ester (0.055 g, 0.266 mmol) obtained in Preparation Example 50 were used to react sequentially in the same manner as in Steps A and B of Example 37 to obtain the title compound (0.043 g, 40%).

$^1$H-NMR (CDCl$_3$) δ 8.40 (1H, m), 7.30 (1H, m), 6.98 (3H, m), 4.41 (1H, m), 4.26 (2H, m), 2.89 (1H, m), 2.50 (2H, m), 2.25 (1H, m), 2.02 (4H, m), 1.90 (1H, m), 1.31 (3H, d)

Example 60

2-[4-(2-cyclobutylsulfanyl-pyridin-3-yl)-2,6-difluoro-phenoxymethyl]-cyclopropanecarboxylic acid

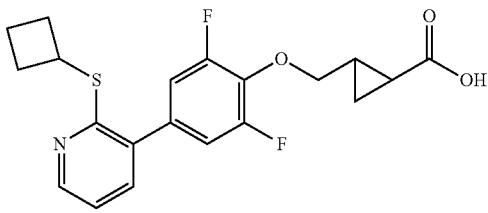 [SMILES: O=C(O)C1CC1COc1c(F)cc(-c2cccnc2SC2CCC2)cc1F]

2-Cyclobutylsulfanyl-3-iodo-pyridine (0.035 g, 0.12 mmol) obtained in Preparation Example 44 and 2-[2,6-difluoro-4-(4,4,5,5-tetramethyl-[1,3,2]dioxaborolan-2-yl)-phenoxymethyl]-cyclopropanecarboxylic acid ethyl ester (0.042 g, 0.112 mmol) obtained in Step D of Preparation Example 52 were used to react sequentially in the same manner as in Step A of Example 50 and Step B of Example 37 to obtain the title compound (0.013 g, 27%).

$^1$H-NMR (CDCl$_3$) δ 8.40 (1H, m), 7.32 (1H, m), 7.00 (3H, m), 4.40 (1H, m), 4.16 (1H, m), 4.05 (1H, m), 2.50 (2H, m), 2.03 (5H, m), 1.72 (1H, m), 1.35 (1H, m), 1.06 (1H, m)

Example 61

4-[4-(2-cyclobutylsulfanyl-pyridin-3-yl)-2,5-difluoro-phenoxy]-butyric acid

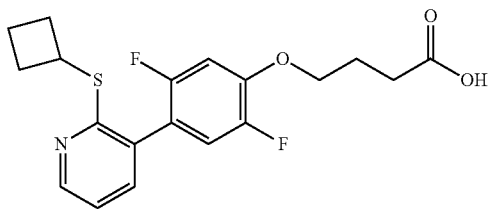 [SMILES: O=C(O)CCCOc1cc(F)c(-c2cccnc2SC2CCC2)cc1F]

2-Cyclobutylsulfanyl-3-iodo-pyridine (0.11 g, 0.38 mmol) obtained in Preparation Example 44 and 4-[2,5-difluoro-4-(4,4,5,5-tetramethyl-[1,3,2]dioxaborolan-2-yl)-phenoxy]-butyric acid ethyl ester (0.132 g, 0.35 mmol) obtained in Step C of Preparation Example 53 were used to react sequentially in the same manner as in Step A of Example 50 and Step B of Example 37 to obtain the title compound (0.061 g, 44%).

$^1$H-NMR (CDCl$_3$) δ 8.41 (1H, m), 7.35 (1H, m), 7.00 (2H, m), 6.78 (1H, m), 4.41 (1H, m), 4.11 (2H, m), 2.64 (2H, m), 2.48 (2H, m), 2.19 (2H, m), 2.02 (4H, m)

Example 62

4-[4-(6-cyclobutylsulfanyl-pyridin-2-yl)-2,5-difluoro-phenoxy]-butyric acid

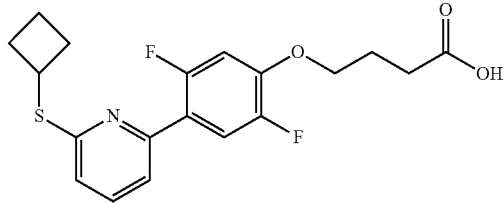 [SMILES: O=C(O)CCCOc1cc(F)c(-c2cccc(SC3CCC3)n2)cc1F]

2-Chloro-6-cyclobutylsulfanyl-pyridine (0.081 g, 0.40 mmol) obtained in Preparation Example 19 and 4-[2,5-difluoro-4-(4,4,5,5-tetramethyl-[1,3,2]dioxaborolan-2-yl)-phenoxy]-butyric acid ethyl ester (0.14 g, 0.37 mmol) obtained in Step C of Preparation Example 53 were used to react sequentially in the same manner as in Step A of Example 50 and Step B of Example 37 to obtain the title compound (0.057 g, 39%).

1H-NMR δ (CDCl$_3$) 7.89 (1H, m), 7.49 (2H, m), 7.00 (1H, m), 6.78 (1H, m), 4.38 (1H, m), 4.11 (2H, m), 2.63 (4H, m), 2.19 (6H, m)

Example 63

4-[4-(2-tert-butylsulfanyl-pyridin-3-yl)-2,6-difluorophenoxy]-butyric acid

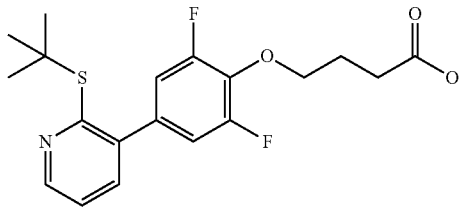 [SMILES: CC(C)(C)Sc1ncccc1-c1cc(F)c(OCCCC(=O)O)c(F)c1]

2-Methyl-propane-2-thiol (27 mg, 0.29 mmol) and 4-[2,6-difluoro-4-(2-fluoro-3-pyridyl)phenoxy]butyric acid ethyl ester (100 mg, 0.29 mmol) obtained in Preparation Example 109 were used to react sequentially in the same manner as in Preparation Example 5 and Step B of Example 1 to obtain the title compound (55 mg, 46%).

1H NMR (CDCl$_3$) δ 8.45 (1H, m), 7.33 (1H, m), 7.04 (1H, m), 6.95 (2H, m), 4.27 (2H, t), 2.69 (2H, t), 2.15 (2H, m), 1.55 (9H, s)

Example 64

6-[2,6-difluoro-4-(2-propylsulfanyl-3-pyridyl)phenoxy]hexanoic acid

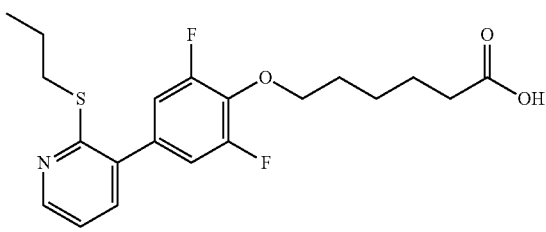 [SMILES: CCCSc1ncccc1-c1cc(F)c(OCCCCCC(=O)O)c(F)c1]

Step A: ethyl 6-[2,6-difluoro-4-(2-propylsulfanyl-3-pyridyl)phenoxy]hexanoate

3-Iodo-2-propylsulfanyl-pyridine (0.073 g, 0.26 mmol) obtained in Preparation Example 203 and ethyl 6-[2,6-difluoro-4-(4,4,5,5-tetramethyl-1,3,2-dioxaborolan-2-yl)phenoxy]hexanoate (0.11 g, 0.27 mmol) obtained in Preparation Example 146 were used to react in the same manner as in Step A of Example 28 to obtain the title compound (0.076 g, 69%).

$^1$H-NMR (CDCl$_3$) δ 8.43 (1H, m), 7.33 (1H, m), 7.04 (1H, m), 7.00 (2H, m), 4.19 (2H, t), 4.13 (2H, q), 3.14 (2H, t), 2.34 (2H, t), 1.81 (2H, m), 1.73 (4H, m), 1.53 (2H, m), 1.28 (3H, t), 1.02 (3H, t)

Step B: 6-[2,6-difluoro-4-(2-propylsulfanyl-3-pyridyl)phenoxy]hexanoic acid

Ethyl 6-[2,6-difluoro-4-(2-propylsulfanyl-3-pyridyl)phenoxy]hexanoate (0.076 g, 0.18 mmol) obtained in Step A was used to react in the same manner as in Step B of Example 1 to obtain the title compound (0.068 g, 96%).

$^1$H-NMR (CDCl$_3$) δ 8.44 (1H, m), 7.35 (1H, m), 7.04 (1H, m), 6.99 (2H, m), 4.20 (2H, t), 3.15 (2H, t), 2.42 (2H, t), 1.83 (2H, m), 1.72 (4H, m), 1.58 (2H, m), 1.02 (3H, t)

Example 65

4-{2,6-difluoro-4-[6-(2-methyl-propenyl)-pyridin-2-yl]-phenoxy}-butyric acid

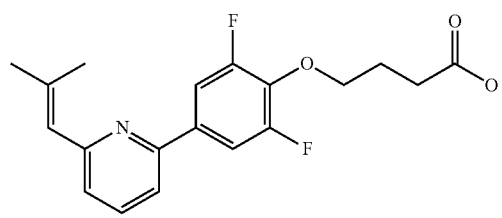 [SMILES: CC(C)=Cc1cccc(-c2cc(F)c(OCCCC(=O)O)c(F)c2)n1]

Step A: 4-{2,6-difluoro-4-[6-(2-methyl-propenyl)-pyridin-2-yl]-phenoxy}-butyric acid ethyl ester 4-[2,6-Difluoro-4-(6-formyl-pyridin-2-yl)-phenoxy]-butyric acid ethyl ester (0.25 g, 0.72 mmol) obtained in Preparation Example 57 was used to react in the same manner as in Preparation Example 101 to obtain the title compound (80 mg, 30%).

Step B: 4-{2,6-difluoro-4-[6-(2-methyl-propenyl)-pyridin-2-yl]-phenoxy}-butyric acid 4-{2,6-Difluoro-4-[6-(2-methyl-propenyl)-pyridin-2-yl]-phenoxy}-butyric acid ethyl ester (20 mg, 0.05 mmol) obtained in Step A was used to react in the same manner as in Step B of Example 1 to obtain the title compound (17 mg, 97%).

1H NMR (CDCl$_3$) δ 7.68 (1H, t), 7.62 (2H, m), 7.41 (1H, m), 7.10 (1H, d), 6.35 (1H, s), 4.25 (2H, t), 2.68 (2H, t), 2.21 (3H, s), 2.13 (2H, m), 1.98 (3H, s)

Example 66

4-[2,6-difluoro-4-(6-isobutyl-pyridin-2-yl)-phenoxy]-butyric acid

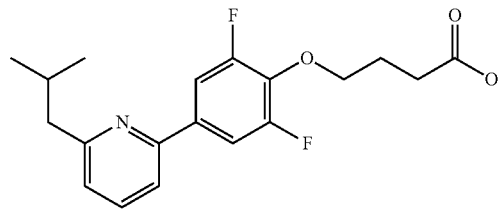 [SMILES: CC(C)Cc1cccc(-c2cc(F)c(OCCCC(=O)O)c(F)c2)n1]

4-{2,6-Difluoro-4-[6-(2-methyl-propenyl)-pyridin-2-yl]-phenoxy}-butyric acid ethyl ester (60 mg, 0.16 mmol) obtained in Step A of Example 65 was used to react sequentially in the same manner as in Step B of Preparation Example 50 and Step B of Example 1 to obtain the title compound (40 mg, 86%).

1H NMR (CDCl$_3$) δ 7.65 (1H, t), 7.59 (2H, m), 7.43 (1H, d), 7.06 (1H, d), 4.24 (2H, t), 2.70 (4H, m), 2.22 (1H, m), 2.12 (2H, m), 0.96 (6H, d)

Example 67

4-[4-(2-cyclobutylsulfanyl-pyridin-3-yl)-3,5-difluoro-phenoxy]-butyric acid

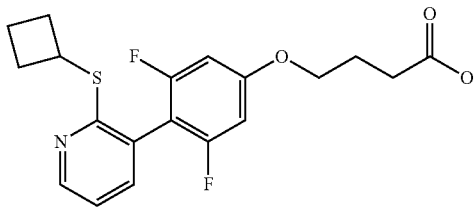 [SMILES: O=C(O)CCCOc1cc(F)c(-c2cccnc2SC2CCC2)c(F)c1]

2-Cyclobutylsulfanyl-3-iodo-pyridine (0.040 g, 0.14 mmol) obtained in Preparation Example 44 and 4-[3,5-difluoro-4-(4,4,5,5-tetramethyl-1,3,2-dioxaborolan-2-yl)phenoxy]butyric acid ethyl ester (0.051 g, 0.14 mmol) obtained in Preparation Example 54 were reacted in the same manner as in Example 1 to obtain the title compound (0.005 g, 10%).

1H NMR (CDCl$_3$) δ 8.45 (1H, m), 7.37 (1H, m), 7.04 (1H, m), 6.56 (2H, m), 4.45 (1H, m), 4.06 (2H, t), 2.61 (2H, t), 2.59 (2H, m), 2.17 (2H, m), 2.05 (4H, m)

Example 68

4-{2,6-difluoro-4-[2-(tetrahydro-pyran-4-yloxy)-pyridin-3-yl]-phenoxy}-butyric acid

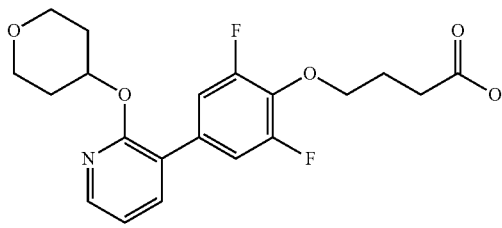 [SMILES: O=C(O)CCCOc1c(F)cc(-c2cccnc2OC2CCOCC2)cc1F]

3-Iodo-2-(tetrahydro-pyran-4-yloxy)-pyridine (0.040 g, 0.13 mmol) obtained in Preparation Example 58 and 4-[2,6-difluoro-4-(4,4,5,5-tetramethyl-1,3,2-dioxaborolan-2-yl)phenoxy]butyric acid ethyl ester (0.049 g, 0.13 mmol) obtained in Preparation Example 2 were reacted in the same manner as in Example 1 to obtain the title compound (0.035 g, 68%).

1H NMR (CDCl$_3$) δ 8.12 (1H, m), 7.57 (1H, m), 7.14 (2H, m), 6.95 (1H, m), 5.37 (1H, m), 4.24 (2H, t), 3.90 (2H, m), 3.64 (2H, m), 2.67 (2H, t), 2.13 (4H, m), 1.82 (2H, m)

Example 69

4-{2,6-difluoro-4-[2-(tetrahydro-furan-3-yloxy)-pyridin-3-yl]-phenoxy}-butyric acid

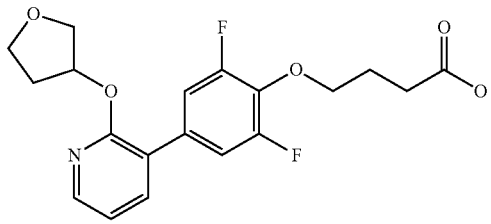 [SMILES: O=C(O)CCCOc1c(F)cc(-c2cccnc2OC2CCOC2)cc1F]

3-Iodo-2-(tetrahydro-furan-3-yloxy)-pyridine (0.040 g, 0.14 mmol) obtained in Preparation Example 59 and 4-[2,6-difluoro-4-(4,4,5,5-tetramethyl-1,3,2-dioxaborolan-2-yl)phenoxy]butyric acid ethyl ester (0.051 g, 0.14 mmol) obtained in Preparation Example 2 were reacted in the same manner as in Example 1 to obtain the title compound (0.030 g, 58%).

1H NMR (CDCl$_3$) δ 8.12 (1H, m), 7.57 (1H, m), 7.13 (2H, m), 6.98 (1H, m), 5.63 (1H, m), 4.24 (2H, t), 4.07 (1H, m), 3.94 (3H, m), 2.68 (2H, t), 2.25 (1H, m), 2.14 (3H, m)

Example 70

4-[4-(2-cyclobutoxy-pyridin-3-yl)-2,6-difluoro-phenoxy]-butyric acid

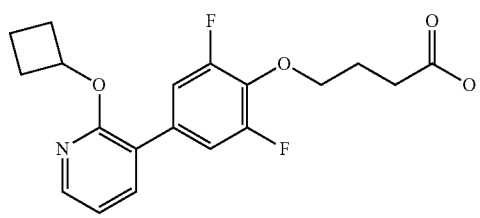 [SMILES: O=C(O)CCCOc1c(F)cc(-c2cccnc2OC2CCC2)cc1F]

2-Cyclobutoxy-3-iodo-pyridine (0.040 g, 0.15 mmol) obtained in Preparation Example 200 and 4-[2,6-difluoro-4-(4,4,5,5-tetramethyl-1,3,2-dioxaborolan-2-yl)phenoxy]butyric acid ethyl ester (0.054 g, 0.15 mmol) obtained in Preparation Example 2 were reacted in the same manner as in Example 1 to obtain the title compound (0.020 g, 38%).

1H NMR (CDCl$_3$) δ 8.12 (1H, m), 7.57 (1H, m), 7.18 (2H, m), 6.93 (1H, m), 5.28 (1H, m), 4.24 (2H, t), 2.69 (2H, t), 2.47 (2H, m), 2.12 (4H, m), 1.83 (1H, m), 1.69 (1H, m)

Example 71

4-{2,6-difluoro-4-[2-(2-methoxy-ethoxy)-pyridin-3-yl]-phenoxy}-butyric acid

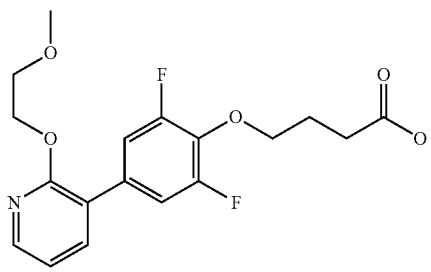 [SMILES: COCCOc1ncccc1-c1cc(F)c(OCCCC(=O)O)c(F)c1]

2-Methoxy-ethanol (51 mg, 0.67 mmol) and 4-[2,6-difluoro-4-(2-fluoro-3-pyridyl)phenoxy]butyric acid (70 mg, 0.22 mmol) obtained in Preparation Example 56 were used to react in the same manner as in Preparation Example 37 to obtain the title compound (55 mg, 67%).

1H NMR (CDCl$_3$) δ 8.14 (1H, m), 7.59 (1H, m), 7.22 (2H, m), 6.96 (1H, m), 4.54 (2H, t), 4.24 (2H, t), 3.76 (2H, t), 3.42 (3H, s), 2.68 (2H, t), 2.12 (2H, m)

Example 72

4-[2,6-difluoro-4-(2-pyrrolidin-1-yl-3-pyridyl)phenoxy]butanoic Acid

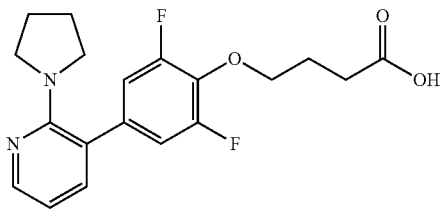 [SMILES: O=C(O)CCCOc1c(F)cc(-c2cccnc2N2CCCC2)cc1F]

Step A: ethyl 4-[2,6-difluoro-4-(2-pyrrolidin-1-yl-3-pyridyl)phenoxy]butanoate 1.2 mL of DMF was added to ethyl 4-[2,6-difluoro-4-(2-fluoro-3-pyridyl)phenoxy]butanoate (0.078 g, 0.23 mmol) obtained in Preparation Example 109, pyrrolidine (0.022 g, 0.32 mmol) and Cs$_2$CO$_3$ (0.15 g, 0.46 mmol), and the resultant was agitated at 50° C. for 8 hours. The reaction solution was concentrated under reduced pressure and purified by column chromatography to obtain the title compound (0.056 g, 62%).

$^1$H-NMR (CDCl$_3$) δ 8.16 (1H, m), 7.31 (1H, m), 6.90 (2H, m), 6.69 (1H, m), 4.21 (2H, t), 4.17 (2H, q), 3.15 (4H, m), 2.59 (2H, t), 2.12 (2H, m), 1.80 (4H, m), 1.27 (3H, t)

Step B: 4-[2,6-difluoro-4-(2-pyrrolidin-1-yl-3-pyridyl)phenoxy]butanoic acid

Ethyl 4-[2,6-difluoro-4-(2-pyrrolidin-1-yl-3-pyridyl)phenoxy]butanoate (0.056 g, 0.14 mmol) obtained in Step A was used to react in the same manner as in Step B of Example 1 to obtain the title compound (0.038 g, 73%).

$^1$H-NMR (CDCl$_3$) δ 8.19 (1H, m), 7.33 (1H, m), 6.90 (2H, m), 6.70 (1H, m), 4.23 (2H, t), 3.17 (4H, m), 2.67 (2H, t), 2.12 (2H, m), 1.81 (4H, m)

Example 73

4-[4-[2-(cyclopentylamino)-3-pyridyl]-2,6-difluorophenoxy]butanoic acid

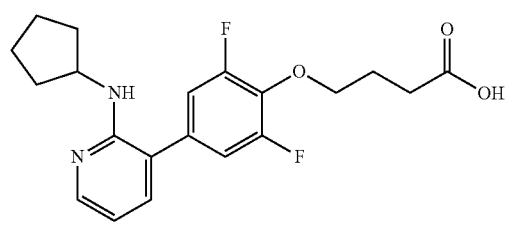 [SMILES: O=C(O)CCCOc1c(F)cc(-c2cccnc2NC2CCCC2)cc1F]

N-Cyclopentyl-3-iodo-pyridin-2-amine (0.03 g, 0.1 mmol) obtained in Preparation Example 64 and 4-[2,6-difluoro-4-(4,4,5,5-tetramethyl-1,3,2-dioxaborolan-2-yl)phenoxy]butyric acid ethyl ester (0.043 g, 0.11 mmol) obtained in Preparation Example 2 were used to react sequentially in the same manner as in Step A of Example 29 and Step B of Example 1 to obtain the title compound (0.02 g, 50%).

$^1$H-NMR (CDCl$_3$) δ 8.15 (1H, m), 7.19 (1H, m), 6.94 (2H, m), 6.60 (1H, m), 4.45 (1H, brs), 4.33 (1H, m), 4.25 (2H, t), 2.68 (2H, t), 2.15 (2H, m), 2.05 (2H, m), 1.64 (4H, m), 1.34 (2H, m)

Example 74

4-[4-[2-(cyclopropylmethylamino)-3-pyridyl]-2,6-difluoro-phenoxy]butanoic acid

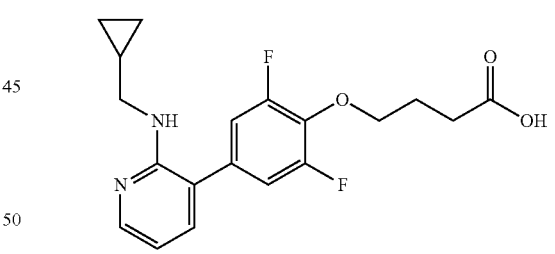

Step A: ethyl 4-[4-[2-(cyclopropylmethylamino)-3-pyridyl]-2,6-difluoro-phenoxy]butanoate Ethyl 4-[2,6-difluoro-4-(2-fluoro-3-pyridyl)phenoxy]butanoate (0.078 g, 0.23 mmol) obtained in Preparation Example 109 and tert-butyl N(cyclopropylmethyl)carbamate (0.047 g, 0.27 mmol) were used to react in the same manner as in Step A of Example 72 to obtain the title compound (0.025 g, 29%).

$^1$H-NMR (CDCl$_3$) δ 8.13 (1H, m), 7.21 (1H, m), 6.98 (2H, m), 6.62 (1H, m), 4.62 (1H, m), 4.24 (2H, t), 4.17 (2H, q), 3.26 (2H, m), 2.59 (2H, t), 2.12 (2H, m), 1.27 (3H, t), 1.05 (1H, m), 0.49 (2H, m), 0.20 (2H, m)

Step B: 4-[4-[2-(cyclopropylmethylamino)-3-pyridyl]-2,6-difluoro-phenoxy]butanoic acid Ethyl 4-[4-[2-(cyclopropylmethylamino)-3-pyridyl]-2,6-difluoro-phenoxy]butanoate (0.026 g, 0.066 mmol) obtained in Step A was used to react in the same manner as in Step B of Example 1 to obtain the title compound (0.02 g, 82%).

¹H-NMR (CDCl₃) δ 8.12 (1H, m), 7.22 (1H, m), 6.99 (2H, m), 6.62 (1H, m), 4.64 (1H, brs), 4.24 (2H, t), 3.24 (2H, d), 2.63 (2H, t), 2.12 (2H, m), 1.05 (1H, m), 0.48 (2H, m), 0.20 (2H, m)

Example 75

4-[4-[6-(cyclopropylmethylamino)-2-pyridyl]-2,6-difluoro-phenoxy]butanoic acid

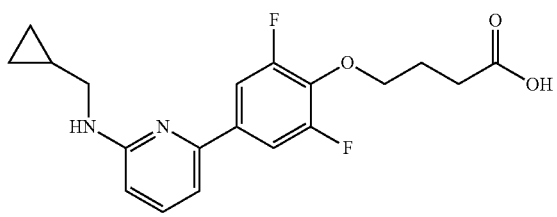 [SMILES: O=C(O)CCCOc1c(F)cc(-c2cccc(NCC3CC3)n2)cc1F]

Step A: ethyl 4-[4-[6-(cyclopropylmethylamino)-2-pyridyl]-2,6-difluoro-phenoxy]butanoate 6-Chloro-N-(cyclopropylmethyl)pyridin-2-amine (0.17 g, 0.93 mmol) obtained in Preparation Example 65 and 4-[2,6-difluoro-4-(4,4,5,5-tetramethyl-1,3,2-dioxaborolan-2-yl)phenoxy]butyric acid ethyl ester (0.34 g, 0.93 mmol) obtained in Preparation Example 2 were used to react in the same manner as in Step A of Example 29 to obtain the title compound (0.125 g, 34%).

¹H-NMR (CDCl₃) δ 7.54 (2H, m), 7.45 (1H, t), 6.91 (1H, d), 6.34 (1H, m), 4.70 (1H, m), 4.20 (2H, t), 4.15 (2H, q), 3.19 (2H, t), 2.58 (2H, t), 2.09 (2H, m), 1.28 (3H, t), 1.13 (1H, m), 0.55 (2H, m), 0.28 (2H, m)

Step B: 4-[4-[6-(cyclopropylmethylamino)-2-pyridyl]-2,6-difluoro-phenoxy]butanoic acid Ethyl 4-[4-[6-(cyclopropylmethylamino)-2-pyridyl]-2,6-difluoro-phenoxy]butanoate (0.32 g, 0.34 mmol) obtained in Step A was used to react in the same manner as in Step B of Example 1 to obtain the title compound (0.115 g, 99%).

¹H-NMR (CDCl₃) δ 7.50 (3H, m), 6.90 (1H, d), 6.35 (1H, d), 4.22 (2H, t), 3.20 (2H, d), 2.66 (2H, t), 2.10 (2H, m), 1.12 (1H, m), 0.55 (2H, m), 0.29 (2H, m)

Example 76

4-[2,6-difluoro-4-[2-(isopropylamino)-3-pyridyl]phenoxy]butanoic acid

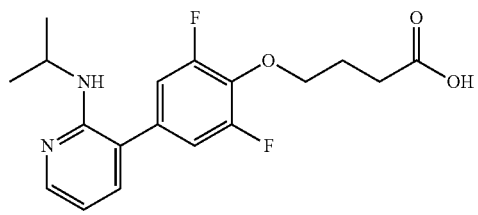 [SMILES: CC(C)Nc1ncccc1-c1cc(F)c(OCCCC(=O)O)c(F)c1]

Step A: ethyl 4-[2,6-difluoro-4-[2-(isopropylamino)-3-pyridyl]phenoxy]butanoate 3-Iodo-N-isopropyl-pyridin-2-amine (0.045 g, 0.17 mmol) obtained in Preparation Example 66 and 4-[2,6-difluoro-4-(4,4,5,5-tetramethyl-1,3,2-dioxaborolan-2-yl)phenoxy]butyric acid ethyl ester (0.063 g, 0.17 mmol) obtained in Preparation Example 2 were used to react in the same manner as in Step A of Example 29 to obtain the title compound (0.047 g, 74%).

¹H-NMR (CDCl₃) δ 8.13 (1H, m), 7.19 (1H, m), 6.93 (2H, m), 6.60 (1H, m), 4.25 (4H, m), 4.17 (2H, q), 2.59 (2H, t), 2.12 (2H, m), 1.27 (3H, t), 1.20 (6H, d)

Step B: 4-[2,6-difluoro-4-[2-(isopropylamino)-3-pyridyl]phenoxy]butanoic acid Ethyl 4-[2,6-difluoro-4-[2-(isopropylamino)-3-pyridyl]phenoxy]butanoate (0.046 g, 0.12 mmol) obtained in Step A was used to react in the same manner as in Step B of Example 1 to obtain the title compound (0.023 g, 54%).

¹H-NMR (CDCl₃) δ 8.14 (1H, m), 7.20 (1H, m), 6.95 (2H, m), 6.62 (1H, m), 4.25 (3H, m), 2.65 (2H, t), 2.13 (2H, m), 1.18 (6H, d)

Example 77

4-[4-[2-(cyclopropylamino)-3-pyridyl]-2,6-difluoro-phenoxy]butanoic acid

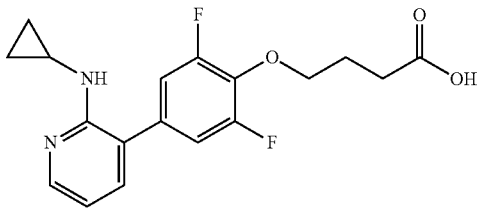 [SMILES: O=C(O)CCCOc1c(F)cc(-c2cccnc2NC2CC2)cc1F]

Step A: ethyl 4-[4-[2-(cyclopropylamino)-3-pyridyl]-2,6-difluoro-phenoxy]butanoate N-Cyclopropyl-3-iodo-pyridin-2-amine (0.05 g, 0.19 mmol) obtained in Preparation Example 67 and 4-[2,6-difluoro-4-(4,4,5,5-tetramethyl-1,3,2-dioxaborolan-2-yl)phenoxy]butyric acid ethyl ester (0.07 g, 0.19 mmol)

obtained in Preparation Example 2 were used to react in the same manner as in Step A of Example 29 to obtain the title compound (0.043 g, 60%).

¹H-NMR (CDCl₃) δ 8.24 (1H, m), 7.22 (1H, m), 6.92 (2H, m), 6.69 (1H, m), 4.76 (1H, brs), 4.23 (2H, t), 4.16 (2H, q), 2.75 (1H, m), 2.58 (2H, t), 2.11 (2H, m), 1.27 (3H, t), 0.80 (2H, m), 0.47 (2H, m)

Step B: 4-[4-[2-(cyclopropylamino)-3-pyridyl]-2,6-difluoro-phenoxy]butanoic acid Ethyl 4-[4-[2-(cyclopropylamino)-3-pyridyl]-2,6-difluoro-phenoxy]butanoate (0.043 g, 0.11 mmol) obtained in Step A was used to react in the same manner as in Step B of Example 1 to obtain the title compound (0.015 g, 39%).

¹H-NMR (CDCl₃) δ 8.25 (1H, m), 7.22 (1H, m), 6.90 (2H, m), 6.69 (1H, m), 4.82 (1H, brs), 4.25 (2H, t), 2.75 (1H, m), 2.66 (2H, t), 2.13 (2H, m), 0.80 (2H, m), 0.47 (2H, m)

Example 78

4-[2,6-difluoro-4-[6-(isopropylamino)-2-pyridyl]phenoxy]butanoic acid

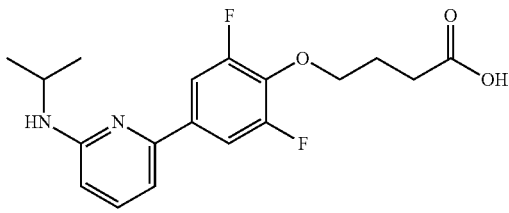 [SMILES: CC(C)Nc1cccc(-c2cc(F)c(OCCCC(=O)O)c(F)c2)n1]

Step A: ethyl 4-[2,6-difluoro-4-[6-(isopropylamino)-2-pyridyl]phenoxy]butanoate tert-butyl N-(6-bromo-2-pyridyl)-N-isopropyl-carbamate (0.06 g, 0.19 mmol) obtained in Preparation Example 69 was dissolved in 0.4 mL of TFA and 0.4 mL of DCM, and the resultant was agitated at room temperature for 5 hours. The reactant which was concentrated under reduced pressure and 4-[2,6-difluoro-4-(4,4,5,5-tetramethyl-1,3,2-dioxaborolan-2-yl)phenoxy]butyric acid ethyl ester (0.07 g, 0.19 mmol) obtained in Preparation Example 2 were used to react in the same manner as in Step A of Example 29 to obtain the title compound (0.028 g, 39%).

¹H-NMR (CDCl₃) δ 7.54 (2H, m), 7.45 (1H, t), 6.90 (1H, d), 6.31 (1H, d), 4.43 (1H, brs), 4.21 (2H, t), 4.15 (2H, q), 4.00 (1H, m), 2.58 (2H, t), 2.10 (2H, m), 1.26 (9H, m)

Step B: 4-[2,6-difluoro-4-[6-(isopropylamino)-2-pyridyl]phenoxy]butanoic acid

Ethyl 4-[2,6-difluoro-4-[6-(isopropylamino)-2-pyridyl]phenoxy]butanoate (0.028 g, 0.07 mmol) obtained in Step A was used to react in the same manner as in Step B of Example 1 to obtain the title compound (0.017 g, 65%).

¹H-NMR (CDCl₃) δ 7.52 (2H, m), 7.46 (1H, t), 6.88 (1H, d), 6.33 (1H, d), 4.22 (2H, t), 3.97 (1H, m), 2.66 (2H, t), 2.10 (2H, m), 1.26 (6H, d)

Example 79

4-[4-[2-(cyclopentylamino)phenyl]-2,6-difluoro-phenoxy]butanoic acid

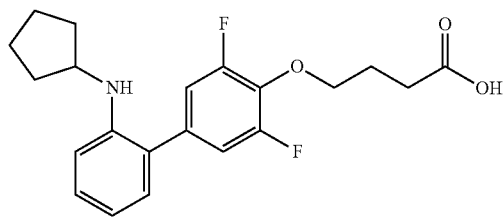 [SMILES: O=C(O)CCCOc1c(F)cc(-c2ccccc2NC2CCCC2)cc1F]

Step A: ethyl 4-[4-[2-(cyclopentylamino)phenyl]-2,6-difluoro-phenoxy]butanoate

N-Cyclopentyl-2-iodo-aniline (0.046 g, 0.16 mmol) obtained in Preparation Example 70 and 4-[2,6-difluoro-4-(4,4,5,5-tetramethyl-1,3,2-dioxaborolan-2-yl)phenoxy]butyric acid ethyl ester (0.05 g, 0.135 mmol) obtained in Preparation Example 2 were used to react in the same manner as in Step A of Example 28 to obtain the title compound (0.044 g, 81%).

¹H-NMR (CDCl₃) δ 7.21 (1H, t), 7.00 (3H, m), 6.71 (2H, m), 4.23 (2H, t), 4.15 (2H. q), 3.79 (2H, m), 2.60 (2H, t), 2.12 (2H, m), 1.98 (2H, m), 1.62 (4H, m), 1.41 (2H, m), 1.27 (3H, t)

Step B: 4-[4-[2-(cyclopentylamino)phenyl]-2,6-difluoro-phenoxy]butanoic acid

Ethyl 4-[4-[2-(cyclopentylamino)phenyl]-2,6-difluoro-phenoxy]butanoate (0.044 g, 0.11 mmol) obtained in Step A was used to react in the same manner as in Step B of Example 1 to obtain the title compound (0.035 g, 85%).

¹H-NMR (CDCl₃) δ 7.21 (1H, t), 7.00 (1H, m), 6.98 (2H, m), 6.75 (2H, m), 4.24 (2H, t), 3.76 (1H, m), 2.68 (2H, t), 2.13 (2H, m), 1.99 (2H, m), 1.67 (2H, m), 1.60 (2H, m), 1.41 (2H, m)

Example 80

4-[4-[3-(cyclopentylamino)phenyl]-2,6-difluoro-phenoxy]butanoic acid

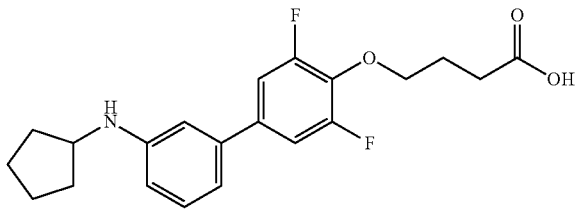 [SMILES: O=C(O)CCCOc1c(F)cc(-c2cccc(NC3CCCC3)c2)cc1F]

Step A: ethyl 4-[4-[3-(cyclopentylamino)phenyl]-2,6-difluoro-phenoxy]butanoate

3-Bromo-N-cyclopentyl-aniline (0.039 g, 0.16 mmol) obtained in Preparation Example 71 and 4-[2,6-difluoro-4-

(4,4,5,5-tetramethyl-1,3,2-dioxaborolan-2-yl)phenoxy]butyric acid ethyl ester (0.05 g, 0.135 mmol) obtained in Preparation Example 2 were used to react in the same manner as in Step A of Example 28 to obtain the title compound (0.024 g, 44%).

$^1$H-NMR (CDCl$_3$) δ 7.20 (1H, t), 7.07 (2H, m), 6.79 (1H, d), 6.68 (1H, m), 6.59 (1H, m), 4.20 (2H, t), 4.15 (2H, q), 3.85 (1H, m), 3.77 (1H, brs), 2.58 (2H, t), 2.10 (4H, m), 1.74 (2H, m), 1.65 (2H, m), 1.48 (2H, m), 1.27 (3H, t)

Step B: 4-[4-[3-(cyclopentylamino)phenyl]-2,6-difluoro-phenoxy]butanoic acid

Ethyl 4-[4-[3-(cyclopentylamino)phenyl]-2,6-difluorophenoxy]butanoate (0.024 g, 0.06 mmol) obtained in Step A was used to react in the same manner as in Step B of Example 1 to obtain the title compound (0.021 g, 94%).

$^1$H-NMR (CDCl$_3$) δ 7.23 (1H, t), 7.09 (2H, m), 6.87 (1H, m), 6.82 (1H, m), 6.72 (1H, m), 4.21 (2H, t), 3.82 (1H, m), 2.67 (2H, t), 2.12 (2H, m), 2.04 (2H, m), 1.76 (2H, m), 1.63 (2H, m), 1.58 (2H, m)

Example 81

4-[2,6-difluoro-4-[2-(propylamino)phenyl]phenoxy]butanoic acid

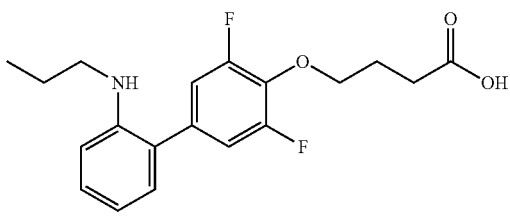 [SMILES: CCCNc1ccccc1-c1cc(F)c(OCCCC(=O)O)c(F)c1]

Step A: ethyl 4-[2,6-difluoro-4-[2-(propylamino)phenyl]phenoxy]butanoate

2-Iodo-N-propyl-aniline (0.056 g, 0.21 mmol) obtained in Preparation Example 72 and 4-[2,6-difluoro-4-(4,4,5,5-tetramethyl-1,3,2-dioxaborolan-2-yl)phenoxy]butyric acid ethyl ester (0.066 g, 0.18 mmol) obtained in Preparation Example 2 were used to react in the same manner as in Step A of Example 28 to obtain the title compound (0.048 g, 57%).

$^1$H-NMR (CDCl$_3$) δ 7.25 (1H, t), 7.02 (1H, d), 6.99 (2H, m), 6.73 (1H, t), 6.69 (1H, d), 4.23 (2H, t), 4.16 (2H, q), 3.82 (1H, brs), 3.07 (2H, t), 2.59 (2H, t), 2.11 (2H, m), 1.62 (2H, m), 1.27 (3H, t), 0.96 (3H, t)

Step B: 4-[2,6-difluoro-4-[2-(propylamino)phenyl]phenoxy]butanoic acid

Ethyl 4-[2,6-difluoro-4-[2-(propylamino)phenyl]phenoxy]butanoate (0.048 g, 0.12 mmol) obtained in Step A was used to react in the same manner as in Step B of Example 1 to obtain the title compound (0.023 g, 51%).

$^1$H-NMR (CDCl$_3$) δ 7.23 (1H, t), 7.00 (3H, m), 6.74 (1H, t), 6.69 (1H, d), 4.23 (2H, t), 3.07 (2H, t), 2.68 (2H, t), 2.13 (2H, m), 1.60 (2H, m), 0.94 (3H, t)

Example 82

4-[4-[2-(cyclopropylmethylamino)phenyl]-2,6-difluoro-phenoxy]butanoic acid

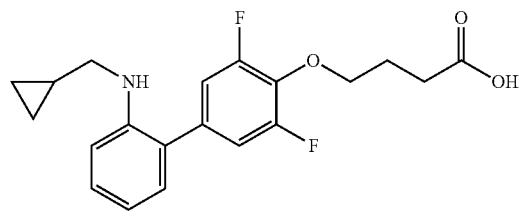 [SMILES: O=C(O)CCCOc1c(F)cc(-c2ccccc2NCC2CC2)cc1F]

Step A: ethyl 4-[4-[2-(cyclopropylmethylamino)phenyl]-2,6-difluoro-phenoxy]butanoate N-(Cyclopropylmethyl)-2-iodo-aniline (0.059 g, 0.21 mmol) obtained in Preparation Example 73 and 4-[2,6-difluoro-4-(4,4,5,5-tetramethyl-1,3,2-dioxaborolan-2-yl)phenoxy]butyric acid ethyl ester (0.066 g, 0.18 mmol) obtained in Preparation Example 2 were used to react in the same manner as in Step A of Example 28 to obtain the title compound (0.048 g, 58%).

$^1$H-NMR (CDCl$_3$) δ 7.22 (1H, t), 7.00 (3H, m), 6.74 (1H, t), 6.69 (1H, d), 4.23 (2H, t), 4.16 (2H, q), 3.97 (1H, brs), 2.96 (2H, d), 2.60 (2H, t), 2.12 (2H, m), 1.27 (3H, t), 1.04 (1H, m), 0.50 (2H, m), 0.18 (2H, m)

Step B: 4-[4-[2-(cyclopropylmethylamino)phenyl]-2,6-difluoro-phenoxy]butanoic acid Ethyl 4-[4-[2-(cyclopropylmethylamino)phenyl]-2,6-difluoro-phenoxy]butanoate (0.048 g, 0.12 mmol) obtained in Step A was used to react in the same manner as in Step B of Example 1 to obtain the title compound (0.042 g, 97%).

$^1$H-NMR (CDCl$_3$) δ 7.23 (1H, t), 7.00 (3H, m), 6.76 (1H, t), 6.70 (1H, d), 4.24 (2H, t), 2.96 (2H, d), 2.68 (2H, t), 2.13 (2H, m), 1.03 (1H, m), 0.52 (2H, m), 0.18 (2H, m)

Example 83

4-[2,6-difluoro-4-[2-(isopropylamino)phenyl]phenoxy]butanoic Acid

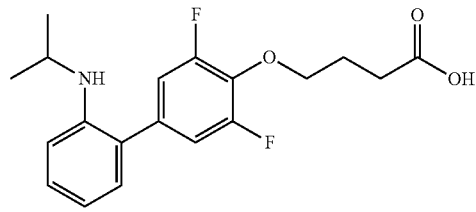 [SMILES: CC(C)Nc1ccccc1-c1cc(F)c(OCCCC(=O)O)c(F)c1]

Step A: ethyl 4-[2,6-difluoro-4-[2-(isopropylamino)phenyl]phenoxy]butanoate

2-Iodo-N-isopropyl-aniline (0.05 g, 0.19 mmol) obtained in Preparation Example 74 and 4-[2,6-difluoro-4-(4,4,5,5-tetramethyl-1,3,2-dioxaborolan-2-yl)phenoxy]butyric acid ethyl ester (0.059 g, 0.16 mmol) obtained in Preparation Example 2 were used to react in the same manner as in Step A of Example 28 to obtain the title compound (0.043 g, 60%).

¹H-NMR (CDCl₃) δ 7.22 (1H, t), 7.00 (1H, d), 6.95 (2H, m), 6.70 (2H, m), 4.23 (2H, t), 4.17 (2H, q), 3.03 (2H, m), 2.59 (2H, t), 2.11 (2H, m), 1.26 (3H, t), 1.17 (6H, d)

Step B: 4-[2,6-difluoro-4-[2-(isopropylamino)phenyl]phenoxy]butanoic acid

Ethyl 4-[2,6-difluoro-4-[2-(isopropylamino)phenyl]phenoxy]butanoate (0.043 g, 0.11 mmol) obtained in Step A was used to react in the same manner as in Step B of Example 1 to obtain the title compound (0.038 g, 99%).

¹H-NMR (CDCl₃) δ 7.23 (1H, t), 7.00 (1H, d), 6.95 (2H, m), 6.72 (2H, m), 4.24 (2H, t), 3.63 (1H, m), 2.68 (2H, t), 2.13 (2H, m), 1.17 (6H, d)

Example 84

4-[4-[2-(cyclopentylamino)phenyl]phenoxy]butanoic acid

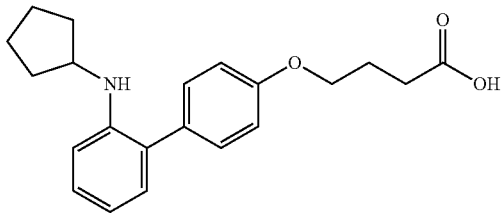 [SMILES: O=C(O)CCCOc1ccc(-c2ccccc2NC2CCCC2)cc1]

N-Cyclopentyl-2-iodo-aniline (0.068 g, 0.24 mmol) obtained in Preparation Example 70 and 4-[4-(4,4,5,5-tetramethyl-1,3,2-dioxaborolan-2-yl)phenoxy]butyric acid ethyl ester (0.061 g, 0.18 mmol) obtained in Preparation Example 1 were used to react sequentially in the same manner as in Step A of Example 28 and Step B of Example 1 to obtain the title compound (0.01 g, 15%).

¹H-NMR (CDCl₃) δ 7.31 (2H, m), 7.20 (1H, t), 7.02 (1H, d), 6.95 (2H, m), 6.72 (2H, m), 4.07 (2H, t), 3.78 (1H, m), 2.62 (2H, t), 2.17 (2H, m), 1.95 (2H, m), 1.58 (4H, m), 1.38 (2H, m)

Example 85

4-[4-[2-(cyclopropylmethylamino)phenyl]phenoxy]butanoic acid

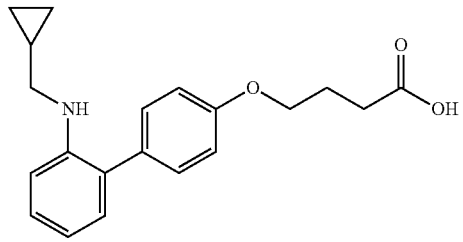 [SMILES: O=C(O)CCCOc1ccc(-c2ccccc2NCC2CC2)cc1]

N-(Cyclopropylmethyl)-2-iodo-aniline (0.057 g, 0.21 mmol) obtained in Preparation Example 73 and 4-[4-(4,4,5,5-tetramethyl-1,3,2-dioxaborolan-2-yl)phenoxy]butyric acid ethyl ester (0.061 g, 0.18 mmol) obtained in Preparation Example 1 were used to react sequentially in the same manner as in Step A of Example 28 and Step B of Example 1 to obtain the title compound (0.015 g, 23%).

¹H-NMR (CDCl₃) δ 7.35 (2H, m), 7.20 (1H, t), 7.06 (1H, m), 6.97 (2H, m), 6.73 (1H, t), 6.68 (1H, d), 4.07 (2H, t), 2.95 (2H, d), 2.63 (2H, m), 2.16 (2H, m), 1.02 (1H, m), 0.47 (2H, m), 0.15 (2H, m)

Example 86

4-[4-[2-(propylamino)phenyl]phenoxy]butanoic acid

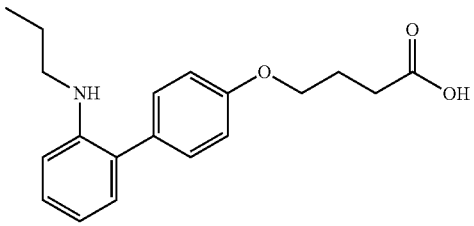 [SMILES: CCCNc1ccccc1-c1ccc(OCCCC(=O)O)cc1]

2-Iodo-N-propyl-aniline (0.056 g, 0.21 mmol) obtained in Preparation Example 72 and 4-[4-(4,4,5,5-tetramethyl-1,3,2-dioxaborolan-2-yl)phenoxy]butyric acid ethyl ester (0.061 g, 0.18 mmol) obtained in Preparation Example 1 were used to react sequentially in the same manner as in Step A of Example 28 and Step B of Example 1 to obtain the title compound (0.007 g, 11%).

¹H-NMR (CDCl₃) δ 7.32 (2H, m), 7.21 (1H, t), 7.05 (1H, d), 6.95 (2H, m), 6.72 (1H, t), 6.68 (1H, d), 4.07 (2H, t), 3.05 (2H, t), 2.62 (2H, t), 2.17 (2H, m), 1.55 (2H, m), 0.91 (3H, t)

Example 87

4-[4-[2-(isopropylamino)phenyl]phenoxy]butanoic acid

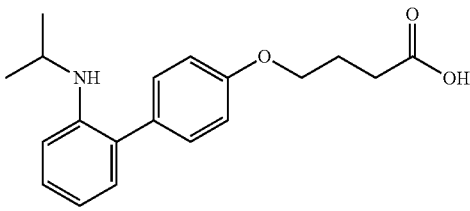 [SMILES: CC(C)Nc1ccccc1-c1ccc(OCCCC(=O)O)cc1]

2-Iodo-N-isopropyl-aniline (0.05 g, 0.19 mmol) obtained in Preparation Example 74 and 4-[4-(4,4,5,5-tetramethyl-1,3,2-dioxaborolan-2-yl)phenoxy]butyric acid ethyl ester (0.053 g, 0.16 mmol) obtained in Preparation Example 1 were used to react sequentially in the same manner as in Step A of Example 28 and Step B of Example 1 to obtain the title compound (0.008 g, 15%).

¹H-NMR (CDCl₃) δ 7.30 (2H, m), 7.19 (1H, t), 7.04 (1H, d), 6.95 (2H, m), 6.69 (2H, m), 4.07 (2H, t), 3.63 (1H, m), 2.63 (2H, t), 2.16 (2H, m), 1.14 (6H, d)

Example 88

4-[4-[2-(cyclobutylamino)phenyl]phenoxy]butanoic acid

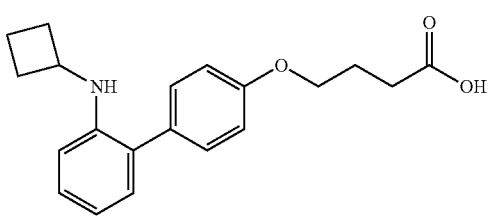 [SMILES: O=C(O)CCCOc1ccc(-c2ccccc2NC2CCC2)cc1]

2-Bromo-N-cyclobutyl-aniline (0.07 g, 0.21 mmol) obtained in Preparation Example 75 and 4-[4-(4,4,5,5-tetramethyl-1,3,2-dioxaborolan-2-yl)phenoxy]butyric acid ethyl ester (0.095 g, 0.42 mmol) obtained in Preparation Example 1 were used to react sequentially in the same manner as in Step A of Example 28 and Step B of Example 1 to obtain the title compound (0.007 g, 0.1%).

$^1$H-NMR (CDCl$_3$) δ 7.33 (2H, m), 7.19 (1H, t), 7.06 (1H, d), 6.97 (2H, m), 6.73 (1H, t), 6.58 (1H, d), 4.12 (2H, t), 3.91 (1H, m), 2.63 (2H, t), 2.36 (2H, m), 2.17 (2H, m), 1.75 (4H, m)

Example 89

4-[4-[2-(cyclobutylamino)phenyl]-2,6-difluoro-phenoxy]butanoic acid

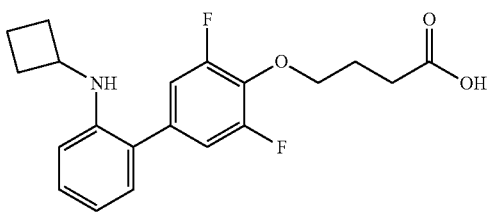 [SMILES: O=C(O)CCCOc1c(F)cc(-c2ccccc2NC2CCC2)cc1F]

2-Bromo-N-cyclobutyl-aniline (0.136 g, 0.6 mmol) obtained in Preparation Example 75 and 4-[2,6-difluoro-4-(4,4,5,5-tetramethyl-1,3,2-dioxaborolan-2-yl)phenoxy]butyric acid ethyl ester (0.1 g, 0.27 mmol) obtained in Preparation Example 2 were used to react sequentially in the same manner as in Step A of Example 28 and Step B of Example 1 to obtain the title compound (0.004 g, 0.04%).

$^1$H-NMR (CDCl$_3$) δ 7.21 (1H, t), 6.99 (3H, m), 6.73 (1H, t), 6.58 (1H, d), 4.24 (2H, t), 3.89 (1H, m), 2.68 (2H, t), 2.40 (2H, m), 2.13 (2H, m), 1.77 (4H, m)

Example 90

4-[4-[3-(cyclopropylmethylamino)phenyl]-2,6-difluoro-phenoxy]butanoic acid

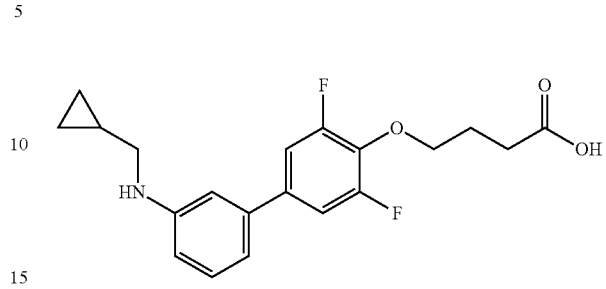

Step A: ethyl 4-[4-[3-(cyclopropylmethylamino)phenyl]-2,6-difluoro-phenoxy]butanoate 3-Bromo-N-(cyclopropylmethyl)aniline (0.063 g, 0.23 mmol) obtained in Preparation Example 76 and 4-[2,6-difluoro-4-(4,4,5,5-tetramethyl-1,3,2-dioxaborolan-2-yl)phenoxy]butyric acid ethyl ester (0.072 g, 0.19 mmol) obtained in Preparation Example 2 were used to react in the same manner as in Step A of Example 29 to obtain the title compound (0.04 g, 54%).

$^1$H-NMR (CDCl$_3$) δ 7.21 (1H, t), 7.09 (2H, m), 6.80 (1H, d), 6.70 (1H, m), 6.60 (1H, m), 4.18 (4H, m), 3.95 (1H, brs), 3.00 (2H, d), 2.59 (2H, t), 2.10 (2H, m), 1.27 (3H, t), 1.10 (1H, m), 0.57 (2H, m), 0.26 (2H, m)

Step B: 4-[4-[3-(cyclopropylmethylamino)phenyl]-2,6-difluoro-phenoxy]butanoic acid Ethyl 4-[4-[3-(cyclopropylmethylamino)phenyl]-2,6-difluoro-phenoxy]butanoate (0.04 g, 0.1 mmol) obtained in Step A was used to react in the same manner as in Step B of Example 1 to obtain the title compound (0.026 g, 72%).

$^1$H-NMR (CDCl$_3$) δ 7.21 (1H, t), 7.11 (2H, m), 6.80 (1H, d), 6.70 (1H, m), 6.61 (1H, m), 4.21 (2H, t), 3.00 (2H, d), 2.67 (2H, t), 2.12 (2H, m), 1.18 (1H, m), 0.57 (2H, m), 0.27 (2H, m)

Example 91

4-[2,6-difluoro-4-[3-(isopropylamino)phenyl]phenoxy]butanoic acid

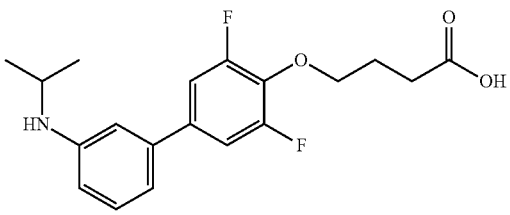 [SMILES: CC(C)Nc1cccc(-c2cc(F)c(OCCCC(=O)O)c(F)c2)c1]

Step A: ethyl 4-[2,6-difluoro-4-[3-(isopropylamino)phenyl]phenoxy]butanoate

3-Bromo-N-isopropyl-aniline (0.06 g, 0.23 mmol) obtained in Preparation Example 77 and 4-[2,6-difluoro-4-(4,4,5,5-tetramethyl-1,3,2-dioxaborolan-2-yl)phenoxy]butyric acid ethyl ester (0.072 g, 0.19 mmol) obtained in Preparation Example 2 were used to react in the same manner as in Step A of Example 29 to obtain the title compound (0.043 g, 60%).

¹H-NMR (CDCl₃) δ 7.20 (1H, t), 7.09 (2H, m), 6.78 (1H, d), 6.66 (1H, m), 6.57 (1H, m), 4.18 (4H, m), 3.68 (1H, m), 3.60 (1H, brs), 2.59 (2H, t), 2.12 (2H, m), 1.27 (9H, m)

Step B: 4-[2,6-difluoro-4-[3-(isopropylamino)phenyl]phenoxy]butanoic acid

Ethyl 4-[2,6-difluoro-4-[3-(isopropylamino)phenyl]phenoxy]butanoate (0.043 g, 0.11 mmol) obtained in Step A was used to react in the same manner as in Step B of Example 1 to obtain the title compound (0.032 g, 83%).

¹H-NMR (CDCl₃) δ 7.20 (1H, t), 7.10 (2H, m), 6.78 (1H, d), 6.67 (1H, m), 6.58 (1H, m), 4.21 (2H, t), 3.69 (1H, m), 2.67 (2H, t), 2.11 (2H, m), 1.24 (6H, d)

Example 92

4-[2,6-difluoro-4-(3-pyrrolidin-1-ylphenyl)phenoxy]butanoic acid

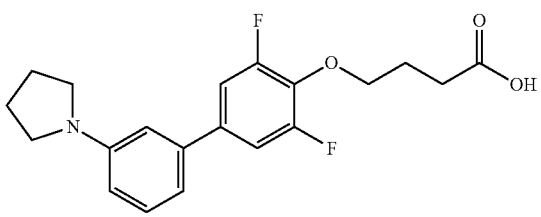 [SMILES: O=C(O)CCCOc1c(F)cc(-c2cccc(N3CCCC3)c2)cc1F]

Step A: ethyl 4-[2,6-difluoro-4-(3-pyrrolidin-1-ylphenyl)phenoxy]butanoate 1-(3-Bromophenyl)pyrrolidine (0.039 g, 0.17 mmol) obtained in Preparation Example 78 and 4-[2,6-difluoro-4-(4,4,5,5-tetramethyl-1,3,2-dioxaborolan-2-yl)phenoxy]butyric acid ethyl ester (0.053 g, 0.14 mmol) obtained in Preparation Example 2 were used to react in the same manner as in Step A of Example 29 to obtain the title compound (0.037 g, 60%).

¹H-NMR (CDCl₃) δ 7.26 (1H, m), 7.13 (2H, m), 6.77 (1H, d), 6.63 (1H, m), 6.57 (1H, m), 4.18 (4H, m), 3.33 (4H, m), 2.59 (2H, t), 2.11 (2H, m), 2.03 (4H, m), 1.26 (3H, t)

Step B: 4-[2,6-difluoro-4-(3-pyrrolidin-1-ylphenyl)phenoxy]butanoic acid

Ethyl 4-[2,6-difluoro-4-(3-pyrrolidin-1-ylphenyl)phenoxy]butanoate (0.033 g, 0.09 mmol) obtained in Step A was used to react in the same manner as in Step B of Example 1 to obtain the title compound (0.014 g, 45%).

¹H-NMR (CDCl₃) δ 7.26 (1H, m), 7.14 (2H, m), 6.76 (1H, d), 6.62 (1H, m), 6.58 (1H, m), 4.21 (2H, t), 3.33 (4H, m), 2.67 (2H, t), 2.12 (2H, m), 2.03 (4H, m)

Example 93

4-[4-[3-(cyclobutylamino)phenyl]-2,6-difluoro-phenoxy]butanoic acid

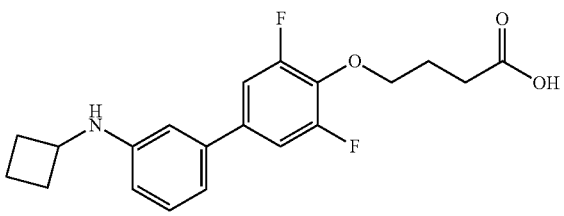 [SMILES: O=C(O)CCCOc1c(F)cc(-c2cccc(NC3CCC3)c2)cc1F]

Step A: ethyl 4-[4-[3-(cyclobutylamino)phenyl]-2,6-difluoro-phenoxy]butanoate 3-Bromo-N-cyclobutyl-aniline (0.028 g, 0.12 mmol) obtained in Preparation Example 80 and 4-[2,6-difluoro-4-(4,4,5,5-tetramethyl-1,3,2-dioxaborolan-2-yl)phenoxy]butyric acid ethyl ester (0.045 g, 0.12 mmol) obtained in Preparation Example 2 were used to react in the same manner as in Step A of Example 29 to obtain the title compound (0.019 g, 40%).

¹H-NMR (CDCl₃) δ 7.19 (1H, t), 7.10 (2H, m), 6.81 (1H, d), 6.63 (1H, m), 6.55 (1H, m), 4.20 (2H, t), 4.14 (2H, q), 3.95 (2H, m), 2.60 (2H, t), 2.44 (2H, m), 2.10 (2H, m), 1.85 (4H, m), 1.27 (3H, t)

Step B: 4-[4-[3-(cyclobutylamino)phenyl]-2,6-difluoro-phenoxy]butanoic acid

Ethyl 4-[4-[3-(cyclobutylamino)phenyl]-2,6-difluoro-phenoxy]butanoate (0.019 g, 0.05 mmol) obtained in Step A was used to react in the same manner as in Step B of Example 1 to obtain the title compound (0.014 g, 77%).

¹H-NMR (CDCl₃) δ 7.20 (1H, t), 7.07 (2H, m), 6.81 (1H, d), 6.63 (1H, m), 6.54 (1H, m), 4.21 (2H, t), 3.96 (1H, m), 2.67 (2H, t), 2.45 (2H, m), 2.11 (2H, m), 1.84 (4H, m)

Example 94

4-[2,6-difluoro-4-[3-(propylamino)phenyl]phenoxy]butanoic acid

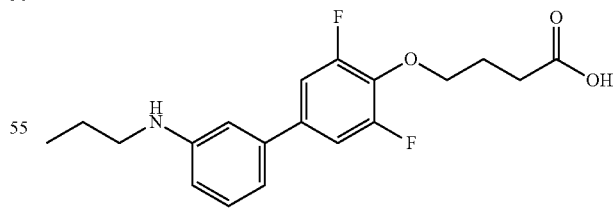

Step A: ethyl 4-[2,6-difluoro-4-[3-(propylamino)phenyl]phenoxy]butanoate

3-Bromo-N-propyl-aniline (0.07 g, 0.3 mmol) obtained in Preparation Example 79 and 4-[2,6-difluoro-4-(4,4,5,5-tetramethyl-1,3,2-dioxaborolan-2-yl)phenoxy]butyric acid ethyl ester (0.08 g, 0.21 mmol) obtained in Preparation Example 2 were used to react in the same manner as in Step A of Example 29 to obtain the title compound (0.029 g, 37%).

¹H-NMR (CDCl₃) δ 7.21 (1H, t), 7.09 (2H, m), 6.80 (1H, d), 6.69 (1H, m), 6.61 (1H, m), 4.20 (2H, t), 4.14 (2H, q), 3.75 (1H, brs), 3.13 (2H, t), 2.58 (2H, t), 2.10 (2H, m), 1.66 (2H, m), 1.27 (3H, t), 1.02 (3H, t)

Step B: 4-[2,6-difluoro-4-[3-(propylamino)phenyl]phenoxy]butanoic acid

Ethyl 4-[2,6-difluoro-4-[3-(propylamino)phenyl]phenoxy]butanoate (0.029 g, 0.076 mmol) obtained in Step A was used to react in the same manner as in Step B of Example 1 to obtain the title compound (0.021 g, 78%).

¹H-NMR (CDCl₃) δ 7.21 (1H, t), 7.11 (2H, m), 6.80 (1H, d), 6.69 (1H, m), 6.60 (1H, m), 4.21 (2H, t), 3.13 (2H, t), 2.67 (2H, t), 2.11 (2H, m), 1.66 (2H, m), 1.02 (3H, t)

Example 95

4-[4-[5-chloro-2-(cyclopentylamino)phenyl]-2,6-difluoro-phenoxy]butanoic acid

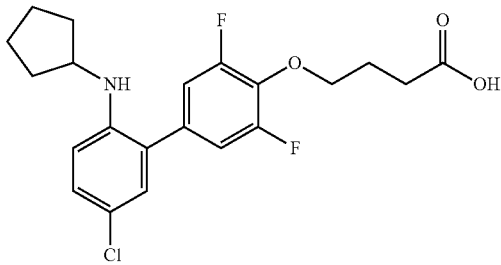 [SMILES: O=C(O)CCCOc1c(F)cc(-c2cc(Cl)ccc2NC2CCCC2)cc1F]

Step A: ethyl 4-[4-[5-chloro-2-(cyclopentylamino)phenyl]-2,6-difluoro-phenoxy]butanoate 2-Bromo-4-chloro-N-cyclopentyl-aniline (0.083 g, 0.3 mmol) obtained in Preparation Example 81 and 4-[2,6-difluoro-4-(4,4,5,5-tetramethyl-1,3,2-dioxaborolan-2-yl)phenoxy]butyric acid ethyl ester (0.112 g, 0.3 mmol) obtained in Preparation Example 2 were used to react in the same manner as in Step A of Example 28 to obtain the title compound (0.1 g, 76%).

¹H-NMR (CDCl₃) δ 7.16 (1H, m), 6.97 (1H, m), 6.92 (2H, m), 6.61 (1H, d), 4.24 (2H, t), 4.15 (2H, q), 3.74 (2H, m), 2.57 (2H, t), 2.13 (2H, m), 1.98 (2H, m), 1.62 (4H, m), 1.39 (2H, m), 1.26 (3H, t)

Step B: 4-[4-[5-chloro-2-(cyclopentylamino)phenyl]-2,6-difluoro-phenoxy]butanoic acid Ethyl 4-[4-[5-chloro-2-(cyclopentylamino)phenyl]-2,6-difluoro-phenoxy]butanoate (0.1 g, 0.23 mmol) obtained in Step A was used to react in the same manner as in Step B of Example 1 to obtain the title compound (0.059 g, 63%).

¹H-NMR (CDCl₃) δ 7.15 (1H, m), 6.98 (1H, m), 6.92 (2H, m), 6.62 (1H, d), 4.25 (2H, t), 3.73 (1H, m), 2.67 (2H, t), 2.13 (2H, m), 1.92 (2H, m), 1.64 (4H, m), 1.38 (2H, m)

Example 96

4-[4-[2-(cyclopentylamino)-5-fluoro-phenyl]-2,6-difluoro-phenoxy]butanoic acid

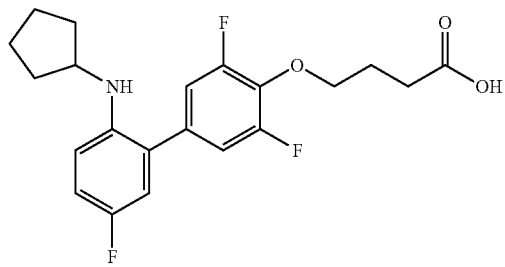 [SMILES: O=C(O)CCCOc1c(F)cc(-c2cc(F)ccc2NC2CCCC2)cc1F]

Step A: ethyl 4-[4-[2-(cyclopentylamino-5-fluoro-phenyl]-2,6-difluoro-phenoxy]butanoate N-cyclopentyl-4-fluoro-2-iodo-aniline (0.055 g, 0.18 mmol) obtained in Preparation Example 82 and 4-[2,6-difluoro-4-(4,4,5,5-tetramethyl-1,3,2-dioxaborolan-2-yl)phenoxy]butyric acid ethyl ester (0.066 g, 0.18 mmol) obtained in Preparation Example 2 were used to react in the same manner as in Step A of Example 28 to obtain the title compound (0.053 g, 70%).

¹H-NMR (CDCl₃) δ 6.96 (3H, m), 6.77 (1H, m), 6.63 (1H, m), 4.23 (2H, t), 4.15 (2H, q), 3.72 (1H, m), 3.60 (1H, brs), 2.59 (2H, t), 2.11 (2H, m), 1.96 (2H, m), 1.64 (4H, m), 1.38 (2H, m), 1.27 (3H, t)

Step B: 4-[4-[2-(cyclopentylamino)-5-fluoro-phenyl]-2,6-difluoro-phenoxy]butanoic acid Ethyl 4-[4-[2-(cyclopentylamino)-5-fluoro-phenyl]-2,6-difluoro-phenoxy]butanoate (0.053 g, 0.125 mmol) obtained in Step A was used to react in the same manner as in Step B of Example 1 to obtain the title compound (0.004 g, 8%).

¹H-NMR (CDCl₃) δ 6.96 (3H, m), 6.76 (1H, m), 6.64 (1H, m), 4.25 (2H, t), 3.71 (1H, m), 2.68 (2H, t), 2.13 (2H, m), 1.99 (2H, m), 1.62 (4H, m), 1.38 (2H, m)

Example 97

4-[4-(3-cyclopentylphenyl)-2,6-difluoro-phenoxy]butanoic acid

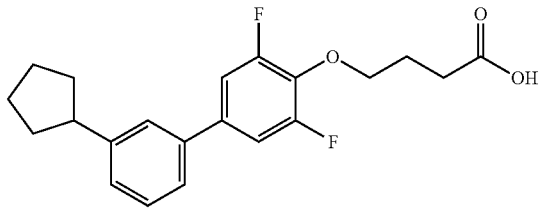 [SMILES: O=C(O)CCCOc1c(F)cc(-c2cccc(C3CCCC3)c2)cc1F]

1-Cyclopentyl-3-iodo-benzene (0.045 g, 0.16 mmol) obtained in Preparation Example 86 and 4-[2,6-difluoro-4-(4,4,5,5-tetramethyl-1,3,2-dioxaborolan-2-yl)phenoxy]butyric acid ethyl ester (0.061 g, 0.16 mmol) obtained in Preparation Example 2 were used to react sequentially in the same manner as in Step A of Example 29 and Step B of Example 1 to obtain the title compound (0.017 g, 30%).

¹H-NMR (CDCl₃) δ 7.36 (2H, m), 7.30 (1H, m), 7.26 (1H, m), 7.12 (2H, m), 4.23 (2H, t), 3.04 (1H, m), 2.67 (2H, t), 2.11 (4H, m), 1.83 (2H, m), 1.72 (2H, m), 1.62 (2H, m)

Example 98

4-[4-[3-(cyclopentylmethyl)phenyl]-2,6-difluoro-phenoxy]butanoic acid

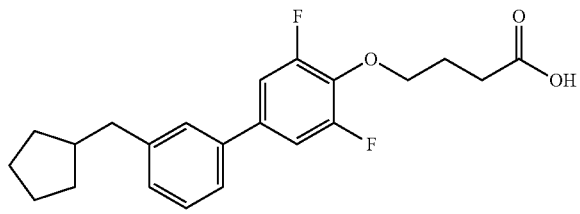 [SMILES: O=C(O)CCCOc1c(F)cc(-c2cccc(CC3CCCC3)c2)cc1F]

Step A: ethyl 4-[4-[3-(cyclopentylmethyl)phenyl]-2,6-difluoro-phenoxy]butanoate

1-Bromo-3-(cyclopentylmethyl)benzene (0.115 g, 0.48 mmol) obtained in Preparation Example 87 and 4-[2,6-difluoro-4-(4,4,5,5-tetramethyl-1,3,2-dioxaborolan-2-yl)phenoxy]butyric acid ethyl ester (0.118 g, 0.32 mmol) obtained in Preparation Example 2 were used to react in the same manner as in Step A of Example 29 to obtain the title compound (0.08 g, 62%).

¹H-NMR (CDCl₃) δ 7.31 (3H, m), 7.15 (1H, d), 7.11 (2H, m), 4.21 (2H, t), 4.15 (2H, q), 2.66 (2H, d), 2.58 (2H, t), 2.10 (3H, m), 1.72 (2H, m), 1.65 (2H, m), 1.52 (2H, m), 1.27 (3H, t), 1.20 (2H, m)

Step B: 4-[4-[3-(cyclopentylmethyl)phenyl]-2,6-difluoro-phenoxy]butanoic acid

Ethyl 4-[4-[3-(cyclopentylmethyl)phenyl]-2,6-difluoro-phenoxy]butanoate (0.08 g, 0.2 mmol) obtained in Step A was used to react in the same manner as in Step B of Example 1 to obtain the title compound (0.07 g, 94%).

¹H-NMR (CDCl₃) δ 7.31 (3H, m), 7.17 (1H, m), 7.11 (2H, m), 4.22 (2H, t), 2.67 (4H, m), 2.11 (3H, m), 1.72 (2H, m), 1.65 (2H, m), 1.53 (2H, m), 1.22 (2H, m)

Example 99

4-[4-[2-(cyclopentylmethyl)phenyl]-2,6-difluoro-phenoxy]butanoic acid

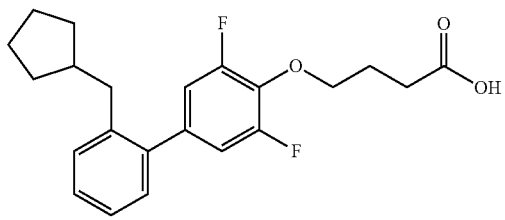 [SMILES: O=C(O)CCCOc1c(F)cc(-c2ccccc2CC2CCCC2)cc1F]

Step A: ethyl 4-[4-[2-(cyclopentylmethyl)phenyl]-2,6-difluoro-phenoxy]butanoate

1-Bromo-2-(cyclopentylmethyl)benzene (0.24 g, 1 mmol) obtained in Preparation Example 88 and 4-[2,6-difluoro-4-(4,4,5,5-tetramethyl-1,3,2-dioxaborolan-2-yl)phenoxy]butyric acid ethyl ester (0.24 g, 0.66 mmol) obtained in Preparation Example 2 were used to react in the same manner as in Step A of Example 28 to obtain the title compound (0.13 g, 49%).

¹H-NMR (CDCl₃) δ 7.29 (2H, m), 7.21 (1H, m), 7.12 (1H, d), 6.84 (2H, m), 4.22 (2H, t), 4.17 (2H, q), 2.60 (4H, m), 2.12 (2H, m), 1.89 (1H, m), 1.58 (4H, m), 1.43 (2H, m), 1.28 (3H, t), 1.02 (2H, m)

Step B: 4-[4-[2-(cyclopentylmethyl)phenyl]-2,6-difluoro-phenoxy]butanoic acid

Ethyl 4-[4-[2-(cyclopentylmethyl)phenyl]-2,6-difluoro-phenoxy]butanoate (0.13 g, 0.32 mmol) obtained in Step A was used to react in the same manner as in Step B of Example 1 to obtain the title compound (0.1 g, 83%).

¹H-NMR (CDCl₃) δ 7.28 (2H, m), 7.21 (1H, m), 7.12 (1H, d), 6.82 (2H, m), 4.24 (2H, t), 2.68 (2H, t), 2.59 (2H, d), 2.14 (2H, m), 1.90 (1H, m), 1.57 (2H, m), 1.52 (2H, m), 1.43 (2H, m), 1.02 (2H, m)

Example 100

4-[4-[6-(cyclopentylmethyl)-2-pyridyl]-2,6-difluoro-phenoxy]butanoic acid

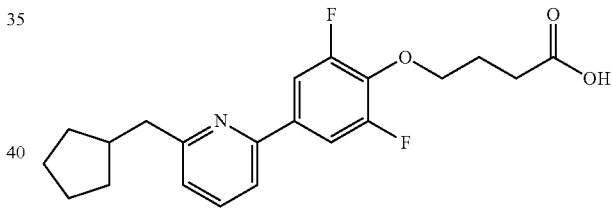

Step A: ethyl 4-[4-[6-(cyclopentylidenemethyl)-2-pyridyl]-2,6-difluoro-phenoxy]butanoate 2-Bromo-6-(cyclopentylidenemethyl)pyridine (0.13 g, 0.54 mmol) obtained in Preparation Example 91 and 4-[2,6-difluoro-4-(4,4,5,5-tetramethyl-1,3,2-dioxaborolan-2-yl)phenoxy]butyric acid ethyl ester (0.155 g, 0.42 mmol) obtained in Preparation Example 2 were used to react in the same manner as in Step A of Example 29 to obtain the title compound (0.15 g, 89%).

¹H-NMR (CDCl₃) δ 7.63 (3H, m), 7.39 (1H, d), 7.12 (1H, d), 6.50 (1H, m), 4.23 (2H, t), 4.16 (2H, q), 2.88 (2H, m), 2.57 (4H, m), 2.10 (2H, m), 1.84 (2H, m), 1.71 (2H, m), 1.27 (3H, t)

Step B: ethyl 4-[4-[6-(cyclopentylmethyl)-2-pyridyl]-2,6-difluoro-phenoxy]butanoate Ethyl 4-[4-[6-(cyclopentylidenemethyl)-2-pyridyl]-2,6-difluoro-phenoxy]butanoate (0.15 g, 0.37 mmol) obtained in Step A was used to react in the same manner as in Step B of Preparation Example 50 to obtain the title compound (0.15 g, 99%).

¹H-NMR (CDCl₃) δ 7.63 (1H, t), 7.59 (2H, m), 7.43 (1H, d), 7.07 (1H, t), 4.21 (2H, t), 4.14 (2H, q), 2.82 (2H, d), 2.58 (2H, t), 2.34 (1H, m), 2.10 (2H, m), 1.65 (8H, m), 1.27 (3H, t)

Step C: 4-[4-[6-(cyclopentylmethyl)-2-pyridyl]-2,6-difluoro-phenoxy]butanoic acid Ethyl 4-[4-[6-(cyclopentylmethyl)-2-pyridyl]-2,6-difluoro-phenoxy]butanoate (0.15 g, 0.37 mmol) obtained in Step B was used to react in the same manner as in Step B of Example 1 to obtain the title compound (0.106 g, 76%).

¹H-NMR (CDCl₃) δ 7.63 (1H, t), 7.57 (2H, m), 7.43 (1H, d), 7.07 (1H, d), 4.23 (2H, t), 2.82 (2H, d), 2.66 (2H, t), 2.34 (1H, m), 2.12 (2H, m), 1.74 (2H, m), 1.66 (2H, m), 1.54 (2H, m), 1.27 (2H, m)

Example 101

4-[4-[2-(cyclobutylmethyl)phenyl]-2,6-difluoro-phenoxy]butanoic acid

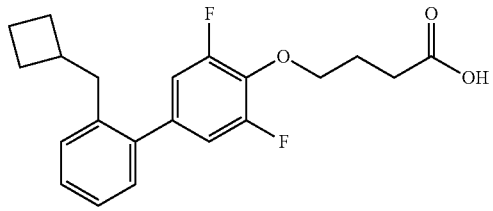 [SMILES: O=C(O)CCCOc1c(F)cc(-c2ccccc2CC2CCC2)cc1F]

Step A: ethyl 4-[4-[2-(cyclobutylmethyl)phenyl]-2,6-difluoro-phenoxy]butanoate

1-Bromo-2-(cyclobutylmethyl)benzene (0.06 g, 0.26 mmol) obtained in Preparation Example 92 and 4-[2,6-difluoro-4-(4,4,5,5-tetramethyl-1,3,2-dioxaborolan-2-yl)phenoxy]butyric acid ethyl ester (0.08 g, 0.21 mmol) obtained in Preparation Example 2 were used to react in the same manner as in Step A of Example 28 to obtain the title compound (0.035 g, 43%).

¹H-NMR (CDCl₃) δ 7.28 (1H, m), 7.21 (2H, m), 7.12 (1H, m), 6.82 (2H, m), 4.23 (2H, t), 4.16 (2H, q), 2.66 (2H, d), 2.60 (2H, t), 2.41 (1H, m), 2.13 (2H, m), 1.95 (2H, m), 1.76 (2H, m), 1.57 (2H, m), 1.27 (3H, t)

Step B: 4-[4-[2-(cyclobutylmethyl)phenyl]-2,6-difluoro-phenoxy]butanoic acid

Ethyl 4-[4-[2-(cyclobutylmethyl)phenyl]-2,6-difluoro-phenoxy]butanoate (0.035 g, 0.09 mmol) obtained in Step A was used to react in the same manner as in Step B of Example 1 to obtain the title compound (0.02 g, 61%).

¹H-NMR (CDCl₃) δ 7.78 (1H, m), 7.21 (2H, m), 7.12 (1H, m), 6.84 (2H, m), 4.24 (2H, t), 2.67 (4H, m), 2.41 (1H, m), 2.13 (2H, m), 1.95 (2H, m), 1.75 (2H, m), 1.57 (2H, m)

Example 102

4-[4-[3-(cyclobutylmethyl)phenyl]-2,6-difluoro-phenoxy]butanoic acid

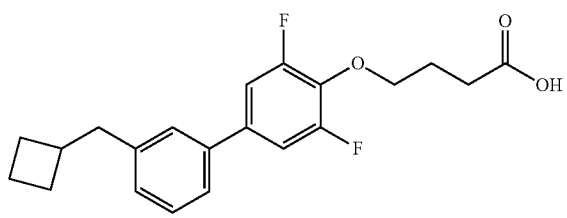 [SMILES: O=C(O)CCCOc1c(F)cc(-c2cccc(CC3CCC3)c2)cc1F]

Step A: ethyl 4-[4-[3-(cyclobutylmethyl)phenyl]-2,6-difluoro-phenoxy]butanoate

1-Bromo-3-(cyclobutylmethyl)benzene (0.03 g, 0.13 mmol) obtained in Preparation Example 93 and 4-[2,6-difluoro-4-(4,4,5,5-tetramethyl-1,3,2-dioxaborolan-2-yl)phenoxy]butyric acid ethyl ester (0.041 g, 0.11 mmol) obtained in Preparation Example 2 were used to react in the same manner as in Step A of Example 29 to obtain the title compound (0.012 g, 28%).

¹H-NMR (CDCl₃) δ 7.32 (3H, m), 7.10 (3H, m), 4.21 (2H, t), 4.15 (2H, q), 2.75 (2H, d), 2.59 (3H, m), 2.10 (4H, m), 1.85 (2H, m), 1.74 (2H, m), 1.27 (3H, t)

Step B: 4-[4-[3-(cyclobutylmethyl)phenyl]-2,6-difluoro-phenoxy]butanoic acid

Ethyl 4-[4-[3-(cyclobutylmethyl)phenyl]-2,6-difluoro-phenoxy]butanoate (0.012 g, 0.03 mmol) obtained in Step A was used to react in the same manner as in Step B of Example 1 to obtain the title compound (0.01 g, 92%).

1H-NMR (MeOH-d₄) δ 7.34 (3H, m), 7.22 (2H, m), 7.16 (1H, m), 4.19 (2H, t), 2.75 (2H, d), 2.61 (1H, m), 2.56 (2H, t), 2.06 (4H, m), 1.85 (2H, m), 1.76 (2H, m)

Example 103

4-[4-[6-(cyclobutylmethyl)-2-pyridyl]-2,6-difluoro-phenoxy]butanoic acid

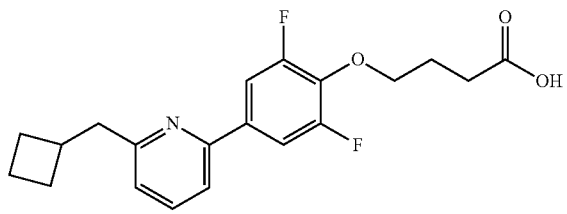 [SMILES: O=C(O)CCCOc1c(F)cc(-c2cccc(CC3CCC3)n2)cc1F]

Step A: ethyl 4-[4-[6-(cyclobutylidenemethyl)-2-pyridyl]-2,6-difluoro-phenoxy]butanoate 2-Bromo-6-(cyclobutylidenemethyl)pyridine (0.096 g, 0.43 mmol) obtained in Preparation Example 94 and 4-[2,6-difluoro-4-(4,4,5,5-tetramethyl-1,3,2-dioxaborolan-2-yl)phenoxy]butyric acid ethyl ester (0.105 g, 0.28 mmol)

obtained in Preparation Example 2 were used to react in the same manner as in Step A of Example 29 to obtain the title compound (0.085 g, 75%).

$^1$H-NMR (CDCl$_3$) δ 7.64 (1H, t), 7.60 (2H, m), 7.38 (1H, d), 7.04 (1H, d), 6.27 (1H, m), 4.23 (2H, t), 4.17 (2H, q), 3.27 (2H, m), 2.94 (2H, m), 2.59 (2H, t), 2.18 (2H, m), 2.10 (2H, m), 1.27 (3H, t)

Step B: ethyl 4-[4-[6-(cyclobutylmethyl)-2-pyridyl]-2,6-difluoro-phenoxy]butanoate Ethyl 4-[4-[6-(cyclobutylidenemethyl)-2-pyridyl]-2,6-difluoro-phenoxy]butanoate (0.085 g, 0.22 mmol) obtained in Step A was used to react in the same manner as in Step B of Preparation Example 50 to obtain the title compound (0.082 g, 95%).

$^1$H-NMR (CDCl$_3$) δ 7.62 (1H, t), 7.57 (2H, m), 7.42 (1H, d), 7.04 (1H, d), 4.22 (2H, t), 2.16 (2H, q), 2.92 (2H, d), 2.79 (1H, m), 2.57 (2H, t), 2.10 (4H, m), 1.88 (2H, m), 1.80 (2H, m), 1.27 (3H, t)

Step C: 4-[4-[6-(cyclobutylmethyl)-2-pyridyl]-2,6-difluoro-phenoxy]butanoic acid Ethyl 4-[4-[6-(cyclobutylmethyl)-2-pyridyl]-2,6-difluoro-phenoxy]butanoate (0.08 g, 0.2 mmol) obtained in Step B was used to react in the same manner as in Step B of Example 1 to obtain the title compound (0.075 g, 99%).

$^1$H-NMR (CDCl$_3$) δ 7.62 (1H, t), 7.57 (2H, m), 7.42 (1H, d), 7.04 (1H, d), 4.23 (2H, t), 2.93 (2H, d), 2.78 (1H, m), 2.67 (2H, t), 2.11 (4H, m), 1.89 (2H, m), 1.80 (2H, m)

Example 104

4-[4-(2-cyclopentylphenyl)-2,6-difluoro-phenoxy]butanoic acid

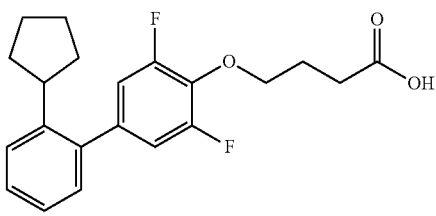 [SMILES: O=C(O)CCCOc1c(F)cc(-c2ccccc2C2CCCC2)cc1F]

Step A: ethyl 4-[4-(2-cyclopentylphenyl)-2,6-difluoro-phenoxy]butanoate

1-Cyclopentyl-2-iodo-benzene (0.065 g, 0.23 mmol) obtained in Preparation Example 97 and 4-[2,6-difluoro-4-(4,4,5,5-tetramethyl-1,3,2-dioxaborolan-2-yl)phenoxy]butyric acid ethyl ester (0.073 g, 0.2 mmol) obtained in Preparation Example 2 were used to react in the same manner as in Step A of Example 28 to obtain the title compound (0.036 g, 46%).

$^1$H-NMR (CDCl$_3$) δ 7.37 (2H, m), 7.18 (1H, t), 7.11 (1H, d), 6.82 (2H, m), 4.22 (2H, t), 4.15 (2H, q), 3.00 (1H, m), 2.60 (2H, t), 2.12 (2H, m), 1.91 (2H, m), 1.79 (2H, m), 1.58 (4H, m), 1.27 (3H, t)

Step B: 4-[4-(2-cyclopentylphenyl)-2,6-difluoro-phenoxy]butanoic acid

Ethyl 4-[4-(2-cyclopentylphenyl)-2,6-difluoro-phenoxy]butanoate (0.036 g, 0.09 mmol) obtained in Step A was used to react in the same manner as in Step B of Example 1 to obtain the title compound (0.03 g, 92%).

$^1$H-NMR (CDCl$_3$) δ 7.36 (2H, m), 7.18 (1H, t), 7.11 (1H, d), 6.82 (2H, m), 4.23 (2H, t), 2.99 (1H, m), 2.67 (2H, t), 2.14 (2H, m), 1.92 (2H, m), 1.80 (2H, m), 1.59 (4H, m)

Example 105

4-[4-(6-cyclopentyl-2-pyridyl)-2,6-difluoro-phenoxy]butanoic acid

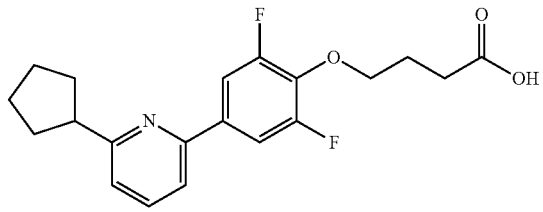

Step A: ethyl 4-[4-(6-cyclopentyl-2-pyridyl)-2-difluoro-phenoxy]butanoate

2-Bromo-6-cyclopentyl-pyridine (0.1 g, 0.44 mmol) obtained in Preparation Example 98 and 4-[2,6-difluoro-4-(4,4,5,5-tetramethyl-1,3,2-dioxaborolan-2-yl)phenoxy]butyric acid ethyl ester (0.125 g, 0.34 mmol) obtained in Preparation Example 2 were used to react in the same manner as in Step A of Example 29 to obtain the title compound (0.091 g, 68%).

$^1$H-NMR (CDCl$_3$) δ 7.60 (3H, m), 7.43 (1H, d), 7.10 (1H, d), 4.20 (2H, t), 4.14 (2H, q), 3.21 (1H, m), 2.56 (2H, t), 2.09 (4H, m), 1.86 (4H, m), 1.72 (2H, m), 1.26 (3H, t)

Step B: 4-[4-(6-cyclopentyl-2-pyridyl)-2,6-difluoro-phenoxy]butanoic acid

Ethyl 4-[4-(6-cyclopentyl-2-pyridyl)-2,6-difluoro-phenoxy]butanoate (0.09 g, 0.23 mmol) obtained in Step A was used to react in the same manner as in Step B of Example 1 to obtain the title compound (0.07 g, 84%).

$^1$H-NMR (CDCl$_3$) δ 7.62 (3H, m), 7.42 (1H, d), 7.11 (1H, d), 4.23 (2H, t), 3.22 (1H, m), 2.67 (2H, t), 2.12 (4H, m), 1.86 (4H, m), 1.71 (2H, m)

Example 106

4-[2,6-difluoro-4-(2-isobutyl-3-pyridyl)phenoxy]butanoic acid

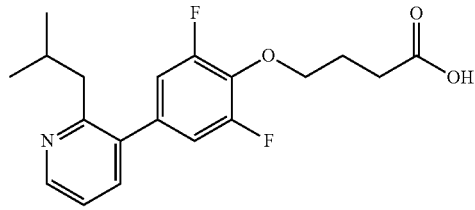 [SMILES: CC(C)Cc1ncccc1-c1cc(F)c(OCCCC(=O)O)c(F)c1]

Step A: ethyl 4-[2,6-difluoro-4-(2-isobutyl-3-pyridyl)phenoxy]butanoate (2-Isobutyl-3-pyridyl)trifluoromethanesulfonate (0.017 g, 0.06 mmol) obtained in Preparation Example 103 and 4-[2, 6-difluoro-4-(4,4,5,5-tetramethyl-1,3,2-dioxaborolan-2-yl) phenoxy]butyric acid ethyl ester (0.026 g, 0.07 mmol) obtained in Preparation Example 2 were used to react in the same manner as in Step A of Example 29 to obtain the title compound (0.013 g, 57%).

$^1$H-NMR (CDCl$_3$) δ 8.57 (1H, m), 7.44 (1H, m), 7.16 (1H, m), 6.83 (2H, m), 4.26 (2H, t), 4.16 (2H, q), 2.65 (2H, d), 2.61 (2H, t), 2.13 (3H, m), 1.26 (3H, t), 0.80 (6H, d)

Step B: 4-[2,6-difluoro-4-(2-isobutyl-3-pyridyl)phenoxy]butanoic acid

Ethyl 4-[2,6-difluoro-4-(2-isobutyl-3-pyridyl)phenoxy]butanoate (0.013 g, 0.034 mmol) obtained in Step A was used to react in the same manner as in Step B of Example 1 to obtain the title compound (0.004 g, 32%).

$^1$H-NMR (CDCl$_3$) δ 8.60 (1H, m), 7.42 (1H, m), 7.20 (1H, m), 6.82 (2H, m), 4.27 (2H, t), 2.67 (4H, m), 2.15 (2H, m), 2.05 (1H, m), 0.78 (6H, d)

Example 107

4-[4-(2-cyclopentyl-3-pyridyl)-2,6-difluoro-phenoxy]butanoic acid

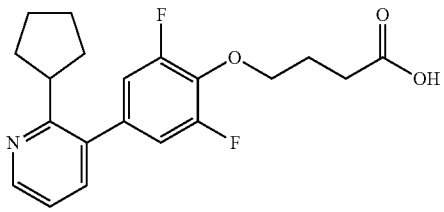 [SMILES: O=C(O)CCCOc1c(F)cc(-c2cccnc2C2CCCC2)cc1F]

Step A: ethyl 4-[4-(2-cyclopentyl-3-pyridyl)-2,6-difluoro-phenoxy]butanoate (2-Cyclopentyl-3-pyridyl)trifluoromethanesulfonate (0.376 g, 1.27 mmol) obtained in Preparation Example 106 and 4-[2,6-difluoro-4-(4,4,5,5-tetramethyl-1,3,2-dioxaborolan-2-yl)phenoxy]butyric acid ethyl ester (0.51 g, 1.4 mmol) obtained in Preparation Example 2 were used to react in the same manner as in Step A of Example 29 to obtain the title compound (0.284 g, 57%).

$^1$H-NMR (CDCl$_3$) δ 8.60 (1H, m), 7.41 (1H, m), 7.12 (1H, m), 6.83 (2H, m), 4.24 (2H, t), 4.16 (2H, q), 3.16 (1H, m), 2.60 (2H, t), 2.12 (2H, m), 1.87 (6H, m), 1.59 (2H, m), 1.27 (3H, t)

Step B: 4-[4-(2-cyclopentyl-3-pyridyl)-2,6-difluoro-phenoxy]butanoic acid

Ethyl 4-[4-(2-cyclopentyl-3-pyridyl)-2,6-difluoro-phenoxy]butanoate (0.18 g, 0.46 mmol) obtained in Step A was used to react in the same manner as in Step B of Example 1 to obtain the title compound (0.15 g, 90%).

$^1$H-NMR (CDCl$_3$) δ 8.62 (1H, m), 7.41 (1H, m), 7.14 (1H, m), 6.84 (2H, m), 4.27 (2H, t), 3.16 (1H, m), 2.69 (2H, t), 2.14 (2H, m), 1.89 (6H, m), 1.60 (2H, m)

Example 108

4-[4-[2-(cyclopentylmethyl)-3-pyridyl]-2,6-difluoro-phenoxy]butanoic acid

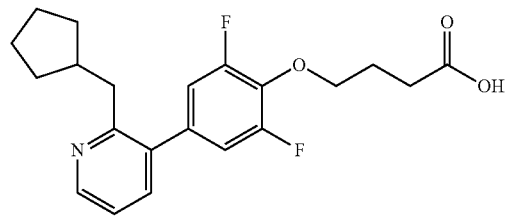

Step A: ethyl 4-[4-[2-(cyclopentylmethyl)-3-pyridyl]-2,6-difluoro-phenoxy]butanoate

[2-(Cyclopentylmethyl)-3-pyridyl]trifluoromethanesulfonate (0.04 g, 0.13 mmol) obtained in Preparation Example 108 and 4-[2,6-difluoro-4-(4,4,5,5-tetramethyl-1,3,2-dioxaborolan-2-yl)phenoxy]butyric acid ethyl ester (0.052 g, 0.14 mmol) obtained in Preparation Example 2 were used to react in the same manner as in Step A of Example 29 to obtain the title compound (0.037 g, 70%).

$^1$H-NMR (CDCl$_3$) δ 8.56 (1H, m), 7.43 (1H, m), 7.16 (1H, m), 6.82 (2H, m), 4.24 (2H, t), 4.15 (2H, q), 2.78 (2H, d), 2.60 (2H, t), 2.23 (1H, m), 2.12 (2H, m), 1.53 (6H, m), 1.27 (3H, t), 1.04 (2H, m)

Step B: 4-[4-[2-(cyclopentylmethyl)-3-pyridyl]-2,6-difluoro-phenoxy]butanoic acid Ethyl 4-[4-[2-(cyclopentylmethyl)-3-pyridyl]-2,6-difluoro-phenoxy]butanoate (0.037 g, 0.09 mmol) obtained in Step A was used to react in the same manner as in Step B of Example 1 to obtain the title compound (0.022 g, 65%).

$^1$H-NMR (CDCl$_3$) δ 8.58 (1H, m), 7.45 (1H, m), 7.17 (1H, m), 6.85 (2H, m), 4.26 (2H, t), 2.80 (2H, d), 2.67 (2H, t), 2.16 (3H, m), 1.55 (6H, m), 1.03 (2H, m)

Example 109

4-[2,6-difluoro-4-(2-pyrrol-1-yl-3-pyridyl)phenoxy]butanoic acid

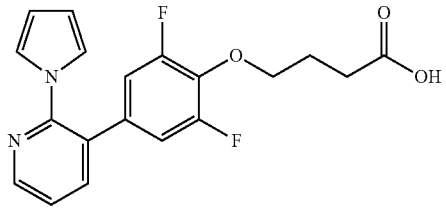 [SMILES: O=C(O)CCCOc1c(F)cc(-c2cccnc2-n2cccc2)cc1F]

Ethyl 4-[2,6-difluoro-4-(2-fluoro-3-pyridyl)phenoxy]butanoate (0.1 g, 0.29 mmol) obtained in Preparation Example 109 and pyrrole (0.04 g, 0.59 mmol) were used to react in the same manner as in Preparation Example 37 to obtain 2,6-difluoro-4-(2-pyrrol-1-yl-3-pyridyl)phenol. The obtained 2,6-difluoro-4-(2-pyrrol-1-yl-3-pyridyl)phenol was reacted with 4-bromo-butyric acid ethyl ester in the same manner as in Preparation Example 12 to obtain ethyl 4-[2,6-difluoro-4-(2-pyrrol-1-yl-3-pyridyl)phenoxy]butanoate. The obtained ethyl 4-[2,6-difluoro-4-(2-pyrrol-1-yl-3-pyridyl)phenoxy]butanoate was reacted in the same manner as in Step B of Example 1 to obtain the title compound (0.07 g, 0.07%).

$^{1}$H-NMR (CDCl$_{3}$) δ 8.51 (1H, m), 7.71 (1H, m), 7.30 (1H, m), 6.82 (2H, m), 6.71 (2H, m), 6.19 (2H, m), 4.23 (2H, t), 2.65 (2H, t), 2.12 (2H, m)

Example 110

4-[2,6-difluoro-4-[2-(4-methylpyrazol-1-yl)-3-pyridyl]phenoxy]butanoic acid

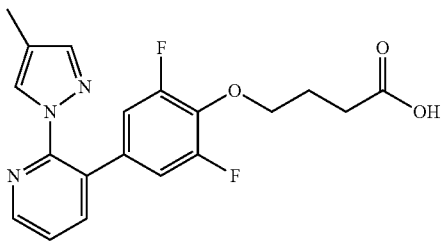 [SMILES: Cc1cnn(-c2ncccc2-c2cc(F)c(OCCCC(=O)O)c(F)c2)c1]

Step A: ethyl 4-[2,6-difluoro-4-[2-(4-methylpyrazol-1-yl)-3-pyridyl]phenoxy]butanoate Ethyl 4-[2,6-difluoro-4-(2-fluoro-3-pyridyl)phenoxy]butanoate (0.071 g, 0.21 mmol) obtained in Preparation Example 109 and 4-methylpyrazole (0.021 g, 0.25 mmol) were used to react in the same manner as in Step A of Example 72 to obtain the title compound (0.054 g, 64%).

$^{1}$H-NMR (CDCl$_{3}$) δ 8.50 (1H, m), 7.76 (1H, m), 7.70 (1H, s), 7.37 (1H, s), 7.36 (1H, m), 6.68 (2H, m), 4.20 (2H, t), 4.15 (2H, q), 2.57 (2H, t), 2.10 (5H, m), 1.27 (3H, t)

Step B: 4-[2,6-difluoro-4-[2-(4-methylpyrazole-1-yl)-3-pyridyl]phenoxy]butanoic acid Ethyl 4-[2,6-difluoro-4-[2-(4-methylpyrazole-1-yl)-3-pyridyl]phenoxy]butanoate (0.054 g, 0.13 mmol) obtained in Step A was used to react in the same manner as in Step B of Example 1 to obtain the title compound (0.016 g, 33%).

$^{1}$H-NMR (CDCl$_{3}$) δ 8.51 (1H, m), 7.76 (1H, m), 7.70 (1H, s), 7.38 (1H, s), 7.36 (1H, m), 6.69 (2H, m), 4.22 (2H, t), 2.64 (2H, m), 2.11 (5H, m)

Example 111

4-[2,6-difluoro-4-(2-morpholino-3-pyridyl)phenoxy]butanoic acid

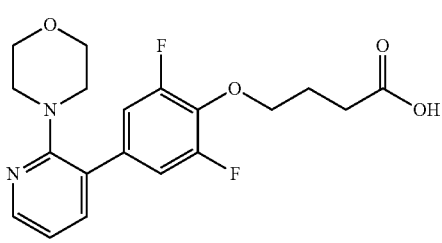 [SMILES: O=C(O)CCCOc1c(F)cc(-c2cccnc2N2CCOCC2)cc1F]

4-(3-Iodo-2-pyridyl)morpholine (0.056 g, 0.19 mmol) obtained in Preparation Example 110 and 4-[2,6-difluoro-4-(4,4,5,5-tetramethyl-1,3,2-dioxaborolan-2-yl)phenoxy] butyric acid ethyl ester (0.072 g, 0.19 mmol) obtained in Preparation Example 2 were used to react sequentially in the same manner as in Example 72 and Step B of Example 1 to obtain the title compound (0.009 g, 12%).

$^{1}$H-NMR (CDCl$_{3}$) δ 8.26 (1H, m), 7.43 (1H, m), 7.19 (2H, m), 6.96 (1H, m), 4.25 (2H, t), 3.67 (4H, m), 3.10 (4H, m), 2.67 (2H, t), 2.12 (2H, m)

Example 112

4-[2,6-difluoro-4-[2-(tetrahydropyran-4-ylmethyl-amino)-3-pyridyl]phenoxy]butanoic acid

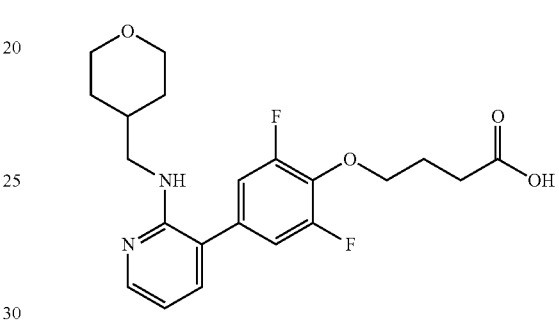

3-Iodo-N-(tetrahydropyran-4-ylmethyl)pyridin-2-amine (0.063 g, 0.2 mmol) obtained in Preparation Example 111 and 4-[2,6-difluoro-4-(4,4,5,5-tetramethyl-1,3,2-dioxaborolan-2-yl)phenoxy]butyric acid ethyl ester (0.075 g, 0.2 mmol) obtained in Preparation Example 2 were used to react sequentially in the same manner as in Example 72 and Step B of Example 1 to obtain the title compound (0.003 g, 4%).

$^{1}$H-NMR (CDCl$_{3}$) δ 8.13 (1H, m), 7.22 (1H, m), 6.94 (2H, m), 6.64 (1H, m), 4.57 (1H, brs), 4.28 (2H, t), 3.97 (2H, m), 3.38 (2H, m), 3.31 (2H, m), 2.67 (2H, t), 2.13 (2H, m), 1.88 (1H, m), 1.61 (2H, m), 1.34 (2H, m)

Example 113

4-[2,6-difluoro-4-[2-(1-piperidyl)-3-pyridyl]phenoxy]butanoic acid

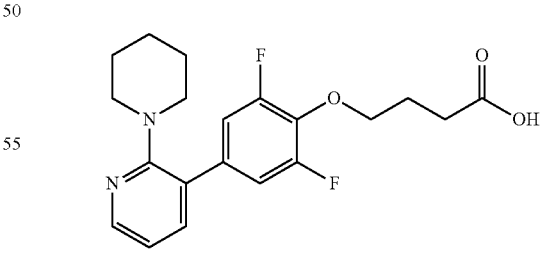

Step A: ethyl 4-[2,6-difluoro-4-[2-(1-piperidyl)-3-pyridyl]phenoxy]butanoate

Ethyl 4-[2,6-difluoro-4-(2-fluoro-3-pyridyl)phenoxy]butanoate (0.1 g, 0.29 mmol) obtained in Preparation Example 109, piperidine (0.05 g, 0.58 mmol) and DMSO were used to react in the same manner as in Step A of Example 72 to obtain the title compound (0.022 g, 19%).

¹H-NMR (CDCl₃) δ 8.22 (1H, m), 7.38 (1H, m), 7.19 (2H, m), 6.87 (1H, m), 4.22 (2H, t), 4.15 (2H, q), 3.03 (4H, m), 2.60 (2H, t), 2.11 (2H, m), 1.52 (6H, m), 1.27 (3H, t)

Step B: 4-[2,6-difluoro-4-[2-(1-piperidyl)-3-pyridyl]phenoxy]butanoic acid

Ethyl 4-[2,6-difluoro-4-[2-(1-piperidyl)-3-pyridyl]phenoxy]butanoate (0.021 g, 0.05 mmol) obtained in Step A was used to react in the same manner as in Step B of Example 1 to obtain the title compound (0.014 g, 74%).

¹H-NMR (CDCl₃) δ 8.24 (1H, m), 7.40 (1H, m), 7.19 (2H, m), 6.89 (1H, m), 4.23 (2H, t), 3.05 (4H, m), 2.67 (2H, t), 2.13 (2H, m), 1.53 (6H, m)

Example 114

(4S)-4-[4-(2-cyclobutylsulfanyl-3-pyridyl)-2,6-difluoro-phenoxy]pentanoic acid

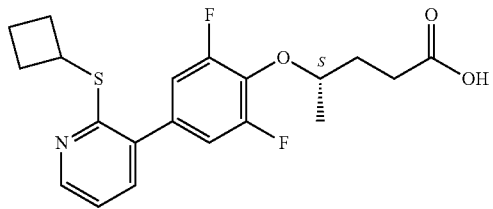

Step A: ethyl (4S)-4-[4-(2-cyclobutylsulfanyl-3-pyridyl)-2,6-difluoro-phenoxy]pentanoate 2-Cyclobutylsulfanyl-3-iodo-pyridine (0.077 g, 0.26 mmol) obtained in Preparation Example 44 and ethyl (4S)-4-[2,6-difluoro-4-(4,4,5,5-tetramethyl-1,3,2-dioxaborolan-2-yl)phenoxy]pentanoate (0.095 g, 0.24 mmol) obtained in Preparation Example 123 were used to react in the same manner as in Step A of Example 28 to obtain the title compound (0.067 g, 60%).

1H NMR (CDCl₃) δ 8.41 (1H, m), 7.33 (1H, m), 7.00 (3H, m), 4.41 (2H, m), 4.16 (2H, q), 2.61 (2H, t), 2.60 (2H, m), 2.05 (6H, m), 1.33 (3H, d), 1.27 (3H, t)

Step B: (4S)-4-[4-(2-cyclobutylsulfanyl-3-pyridyl-2,6-difluoro-phenoxy]pentanoic acid Ethyl (4S)-4-[4-(2-cyclobutylsulfanyl-3-pyridyl)-2,6-difluoro-phenoxy]pentanoate (0.067 g, 0.16 mmol) obtained in Step A was used to react in the same manner as in Step B of Example 1 to obtain the title compound (0.033 g, 52%).

1H NMR (CDCl₃) δ 8.41 (1H, m), 7.33 (1H, m), 7.00 (3H, m), 4.41 (2H, m), 2.71 (2H, t), 2.52 (2H, m), 2.05 (6H, m), 1.35 (3H, d)

Example 115

(4R)-4-[4-(2-cyclobutylsulfanyl-3-pyridyl)-2,6-difluoro-phenoxy]pentanoic acid

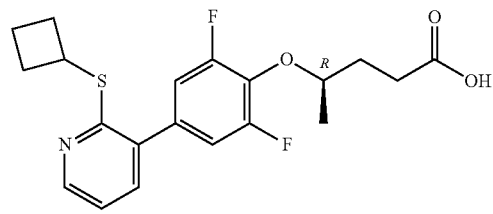

Step A: methyl (4R)-4-[4-(2-cyclobutylsulfanyl-3-pyridyl)-2,6-difluoro-phenoxy]pentanoate 2-Cyclobutylsulfanyl-3-iodo-pyridine (0.051 g, 0.18 mmol) obtained in Preparation Example 44 and methyl (4R)-4-[2,6-difluoro-4-(4,4,5,5-tetramethyl-1,3,2-dioxaborolan-2-yl)phenoxy]pentanoate (0.062 g, 0.16 mmol) obtained in Preparation Example 117 were used to react in the same manner as in Step A of Example 28 to obtain the title compound (0.04 g, 61%).

1H NMR (CDCl₃) δ 8.41 (1H, m), 7.33 (1H, m), 7.01 (3H, m), 4.41 (2H, m), 3.69 (3H, s), 2.63 (2H, t), 2.51 (2H, m), 2.05 (6H, m), 1.33 (3H, d)

Step B: (4R)-4-[4-(2-cyclobutylsulfanyl-3-pyridyl-2,6-difluoro-phenoxy]pentanoic acid Methyl (4R)-4-[4-(2-cyclobutylsulfanyl-3-pyridyl)-2,6-difluoro-phenoxy]pentanoate (0.04 g, 0.1 mmol) obtained in Step A was used to react in the same manner as in Step B of Example 1 to obtain the title compound (0.039 g, 99%).

1H NMR (CDCl₃) δ 8.41 (1H, m), 7.33 (1H, m), 7.00 (3H, m), 4.41 (2H, m), 2.71 (2H, t), 2.52 (2H, m), 2.05 (6H, m), 1.35 (3H, d)

Example 116

(4R)-4-[4-[3-(cyclobutoxy)phenyl]-2,6-difluoro-phenoxy]pentanoic acid

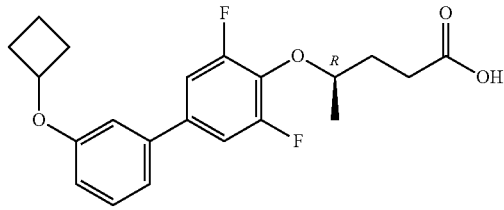

Step A: methyl (4R)-4-[4-[3-(cyclobutoxy)phenyl]-2,6-difluoro-phenoxy]pentanoate 1-Cyclobutoxy-3-iodo-benzene (0.049 g, 0.18 mmol) obtained in Preparation Example 60 and methyl (4R)-4-[2,6-difluoro-4-(4,4,5,5-tetramethyl-1,3,2-dioxaborolan-2-yl)phenoxy]pentanoate (0.055 g, 0.15 mmol) obtained in Preparation Example 117 were used to react in the same manner as in Step A of Example 29 to obtain the title compound (0.039 g, 71%).

1H NMR (CDCl₃) δ 7.31 (1H, t), 7.09 (3H, m), 6.94 (1H, m), 6.80 (1H, m), 4.69 (1H, m), 4.34 (1H, m), 3.70 (3H, s), 2.62 (2H, t), 2.47 (2H, m), 2.20 (2H, m), 2.04 (2H, m), 1.88 (1H, m), 1.71 (1H, m), 1.31 (3H, d)

Step B: (4R)-4-[4-[3-(cyclobutoxy)phenyl]-2,6-difluoro-phenoxy]pentanoic acid

Methyl (4R)-4-[4-[3-(cyclobutoxy)phenyl]-2,6-difluoro-phenoxy]pentanoate (0.039 g, 0.1 mmol) obtained in Step A was used to react in the same manner as in Step B of Example 1 to obtain the title compound (0.031 g, 82%).

1H NMR (CDCl₃) δ 7.31 (1H, t), 7.12 (3H, m), 6.95 (1H, m), 6.80 (1H, m), 4.69 (1H, m), 4.36 (1H, m), 2.70 (2H, t), 2.46 (2H, m), 2.20 (2H, m), 2.05 (2H, m), 1.88 (1H, m), 1.71 (1H, m), 1.30 (3H, d)

Example 117

(4R)-4-[4-(2-cyclopentylsulfanyl-3-pyridyl)-2,6-difluoro-phenoxy]pentanoic acid

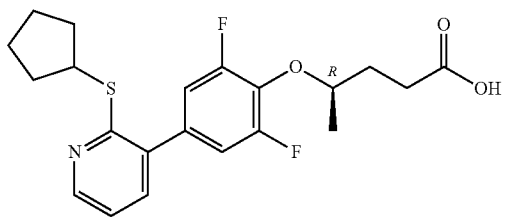

Step A: methyl (4R)-4-[4-(2-cyclopentylsulfanyl-3-pyridyl-2,6-difluoro-phenoxy]pentanoate 2-cyclopentylsulfanyl-3-iodo-pyridine (0.054 g, 0.18 mmol) obtained in Preparation Example 39 and methyl (4R)-4-[2,6-difluoro-4-(4,4,5,5-tetramethyl-1,3,2-dioxaborolan-2-yl)phenoxy]pentanoate (0.055 g, 0.15 mmol) obtained in Preparation Example 117 were used to react in the same manner as in Step A of Example 28 to obtain the title compound (0.045 g, 66%).

1H NMR (CDCl₃) δ 8.42 (1H, m), 7.32 (1H, m), 7.00 (3H, m), 4.37 (1H, m), 4.08 (1H, m), 3.70 (3H, s), 2.63 (2H, t), 2.20 (2H, m), 2.04 (2H, m), 1.72 (2H, m), 1.64 (2H, m), 1.57 (2H, m), 1.33 (3H, d)

Step B: (4R)-4-[4-(2-cyclopentylsulfanyl-3-pyridyl-2,6-difluoro-phenoxy]pentanoic acid Methyl (4R)-4-[4-(2-cyclopentylsulfanyl-3-pyridyl)-2,6-difluoro-phenoxy]pentanoate (0.045 g, 0.1 mmol) obtained in Step A was used to react in the same manner as in Step B of Example 1 to obtain the title compound (0.041 g, 95%).

1H NMR (CDCl₃) δ 8.43 (1H, m), 7.32 (1H, m), 7.00 (3H, m), 4.39 (1H, m), 4.09 (1H, m), 2.70 (2H, t), 2.20 (2H, m), 2.04 (2H, m), 1.71 (2H, m), 1.62 (4H, m), 1.34 (3H, d)

Example 118

(4R)-4-[2,6-difluoro-4-(3-phenoxyphenyl)phenoxy]pentanoic acid

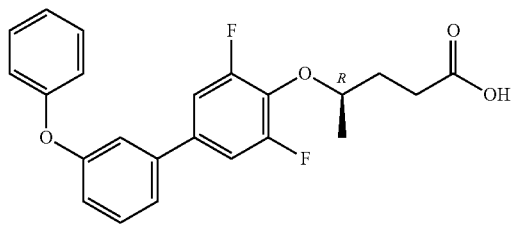

Step A: methyl (4R)-4-[2,6-difluoro-4-(3-phenoxyphenyl)phenoxy]pentanoate

Methyl (4R)-4-[2,6-difluoro-4-(4,4,5,5-tetramethyl-1,3,2-dioxaborolan-2-yl)phenoxy]pentanoate (0.055 g, 0.15 mmol) obtained in Preparation Example 117 and 1-bromo-3-phenoxy-benzene (0.044 g, 0.18 mmol) were used to react in the same manner as in Step A of Example 29 to obtain the title compound (0.044 g, 72%).

1H NMR (CDCl₃) δ 7.37 (3H, m), 7.23 (1H, m), 7.14 (2H, m), 7.08 (2H, m), 7.04 (2H, m), 6.99 (1H, m), 4.34 (1H, m), 3.69 (3H, s), 2.62 (2H, t), 2.02 (2H, m), 1.30 (3H, d)

Step B: (4R)-4-[2,6-difluoro-4-(3-phenoxyphenyl)phenoxy]pentanoic acid

Methyl (4R)-4-[2,6-difluoro-4-(3-phenoxyphenyl)phenoxy]pentanoate (0.044 g, 0.1 mmol) obtained in Step A was used to react in the same manner as in Step B of Example 1 to obtain the title compound (0.041 g, 96%).

1H NMR (CDCl₃) δ 7.36 (3H, m), 7.23 (1H, m), 7.14 (2H, m), 7.09 (2H, m), 7.04 (2H, m), 6.99 (1H, m), 4.35 (1H, m), 2.68 (2H, t), 2.03 (2H, m), 1.30 (3H, d)

Example 119

4-(3'-cyclobutoxy-biphenyl-4-ylsulfanyl)-butyric acid

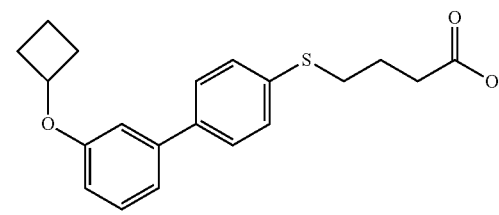 [SMILES: O=C(O)CCCSc1ccc(-c2cccc(OC3CCC3)c2)cc1]

Step A: 4-(3'-cyclobutoxy-biphenyl-4-ylsulfanyl)-butyric acid ethyl ester 4-(3'-Hydroxy-biphenyl-4-ylsulfanyl)-butyric acid ethyl ester (0.1 g, 0.32 mmol) obtained in Preparation Example 149, bromo-cyclobutane (0.044 mL) and Cs₂CO₃ (0.31 g, 0.95 mmol) were used to react in the same manner as in Step B of Preparation Example 44 to obtain the title compound (0.075 g, 64%).

¹H-NMR (CDCl₃) δ 7.48 (2H, d), 7.38 (2H, d), 7.30 (1H, t), 7.12 (1H, m), 7.00 (1H, s), 6.78 (1H, m), 4.69 (1H, m), 4.12 (2H, q), 3.00 (2H, t), 2.47 (4H, m), 2.20 (2H, m), 1.98 (2H, m), 1.86 (1H, m), 1.70 (1H, m), 1.24 (3H, t).

Step B: 4-(3'-cyclobutoxy-biphenyl-4-ylsulfanyl)-butyric acid 4-(3'-Cyclobutoxy-biphenyl-4-ylsulfanyl)-butyric acid ethyl ester (0.075 g, 0.20 mmol) obtained in Step A was used to react in the same manner as in Step B of Example 1 to obtain the title compound (0.02 g, 28%).

¹H-NMR (CDCl₃) δ 7.48 (2H, d), 7.38 (2H, d), 7.30 (1H, t), 7.12 (1H, m), 7.00 (1H, s), 6.78 (1H, m), 4.68 (1H, m), 3.01 (2H, t), 2.54 (2H, t), 2.46 (2H, m), 2.20 (2H, m), 2.00 (2H, m), 1.85 (1H, m), 1.70 (1H, m).

Example 120

4-(3'-isopropoxy-biphenyl-4-ylsulfanyl)-butyric acid

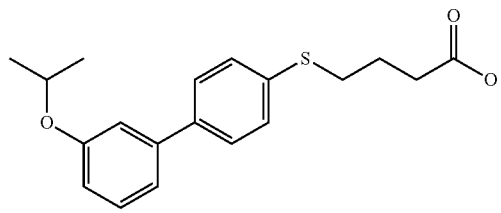 [SMILES: CC(C)Oc1cccc(-c2ccc(SCCCC(=O)O)cc2)c1]

Step A: 4-(3'-isopropoxy-biphenyl-4-ylsulfanyl)-butyric acid ethyl ester 4-(3'-Hydroxy-biphenyl-4-ylsulfanyl)-butyric acid ethyl ester (0.11 g, 0.35 mmol) obtained in Preparation Example 149, 2-bromo-propane (0.049 mL) and Cs₂CO₃ (0.34 g, 1.04 mmol) were used to react in the same manner as in Step B of Preparation Example 44 to obtain the title compound (0.12 g, 96%).

¹H-NMR (CDCl₃) δ 7.50 (2H, d), 7.39 (2H, d), 7.31 (1H, t), 7.12 (1H, m), 7.07 (1H, s), 6.86 (1H, m), 4.60 (1H, m), 4.13 (2H, q), 3.00 (2H, t), 2.47 (2H, t), 1.98 (2H, m), 1.36 (6H, d), 1.24 (3H, t).

Step B: 4-(3'-isopropoxy-biphenyl-4-ylsulfanyl)-butyric acid 4-(3'-Isopropoxy-biphenyl-4-ylsulfanyl)-butyric acid ethyl ester (0.12 g, 0.33 mmol) obtained in Step A was used to react in the same manner as in Step B of Example 1 to obtain the title compound (0.10 g, 95%).

¹H-NMR (CDCl₃) δ 7.50 (2H, d), 7.39 (2H, d), 7.31 (1H, t), 7.12 (1H, m), 7.07 (1H, s), 6.86 (1H, m), 4.60 (1H, m), 3.01 (2H, t), 2.54 (2H, t), 2.00 (2H, m), 1.34 (6H, d).

Example 121

[1-(3,5-difluoro-3'-isopropoxy-biphenyl-4-ylsulfanylmethyl)-cyclopropyl]-acetic acid

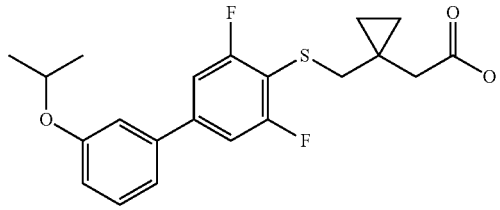 [SMILES: CC(C)Oc1cccc(-c2cc(F)c(SCC3(CC(=O)O)CC3)c(F)c2)c1]

Step A: [1-(3,5-difluoro-3'-isopropoxy-biphenyl-4-ylsulfanylmethyl)-cyclopropyl]-acetic acid methyl ester

[1-(3,5-Difluoro-3'-hydroxy-biphenyl-4-ylsulfanylmethyl)-cyclopropyl]-acetic acid methyl ester (0.02 g, 0.05 mmol) obtained in Preparation Example 152, 2-bromopropane (0.008 mL) and Cs₂CO₃ (0.05 g, 0.16 mmol) were used to react in the same manner as in Step B of Preparation Example 44 to obtain the title compound (0.006 g, 27%).

¹H-NMR (CDCl₃) δ 7.34 (1H, t), 7.13-7.08 (3H, m), 7.04 (1H, s), 6.91 (1H, m), 4.61 (1H, m), 3.64 (3H, s), 3.01 (2H, s), 2.56 (2H, s), 1.35 (6H, d), 0.45-0.38 (4H, m).

Step B: [1-(3,5-difluoro-3'-isopropoxy-biphenyl-4-ylsulfanylmethyl)-cyclopropyl]-acetic acid

[1-(3,5-Difluoro-3'-isopropoxy-biphenyl-4-ylsulfanylmethyl)-cyclopropyl]-acetic acid methyl ester (0.006 g, 0.015 mmol) obtained in Step A was used to react in the same manner as in Step B of Example 1 to obtain the title compound (0.004 g, 69%).

¹H-NMR (CDCl₃) δ 7.33 (1H, t), 7.13-7.05 (4H, m), 6.90 (1H, m), 4.60 (1H, m), 3.01 (2H, s), 2.62 (2H, s), 1.36 (6H, d), 0.46-0.35 (4H, m).

Example 122

4-(3'-cyclopentyloxy-3,5-difluoro-biphenyl-4-ylsulfanyl)-butyric acid

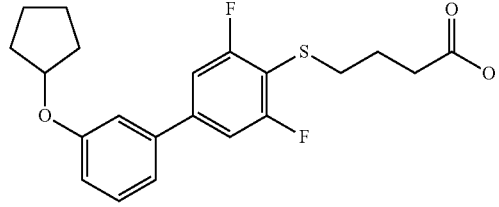 [SMILES: O=C(O)CCCSc1c(F)cc(-c2cccc(OC3CCCC3)c2)cc1F]

Step A: 2-[2-(3'-cyclopentyloxy-3,5-difluoro-biphenyl-ylsulfanyl)-ethyl]-malonic acid dimethyl ester NaH (60% in mineral oil, 0.005 g, 0.12 mmol) was dissolved in 1 mL of DMF. Dimethylmalonate (0.013 mL, 0.12 mmol) was added thereto and the resultant was agitated at room temperature for 15 minutes. 4-(2-Chloro-ethylsulfanyl)-3'-cyclopentyloxy-3,5-difluoro-biphenyl (0.03 g, 0.08 mmol) obtained in Preparation Example 158 was added thereto, and the resultant was agitated at 65° C. for 18 hours. The reaction solution was added with water and extracted with EtOAc. The organic layer was dried with MgSO$_4$ and purified by column chromatography to obtain the title compound (0.01 g, 25%).

Step B: 4-(3'-cyclopentyloxy-3,5-difluoro-biphenyl-ylsulfanyl)-butyric acid

2-[2-(3'-Cyclopentyloxy-3,5-difluoro-biphenyl-ylsulfanyl)-ethyl]-malonic acid dimethyl ester (0.01 g, 0.02 mmol) obtained in Step A was dissolved in each 0.3 mL of EtOH and THF. 0.2 mL of 4N KOH was added thereto, and the resultant was agitated at 60° C. for 1 hour. The reaction solution was concentrated under reduced pressure, and water was then added thereto. The pH was adjusted to 3 by the use of 2N HCl, and the resultant was then extracted with EtOAc. The separated organic layer was dried with MgSO$_4$ and concentrated under reduced pressure. The concentrated organic layer was dissolved in 1 mL of pyridine, and the resultant was agitated at 80° C. for 18 hours. The reaction solution was concentrated under reduced pressure, and then water was added thereto. The pH was adjusted to 3 by the use of 2N HCl, and the resultant was then extracted with EtOAc. The separated organic layer was dried with MgSO$_4$ and purified by column chromatography to obtain the title compound (0.002 g, 20%).

$^1$H-NMR (CDCl$_3$) δ 7.32 (1H, t), 7.13 (2H, m), 7.08 (1H, m), 7.02 (1H, s), 6.90 (1H, m), 4.81 (1H, m), 2.94 (2H, t), 2.55 (2H, t), 1.92-1.81 (8H, m), 1.64 (2H, m).

Example 123

4-[4-(2-cyclopentyloxy-pyridin-3-yl)-phenylsulfanyl]-butyric acid

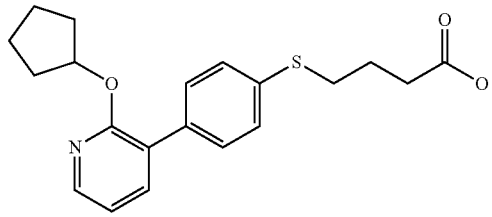 [SMILES: O=C(O)CCCSc1ccc(-c2cccnc2OC2CCCC2)cc1]

4-[4-(4,4,5,5-Tetramethyl-[1,3,2]dioxaborolan-2-yl)-phenylsulfanyl]-butyric acid ethyl ester (0.056 g, 0.16 mmol) obtained in Preparation Example 159 and 2-cyclopentoxy-3-iodo-pyridine (0.046 g, 0.16 mmol) obtained in Preparation Example 38 were used to react sequentially in the same manner as in Steps A and B of Example 1 to obtain the title compound (0.025 g, 44%).

$^1$H-NMR (CDCl$_3$) δ 8.12 (1H, m), 7.56 (1H, m), 7.49 (2H, d), 7.36 (2H, d), 6.90 (1H, m), 5.50 (1H, m), 3.02 (2H, t), 2.56 (2H, t), 2.03-1.92 (4H, m), 1.84-1.60 (6H, m).

Example 124

4-[4-(2-cyclopropylmethoxy-pyridin-3-yl)-phenyl-sulfanyl]-butyric acid

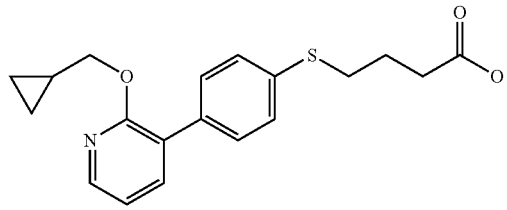 [SMILES: O=C(O)CCCSc1ccc(-c2cccnc2OCC2CC2)cc1]

4-[4-(4,4,5,5-Tetramethyl-[1,3,2]dioxaborolan-2-yl)-phenylsulfanyl]-butyric acid ethyl ester (0.08 g, 0.29 mmol) obtained in Preparation Example 159 and 2-cyclopropyl-methoxy-3-iodo-pyridine (0.10 g, 0.29 mmol) obtained in Preparation Example 40 were used to react sequentially in the same manner as in Steps A and B of Example 1 to obtain the title compound (0.02 g, 25%).

$^1$H-NMR (CDCl$_3$) δ 8.10 (1H, m), 7.59 (1H, m), 7.55 (2H, d), 7.38 (2H, d), 6.95 (1H, m), 4.20 (2H, d), 3.04-3.01 (2H, t), 2.57-2.54 (2H, t), 2.02-1.99 (2H, m), 1.27 (1H, m), 0.55 (2H, m), 0.33 (2H, m).

Example 125

4-(3'-phenoxy-biphenyl-4-ylsulfanyl)-butyric acid

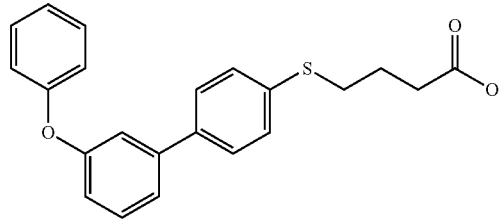 [SMILES: O=C(O)CCCSc1ccc(-c2cccc(Oc3ccccc3)c2)cc1]

4-[4-(4,4,5,5-Tetramethyl-[1,3,2]dioxaborolan-2-yl)-phenylsulfanyl]-butyric acid ethyl ester (0.03 g, 0.11 mmol) obtained in Preparation Example 159 and 1-bromo-3-phenoxy-benzene (0.03 g, 0.12 mmol) were used to react sequentially in the same manner as in Steps A and B of Example 1 to obtain the title compound (0.005 g, 16%).

$^1$H-NMR (CDCl$_3$) δ 7.48 (2H, d), 7.38-7.26 (6H, m), 7.25 (1H, s), 7.1 (1H, t), 7.05 (2H, d), 6.97 (1H, m), 3.00 (2H, t), 2.54 (2H, t), 1.98 (2H, m).

Example 126

4-(3'-cyclopentyloxy-biphenyl-4-ylsulfanyl)-butyric acid

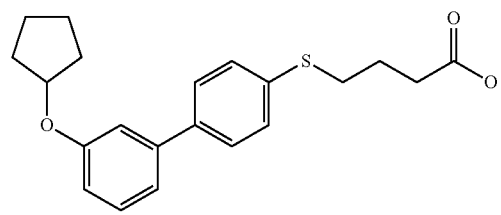 [SMILES: O=C(O)CCCSc1ccc(-c2cccc(OC3CCCC3)c2)cc1]

4-(3'-Hydroxy-biphenyl-4-ylsulfanyl)-butyric acid ethyl ester (0.056 g, 0.17 mmol) obtained in Preparation Example 149, bromo-cyclopentane (0.030 mL) and Cs$_2$CO$_3$ (0.17 g, 0.53 mmol) were used to react sequentially in the same manner as in Steps A and B of Example 119 to obtain the title compound (0.052 g, 82%).

$^1$H-NMR (CDCl$_3$) δ 7.49 (2H, d), 7.38 (2H, d), 7.30 (1H, t), 7.12 (1H, m), 7.06 (1H, s), 6.85 (1H, m), 4.81 (1H, m), 3.01 (2H, t), 2.54 (2H, t), 2.00-1.81 (8H, m), 1.62 (2H, m).

Example 127

4-(3'-propoxy-biphenyl-4-ylsulfanyl)-butyric acid

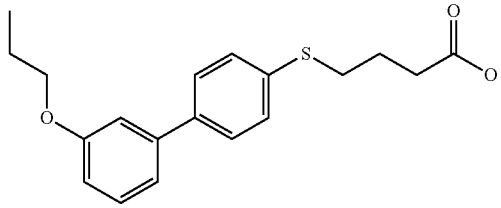 [SMILES: CCCOc1cccc(-c2ccc(SCCCC(=O)O)cc2)c1]

4-(3'-Hydroxy-biphenyl-4-ylsulfanyl)-butyric acid ethyl ester (0.053 g, 0.17 mmol) obtained in Preparation Example 149, 2-bromo-propane (0.023 mL) and $Cs_2CO_3$ (0.16 g, 0.50 mmol) were used to react sequentially in the same manner as in Steps A and B of Example 119 to obtain the title compound (0.045 g, 81%).

$^1$H-NMR (CDCl$_3$) δ 7.50 (2H, d), 7.38 (2H, d), 7.32 (1H, t), 7.12 (1H, m), 7.09 (1H, s), 6.87 (1H, m), 3.97 (2H, t), 3.01 (2H, t), 2.55 (2H, t), 2.00 (2H, m), 1.82 (2H, m), 1.05 (3H, t).

Example 128

4-[4-(6-cyclobutoxy-pyridin-2-yl)-phenylsulfanyl]-butyric acid

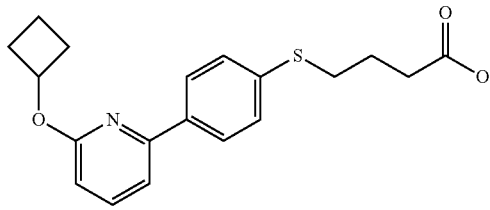 [SMILES: O=C(O)CCCSc1ccc(-c2cccc(OC3CCC3)n2)cc1]

4-[4-(4,4,5,5-Tetramethyl-[1,3,2]dioxaborolan-2-yl)-phenylsulfanyl]-butyric acid ethyl ester (0.05 g, 0.14 mmol) obtained in Preparation Example 159 and 2-chloro-6-(cyclobutoxy)-pyridine (0.033 g, 0.16 mmol) obtained in Preparation Example 24 were used to react sequentially in the same manner as in Steps A and B of Example 1 to obtain the title compound (0.005 g, 10%).

$^1$H-NMR (CDCl$_3$) δ 7.93 (2H, d), 7.59 (1H, t), 7.38 (2H, d), 7.28 (1H, d), 6.61 (1H, d), 5.26 (1H, m), 3.02 (2H, t), 2.56-2.53 (4H, m), 2.19 (2H, m), 2.01 (2H, m), 1.85 (1H, q), 1.73 (1H, m).

Example 129

4-[4-(6-cyclopentyloxy-pyridin-2-yl)-phenylsulfanyl]-butyric acid

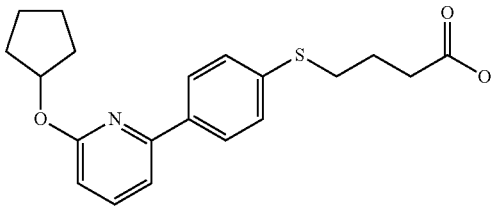

4-[4-(4,4,5,5-Tetramethyl-[1,3,2]dioxaborolan-2-yl)-phenylsulfanyl]-butyric acid ethyl ester (0.05 g, 0.14 mmol) obtained in Preparation Example 159 and 2-chloro-6-(cyclopentoxy)pyridine (0.036 g, 0.16 mmol) obtained in Preparation Example 8 were used to react sequentially in the same manner as in Steps A and B of Example 1 to obtain the title compound (0.004 g, 8%).

$^1$H-NMR (CDCl$_3$) δ 7.95 (2H, d), 7.57 (1H, t), 7.38 (2H, d), 7.26 (1H, d), 6.60 (1H, d), 5.50 (1H, m), 3.02 (2H, t), 2.54 (2H, t), 2.10-1.97 (4H, m), 1.82 (4H, m), 1.63 (2H, m).

Example 130

4-[4-(6-isopropoxy-pyridin-2-yl)-phenylsulfanyl]-butyric acid

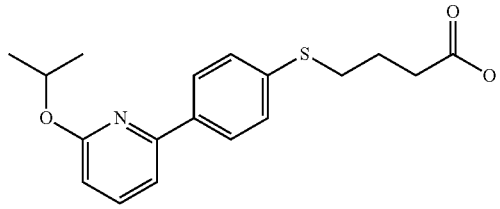 [SMILES: CC(C)Oc1cccc(-c2ccc(SCCCC(=O)O)cc2)n1]

4-[4-(4,4,5,5-Tetramethyl-[1,3,2]dioxaborolan-2-yl)-phenylsulfanyl]-butyric acid ethyl ester (0.031 g, 0.09 mmol) obtained in Preparation Example 159 and 2-bromo-6-isopropoxy-pyridine (0.021 g, 0.10 mmol) obtained in Preparation Example 228 were used to react sequentially in the same manner as in Steps A and B of Example 1 to obtain the title compound (0.011 g, 37%).

$^1$H-NMR (CDCl$_3$) δ 7.94 (2H, d), 7.59 (1H, t), 7.38 (2H, d), 7.26 (1H, d), 6.60 (1H, d), 5.46 (1H, m), 3.02 (2H, t), 2.54 (2H, t), 2.00 (2H, m), 1.39 (6H, d).

Example 131

4-[4-(2-isopropoxy-pyridin-3-yl)-phenylsulfanyl]-butyric acid

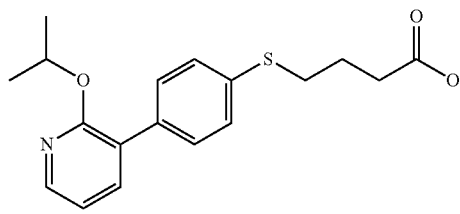 [SMILES: CC(C)Oc1ncccc1-c1ccc(SCCCC(=O)O)cc1]

4-[4-(4,4,5,5-Tetramethyl-[1,3,2]dioxaborolan-2-yl)-phenylsulfanyl]-butyric acid ethyl ester (0.11 g, 0.32 mmol) obtained in Preparation Example 159 and 3-iodo-2-isopropoxy-pyridine (0.12 g, 0.35 mmol) obtained in Preparation Example 37 were used to react sequentially in the same manner as in Steps A and B of Example 1 to obtain the title compound (0.05 g, 34%).

$^1$H-NMR (CDCl$_3$) δ 8.11 (1H, m), 7.57 (1H, m), 7.50 (2H, d), 7.35 (2H, d), 6.90 (1H, m), 5.38 (1H, m), 3.02 (2H, t), 2.56 (2H, t), 2.02 (2H, m), 1.33 (6H, d).

Example 132

4-[4-(6-propoxy-pyridin-2-yl)-phenylsulfanyl]-butyric acid

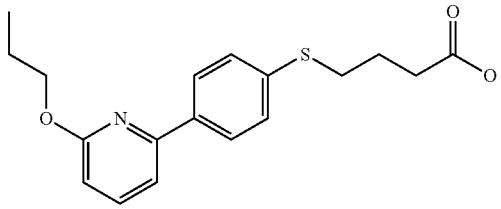

4-[4-(4,4,5,5-Tetramethyl-[1,3,2]dioxaborolan-2-yl)-phenylsulfanyl]-butyric acid ethyl ester (0.06 g, 0.17 mmol) obtained in Preparation Example 159 and 2-bromo-6-propoxy-pyridine (0.041 g, 0.19 mmol) obtained in Preparation Example 227 were used to react sequentially in the same manner as in Steps A and B of Example 1 to obtain the title compound (0.03 g, 52%).

$^1$H-NMR (CDCl$_3$) δ 7.94 (2H, d), 7.59 (1H, t), 7.39 (2H, d), 7.28 (1H, d), 6.65 (1H, d), 4.36 (2H, t), 3.02 (2H, t), 2.54 (2H, t), 2.00 (2H, m), 1.82 (2H, m), 1.04 (3H, t).

Example 133

4-[4-(6-cyclopentylsulfanyl-pyridin-2-yl)-phenylsulfanyl]-butyric acid

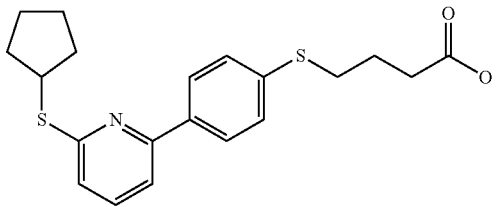 [SMILES: O=C(O)CCCSc1ccc(-c2cccc(SC3CCCC3)n2)cc1]

4-[4-(4,4,5,5-Tetramethyl-[1,3,2]dioxaborolan-2-yl)-phenylsulfanyl]-butyric acid ethyl ester (0.06 g, 0.17 mmol) obtained in Preparation Example 159 and 2-bromo-6-cyclopentylsulfanyl-pyridine (0.049 g, 0.19 mmol) obtained in Preparation Example 234 were used to react sequentially in the same manner as in Steps A and B of Example 1 to obtain the title compound (0.02 g, 28%).

$^1$H-NMR (CDCl$_3$) δ 7.95 (2H, d), 7.50 (1H, t), 7.40-7.38 (3H, m), 7.05 (1H, d), 4.17 (1H, m), 3.03 (2H, t), 2.55 (2H, t), 2.24 (2H, m), 2.00 (2H, m), 1.82-1.63 (6H, m).

Example 134

4-(3'-cyclobutoxy-3,5-difluoro-biphenyl-4-ylsulfanyl)-butyric acid

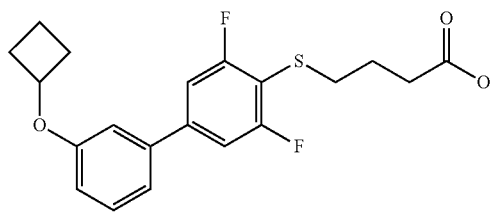 [SMILES: O=C(O)CCCSc1c(F)cc(-c2cccc(OC3CCC3)c2)cc1F]

3'-Cyclobutoxy-3,4,5-trifluoro-biphenyl (0.02 g, 0.07 mmol) obtained in Preparation Example 163, Cs$_2$CO$_3$ (0.022 g, 0.07 mmol) and 4-mercapto-butyric acid ethyl ester (0.01 g, 0.07 mmol) obtained in Preparation Example 161 were used to react sequentially in the same manner as in Steps A and B of Example 137 to obtain the title compound (0.001 g, 4%).

$^1$H-NMR (CDCl$_3$) δ 7.32 (1H, t), 7.13 (2H, d), 7.12 (1H, m), 6.96 (1H, s), 6.84 (1H, m), 4.68 (1H, m), 2.94 (2H, t), 2.55 (2H, t), 2.47 (2H, m), 2.19 (2H, m), 1.87 (3H, m), 1.71 (1H, m).

Example 135

4-(3,5-difluoro-3'-isopropoxy-biphenyl-4-ylsulfanyl)-butyric acid

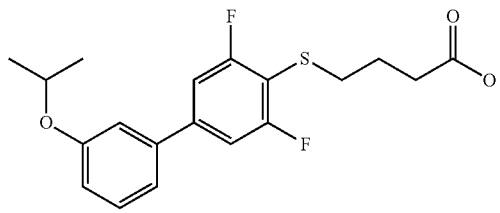 [SMILES: CC(C)Oc1cccc(-c2cc(F)c(SCCCC(=O)O)c(F)c2)c1]

3,4,5-Trifluoro-3'-isopropoxy-biphenyl (0.06 g, 0.23 mmol) obtained in Preparation Example 164, Cs$_2$CO$_3$ (0.074 g, 0.23 mmol) and 4-mercapto-butyric acid ethyl ester (0.034 g, 0.23 mmol) obtained in Preparation Example 161 were used to react sequentially in the same manner as in Steps A and B of Example 137 to obtain the title compound (0.011 g, 13%).

$^1$H-NMR (CDCl$_3$) δ 7.33 (1H, t), 7.13 (2H, d), 7.09 (1H, m), 7.04 (1H, s), 6.92 (1H, m), 4.60 (1H, m), 2.94 (2H, t), 2.55 (2H, t), 1.87 (2H, m), 1.35 (6H, d).

Example 136

4-[2,6-difluoro-4-(6-propoxy-pyridin-2-yl)-phenylsulfanyl]-butyric acid

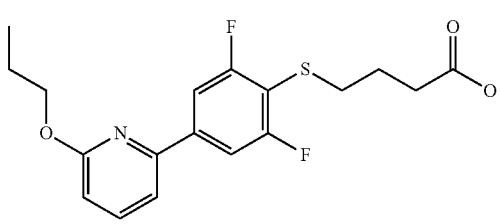 [SMILES: CCCOc1cccc(-c2cc(F)c(SCCCC(=O)O)c(F)c2)n1]

2-Propoxy-6-(3,4,5-trifluoro-phenyl)-pyridine (0.02 g, 0.08 mmol) obtained in Preparation Example 166, Cs$_2$CO$_3$ (0.028 g, 0.08 mmol) and 4-mercapto-butyric acid ethyl ester (0.01 g, 0.08 mmol) obtained in Preparation Example 161 were used to react sequentially in the same manner as in Steps A and B of Example 137 to obtain the title compound (0.008 g, 24%).

$^1$H-NMR (CDCl$_3$) δ 7.63-7.59 (3H, m), 7.27 (1H, d), 6.71 (1H, d), 4.35 (2H, t), 2.96 (2H, t), 2.54 (2H, t), 1.88-1.82 (4H, m), 1.05 (3H, t).

Example 137

4-[2,6-difluoro-4-(6-isopropoxy-pyridin-2-yl)-phenylsulfanyl]-butyric acid

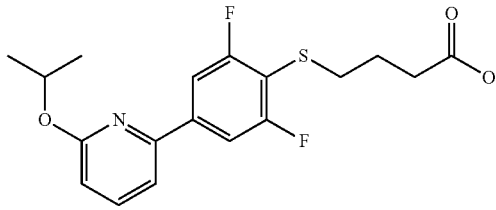 [SMILES: CC(C)Oc1cccc(-c2cc(F)c(SCCCC(=O)O)c(F)c2)n1]

Step A: 4-[2,6-difluoro-4-(6-isopropoxy-pyridin-2-yl)-phenylsulfanyl]-butyric acid ethyl ester 2-Isopropoxy-6-(3,4,5-trifluoro-phenyl)-pyridine (0.02 g, 0.07 mmol) obtained in Preparation Example 167 was dissolved in 1 mL of DMF, and $Cs_2CO_3$ (0.024 g, 0.07 mmol) and 4-mercapto-butyric acid ethyl ester (0.011 g, 0.07 mmol) obtained in Preparation Example 161 were added thereto. The resultant was agitated at 65° C. for 4 hours. The reaction solution was added with water and extracted with EtOAc. The separated organic layer was dried with $MgSO_4$ and purified by column chromatography to obtain the title compound (0.017 g, 58%).

Step B: 4-[2,6-difluoro-4-(6-isopropoxy-pyridin-2-yl-phenylsulfanyl]-butyric acid 4-[2,6-Difluoro-4-(6-isopropoxy-pyridin-2-yl)-phenylsulfanyl]-butyric acid ethyl ester (0.017 g, 0.04 mmol) obtained in Step A was reacted in the same manner as in Step B of Example 1 to obtain the title compound (0.011 g, 73%).

$^1$H-NMR ($CDCl_3$) δ 7.63-7.57 (3H, m), 7.23 (1H, d), 6.67 (1H, d), 5.44 (1H, m), 2.97 (2H, t), 2.55 (2H, t), 1.88 (2H, m), 1.40 (6H, d).

Example 138

4-[2,6-difluoro-4-(2-isopropoxy-pyridin-3-yl)-phenylsulfanyl]-butyric acid

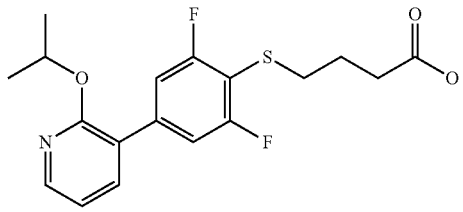 [SMILES: CC(C)Oc1ncccc1-c1cc(F)c(SCCCC(=O)O)c(F)c1]

4-[2,6-Difluoro-4-(4,4,5,5-tetramethyl-[1,3,2]dioxaborolan-2-yl)-phenylsulfanyl]-butyric acid ethyl ester (1.22 g, 3.16 mmol) obtained in Preparation Example 170 and 3-iodo-2-isopropoxy-pyridine (1.24 g, 4.74 mmol) obtained in Preparation Example 37 were used to react sequentially in the same manner as in Steps A and B of Example 1 to obtain the title compound (0.78 g, 67%).

$^1$H-NMR ($CDCl_3$) δ 8.15 (1H, m), 7.60 (1H, m), 7.19 (2H, d), 6.93 (1H, m), 5.40 (1H, m), 2.96 (2H, t), 2.56 (2H, t), 1.90 (2H, m), 1.36 (6H, d).

Example 139

4-[2,6-difluoro-4-(2-propoxy-pyridin-3-yl)-phenylsulfanyl]-butyric acid

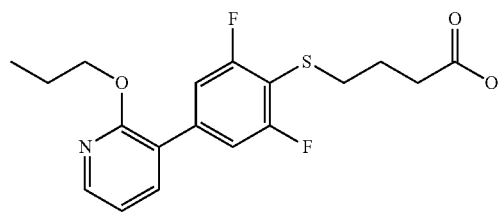

2-Propoxy-3-(3,4,5-trifluoro-phenyl)-pyridine (0.02 g, 0.08 mmol) obtained in Preparation Example 171, $Cs_2CO_3$ (0.027 g, 0.08 mmol) and 4-mercapto-butyric acid ethyl ester (0.012 g, 0.08 mmol) obtained in Preparation Example 161 were used to react sequentially in the same manner as in Steps A and B of Example 137 to obtain the title compound (0.009 g, 30%).

$^1$H-NMR ($CDCl_3$) δ 8.16 (1H, m), 7.60 (1H, m), 7.20 (2H, d), 6.95 (1H, m), 4.32 (2H, t), 2.96 (2H, t), 2.54 (2H, t), 1.89 (2H, m), 1.80 (2H, m), 1.00 (3H, t).

Example 140

4-[2,6-difluoro-4-(6-isopropylsulfanyl-pyridin-2-yl)-phenyl sulfanyl]-butyric acid

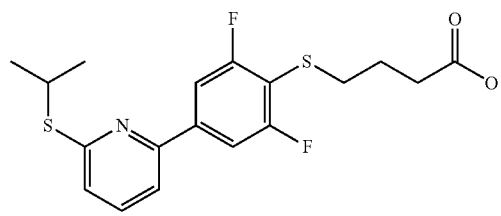 [SMILES: CC(C)Sc1cccc(-c2cc(F)c(SCCCC(=O)O)c(F)c2)n1]

2-Isopropylsulfanyl-6-(3,4,5-trifluoro-phenyl)-pyridine (0.035 g, 0.12 mmol) obtained in Preparation Example 172, $Cs_2CO_3$ (0.04 g, 0.12 mmol) and 4-mercapto-butyric acid ethyl ester (0.018 g, 0.12 mmol) obtained in Preparation Example 161 were used to react sequentially in the same manner as in Steps A and B of Example 137 to obtain the title compound (0.022 g, 46%).

$^1$H-NMR ($CDCl_3$) δ 7.62-7.53 (3H, m), 7.37 (1H, d), 7.13 (1H, d), 4.14 (1H, m), 2.98 (2H, t), 2.56 (2H, t), 1.89 (2H, m), 1.45 (6H, d).

Example 141

4-[2,6-difluoro-4-(6-propylsulfanyl-pyridin-2-yl)-phenyl sulfanyl]-butyric acid

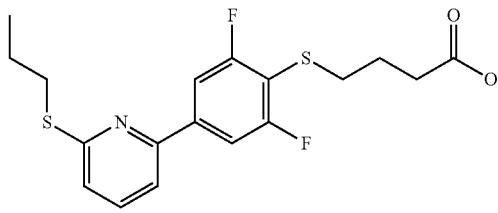

2-Propylsulfanyl-6-(3,4,5-trifluoro-phenyl)-pyridine (0.03 g, 0.11 mmol) obtained in Preparation Example 173, $Cs_2CO_3$ (0.035 g, 0.11 mmol) and 4-mercapto-butyric acid ethyl ester (0.016 g, 0.11 mmol) obtained in Preparation Example 161 were used to react sequentially in the same manner as in Steps A and B of Example 137 to obtain the title compound (0.024 g, 57%).

$^1$H-NMR (CDCl$_3$) δ 7.62-7.53 (3H, m), 7.37 (1H, d), 7.16 (1H, d), 3.24 (2H, t), 2.98 (2H, t), 2.56 (2H, t), 1.92-1.77 (4H, m), 1.09 (3H, t).

Example 142

4-[4-(2-cyclobutylsulfanyl-pyridin-3-yl)-2,6-difluoro-phenyl sulfanyl]-butyric acid

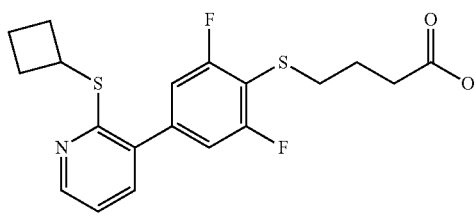 [SMILES: O=C(O)CCCSc1c(F)cc(-c2cccnc2SC2CCC2)cc1F]

2-Cyclobutylsulfanyl-3-(3,4,5-trifluoro-phenyl)-pyridine (0.056 g, 0.19 mmol) obtained in Preparation Example 174, $Cs_2CO_3$ (0.093 g, 0.19 mmol) and 4-mercapto-butyric acid ethyl ester (0.028 g, 0.19 mmol) Preparation Example 161 were used to react sequentially in the same manner as in Steps A and B of Example 137 to obtain the title compound (0.03 g, 40%).

$^1$H-NMR (CDCl$_3$) δ 8.42 (1H, m), 7.34 (1H, m), 7.02 (3H, m), 4.42 (1H, m), 2.98 (2H, t), 2.58-2.48 (4H, m), 2.10-1.89 (6H, m).

Example 143

4-[4-(2-cyclobutoxy-pyridin-3-yl)-phenylsulfanyl]-butyric acid

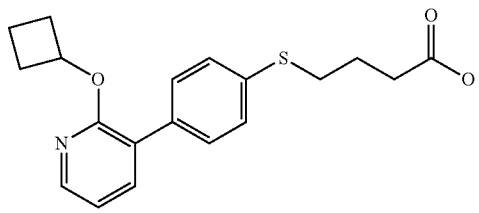 [SMILES: O=C(O)CCCSc1ccc(-c2cccnc2OC2CCC2)cc1]

4-[4-(4,4,5,5-Tetramethyl-[1,3,2]dioxaborolan-2-yl)-phenylsulfanyl]-butyric acid ethyl ester (0.018 g, 0.05 mmol) obtained in Preparation Example 159 and 2-cyclobutoxy-3-iodo-pyridine (0.016 g, 0.06 mmol) obtained in Preparation Example 200 were used to react sequentially in the same manner as in Steps A and B of Example 1 to obtain the title compound (0.004 g, 23%).

$^1$H-NMR (CDCl$_3$) δ 8.09 (1H, m), 7.58 (1H, m), 7.52 (2H, d), 7.36 (2H, d), 6.91 (1H, m), 5.26 (1H, m), 3.02 (2H, t), 2.56-2.42 (4H, m), 2.15-1.99 (4H, m), 1.81 (1H, m), 1.67 (1H, m).

Example 144

4-[4-(2-cyclobutoxy-pyridin-3-yl)-2,6-difluoro-phenyl sulfanyl]-butyric acid

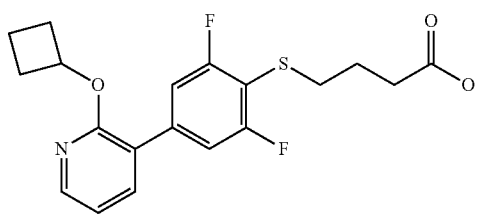 [SMILES: O=C(O)CCCSc1c(F)cc(-c2cccnc2OC2CCC2)cc1F]

2-Cyclobutoxy-3-(3,4,5-trifluoro-phenyl)-pyridine (0.01 g, 0.03 mmol) obtained in Preparation Example 175, $Cs_2CO_3$ (0.012 g, 0.03 mmol) and 4-mercapto-butyric acid ethyl ester (0.005 g, 0.03 mmol) obtained in Preparation Example 161 were used to react sequentially in the same manner as in Steps A and B of Example 137 to obtain the title compound (0.002 g, 17%).

$^1$H-NMR (CDCl$_3$) δ 8.14 (1H, m), 7.60 (1H, m), 7.21 (2H, d), 6.95 (1H, m), 5.27 (1H, m), 2.97 (2H, t), 2.56-2.42 (4H, m), 2.12 (2H, m), 1.91-1.81 (3H, m), 1.69 (1H, m).

Example 145

4-[4-(2-cyclopentyloxy-pyridin-3-yl)-2,6-difluoro-phenyl sulfanyl]-butyric acid

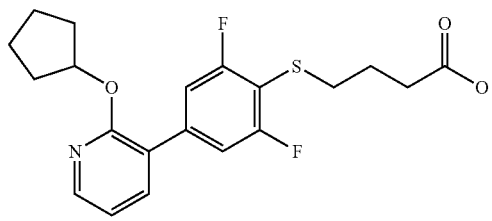 [SMILES: O=C(O)CCCSc1c(F)cc(-c2cccnc2OC2CCCC2)cc1F]

4-[2,6-Difluoro-4-(4,4,5,5-tetramethyl-[1,3,2]dioxaborolan-2-yl)-phenylsulfanyl]-butyric acid ethyl ester (0.063 g, 0.16 mmol) obtained in Preparation Example 170 and 2-cyclopentoxy-3-iodo-pyridine (0.052 g, 0.18 mmol) obtained in Preparation Example 38 were used to react sequentially in the same manner as in Steps A and B of Example 1 to obtain the title compound (0.025 g, 39%).

$^1$H-NMR (CDCl$_3$) δ 8.17 (1H, m), 7.58 (1H, m), 7.17 (2H, d), 6.92 (1H, m), 5.51 (1H, m), 2.96 (2H, t), 2.55 (2H, m), 1.98-1.87 (4H, m), 1.81-1.73 (4H, m), 1.63 (2H, m).

Example 146

4-[2,6-difluoro-4-(2-isopropylsulfanyl-pyridin-3-yl)-phenyl sulfanyl]-butyric acid

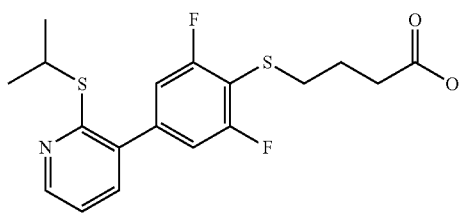 [SMILES: CC(C)Sc1ncccc1-c1cc(F)c(SCCCC(=O)O)c(F)c1]

4-[2,6-Difluoro-4-(4,4,5,5-tetramethyl-[1,3,2]dioxaborolan-2-yl)-phenylsulfanyl]-butyric acid ethyl ester (0.02 g, 0.05 mmol) obtained in Preparation Example 170 and 3-iodo-2-isopropylsulfanyl-pyridine (0.015 g, 0.054 mmol) obtained in Preparation Example 226 were used to react sequentially in the same manner as in Steps A and B of Example 1 to obtain the title compound (0.007 g, 36%).

$^1$H-NMR (CDCl$_3$) δ 8.45 (1H, m), 7.36 (1H, m), 7.04-7.00 (3H, m), 4.06 (1H, m), 2.98 (2H, t), 2.57 (2H, t), 1.91 (2H, m), 1.34 (6H, d).

Example 147

4-[4-(2-cyclopentylsulfanyl-pyridin-3-yl)-2,6-difluoro-phenylsulfanyl]-butyric acid

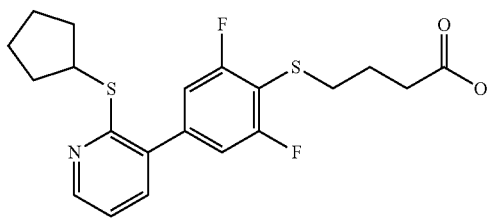

2-Cyclopentylsulfanyl-3-(3,4,5-trifluoro-phenyl)-pyridine (0.02 g, 0.06 mmol) obtained in Preparation Example 176, Cs$_2$CO$_3$ (0.02 g, 0.06 mmol) and 4-mercapto-butyric acid ethyl ester (0.01 g, 0.06 mmol) obtained in Preparation Example 161 were used to react sequentially in the same manner as in Steps A and B of Example 137 to obtain the title compound (0.007 g, 26%).

$^1$H-NMR (CDCl$_3$) δ 8.44 (1H, m), 7.34 (1H, m), 7.03-7.01 (3H, m), 4.09 (1H, m), 2.98 (2H, t), 2.57 (2H, t), 2.18 (2H, m), 1.91 (2H, m), 1.72-1.52 (6H, m).

Example 148

4-[4-(2-isopropylsulfanyl-pyridin-3-yl)-phenylsulfanyl]-butyric acid

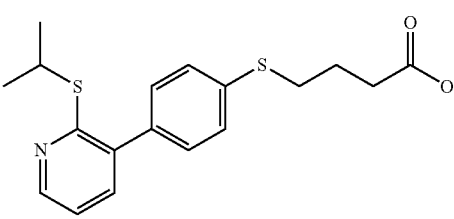

4-[4-(4,4,5,5-Tetramethyl-[1,3,2]dioxaborolan-2-yl)-phenylsulfanyl]-butyric acid ethyl ester (0.05 g, 0.14 mmol) obtained in Preparation Example 159 and 3-iodo-2-isopropylsulfanyl-pyridine (0.044 g, 0.16 mmol) obtained in Preparation Example 226 were used to react sequentially in the same manner as in Steps A and B of Example 1 to obtain the title compound (0.013 g, 27%).

$^1$H-NMR (CDCl$_3$) δ 8.41 (1H, m), 7.39-7.32 (5H, m), 7.02 (1H, m), 4.04 (1H, m), 3.04 (2H, t), 2.55 (2H, t), 2.03 (2H, m), 1.34 (6H, d).

Example 149

4-[4-(2-cyclopentylsulfanyl-pyridin-3-yl)-phenylsulfanyl]-butyric acid

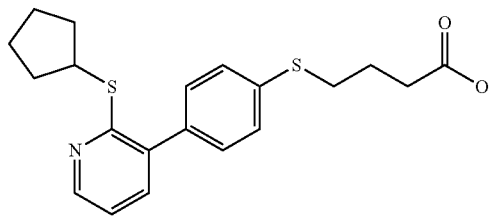

4-[4-(4,4,5,5-Tetramethyl-[1,3,2]dioxaborolan-2-yl)-phenylsulfanyl]-butyric acid ethyl ester (0.05 g, 0.14 mmol) obtained in Preparation Example 159 and 2-cyclopentylsulfanyl-3-iodo-pyridine (0.048 g, 0.16 mmol) obtained in Preparation Example 39 were used to react sequentially in the same manner as in Steps A and B of Example 1 to obtain the title compound (0.011 g, 20%).

$^1$H-NMR (CDCl$_3$) δ 8.41 (1H, m), 7.39-7.32 (5H, m), 7.02 (1H, m), 4.04 (1H, m), 3.03 (2H, t), 2.55 (2H, t), 2.18 (2H, m), 2.02 (2H, m), 1.72-1.52 (6H, m).

Example 150

4-[2-fluoro-4-(6-isopropoxy-pyridin-2-yl)-phenylsulfanyl]-butyric acid

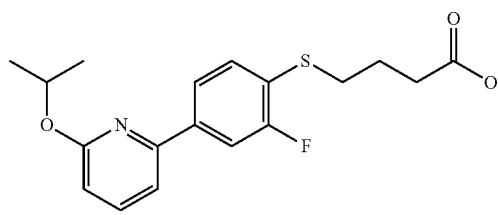 [SMILES: CC(C)Oc1cccc(-c2ccc(SCCCC(=O)O)c(F)c2)n1]

4-[2-Fluoro-4-(4,4,5,5-tetramethyl-[1,3,2]dioxaborolan-2-yl)-phenylsulfanyl]-butyric acid ethyl ester (0.05 g, 0.13 mmol) obtained in Preparation Example 180 and 2-bromo-6-isopropoxy-pyridine (0.032 g, 0.15 mmol) obtained in Preparation Example 228 were used to react sequentially in the same manner as in Steps A and B of Example 1 to obtain the title compound (0.014 g, 29%).

$^1$H-NMR (CDCl$_3$) δ 7.73-7.71 (2H, m), 7.59 (1H, t), 7.42 (1H, t), 7.25 (1H, m), 6.64 (1H, d), 5.45 (1H, m), 3.00 (2H, t), 2.54 (2H, t), 1.95 (2H, m), 1.38 (6H, d).

Example 151

4-[4-(2-cyclopentyloxy-pyridin-3-yl)-2-fluoro-phenylsulfanyl]-butyric acid

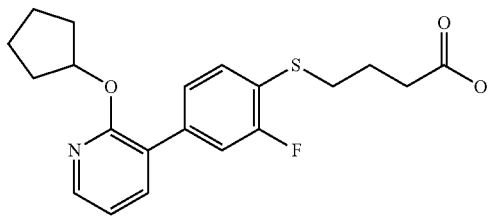

4-[2-Fluoro-4-(4,4,5,5-tetramethyl-[1,3,2]dioxaborolan-2-yl)-phenylsulfanyl]-butyric acid ethyl ester (0.05 g, 0.13 mmol) obtained in Preparation Example 180 and 2-cyclopentoxy-3-iodo-pyridine (0.04 g, 0.15 mmol) obtained in Preparation Example 38 were used to react sequentially in the same manner as in Steps A and B of Example 1 to obtain the title compound (0.027 g, 54%).

$^1$H-NMR (CDCl$_3$) δ 8.14 (1H, m), 7.57 (1H, m), 7.38 (1H, t), 7.29-7.27 (2H, m), 6.91 (1H, m), 5.50 (1H, m), 3.00 (2H, t), 2.55 (2H, t), 1.98-1.93 (4H, m), 1.86-1.59 (6H, m).

Example 152

4-[4-(2-cyclobutylsulfanyl-pyridin-3-yl)-2-fluoro-phenylsulfanyl]-butyric acid

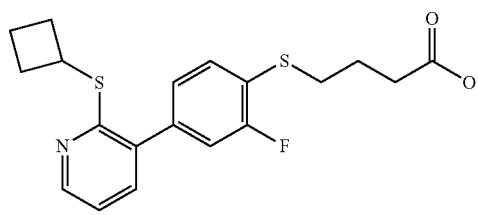 [SMILES: O=C(O)CCCSc1ccc(-c2cccnc2SC2CCC2)cc1F]

4-[2-Fluoro-4-(4,4,5,5-tetramethyl-[1,3,2]dioxaborolan-2-yl)-phenylsulfanyl]-butyric acid ethyl ester (0.05 g, 0.13 mmol) obtained in Preparation Example 180 and 2-cyclobutylsulfanyl-3-iodo-pyridine (0.04 g, 0.15 mmol) obtained in Preparation Example 44 were used to react sequentially in the same manner as in Steps A and B of Example 1 to obtain the title compound (0.032 g, 62%).

$^1$H-NMR (CDCl$_3$) δ 8.40 (1H, m), 7.41 (1H, t), 7.33 (1H, m), 7.15 (2H, m), 7.02 (1H, m), 4.42 (1H, m), 3.02 (2H, t), 2.57 (2H, t), 2.55 (2H, m), 2.10-1.97 (6H, m).

Example 153

4-[4-(2-cyclobutylsulfanyl-pyridin-3-yl)-phenylsulfanyl]-butyric acid

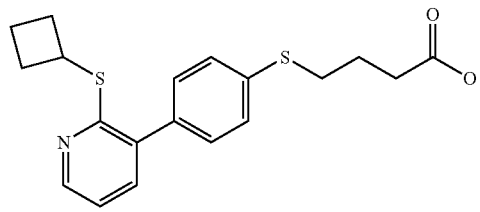 [SMILES: O=C(O)CCCSc1ccc(-c2cccnc2SC2CCC2)cc1]

4-[4-(4,4,5,5-Tetramethyl-[1,3,2]dioxaborolan-2-yl)-phenylsulfanyl]-butyric acid ethyl ester (0.05 g, 0.14 mmol) obtained in Preparation Example 159 and 2-cyclobutylsulfanyl-3-iodo-pyridine (0.046 g, 0.16 mmol) obtained in Preparation Example 44 were used to react sequentially in the same manner as in Steps A and B of Example 1 to obtain the title compound (0.015 g, 29%).

$^1$H-NMR (CDCl$_3$) δ 8.38 (1H, m), 7.37-7.34 (5H, m), 7.02 (1H, m), 4.41 (1H, m), 3.03 (2H, t), 2.57 (2H, t), 2.54 (2H, m), 2.10-1.97 (6H, m).

Example 154

4-[4-(6-cyclobutoxy-pyridin-2-yl)-2,6-difluoro-phenylsulfanyl]- butyric acid

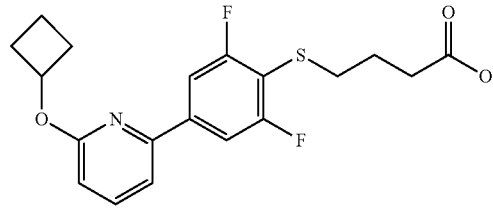 [SMILES: O=C(O)CCCSc1c(F)cc(-c2cccc(OC3CCC3)n2)cc1F]

2-Cyclobutoxy-6-(3,4,5-trifluoro-phenyl)-pyridine (0.03 g, 0.11 mmol) obtained in Preparation Example 181, Cs$_2$CO$_3$ (0.035 g, 0.11 mmol) and 4-mercapto-butyric acid ethyl ester (0.016 g, 0.11 mmol) obtained in Preparation Example 161 were used to react sequentially in the same manner as in Steps A and B of Example 137 to obtain the title compound (0.011 g, 27%).

$^1$H-NMR (CDCl$_3$) δ 7.64-7.57 (3H, m), 7.27 (1H, d), 6.69 (1H, d), 5.26 (1H, m), 2.96 (2H, t), 2.57-2.51 (4H, m), 2.18 (2H, m), 1.87 (3H, m), 1.76 (1H, m).

Example 155

4-[4-(6-cyclopentyloxy-pyridin-2-yl)-2,6-difluoro-phenylsulfanyl]-bytyric acid

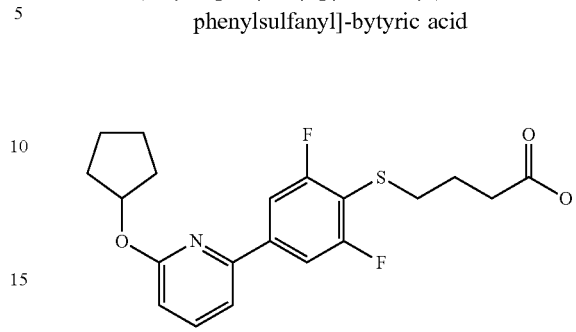

2-Cyclopentyloxy-6-(3,4,5-trifluoro-phenyl)-pyridine (0.035 g, 0.12 mmol) obtained in Preparation Example 182, Cs$_2$CO$_3$ (0.039 g, 0.12 mmol) and 4-mercapto-butyric acid ethyl ester (0.018 g, 0.12 mmol) obtained in Preparation Example 161 were used to react sequentially in the same manner as in Steps A and B of Example 137 to obtain the title compound (0.016 g, 34%).

$^1$H-NMR (CDCl$_3$) δ 7.62-7.58 (3H, m), 7.24 (1H, d), 6.67 (1H, d), 5.50 (1H, m), 2.96 (2H, t), 2.54 (2H, t), 2.03 (2H, m), 1.89-1.78 (6H, m), 1.65 (2H, m).

Example 156

4-[4-(6-cyclobutylsulfanyl-pyridin-2-yl)-phenylsulfanyl]-butyric acid

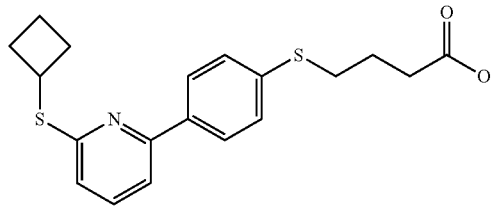

4-[4-(4,4,5,5-Tetramethyl-[1,3,2]dioxaborolan-2-yl)-phenylsulfanyl]-butyric acid ethyl ester (0.011 g, 0.03 mmol) obtained in Preparation Example 159 and 2-bromo-6-cyclobutylsulfanyl-pyridine (0.008 g, 0.03 mmol) obtained in Preparation Example 233 were used to react sequentially in the same manner as in Steps A and B of Example 1 to obtain the title compound (0.003 g, 27%).

$^1$H-NMR (CDCl$_3$) δ 7.94 (2H, d), 7.49 (1H, t), 7.40-7.37 (3H, m), 7.00 (1H, m), 4.44 (1H, m), 3.03 (2H, t), 2.63-2.53 (4H, m), 2.20-1.98 (6H, m).

Example 157

4-[4-(6-cyclopropylmethoxy-pyridin-2-yl)-2,6-difluoro-phenylsulfanyl]-butyric acid

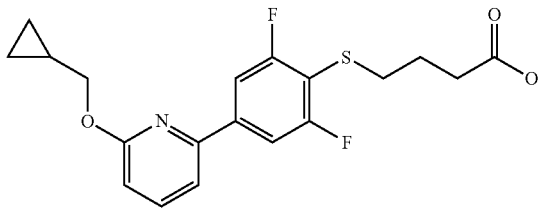 [SMILES: O=C(O)CCCSc1c(F)cc(-c2cccc(OCC3CC3)n2)cc1F]

2-Cyclopropylmethoxy-6-(3,4,5-trifluoro-phenyl)-pyridine (0.034 g, 0.12 mmol) obtained in Preparation Example 183, $Cs_2CO_3$ (0.04 g, 0.12 mmol) and 4-mercapto-butyric acid ethyl ester (0.018 g, 0.12 mmol) obtained in Preparation Example 161 were used to react sequentially in the same manner as in Steps A and B of Example 137 to obtain the title compound (0.012 g, 26%).

$^1$H-NMR (CDCl$_3$) δ 7.65 (1H, t), 7.59 (2H, d), 7.27 (1H, d), 6.76 (1H, d), 4.24 (2H, d), 2.96 (2H, t), 2.54 (2H, t), 1.87 (2H, m), 1.32 (1H, m), 0.64 (2H, m), 0.39 (2H, m).

Example 158

4-[4-(6-cyclobutylsulfanyl-pyridin-2-yl)-2,6-difluoro-phenylsulfanyl]-butyric acid

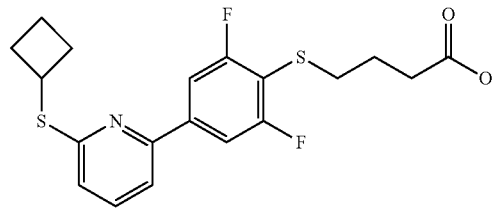

2-Cyclobutylsulfanyl-6-(3,4,5-trifluoro-phenyl)-pyridine (0.03 g, 0.1 mmol) obtained in Preparation Example 184, $Cs_2CO_3$ (0.033 g, 0.1 mmol) and 4-mercapto-butyric acid ethyl ester (0.015 g, 0.1 mmol) obtained in Preparation Example 161 were used to react sequentially in the same manner as in Steps A and B of Example 137 to obtain the title compound (0.016 g, 40%).

$^1$H-NMR (CDCl$_3$) δ 7.60 (2H, d), 7.53 (1H, t), 7.35 (1H, d), 7.07 (1H, d), 4.42 (1H, m), 2.98 (2H, t), 2.63-2.53 (4H, m), 2.20-2.10 (4H, m), 1.88 (2H, m).

Example 159

4-[4-(6-cyclopentylsulfanyl-pyridin-2-yl)-2,6-difluoro-phenylsulfanyl]-butyric acid

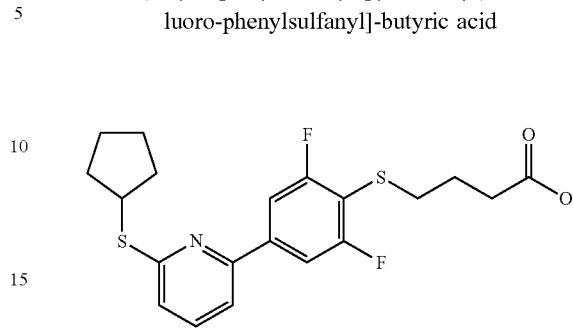

2-Cyclopentylsulfanyl-6-(3,4,5-trifluoro-phenyl)-pyridine (0.04 g, 0.13 mmol) obtained in Preparation Example 185, $Cs_2CO_3$ (0.044 g, 0.13 mmol) and 4-mercapto-butyric acid ethyl ester (0.02 g, 0.13 mmol) obtained in Preparation Example 161 were used to react sequentially in the same manner as in Steps A and B of Example 137 to obtain the title compound (0.016 g, 29%).

$^1$H-NMR (CDCl$_3$) δ 7.61 (2H, d), 7.53 (1H, t), 7.35 (1H, d), 7.13 (1H, d), 4.16 (1H, m), 2.97 (2H, t), 2.54 (2H, t), 2.24 (2H, m), 1.89-1.69 (8H, m)

Example 160

4-(2'-cyclopentylamino-3-fluoro-biphenyl-4-ylsulfanyl)-butyric acid

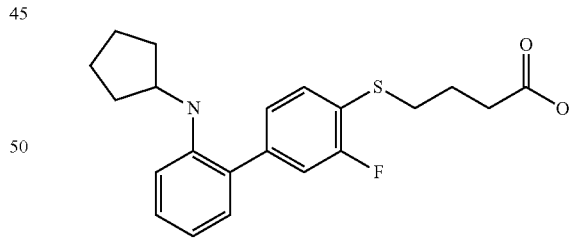

4-[2-Fluoro-4-(4,4,5,5-tetramethyl-[1,3,2]dioxaborolan-2-yl)-phenylsulfanyl]-butyric acid ethyl ester (0.05 g, 0.13 mmol) obtained in Preparation Example 180 and N-cyclopentyl-2-iodo-aniline (0.043 g, 0.15 mmol) obtained in Preparation Example 70 were used to react sequentially in the same manner as in Steps A and B of Example 1 to obtain the title compound (0.022 g, 40%).

$^1$H-NMR (CDCl$_3$) δ 7.42 (1H, t), 7.23 (1H, m), 7.15 (2H, m), 7.02 (1H, m), 6.72 (2H, m), 3.77 (1H, m), 3.01 (2H, t), 2.56 (2H, t), 1.98 (4H, m), 1.60 (4H, m), 1.37 (2H, m).

Example 161

4-(2'-cyclopentylamino-3,5-difluoro-biphenyl-4-ylsulfanyl)-butyric acid

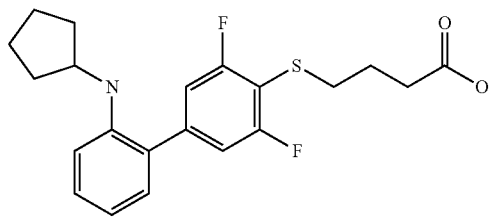 [SMILES: O=C(O)CCCSc1c(F)cc(-c2ccccc2NC2CCCC2)cc1F]

4-[2,6-difluoro-4-(4,4,5,5-Tetramethyl-[1,3,2]dioxaborolan-2-yl)-phenylsulfanyl]-butyric acid ethyl ester (0.06 g, 0.16 mmol) obtained in Preparation Example 170 and N-cyclopentyl-2-iodo-aniline (0.05 g, 0.17 mmol) obtained in Preparation Example 70 were used to react sequentially in the same manner as in Steps A and B of Example 1 to obtain the title compound (0.013 g, 21%).

$^1$H-NMR (CDCl$_3$) δ 7.23 (1H, m), 7.01 (3H, m), 6.72 (2H, m), 3.77 (1H, m), 2.97 (2H, t), 2.56 (2H, t), 2.03-1.89 (4H, m), 1.66-1.58 (4H, m), 1.40 (2H, m).

Example 162

4-[2'-(cyclopropylmethyl-amino)-3,5-difluoro-biphenyl-4-ylsulfanyl]-butyric acid

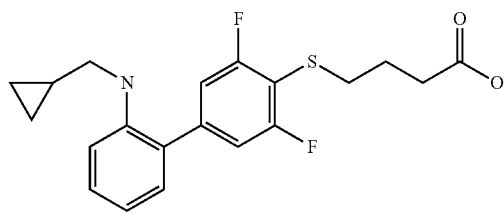 [SMILES: O=C(O)CCCSc1c(F)cc(-c2ccccc2NCC2CC2)cc1F]

4-[2,6-Difluoro-4-(4,4,5,5-tetramethyl-[1,3,2]dioxaborolan-2-yl)-phenylsulfanyl]-butyric acid ethyl ester (0.054 g, 0.14 mmol) obtained in Preparation Example 170 and N(cyclopropylmethyl)-2-iodo-aniline (0.042 g, 0.15 mmol) obtained in Preparation Example 73 were used to react sequentially in the same manner as in Steps A and B of Example 1 to obtain the title compound (0.011 g, 21%).

$^1$H-NMR (CDCl$_3$) δ 7.25 (1H, m), 7.05 (3H, m), 6.74 (1H, t), 6.68 (1H, d), 2.96 (4H, m), 2.57 (2H, t), 1.91 (2H, m), 1.04 (1H, m), 0.49 (2H, m), 0.18 (2H, m).

Example 163

4-[2-fluoro-4-(2-isopropylsulfanyl-pyridin-3-yl)-phenylsulfanyl]butyric acid

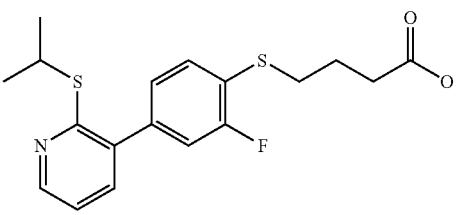 [SMILES: CC(C)Sc1ncccc1-c1ccc(SCCCC(=O)O)c(F)c1]

4-[2-Fluoro-4-(4,4,5,5-tetramethyl-[1,3,2]dioxaborolan-2-yl)-phenylsulfanyl]-butyric acid ethyl ester (0.05 g, 0.14 mmol) obtained in Preparation Example 180 and 3-iodo-2-isopropylsulfanyl-pyridine (0.057 g, 0.2 mmol) obtained in Preparation Example 226 were used to react sequentially in the same manner as in Steps A and B of Example 1 to obtain the title compound (0.023 g, 46%).

$^1$H-NMR (CDCl$_3$) δ 8.44 (1H, m), 7.44-7.35 (2H, m), 7.15 (2H, m), 7.05 (1H, m), 4.07 (1H, m), 3.01 (2H, t), 2.57 (2H, t), 1.99 (2H, m), 1.36 (6H, d).

Example 164

4-[4-(2-cyclopentylsulfanyl-pyridin-3-yl)-2-fluoro-phenylsulfanyl]-butyric acid

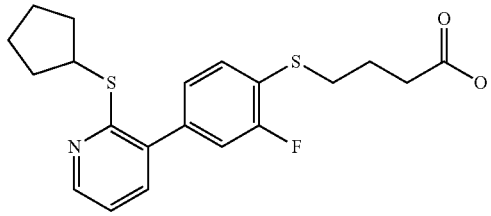 [SMILES: O=C(O)CCCSc1ccc(-c2cccnc2SC2CCCC2)cc1F]

4-[2-Fluoro-4-(4,4,5,5-tetramethyl-[1,3,2]dioxaborolan-2-yl)-phenylsulfanyl]-butyric acid ethyl ester (0.04 g, 0.11 mmol) obtained in Preparation Example 180 and 2-cyclopentylsulfanyl-3-iodo-pyridine (0.05 g, 0.16 mmol) obtained in Preparation Example 39 were used to react sequentially in the same manner as in Steps A and B of Example 1 to obtain the title compound (0.014 g, 33%).

$^1$H-NMR (CDCl$_3$) δ 8.44 (1H, m), 7.43-7.35 (2H, m), 7.17 (2H, m), 7.05 (1H, m), 4.09 (1H, m), 3.01 (2H, t), 2.57 (2H, t), 2.18 (2H, m), 1.99 (2H, m), 1.73-1.53 (6H, m).

Example 165

4-(3,5-difluoro-2'-isopropylamino-biphenyl-4-ylsulfanyl)-butyric acid

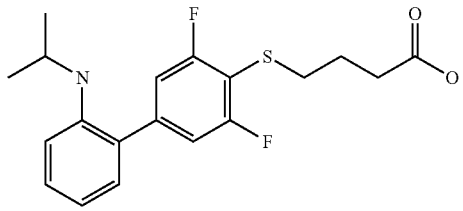

4-[2,6-Difluoro-4-(4,4,5,5-tetramethyl-[1,3,2]dioxaborolan-2-yl)-phenylsulfanyl]-butyric acid ethyl ester (0.05 g, 0.13 mmol) obtained in Preparation Example 170 and 2-iodo-N-isopropyl-aniline (0.05 g, 0.14 mmol) obtained in Preparation Example 74 were used to react sequentially in the same manner as in Steps A and B of Example 1 to obtain the title compound (0.033 g, 70%).

$^1$H-NMR (CDCl$_3$) δ 7.24 (1H, m), 7.02 (3H, m), 6.72 (2H, m), 3.64 (1H, m), 2.98 (2H, t), 2.58 (2H, t), 1.93 (2H, m), 1.17 (6H, d).

Example 166

4-(3,5-difluoro-2'-propylamino-biphenyl-4-ylsulfanyl)-butyric acid

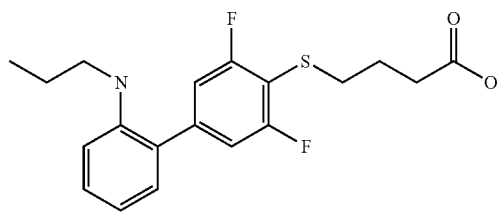

4-[2,6-Difluoro-4-(4,4,5,5-tetramethyl-[1,3,2]dioxaborolan-2-yl)-phenylsulfanyl]-butyric acid ethyl ester (0.05 g, 0.13 mmol) obtained in Preparation Example 170 and 2-iodo-N-propyl-aniline (0.05 g, 0.14 mmol) obtained in Preparation Example 72 were used to react sequentially in the same manner as in Steps A and B of Example 1 to obtain the title compound (0.023 g, 48%).

$^1$H-NMR (CDCl$_3$) δ 7.25 (1H, m), 7.04 (3H, m), 6.73 (2H, m), 3.07 (2H, t), 2.97 (2H, t), 2.58 (2H, t), 1.91 (2H, m), 1.57 (2H, m), 0.94 (3H, t).

Example 167

4-[4-(2-cyclopropylmethoxy-pyridin-3-yl)-2,6-difluoro-phenylsulfanyl]-butyric acid

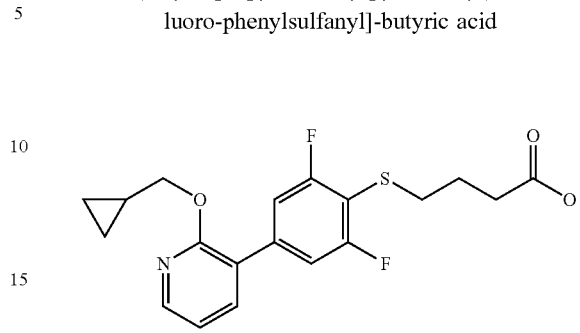

4-[2,6-Difluoro-4-(4,4,5,5-tetramethyl-[1,3,2]dioxaborolan-2-yl)-phenylsulfanyl]-butyric acid ethyl ester (0.05 g, 0.13 mmol) obtained in Preparation Example 170 and 2-cyclopropylmethoxy-3-iodo-pyridine (0.07 g, 0.26 mmol) obtained in Preparation Example 40 were used to react sequentially in the same manner as in Steps A and B of Example 1 to obtain the title compound (0.025 g, 51%).

$^1$H-NMR (CDCl$_3$) δ 8.15 (1H, m), 7.62 (1H, m), 7.24 (2H, d), 6.96 (1H, m), 4.23 (2H, d), 2.97 (2H, t), 2.56 (2H, t), 1.90 (2H, m), 1.29 (1H, m), 0.59 (2H, m), 0.34 (2H, m).

Example 168

4-[2,6-difluoro-4-(2-propylsulfanyl-pyridin-3yl)-phenylsulfanyl]-butyric acid

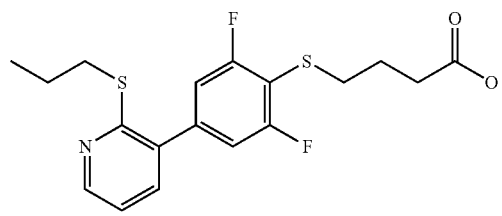 [SMILES: CCCSc1ncccc1-c1cc(F)c(SCCCC(=O)O)c(F)c1]

4-[2,6-Difluoro-4-(4,4,5,5-tetramethyl-[1,3,2]dioxaborolan-2-yl)-phenylsulfanyl]-butyric acid ethyl ester (0.05 g, 0.13 mmol) obtained in Preparation Example 170 and 3-iodo-2-propylsulfanyl-pyridine (0.07 g, 0.26 mmol) obtained in Preparation Example 203 were used to react sequentially in the same manner as in Steps A and B of Example 1 to obtain the title compound (0.03 g, 61%).

$^1$H-NMR (CDCl$_3$) δ 8.45 (1H, m), 7.36 (1H, m), 7.07-7.01 (3H, m), 3.15 (2H, t), 2.99 (2H, t), 2.58 (2H, t), 1.92 (2H, m), 1.71 (2H, m), 1.02 (3H, t).

Example 169

4-[4-(6-cyclobutylsulfanyl-pyridin-2-yl)-2-fluoro-phenylsulfanyl]-butyric acid

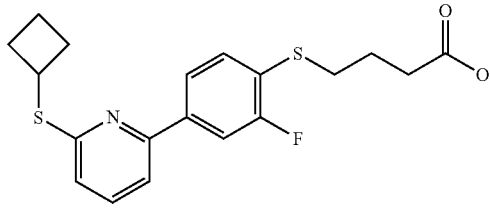 [SMILES: O=C(O)CCCSc1ccc(-c2cccc(SC3CCC3)n2)cc1F]

4-[2-Fluoro-4-(4,4,5,5-tetramethyl-[1,3,2]dioxaborolan-2-yl)-phenylsulfanyl]-butyric acid ethyl ester (0.04 g, 0.11 mmol) obtained in Preparation Example 180 and 2-chloro-6-cyclobutylsulfanyl-pyridine (0.04 g, 0.22 mmol) obtained in Preparation Example 19 were used to react sequentially in the same manner as in Steps A and B of Example 1 to obtain the title compound (0.009 g, 21%).

$^1$H-NMR (CDCl$_3$) δ 7.74 (2H, m), 7.51 (1H, t), 7.43 (1H, t), 7.36 (1H, d), 7.03 (1H, d), 4.41 (1H, m), 3.02 (2H, t), 2.61-2.53 (4H, m), 2.21-2.07 (4H, m), 1.99 (2H, m).

Example 170

4-[4-(2-cyclopentylamino-pyridin-3-yl)-2-fluoro-phenylsulfanyl]-butyric acid

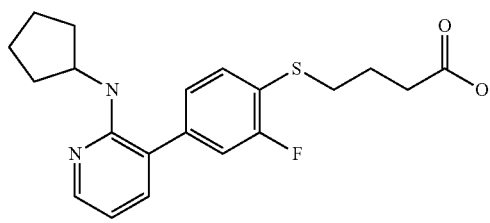 [SMILES: O=C(O)CCCSc1ccc(-c2cccnc2NC2CCCC2)cc1F]

4-[2-Fluoro-4-(4,4,5,5-tetramethyl-[1,3,2]dioxaborolan-2-yl)-phenylsulfanyl]-butyric acid ethyl ester (0.05 g, 0.14 mmol) obtained in Preparation Example 180 and N-cyclopentyl-3-iodo-pyridin-2-amine (0.06 g, 0.2 mmol) obtained in Preparation Example 64 were used to react sequentially in the same manner as in Steps A and B of Example 1 to obtain the title compound (0.016 g, 32%).

$^1$H-NMR (CDCl$_3$) δ 8.14 (1H, m), 7.44 (1H, t), 7.21 (1H, m), 7.12 (2H, m), 6.61 (1H, m), 4.32 (1H, m), 3.02 (2H, t), 2.56 (2H, t), 2.09-1.97 (4H, m), 1.61 (4H, m), 1.33 (2H, m).

Example 171

4-[2-fluoro-4-(2-isopropoxy-pyridin-3-yl)-phenylsulfanyl]-butyric acid

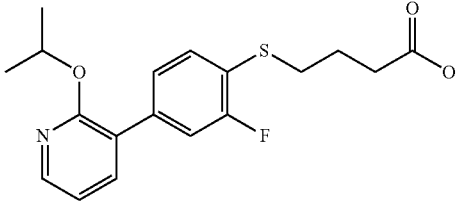 [SMILES: CC(C)Oc1ncccc1-c1ccc(SCCCC(=O)O)c(F)c1]

4-[2-Fluoro-4-(4,4,5,5-tetramethyl-[1,3,2]dioxaborolan-2-yl)-phenylsulfanyl]-butyric acid ethyl ester (0.05 g, 0.14 mmol) obtained in Preparation Example 180 and 3-iodo-2-isopropoxy-pyridine (0.053 g, 0.2 mmol) obtained in Preparation Example 37 were used to react sequentially in the same manner as in Steps A and B of Example 1 to obtain the title compound (0.019 g, 40%).

$^1$H-NMR (CDCl$_3$) δ 8.13 (1H, m), 7.58 (1H, m), 7.39-7.30 (3H, m), 6.92 (1H, m), 5.40 (1H, m), 3.00 (2H, t), 2.56 (2H, t), 1.98 (2H, m), 1.35 (6H, d).

Example 172

4-[4-(2-cyclobutoxy-pyridin-3-yl)-2-fluoro-phenylsulfanyl]-butyric acid

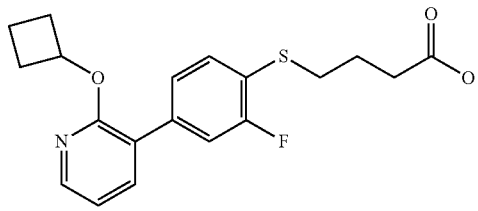 [SMILES: O=C(O)CCCSc1ccc(-c2cccnc2OC2CCC2)cc1F]

4-[2-Fluoro-4-(4,4,5,5-tetramethyl-[1,3,2]dioxaborolan-2-yl)-phenylsulfanyl]-butyric acid ethyl ester (0.05 g, 0.14 mmol) obtained in Preparation Example 180 and 2-cyclobutoxy-3-iodo-pyridine (0.056 g, 0.2 mmol) obtained in Preparation Example 200 were used to react sequentially in the same manner as in Steps A and B of Example 1 to obtain the title compound (0.015 g, 30%).

$^1$H-NMR (CDCl$_3$) δ 8.11 (1H, m), 7.58 (1H, m), 7.40-7.32 (3H, m), 6.93 (1H, m), 5.25 (1H, m), 3.01 (2H, t), 2.57-2.42 (4H, m), 2.11 (2H, m), 1.97 (2H, m), 1.82 (1H, m), 1.67 (1H, m).

Example 173

4-[2-fluoro-4-(2-pyrrolidin-1-yl-pyridin-3-yl)-phenylsulfanyl]-butyric acid

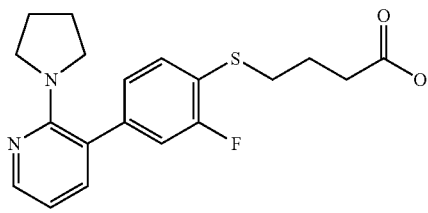 [SMILES: O=C(O)CCCSc1ccc(-c2cccnc2N2CCCC2)cc1F]

4-[2-Fluoro-4-(4,4,5,5-tetramethyl-[1,3,2]dioxaborolan-2-yl)-phenylsulfanyl]-butyric acid ethyl ester (0.05 g, 0.14 mmol) obtained in Preparation Example 180 and 3-iodo-2-pyrrolidin-1-yl-pyridine (0.056 g, 0.2 mmol) obtained in Preparation Example 204 were used to react sequentially in the same manner as in Steps A and B of Example 1 to obtain the title compound (0.03 g, 61%).

$^1$H-NMR (CDCl$_3$) δ 8.20 (1H, m), 7.40-7.36 (2H, m), 7.10-7.05 (2H, m), 6.71 (1H, m), 3.16 (4H, m), 3.01 (2H, t), 2.56 (2H, t), 1.97 (2H, m), 1.80 (4H, m).

Example 174

4-[2-fluoro-4-(2-isopropylamino-pyridin-3-yl)-phenylsulfanyl]-bytyric acid

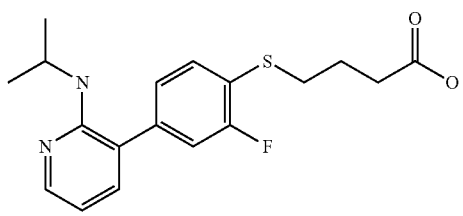 [SMILES: CC(C)Nc1ncccc1-c1ccc(SCCCC(=O)O)c(F)c1]

4-[2-Fluoro-4-(4,4,5,5-tetramethyl-[1,3,2]dioxaborolan-2-yl)-phenylsulfanyl]-butyric acid ethyl ester (0.05 g, 0.14 mmol) obtained in Preparation Example 180 and 3-iodo-N-isopropyl-pyridin-2-amine (0.053 g, 0.2 mmol) obtained in Preparation Example 66 were used to react sequentially in the same manner as in Steps A and B of Example 1 to obtain the title compound (0.029 g, 61%).

$^1$H-NMR (CDCl$_3$) δ 8.14 (1H, m), 7.46 (1H, t), 7.24 (1H, m), 7.15-7.10 (2H, m), 6.62 (1H, m), 4.25 (1H, m), 3.04 (2H, t), 2.57 (2H, t), 2.00 (2H, m), 1.19 (6H, d).

Example 175

4-(2'-cyclopentylamino-3,5'-difluoro-biphenyl-4-ylsulfanyl)-butyric acid

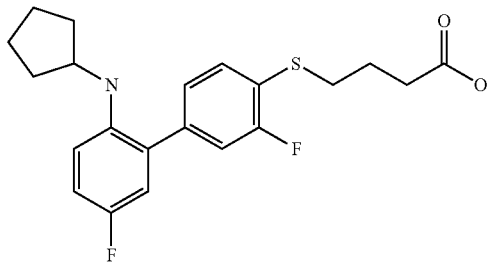 [SMILES: O=C(O)CCCSc1ccc(-c2cc(F)ccc2NC2CCCC2)cc1F]

4-[2-Fluoro-4-(4,4,5,5-tetramethyl-[1,3,2]dioxaborolan-2-yl)-phenylsulfanyl]-butyric acid ethyl ester (0.05 g, 0.14 mmol) obtained in Preparation Example 180 and N-cyclopentyl-4-fluoro-2-iodo-aniline (0.046 g, 0.15 mmol) obtained in Preparation Example 82 were used to react sequentially in the same manner as in Steps A and B of Example 1 to obtain the title compound (0.02 g, 39%).

$^1$H-NMR (CDCl$_3$) δ 7.43 (1H, t), 7.13 (2H, m), 6.92 (1H, m), 6.78 (1H, m), 6.62 (1H, m), 3.71 (1H, m), 3.01 (2H, t), 2.55 (2H, t), 1.99-1.91 (4H, m), 1.61 (4H, m), 1.36 (2H, m).

Example 176

4-(2'-cyclopentylamino-5'-fluoro-biphenyl-4-ylsulfanyl)-butyric acid

4-[4-(4,4,5,5-Tetramethyl-[1,3,2]dioxaborolan-2-yl)-phenylsulfanyl]-butyric acid ethyl ester (0.05 g, 0.14 mmol) obtained in Preparation Example 159 and N-cyclopentyl-4-fluoro-2-iodo-aniline (0.048 g, 0.16 mmol) obtained in Preparation Example 82 were used to react sequentially in the same manner as in Steps A and B of Example 1 to obtain the title compound (0.028 g, 52%).

$^1$H-NMR (CDCl$_3$) δ 7.39 (2H, d), 7.29 (2H, d), 6.91 (1H, m), 6.79 (1H, m), 6.62 (1H, m), 3.71 (1H, m), 3.03 (2H, t), 2.55 (2H, t), 2.02-1.93 (4H, m), 1.59 (4H, m), 1.36 (2H, m).

Example 177

4-(2'-cyclopentyloxy-5'-methyl-biphenyl-4-ylsulfanyl)-butyric acid

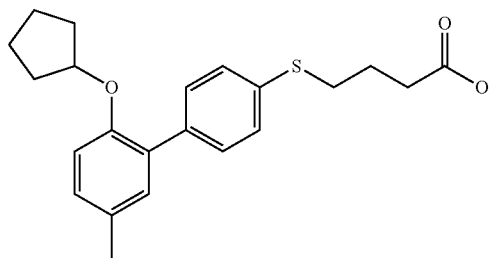 [SMILES: Cc1ccc(OC2CCCC2)c(-c2ccc(SCCCC(=O)O)cc2)c1]

4-(2'-Cyclopentyloxy-5'-methyl-biphenyl-4-ylsulfanyl)-butyric acid ethyl ester (0.02 g, 0.05 mmol) obtained in Preparation Example 187 was used to react in the same manner as in Step B of Example 1 to obtain the title compound (0.01 g, 55%).

$^1$H-NMR (CDCl$_3$) δ 7.45 (2H, d), 7.34 (2H, d), 7.10 (1H, s), 7.04 (1H, m), 6.86 (1H, d), 4.67 (1H, m), 3.00 (2H, t), 2.53 (2H, t), 2.31 (3H, s), 1.98 (2H, m), 1.77 (4H, m), 1.64-1.53 (4H, m).

Example 178

4-(2'-cyclopentyloxy-4'-methoxy-biphenyl-4-ylsulfanyl)-butyric acid

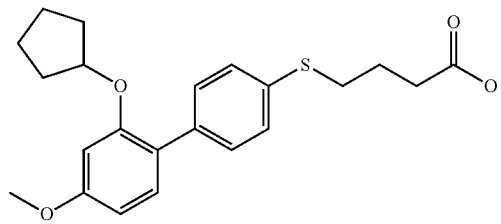 [SMILES: COc1ccc(-c2ccc(SCCCC(=O)O)cc2)c(OC2CCCC2)c1]

4-[4-(4,4,5,5-Tetramethyl-[1,3,2]dioxaborolan-2-yl)-phenylsulfanyl]-butyric acid ethyl ester (0.025 g, 0.07 mmol) obtained in Preparation Example 159 and 1-bromo-2-cyclopentyloxy-4-methoxy-benzene (0.02 g, 0.07 mmol) obtained in Preparation Example 128 were used to react sequentially in the same manner as in Steps A and B of Example 1 to obtain the title compound (0.002 g, 7%).

$^1$H-NMR (CDCl$_3$) δ 7.45 (2H, d), 7.34 (2H, d), 7.10 (1H, s), 7.04 (1H, d), 6.86 (1H, d), 4.67 (1H, m), 3.00 (2H, t), 2.53 (2H, t), 2.31 (3H, s), 1.98 (2H, m), 1.77 (4H, m), 1.64-1.53 (4H, m).

Example 179

4-(2'-cyclopentyloxy-5'-fluoro-biphenyl-4-ylsulfanyl)-butyric acid

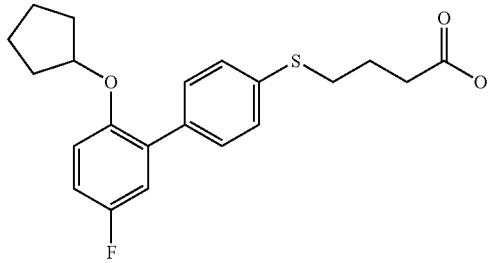 [SMILES: O=C(O)CCCSc1ccc(-c2cc(F)ccc2OC2CCCC2)cc1]

4-[4-(4,4,5,5-Tetramethyl-[1,3,2]dioxaborolan-2-yl)-phenylsulfanyl]-butyric acid ethyl ester (0.05 g, 0.14 mmol) obtained in Preparation Example 159 and 2-bromo-1-cyclopentyloxy-4-fluoro-benzene (0.04 g, 0.16 mmol) obtained in Preparation Example 129 were used to react sequentially in the same manner as in Steps A and B of Example 1 to obtain the title compound (0.003 g, 5%).

$^1$H-NMR (CDCl$_3$) δ 7.43 (2H, d), 7.32 (2H, d), 7.02 (1H, m), 6.95 (1H, m), 6.88 (1H, m), 4.63 (1H, m), 3.01 (2H, t), 2.53 (2H, t), 1.99 (2H, m), 1.75 (4H, m), 1.63-1.52 (4H, m).

Example 180

4-(2'-cyclopentyloxy-3,5'-difluoro-biphenyl-4-ylsulfanyl)-butyric acid

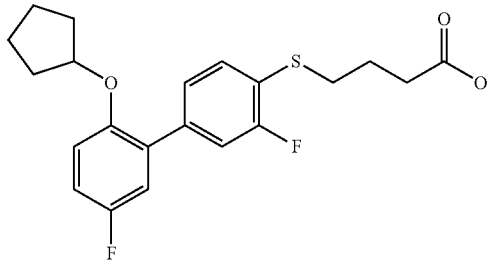

4-[2-Fluoro-4-(4,4,5,5-tetramethyl-[1,3,2]dioxaborolan-2-yl)-phenylsulfanyl]-butyric acid ethyl ester (0.1 g, 0.27 mmol) obtained in Preparation Example 180 and 2-bromo-1-cyclopentyloxy-4-fluoro-benzene (0.1 g, 0.4 mmol) obtained in Preparation Example 129 were used to react sequentially in the same manner as in Steps A and B of Example 1 to obtain the title compound (0.047 g, 44%).

$^1$H-NMR (CDCl$_3$) δ 7.38 (1H, t), 7.27-7.24 (2H, m), 7.03 (1H, m), 6.97 (1H, m), 6.89 (1H, m), 4.66 (1H, m), 3.01 (2H, t), 2.55 (2H, t), 1.98 (2H, m), 1.79 (4H, m), 1.70-1.47 (4H, m).

Example 181

4-[4-(2-cyclopentyloxy-5-methyl-pyridin-3-yl)-phenylsulfanyl]-butyric acid

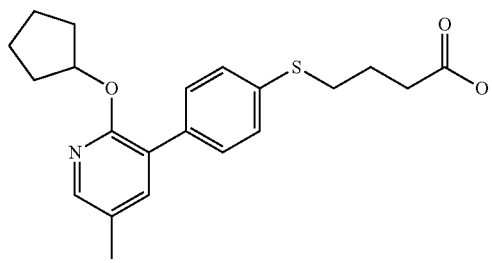 [SMILES: Cc1cnc(OC2CCCC2)c(-c2ccc(SCCCC(=O)O)cc2)c1]

4-[4-(4,4,5,5-Tetramethyl-[1,3,2]dioxaborolan-2-yl)-phenylsulfanyl]-butyric acid ethyl ester (0.1 g, 0.28 mmol) obtained in Preparation Example 159 and 3-bromo-2-cyclopentyloxy-5-methyl-pyridine (0.11 g, 0.43 mmol) obtained in Preparation Example 131 were used to react sequentially in the same manner as in Steps A and B of Example 1 to obtain the title compound (0.03 g, 28%).

$^1$H-NMR (CDCl$_3$) δ 7.91 (1H, s), 7.48 (2H, d), 7.40 (1H, s), 7.34 (2H, d), 5.44 (1H, m), 3.01 (2H, t), 2.54 (2H, t), 2.26 (3H, s), 2.01 (2H, m), 1.90 (2H, m), 1.78-1.58 (6H, m).

Example 182

4-(2'-cyclopentyloxy-3,5,5'-trifluoro-biphenyl-4-ylsulfanyl)-butyric acid

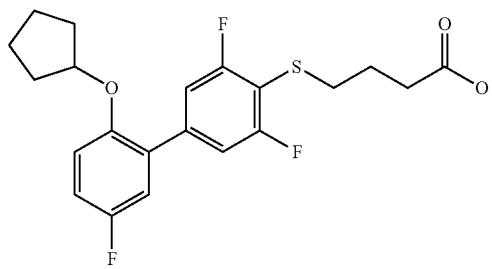 [SMILES: O=C(O)CCCSc1c(F)cc(-c2cc(F)ccc2OC2CCCC2)cc1F]

4-[2,6-Difluoro-4-(4,4,5,5-tetramethyl-[1,3,2]dioxaborolan-2-yl)-phenylsulfanyl]-butyric acid ethyl ester (0.036 g, 0.09 mmol) obtained in Preparation Example 170 and 2-bromo-1-cyclopentyloxy-4-fluoro-benzene (0.026 g, 0.1 mmol) obtained in Preparation Example 129 were used to react sequentially in the same manner as in Steps A and B of Example 1 to obtain the title compound (0.002 g, 4%).

$^1$H-NMR (CDCl$_3$) δ 7.11 (2H, d), 7.02 (2H, m), 6.89 (1H, m), 4.68 (1H, m), 2.95 (2H, t), 2.53 (2H, t), 1.89-1.79 (6H, m), 1.66-1.58 (4H, m).

Example 183

4-(2'-cyclopentyloxy-3-fluoro-4'-methoxy-biphenyl-4-ylsulfanyl)-butyric acid

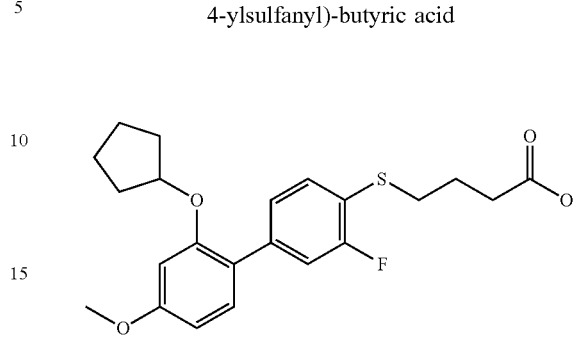

4-[2-Fluoro-4-(4,4,5,5-tetramethyl-[1,3,2]dioxaborolan-2-yl)-phenylsulfanyl]-butyric acid ethyl ester (0.05 g, 0.13 mmol) obtained in Preparation Example 180 and 1-bromo-2-cyclopentyloxy-4-methoxy-benzene (0.04 g, 0.15 mmol) obtained in Preparation Example 128 were used to react sequentially in the same manner as in Steps A and B of Example 1 to obtain the title compound (0.005 g, 9%).

$^1$H-NMR (CDCl$_3$) δ 7.38 (1H, t), 7.28-7.21 (4H, m), 6.53 (1H, m), 4.74 (1H, m), 3.83 (3H, s), 2.98 (2H, t), 2.55 (2H, t), 1.99 (2H, m), 1.84 (4H, m), 1.71-1.58 (4H, m).

Example 184

4-(2'-cyclopentyloxy-3,5-difluoro-4'-methoxy-biphenyl-4-ylsulfanyl)-butyric acid

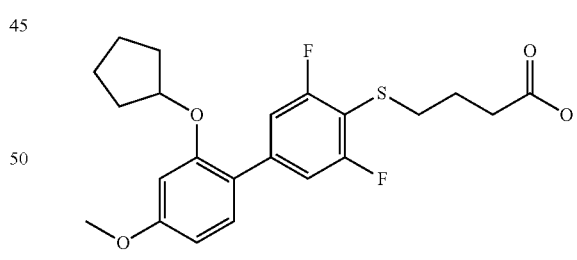

4-[2,6-Difluoro-4-(4,4,5,5-tetramethyl-[1,3,2]dioxaborolan-2-yl)-phenylsulfanyl]-butyric acid ethyl ester (0.05 g, 0.13 mmol) obtained in Preparation Example 170 and 1-bromo-2-cyclopentyloxy-4-methoxy-benzene (0.04 g, 0.14 mmol) obtained Preparation Example 128 in were used to react sequentially in the same manner as in Steps A and B of Example 1 to obtain the title compound (0.004 g, 7%).

$^1$H-NMR (CDCl$_3$) δ 7.22 (1H, m), 7.10 (2H, d), 6.55 (2H, m), 4.76 (1H, m), 3.84 (3H, s), 2.94 (2H, t), 2.56 (2H, t), 1.91-1.86 (6H, m), 1.71 (2H, m), 1.62 (2H, m).

Example 185

4-(3-fluoro-2'-isopropoxy-4'-methoxy-biphenyl-4-ylsulfanyl)-butyric acid

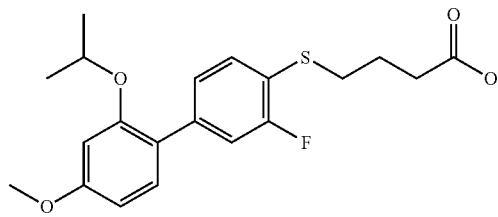 [SMILES: COc1ccc(-c2ccc(SCCCC(=O)O)c(F)c2)c(OC(C)C)c1]

4-[2-Fluoro-4-(4,4,5,5-tetramethyl-[1,3,2]dioxaborolan-2-yl)-phenylsulfanyl]-butyric acid ethyl ester (0.05 g, 0.13 mmol) obtained in Preparation Example 180 and 1-bromo-2-isopropoxy-4-methoxy-benzene (0.04 g, 0.15 mmol) obtained in Preparation Example 132 were used to react sequentially in the same manner as in Steps A and B of Example 1 to obtain the title compound (0.007 g, 13%).

¹H-NMR (CDCl₃) δ 7.37 (1H, t), 7.30-7.22 (3H, m), 6.56 (2H, m), 4.47 (1H, m), 3.84 (3H, s), 2.99 (2H, t), 2.56 (2H, t), 1.96 (2H, m), 1.29 (6H, d).

Example 186

4-[4-(2-cyclopentyloxy-5-methyl-pyridin-3-yl)-2-fluoro-phenylsulfanyl]-butyric acid

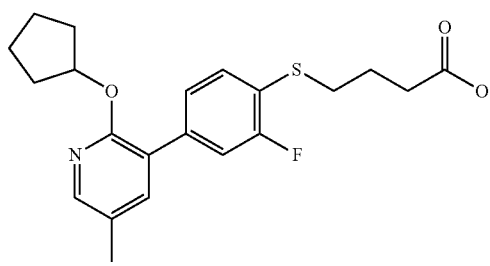 [SMILES: Cc1cnc(OC2CCCC2)c(-c2ccc(SCCCC(=O)O)c(F)c2)c1]

4-[2-Fluoro-4-(4,4,5,5-tetramethyl-[1,3,2]dioxaborolan-2-yl)-phenylsulfanyl]-butyric acid ethyl ester (0.05 g, 0.14 mmol) obtained in Preparation Example 180 and 3-bromo-2-cyclopentyloxy-5-methyl-pyridine (0.05 g, 0.2 mmol) obtained in Preparation Example 131 were used to react sequentially in the same manner as in Steps A and B of Example 1 to obtain the title compound (0.018 g, 34%).

¹H-NMR (CDCl₃) δ 7.96 (1H, s), 7.43 (1H, s), 7.38 (1H, t), 7.31-7.25 (2H, m), 5.47 (1H, m), 3.00 (2H, t), 2.55 (2H, t), 2.27 (3H, s), 1.98-1.93 (4H, m), 1.78-1.61 (6H, m).

Example 187

4-[2-fluoro-4-(2-isopropoxy-5-methyl-pyridin-3-yl)-phenylsulfanyl]-butyric acid

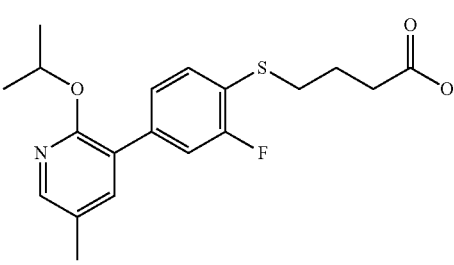 [SMILES: Cc1cnc(OC(C)C)c(-c2ccc(SCCCC(=O)O)c(F)c2)c1]

4-[2-Fluoro-4-(4,4,5,5-tetramethyl-[1,3,2]dioxaborolan-2-yl)-phenylsulfanyl]-butyric acid ethyl ester (0.05 g, 0.14 mmol) obtained in Preparation Example 180 and 3-bromo-2-isopropoxy-5-methyl-pyridine (0.05 g, 0.2 mmol) obtained in Preparation Example 133 were used to react sequentially in the same manner as in Steps A and B of Example 1 to obtain the title compound (0.017 g, 34%).

¹H-NMR (CDCl₃) δ 7.94 (1H, s), 7.43 (1H, s), 7.41 (1H, t), 7.38-7.30 (2H, m), 5.34 (1H, m), 3.00 (2H, t), 2.55 (2H, t), 2.27 (3H, s), 1.97 (2H, m), 1.32 (6H, d).

Example 188

4-(3,5'-difluoro-2'-isopropoxy-biphenyl-4-ylsulfanyl)-butyric acid

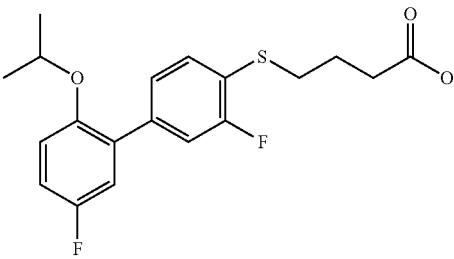 [SMILES: CC(C)Oc1ccc(F)cc1-c1ccc(SCCCC(=O)O)c(F)c1]

4-[2-Fluoro-4-(4,4,5,5-tetramethyl-[1,3,2]dioxaborolan-2-yl)-phenylsulfanyl]-butyric acid ethyl ester (0.05 g, 0.14 mmol) obtained in Preparation Example 180 and 2-bromo-4-fluoro-1-isopropoxy-benzene (0.05 g, 0.2 mmol) obtained in Preparation Example 134 were used to react sequentially in the same manner as in Steps A and B of Example 1 to obtain the title compound (0.02 g, 40%).

¹H-NMR (CDCl₃) δ 7.39 (1H, t), 7.33-7.27 (2H, m), 7.05-6.90 (3H, m), 4.33 (1H, m), 3.01 (2H, t), 2.56 (2H, t), 1.97 (2H, m), 1.24 (6H, d).

Example 189

4-[4-(2-cyclopentyloxy-6-methyl-pyridin-3-yl)-2-fluoro-phenylsulfanyl]-butyric acid

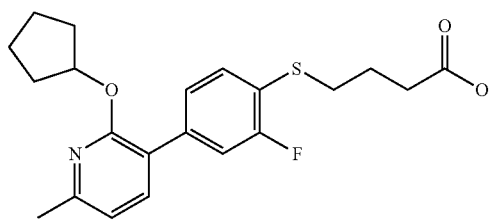 [SMILES: Cc1ccc(-c2ccc(SCCCC(=O)O)c(F)c2)c(OC2CCCC2)n1]

4-[2-fluoro-4-(4,4,5,5-tetramethyl-[1,3,2]dioxaborolan-2-yl)-phenylsulfanyl]-butyric acid ethyl ester (0.05 g, 0.14 mmol) obtained in Preparation Example 180 and 3-bromo-2-cyclopentyloxy-6-methyl-pyridine (0.05 g, 0.2 mmol) obtained Preparation Example 136 in were used to react sequentially in the same manner as in Steps A and B of Example 1 to obtain the title compound (0.011 g, 20%).

$^1$H-NMR (CDCl$_3$) δ 7.39 (2H, m), 7.01 (2H, m), 6.55 (1H, d), 5.34 (1H, m), 2.99 (2H, t), 2.54 (2H, t), 2.39 (3H, s), 2.01-1.91 (4H, m), 1.81 (4H, m), 1.62 (2H, m).

Example 191

4-(3,3'-difluoro-5'-methyl-2'-propoxy-biphenyl-4-ylsulfanyl)-butyric acid

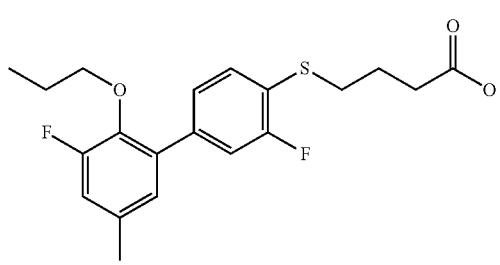

4-[2-Fluoro-4-(4,4,5,5-tetramethyl-[1,3,2]dioxaborolan-2-yl)-phenylsulfanyl]-butyric acid ethyl ester (0.05 g, 0.14 mmol) obtained in Preparation Example 180 and 1-bromo-3-fluoro-5-methyl-2-propoxy-benzene (0.05 g, 0.2 mmol) obtained in Preparation Example 139 were used to react sequentially in the same manner as in Steps A and B of Example 1 to obtain the title compound (0.02 g, 39%).

$^1$H-NMR (CDCl$_3$) δ 7.39 (1H, t), 7.26 (2H, m), 6.91 (2H, m), 3.72 (2H, t), 2.99 (2H, t), 2.55 (2H, t), 2.31 (3H, s), 1.94 (2H, m), 1.55 (2H, m), 0.82 (3H, t).

Example 190

4-(3,3'-difluoro-2'-isopropoxy-5'-methyl-biphenyl-4-ylsulfanyl)-butyric acid

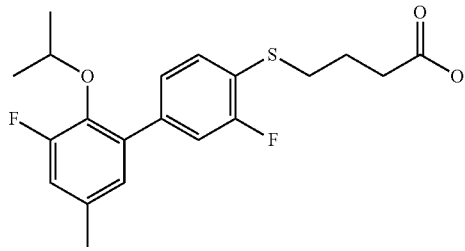 [SMILES: Cc1cc(F)c(OC(C)C)c(-c2ccc(SCCCC(=O)O)c(F)c2)c1]

4-[2-Fluoro-4-(4,4,5,5-tetramethyl-[1,3,2]dioxaborolan-2-yl)-phenylsulfanyl]-butyric acid ethyl ester (0.05 g, 0.14 mmol) obtained in Preparation Example 180 and 1-bromo-3-fluoro-2-isopropoxy-5-methyl-benzene (0.05 g, 0.2 mmol) obtained in Preparation Example 138 were used to react sequentially in the same manner as in Steps A and B of Example 1 to obtain the title compound (0.022 g, 43%).

$^1$H-NMR (CDCl$_3$) δ 7.39 (1H, t), 7.31 (2H, m), 6.91 (2H, m), 3.97 (1H, m), 2.99 (2H, t), 2.55 (2H, t), 2.33 (3H, s), 1.94 (2H, m), 1.05 (6H, d).

Example 192

4-(3-fluoro-2',4'-dipropoxy-biphenyl-4-ylsulfanyl)-butyric acid

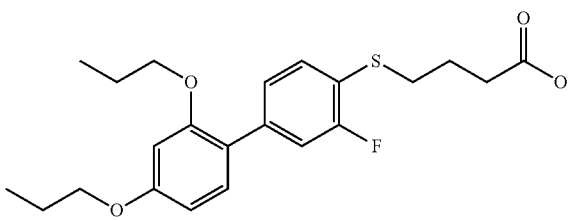 [SMILES: CCCOc1ccc(-c2ccc(SCCCC(=O)O)c(F)c2)c(OCCC)c1]

4-[2-Fluoro-4-(4,4,5,5-tetramethyl-[1,3,2]dioxaborolan-2-yl)-phenylsulfanyl]-butyric acid ethyl ester (0.05 g, 0.14 mmol) obtained in Preparation Example 180 and 2-bromo-1-cyclopentyloxy-3-fluoro-4-methyl-benzene (0.056 g, 0.2 mmol) obtained in Preparation Example 142 were used to react sequentially in the same manner as in Steps A and B of Example 1 to obtain the title compound (0.035 g, 63%).

$^1$H-NMR (CDCl$_3$) δ 7.41 (1H, t), 7.31-7.26 (2H, m), 6.89-6.83 (2H, m), 4.03 (1H, m), 3.00 (2H, t), 2.56 (2H, t), 2.31 (3H, s), 1.94 (2H, m), 1.57 (4H, m), 1.40 (4H, m).

Example 193

4-(6'-cyclopentyloxy-3,2'-difluoro-3'-methyl-biphenyl-4-yl sulfanyl)-butyric acid

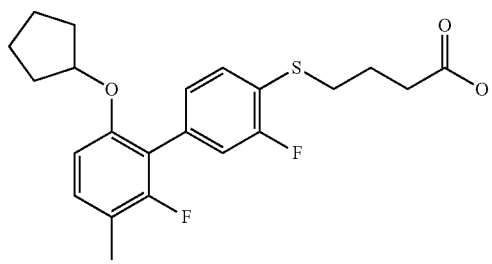 [SMILES: Cc1ccc(OC2CCCC2)c(-c2ccc(SCCCC(=O)O)c(F)c2)c1F]

4-[2-Fluoro-4-(4,4,5,5-tetramethyl-[1,3,2]dioxaborolan-2-yl)-phenylsulfanyl]-butyric acid ethyl ester (0.05 g, 0.14 mmol) obtained in Preparation Example 180 and 2-bromo-1-cyclopentyloxy-3-fluoro-4-methyl-benzene (0.056 g, 0.2 mmol) obtained in Preparation Example 142 were used to react sequentially in the same manner as in Steps A and B of Example 1 to obtain the title compound (0.035 g, 63%).

$^1$H-NMR (CDCl$_3$) δ 7.41 (1H, t), 7.31-7.26 (2H, m), 6.89-6.83 (2H, m), 4.03 (1H, m), 3.00 (2H, t), 2.56 (2H, t), 2.31 (3H, s), 1.94 (2H, m), 1.57 (4H, m), 1.40 (4H, m).

Example 194

4-(2'-cyclopentyloxy-3,3'-difluoro-biphenyl-4-ylsulfanyl)-butyric acid

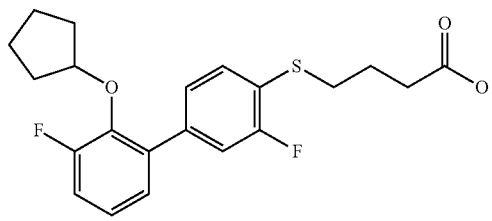 [SMILES: O=C(O)CCCSc1ccc(-c2cccc(F)c2OC2CCCC2)cc1F]

4-[2-Fluoro-4-(4,4,5,5-tetramethyl-[1,3,2]dioxaborolan-2-yl)-phenylsulfanyl]-butyric acid ethyl ester (0.05 g, 0.14 mmol) obtained in Preparation Example 180 and 1-bromo-2-cyclopentyloxy-3-fluoro-benzene (0.053 g, 0.2 mmol) obtained in Preparation Example 144 were used to react sequentially in the same manner as in Steps A and B of Example 1 to obtain the title compound (0.01 g, 18%).

$^1$H-NMR (CDCl$_3$) δ 7.42 (1H, t), 7.30-7.21 (4H, m), 7.01 (1H, t), 4.84 (1H, m), 2.99 (2H, t), 2.55 (2H, t), 1.99-1.83 (8H, m), 1.64 (2H, m).

Example 195

4-(2'-cyclopentyloxy-3,3'-difluoro-5'-methyl-biphenyl-4-ylsulfanyl)-butyric acid

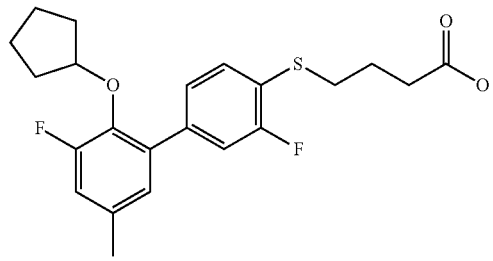 [SMILES: Cc1cc(F)c(OC2CCCC2)c(-c2ccc(SCCCC(=O)O)c(F)c2)c1]

4-[2-Fluoro-4-(4,4,5,5-tetramethyl-[1,3,2]dioxaborolan-2-yl)-phenylsulfanyl]-butyric acid ethyl ester (0.05 g, 0.14 mmol) obtained in Preparation Example 180 and 1-bromo-2-cyclopentyloxy-3-fluoro-5-methyl-benzene (0.053 g, 0.2 mmol) obtained in Preparation Example 145 were used to react sequentially in the same manner as in Steps A and B of Example 1 to obtain the title compound (0.025 g, 45%).

$^1$H-NMR (CDCl$_3$) δ 7.40 (1H, t), 7.38-7.26 (2H, m), 6.91 (2H, m), 4.46 (1H, m), 2.99 (2H, t), 2.55 (2H, t), 2.32 (3H, s), 1.94 (2H, m), 1.65 (2H, m), 1.47-1.39 (6H, m).

Example 196

5-[4-(2-cyclobutylmethoxy-pyridin-3-yl)-2,6-difluoro-phenoxy]-pentanoic acid

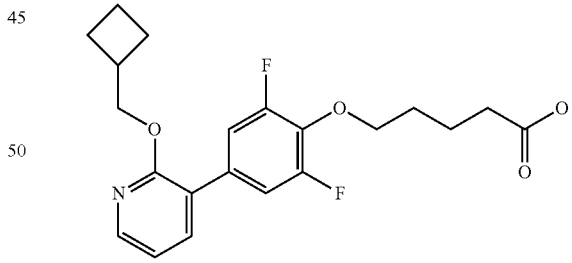

2-Cyclobutylmethoxy-3-iodo-pyridine (0.040 g, 0.14 mmol) obtained in Preparation Example 61 and 4-[2,6-difluoro-4-(4,4,5,5-tetramethyl-1,3,2-dioxaborolan-2-yl) phenoxy]butyric acid ethyl ester (0.053 g, 0.14 mmol) obtained in Preparation Example 2 were used to react in the same manner as in Steps A and B of Example 1 to obtain the title compound (0.029 g, 54%).

1H NMR (CDCl$_3$) δ 8.14 (1H, m), 7.59 (1H, m), 7.16 (2H, m), 6.94 (1H, m), 4.33 (2H, d), 4.20 (2H, t), 2.79 (1H, m), 2.48 (2H, t), 2.14 (2H, m), 2.00-1.80 (8H, m)

Example 197

5-[4-(2-cyclopropoxy-pyridin-3-yl)-2,6-difluoro-phenoxy]-pentanoic acid

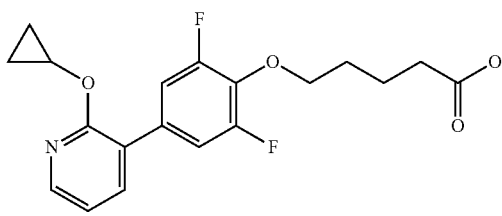 [SMILES: O=C(O)CCCCOc1c(F)cc(-c2cccnc2OC2CC2)cc1F]

2-Cyclopropoxy-3-iodo-pyridine (0.040 g, 0.15 mmol) obtained in Preparation Example 62 and 4-[2,6-difluoro-4-(4,4,5,5-tetramethyl-1,3,2-dioxaborolan-2-yl)phenoxy]butyric acid ethyl ester (0.059 g, 0.15 mmol) obtained in Preparation Example 2 were used to react in the same manner as in Steps A and B of Example 1 to obtain the title compound (0.024 g, 43%).

1H NMR (CDCl$_3$) δ 8.23 (1H, m), 7.57 (1H, m), 7.07 (2H, m), 7.00 (1H, m), 4.34 (1H, m), 4.18 (2H, t), 2.48 (2H, t), 1.89 (4H, m), 0.82 (2H, m), 0.75 (2H, m)

Example 198

4-[4-(2-cyclopentyloxy-5-methyl-pyridin-3-yl)-2,6-difluoro-phenylsulfanyl]-butyric acid

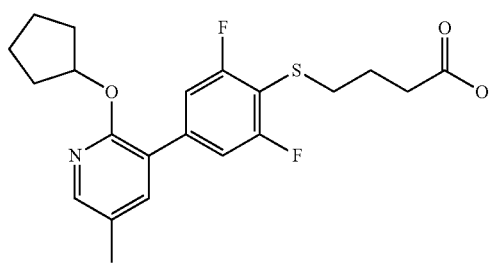

4-[2,6-Difluoro-4-(4,4,5,5-tetramethyl-[1,3,2]dioxaborolan-2-yl)-phenylsulfanyl]-butyric acid ethyl ester (0.05 g, 0.13 mmol) obtained in Preparation Example 170 and 3-bromo-2-cyclopentyloxy-5-methyl-pyridine (0.05 g, 0.26 mmol) obtained in Preparation Example 131 were used to react sequentially in the same manner as in Steps A and B of Example 1 to obtain the title compound (0.02 g, 40%).

$^1$H-NMR (CDCl$_3$) δ 7.97 (1H, s), 7.42 (1H, s), 7.16 (2H, d), 5.47 (1H, m), 2.95 (2H, t), 2.55 (2H, t), 2.27 (3H, s), 1.92 (4H, m), 1.88-1.62 (6H, m).

Example 199

4-[4-(2-cyclopentyloxy-pyridin-3-yl)-phenylsulfanyl]-pentanoic acid

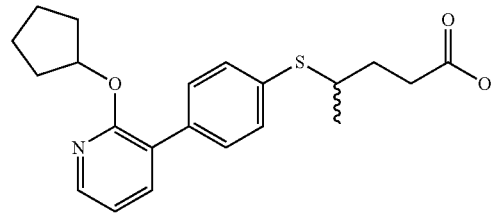 [SMILES: CC(CCC(=O)O)Sc1ccc(-c2cccnc2OC2CCCC2)cc1]

4-[4-(2-Cyclopentyloxy-pyridin-3-yl)-phenylsulfanyl]-pentanoic acid ethyl ester (0.01 g, 0.02 mmol) obtained in Preparation Example 191 was used to react in the same manner as in Step B of Example 1 to obtain the title compound (0.005 g, 48%).

$^1$H-NMR (CDCl$_3$) δ 8.12 (1H, m), 7.57 (1H, m), 7.49 (2H, d), 7.41 (2H, d), 6.90 (1H, m), 5.49 (1H, m), 3.29 (1H, m), 2.59 (2H, t), 1.93-1.91 (4H, m), 1.82-1.59 (6H, m), 1.34 (3H, d).

Example 200

4-[4-(2-isopropoxy-pyridin-3-yl)-phenylsulfanyl]-pentanoic acid

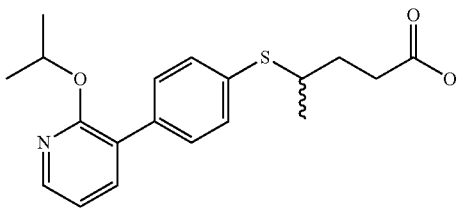 [SMILES: CC(C)Oc1ncccc1-c1ccc(SC(C)CCC(=O)O)cc1]

(E)-4-[4-(2-isopropoxy-pyridin-3-yl)-phenylsulfanyl]-pent-2-enoic acid ethyl ester (0.025 g, 0.07 mmol) obtained in Preparation Example 193 was used to react sequentially in the same manner as in Preparation Example 191 and Step B of Example 1 to obtain the title compound (0.005 g, 20%).

$^1$H-NMR (CDCl$_3$) δ 8.11 (1H, m), 7.57 (1H, m), 7.51 (2H, d), 7.42 (2H, d), 6.90 (1H, m), 5.38 (1H, m), 3.29 (1H, m), 2.60 (2H, t), 1.93 (2H, m), 1.34 (9H, m).

Example 201

4-[4-(2-cyclopentyloxy-pyridin-3-yl)-2,6-difluoro-phenyl sulfanyl]-pentanoic acid

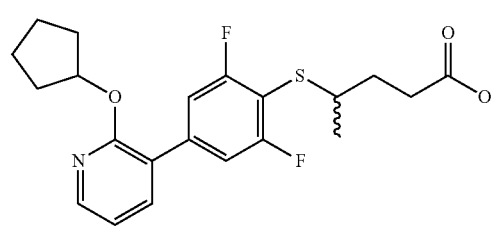

(E)-4-[4-(2-cyclopentyloxy-pyridin-3-yl)-2,6-difluoro-phenylsulfanyl]-pent-2-enoic acid ethyl ester (0.04 g, 0.09 mmol) obtained in Preparation Example 197 was used to react sequentially in the same manner as in Preparation Example 191 and Step B of Example 1 to obtain the title compound (0.01 g, 26%).

¹H-NMR (CDCl₃) δ 8.17 (1H, m), 7.61 (1H, m), 7.19 (2H, d), 6.93 (1H, m), 5.51 (1H, m), 3.31 (1H, m), 2.62 (2H, t), 1.94 (2H, m), 1.86-1.73 (6H, m), 1.63 (2H, m), 1.30 (3H, d).

Example 202

4-[4-(2-cyclopentylsulfanyl-pyridin-3-yl)-2,6-difluoro-phenyl sulfanyl]-pentanoic acid

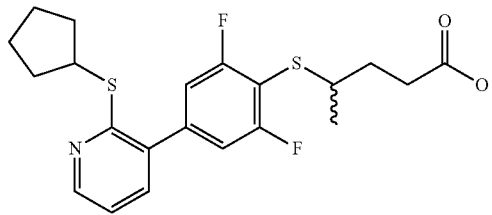 [SMILES: CC(CCC(=O)O)Sc1c(F)cc(-c2cccnc2SC2CCCC2)cc1F]

(E)-4-[4-(2-cyclopentylsulfanyl-pyridin-3-yl)-2,6-difluoro-phenylsulfanyl]-pent-2-enoic acid ethyl ester (0.04 g, 0.09 mmol) obtained in Preparation Example 199 was used to react sequentially in the same manner as in Preparation Example 191 and Step B of Example 1 to obtain the title compound (0.005 g, 12%).

¹H-NMR (CDCl₃) δ 8.44 (1H, m), 7.34 (1H, m), 7.03 (3H, m), 4.08 (1H, m), 3.32 (1H, m), 2.62 (2H, t), 2.19 (2H, m), 1.87 (2H, m), 1.71-1.51 (6H, m), 1.30 (3H, d).

Example 203

4-[4-[2-(2-dimethylaminoethyloxy)-3-pyridyl]-2,6-difluoro-phenoxy]butanoic acid

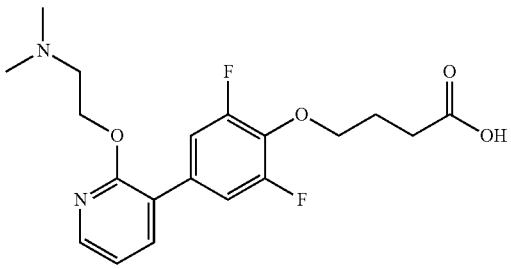 [SMILES: CN(C)CCOc1ncccc1-c1cc(F)c(OCCCC(=O)O)c(F)c1]

Step A: ethyl 4-[4-[2-(2-dimethylaminoethyloxy)-3-pyridyl]-2,6-difluoro-phenoxy]butanoate 2-[(3-Iodo-2-pyridyl)oxy]-N,N-dimethyl-ethanamine (0.117 g, 0.4 mmol) obtained in Preparation Example 206 and 4-[2,6-difluoro-4-(4,4,5,5-tetramethyl-1,3,2-dioxaboro-lan-2-yl)phenoxy]butyric acid ethyl ester (0.163 g, 0.44 mmol) obtained in Preparation Example 2 were used to react in the same manner as in Step A of Example 28 to obtain the title compound (0.06 g, 37%).

¹H-NMR (CDCl₃) δ 8.14 (1H, m), 7.58 (1H, m), 7.22 (2H, m), 6.96 (1H, m), 4.49 (2H, t), 4.21 (2H, t), 4.15 (2H, q), 2.72 (2H, t), 2.59 (2H, t), 2.31 (6H, s), 2.11 (2H, m), 1.27 (3H, t)

Step B: 4-[4-[2-(2-dimethylaminoethyloxy)-3-pyridyl]-2,6-difluoro-phenoxy]butanoic acid Ethyl 4-[4-[2-(2-dimethylaminoethyloxy)-3-pyridyl]-2,6-difluoro-phenoxy]butanoate (0.06 g, 0.15 mmol) obtained in Step A was used to react in the same manner as in Step B of Example 1 to obtain the title compound (0.02 g, 38%).

1H-NMR (MeOH-d₄) δ 8.14 (1H, m), 7.73 (1H, m), 7.21 (2H, m), 7.08 (1H, m), 4.63 (2H, t), 2.19 (2H, t), 3.23 (2H, t), 2.63 (6H, s), 2.40 (2H, t), 2.02 (2H, m)

Example 204

4-[2,6-difluoro-4-(2-propylsulfanyl-pyridin-3-yl)-phenoxy]-butanoic acid

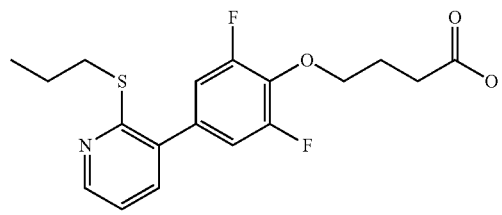 [SMILES: CCCSc1ncccc1-c1cc(F)c(OCCCC(=O)O)c(F)c1]

Step A: 4-[2,6-difluoro-4-(2-propylsulfanyl-pyridin-3-yl)-phenoxy]-butanoic acid ethyl ester 3-Iodo-2-propylsulfanyl-pyridine (0.114 g, 0.410 mmol) obtained in Preparation Example 203 and 4-[2,6-difluoro-4-(4,4,5,5-tetramethyl-1,3,2-dioxaboran-2-yl)phenoxy]bu-tyric acid ethyl ester (0.142 g, 0.383 mmol) obtained in Preparation Example 2 were dissolved in 2 mL of 2M sodium carbonate aqueous solution and 4 mL of 1,2-dime-thoxyethane, and N₂ gas was charged thereto for 5 minutes. Bis(triphenylphosphine)palladium(II) dichloride (0.013 g, 0.019 mmol) was added thereto and the resultant was agitated at 80° C. for 16 hours. After finishing the reaction, the resultant was diluted with water and extracted with ethyl acetate. The organic layer was dried with anhydrous MgSO₄ and purified by column chromatography (eluent: EtOAc/Hex=1/4) to obtain the title compound (0.113 g, 74%).

¹H-NMR (CDCl₃) δ 8.42 (1H, m), 7.32 (1H, m), 7.01 (3H, m), 4.22 (2H, t), 4.15 (2H, q), 3.13 (2H, t), 2.58 (2H, t), 2.11 (2H, m), 1.68 (2H, m), 1.25 (3H, t), 1.01 (3H, t)

Step B: 4-[2,6-difluoro-4-(2-propylsulfanyl-pyridin-3-yl)-phenoxy]-butanoic acid 4-[2,6-Difluoro-4-(2-propylsulfanyl-pyridin-3-yl)-phenoxy]-butanoic acid ethyl ester (0.026 g, 0.065 mmol) obtained in Step A was dissolved in THF/MeOH/water (1:1:1, 3 mL). 1N NaOH (12 mg, 0.50 mmol) was added thereto, and the resultant was agitated at room temperature for 2 hours. After finishing the reaction, the resultant was concentrated under reduced pressure, and the residue was diluted with water. The pH of the aqueous layer was adjusted to 2-3 by the use of 1N HCl, and the resultant was extracted with ethyl acetate. The organic layer was dried with anhydrous MgSO₄ and purified by column chromatography (eluent: EtOAc/Hex=1/1) to obtain the title compound (0.014 g, 58%).

¹H-NMR (CDCl₃) δ 8.43 (1H, m), 7.32 (1H, m), 7.01 (3H, m), 4.26 (2H, t), 3.14 (2H, t), 2.68 (2H, t), 2.14 (2H, m), 1.69 (2H, m), 1.02 (3H, t)

Example 205

4-[4-(2-cyclopropylsulfanyl-pyridin-3-yl)-2,6-difluoro-phenoxy]-butanoic acid

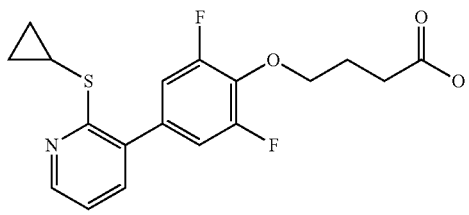 [SMILES: O=C(O)CCCOc1c(F)cc(-c2cccnc2SC2CC2)cc1F]

2-Cyclopropylsulfanyl-3-iodo-pyridine (0.06 g, 0.21 mmol) obtained in Preparation Example 239 and 4-[2,6-difluoro-4-(4,4,5,5-tetramethyl-1,3,2-dioxaboran-2-yl)phenoxy]butyric acid ethyl ester (0.074 g, 0.202 mmol) obtained in Preparation Example 2 were used to react in the same manner as in Example 1 to obtain the title compound (0.03 g, 38%).

¹H-NMR (CDCl₃) δ 8.52 (1H, m), 7.34 (1H, m), 7.09 (1H, m), 6.95 (2H, m), 4.25 (2H, m), 2.67 (2H, t), 2.40 (1H, m), 2.12 (2H, m), 1.07 (2H, m), 0.59 (2H, m)

Example 206

4-[4-(2-ethylsulfanyl-pyridin-3-yl)-2,6-difluoro-phenoxy]-butanoic acid

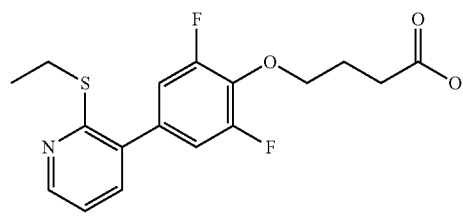 [SMILES: CCSc1ncccc1-c1cc(F)c(OCCCC(=O)O)c(F)c1]

2-Ethylsulfanyl-3-iodo-pyridine (0.098 g, 0.369 mmol) obtained in Preparation Example 240 and 4-[2,6-difluoro-4-(4,4,5,5-tetramethyl-1,3,2-dioxaboran-2-yl) phenoxy]butyric acid ethyl ester (0.127 g, 0.345 mmol) obtained in Preparation Example 2 were used to react in the same manner as in Example 1 to obtain the title compound (0.03 g, 35%).

¹H-NMR (CDCl₃) δ 8.45 (1H, m), 7.34 (1H, m), 7.05 (1H, m), 6.99 (2H, m), 4.26 (2H, t), 3.17 (2H, q), 2.68 (2H, t), 2.13 (2H, m), 1.33 (3H, t)

Example 207

4-[4-(2-butylsulfanyl-pyridin-3-yl)-2,6-difluoro-phenoxy]-butanoic acid

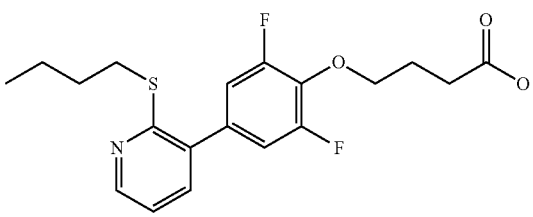 [SMILES: CCCCSc1ncccc1-c1cc(F)c(OCCCC(=O)O)c(F)c1]

2-Butylsulfanyl-3-iodo-pyridine (0.102 g, 0.347 mmol) obtained in Preparation Example 241 and 4-[2,6-difluoro-4-(4,4,5,5-tetramethyl-1,3,2-dioxaboran-2-yl)phenoxy]butyric acid ethyl ester (0.12 g, 0.325 mmol) obtained in Preparation Example 2 were used to react in the same manner as in Example 1 to obtain the title compound (0.052 g, 39%).

¹H-NMR (CDCl₃) δ 8.43 (1H, m), 7.33 (1H, d), 7.04 (1H, m), 6.99 (2H, m), 4.26 (2H, t), 3.17 (2H, t), 2.68 (2H, t), 2.14 (2H, m), 1.66 (2H, m), 1.44 (2H, m), 0.93 (3H, t)

Example 208

4-(2'-cyclopentylamino-biphenyl-4-ylsulfanyl)-butyric acid

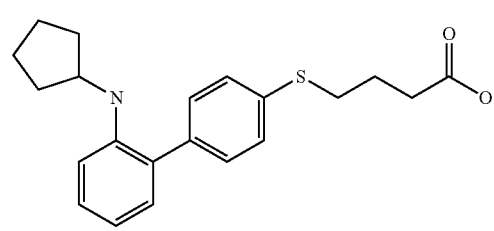 [SMILES: O=C(O)CCCSc1ccc(-c2ccccc2NC2CCCC2)cc1]

4-[4-(4,4,5,5-Tetramethyl-[1,3,2]dioxaborolan-2-yl)-phenylsulfanyl]-butyric acid ethyl ester (0.05 g, 0.14 mmol) obtained in Preparation Example 159 and N-cyclopentyl-2-iodo-aniline (0.045 g, 0.16 mmol) obtained in Preparation Example 70 were used to react sequentially in the same manner as in Steps A and B of Example 1 to obtain the title compound (0.02 g, 40%).

¹H-NMR (CDCl₃) δ 7.39 (2H, d), 7.33 (2H, d), 7.21 (1H, t), 7.03 (1H, m), 6.72 (2H, m), 3.77 (1H, m), 3.03 (2H, t), 2.56 (2H, t), 2.03-1.95 (4H, m), 1.61 (4H, m), 1.38 (2H, m).

Example 209

4-[4-(2-cyclopentyloxy-5-methyl-pyridin-3-yl)-2,6-difluoro-phenoxy]-butyric acid

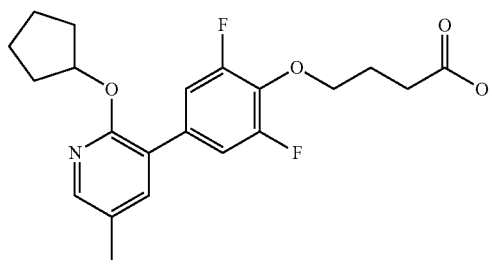 [SMILES: Cc1cnc(OC2CCCC2)c(-c2cc(F)c(OCCCC(=O)O)c(F)c2)c1]

4-[2,6-difluoro-4-(4,4,5,5-tetramethyl-1,3,2-dioxaborolan-2-yl)phenoxy]butyric acid ethyl ester (0.05 g, 0.13 mmol) obtained in Preparation Example 2 and 3-bromo-2-cyclopentyloxy-5-methyl-pyridine (0.05 g, 0.20 mmol) obtained in Preparation Example 131 were used to react sequentially in the same manner as in Steps A and B of Example 1 to obtain the title compound (0.027 g, 52%).

$^1$H-NMR (CDCl$_3$) δ 7.95 (1H, s), 7.39 (1H, s), 7.12 (2H, d), 5.46 (1H, m), 4.22 (2H, t), 2.66 (2H, t), 2.27 (3H, s), 2.12 (2H, m), 1.92 (2H, m), 1.80-1.72 (4H, m), 1.62 (2H, m).

Example 210

4-[4-(6-isopropylsulfanyl-2-pyridyl)phenoxy]butanoic acid

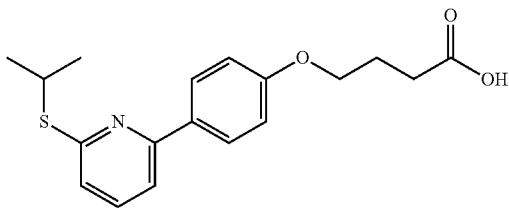 [SMILES: CC(C)Sc1cccc(-c2ccc(OCCCC(=O)O)cc2)n1]

Step A: ethyl 4-[4-(6-isopropylsulfanyl-2-pyridyl)phenoxy]butanoate

4-[4-(4,4,5,5-Tetramethyl-1,3,2-dioxaborolan-2-yl)phenoxy]butyric acid ethyl ester (0.143 g, 0.43 mmol) obtained in Preparation Example 1 and 2-chloro-6-isopropylsulfanyl-pyridine (0.03 g, 0.16 mmol) obtained in Preparation Example 125 were used to react in the same manner as in Step A of Example 29 to obtain the title compound (0.036 g, 62%).

1H NMR (CDCl$_3$) δ 7.97 (2H, d), 7.48 (1H, t), 7.35 (1H, d), 7.02 (1H, d), 6.95 (2H, d), 4.14 (3H, m), 4.07 (2H, t), 2.53 (2H, t), 2.14 (2H, m), 1.46 (6H, d), 1.26 (3H, t)

Step B: 4-[4-(6-isopropylsulfanyl-2-pyridyl)phenoxy]butanoic acid

Ethyl 4-[4-(6-isopropylsulfanyl-2-pyridyl)phenoxy]butanoate (0.036 g, 0.1 mmol) obtained in Step A was used to react in the same manner as in Step B of Example 1 to obtain the title compound (0.019 g, 57%).

1H NMR (CDCl$_3$) δ 7.98 (2H, d), 7.48 (1H, t), 7.35 (1H, m), 7.02 (1H, m), 6.96 (2H, m), 4.16 (1H, m), 4.09 (2H, t), 2.61 (2H, t), 2.14 (2H, m), 1.46 (6H, d)

Example 211

4-[2,6-difluoro-4-(3-phenoxyphenyl)phenoxy]butanoic acid

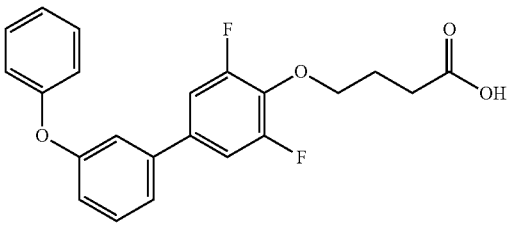 [SMILES: O=C(O)CCCOc1c(F)cc(-c2cccc(Oc3ccccc3)c2)cc1F]

4-[2,6-Difluoro-4-(4,4,5,5-tetramethyl-1,3,2-dioxaborolan-2-yl)phenoxy]butyric acid ethyl ester (0.090 g, 0.24 mmol) obtained in Preparation Example 2 and 1-bromo-3-phenoxy-benzene (0.06 g. 0.24 mmol) were used to react sequentially in the same manner as in Steps A and B of Example 29 to obtain the title compound (0.078 g, 80%).

1H NMR (CDCl$_3$) δ 7.36 (3H, m), 7.23 (1H, m), 7.13 (2H, m), 7.08 (2H, m), 7.04 (2H, m), 6.99 (1H, m), 4.21 (2H, t), 2.66 (2H, t), 2.11 (2H, m)

Example 212

4-[4-[6-[3-(dimethylamino)pyrrolidin-1-yl]-2-pyridyl]-2,6-difluoro-phenoxy]butanoic acid

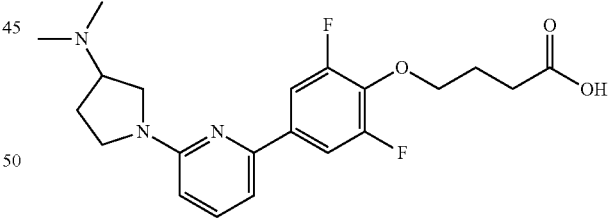

1-(6-Chloro-2-pyridyl)-N,N-dimethyl-pyrrolidin-3-amine (0.04 g, 0.18 mmol) obtained in Preparation Example 124 and 4-[2,6-difluoro-4-(4,4,5,5-tetramethyl-1,3,2-dioxaborolan-2-yl)phenoxy]butyric acid ethyl ester (0.066 g, 0.18 mmol) obtained in Preparation Example 2 were used to react sequentially in the same manner as in Step A of Example 29 and Step B of Example 1 to obtain the title compound (3.3 mg, 5%).

1H NMR (CDCl$_3$) δ 7.43 (3H, m), 6.88 (1H, m), 6.31 (1H, m), 4.21 (2H, t), 3.85 (1H, m), 3.74 (1H, m), 3.48 (2H, m), 3.17 (1H, m), 2.56 (2H, t), 2.47 (6H, s), 2.27 (1H, m), 2.24 (1H, m), 2.08 (2H, m)

Example 213

5-[2,6-difluoro-4-(2-isopropoxy-pyridin-3-yl)-phenoxy]-pentanoic acid

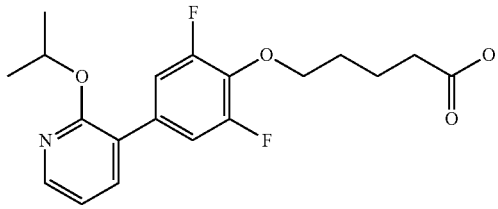 [SMILES: CC(C)Oc1ncccc1-c1cc(F)c(OCCCCC(=O)O)c(F)c1]

3-Iodo-2-isopropoxy-pyridine (0.040 g, 0.15 mmol) obtained in Preparation Example 37 and ethyl 5-[2,6-difluoro-4-(4,4,5,5-tetramethyl-1,3,2-dioxaborolan-2-yl)phenoxy]pentanoate (0.058 g, 0.15 mmol) obtained in Preparation Example 225 were used to react in the same manner as in Example 1 to obtain the title compound (0.038 g, 68%).

1H NMR (CDCl$_3$) 8.13 (1H, m), 7.56 (1H, m), 7.16 (2H, m), 6.92 (1H, m), 5.41 (1H, m), 4.20 (2H, t), 2.49 (2H, t), 1.89 (4H, m), 1.36 (6H, d)

Example 214

5-[4-(2-cyclobutoxy-pyridin-3-yl)-2,6-difluoro-phenoxy]-pentanoic acid

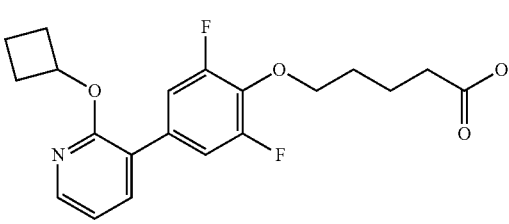 [SMILES: O=C(O)CCCCOc1c(F)cc(-c2cccnc2OC2CCC2)cc1F]

2-Cyclobutoxy-3-iodo-pyridine (0.040 g, 0.15 mmol) obtained in Preparation Example 200 and ethyl 5-[2,6-difluoro-4-(4,4,5,5-tetramethyl-1,3,2-dioxaborolan-2-yl)phenoxy]pentanoate (0.056 g, 0.15 mmol) obtained in Preparation Example 225 were used to react in the same manner as in Example 1 to obtain the title compound (0.033 g, 60%).

1H NMR (CDCl$_3$) 8.12 (1H, m), 7.57 (1H, m), 7.18 (2H, m), 6.94 (1H, m), 5.28 (1H, m), 4.20 (2H, t), 2.48 (4H, m), 2.13 (2H, m), 1.89 (5H, m), 1.72 (1H, m)

Example 215

4-[4-[2-(3,3-difluoropyrrolidin-1-yl)-3-pyridyl]-2,6-difluoro-phenoxy]butanoic acid

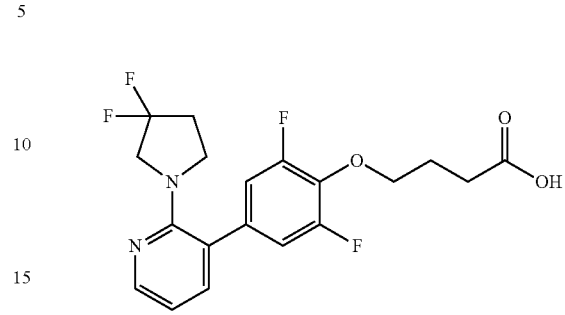

Step A: ethyl 4-[4-[2-(3,3-difluoropyrrolidin-1-yl)-3-pyridyl]-2,6-difluoro-phenoxy]butanoate Ethyl 4-[2,6-difluoro-4-(2-fluoro-3-pyridyl)phenoxy]butanoate (0.09 g, 0.27 mmol) obtained in Preparation Example 109 and 3,3-difluoropyrrolidine hydrochloride (0.11 g, 0.8 mmol) were used to react in the same manner as in Step A of Example 72 to obtain the title compound (0.007 g, 6%).

1H NMR (CDCl$_3$) δ 8.20 (1H, m), 7.38 (1H, m), 6.98 (2H, m), 6.84 (1H, m), 4.24 (2H, t), 4.16 (2H, q), 4.45 (4H, m), 2.59 (2H, t), 2.27 (2H, m), 2.13 (2H, m), 1.27 (3H, t)

Step B: 4-[4-[2-(3,3-difluoropyrrolidin-1-yl)-3-pyridyl]-2,6-difluoro-phenoxy]butanoic acid Ethyl 4-[4-[2-(3,3-difluoropyrrolidin-1-yl)-3-pyridyl]-2,6-difluoro-phenoxy]butanoate (0.007 g, 0.016 mmol) obtained in Step A was used to react in the same manner as in Step B of Example 1 to obtain the title compound (0.006 g, 98%).

1H NMR (CDCl$_3$) δ 8.21 (1H, m), 7.38 (1H, m), 6.95 (2H, m), 6.8 (1H, m), 4.25 (2H, t), 3.43 (4H, m), 2.68 (2H, t), 2.28 (2H, m), 2.14 (2H, m)

Example 216

4-[2,6-difluoro-4-[2-(4-methylpiperazin-1-yl)-3-pyridyl]phenoxy]butanoic acid

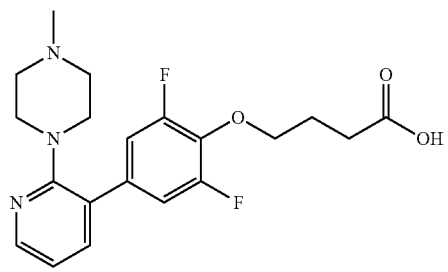 [SMILES: CN1CCN(c2ncccc2-c2cc(F)c(OCCCC(=O)O)c(F)c2)CC1]

Step A: ethyl 4-[2,6-difluoro-4-[2-(4-methylpiperazin-1-yl)-3-pyridyl]phenoxy]butanoate Ethyl 4-[2,6-difluoro-4-(2-fluoro-3-pyridyl)phenoxy]butanoate (0.09 g, 0.27 mmol) obtained in Preparation Example 109 and 1-methylpiperazin (0.088 g, 0.8 mmol) were used to react in the same manner as in Step A of Example 72 to obtain the title compound (0.007 g, 6%).

1H NMR (CDCl$_3$) δ 8.23 (1H, m), 7.38 (1H, m), 7.16 (2H, m), 6.92 (1H, m), 4.23 (2H, t), 4.17 (2H, q), 3.14 (4H, m), 2.60 (2H, t), 2.40 (4H, m), 2.30 (3H, s), 2.11 (2H, m), 1.27 (3H, t)

Step B: 4-[2,6-difluoro-4-[2-(4-methylpiperazin-1-yl)-3-pyridyl]phenoxy]butanoic acid Ethyl 4-[2,6-difluoro-4-[2-(4-methylpiperazin-1-yl)-3-pyridyl]phenoxy]butanoate (0.007 g, 0.016 mmol) obtained in Step A was used to react in the same manner as in Step B of Example 1 to obtain the title compound (0.0013 g, 20%).

1H NMR (CDCl$_3$) δ 8.21 (1H, m), 7.40 (1H, m), 7.08 (2H, m), 6.91 (1H, m), 4.26 (2H, t), 3.23 (4H, m), 2.62 (4H, m), 2.52 (2H, t), 2.39 (3H, s), 2.07 (2H, m)

Example 217

4-[2,6-difluoro-4-[2-(5-methylisoxazol-3-yl)oxy-3-pyridyl]phenoxy]butanoic acid

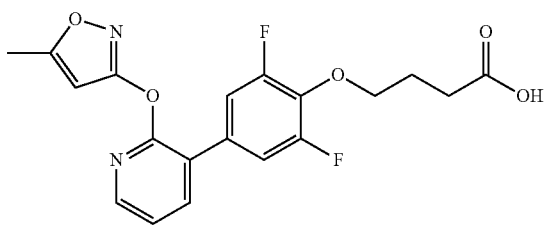 [SMILES: Cc1cc(Oc2ncccc2-c2cc(F)c(OCCCC(=O)O)c(F)c2)no1]

Step A: ethyl 4-[2,6-difluoro-4-[2-(5-methylisoxazol-3-yl)oxy-3-pyridyl]phenoxy]butanoate 3-[(3-Iodo-2-pyridyl)oxy]-5-methyl-isoxazole (0.15 g, 0.5 mmol) obtained in Preparation Example 205 and 4-[2,6-difluoro-4-(4,4,5,5-tetramethyl-1,3,2-dioxaborolan-2-yl)phenoxy]butyric acid ethyl ester (0.20 g, 0.54 mmol) obtained in Preparation Example 2 were used to react in the same manner as in Step A of Example 28 to obtain the title compound (0.14 g, 67%).

$^1$H-NMR (CDCl$_3$) δ 8.21 (1H, m), 7.75 (1H, m), 7.20 (3H, m), 6.02 (1H, s), 4.23 (2H, t), 4.15 (2H, q), 2.58 (2H, t), 2.43 (3H, s), 2.12 (2H, m), 1.27 (3H, t)

Step B: 4-[2,6-difluoro-4-[2-(5-methylisoxazol-3-yl)oxy-3-pyridyl]phenoxy]butanoic acid Ethyl 4-[2,6-difluoro-4-[2-(5-methylisoxazol-3-yl)oxy-3-pyridyl]phenoxy]butanoate (0.14 g, 0.33 mmol) obtained in Step A was used to react in the same manner as in Step B of Example 1 to obtain the title compound (0.1 g, 78%).

$^1$H-NMR (CDCl$_3$) δ 8.21 (1H, m), 7.74 (1H, m), 7.17 (3H, m), 6.02 (1H, s), 4.25 (2H, t), 2.67 (2H, t), 2.43 (3H, s), 2.12 (2H, m)

Example 218

4-[4-[2-[2-(aziridin-1-yl)ethoxy]-3-pyridyl]-2,6-difluoro-phenoxy]butanoic acid

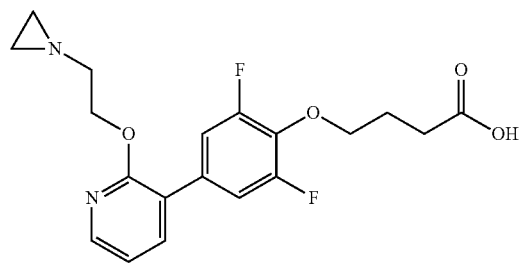 [SMILES: O=C(O)CCCOc1c(F)cc(-c2cccnc2OCCN2CC2)cc1F]

2-[2-(Aziridin-1-yl)ethoxy]-3-iodo-pyridine (0.095 g, 0.33 mmol) obtained in Preparation Example 207 and 4-[2,6-difluoro-4-(4,4,5,5-tetramethyl-1,3,2-dioxaborolan-2-yl)phenoxy]butyric acid ethyl ester (0.133 g, 0.36 mmol) obtained in Preparation Example 2 were used to react sequentially in the same manner as in Step A of Example 28 and Step B of Example 1 to obtain the title compound (0.001 g, 0.1%).

1H-NMR (MeOH-d4) δ 8.11 (1H, m), 7.72 (1H, m), 7.25 (2H, m), 7.04 (1H, m), 4.51 (2H, m), 4.18 (2H, t), 2.67 (2H, t), 2.45 (2H, t), 2.02 (2H, m), 1.73 (2H, m), 1.34 (2H, m)

Example 219

4-[2,6-difluoro-4-[2-(3-furylmethoxy)-3-pyridyl]phenoxy]butanoic acid

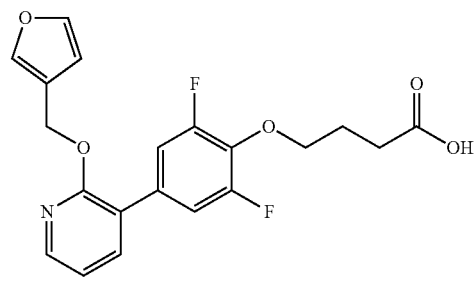 [SMILES: O=C(O)CCCOc1c(F)cc(-c2cccnc2OCc2ccoc2)cc1F]

Step A: ethyl 4-[2,6-difluoro-4-[2-(3-furylmethoxy)-3-pyridyl]phenoxy]butanoate 2-(3-Furylmethoxy)-3-iodo-pyridine (0.107 g, 0.36 mmol) obtained in Preparation Example 208 and 4-[2,6-difluoro-4-(4,4,5,5-tetramethyl-1,3,2-dioxaborolan-2-yl)phenoxy]butyric acid ethyl ester (0.10 g, 0.27 mmol) obtained in Preparation Example 2 were used to react in the same manner as in Step A of Example 28 to obtain the title compound (0.058 g, 51%).

$^1$H-NMR (CDCl$_3$) δ 8.17 (1H, m), 7.59 (1H, m), 7.48 (1H, m), 7.40 (1H, m), 7.14 (2H, m), 6.98 (1H, m), 6.47 (1H, m), 5.34 (2H, s), 4.21 (2H, t), 4.15 (2H, q), 2.58 (2H, t), 2.10 (2H, m), 1.27 (3H, t)

Step B: 4-[2,6-difluoro-4-[2-(3-furylmethoxy)-3-pyridyl]phenoxy]butanoic acid Ethyl 4-[2,6-difluoro-4-[2-(3-furylmethoxy)-3-pyridyl]phenoxy]butanoate (0.058 g, 0.14 mmol) obtained in Step A was used to react in the same manner as in Step B of Example 1 to obtain the title compound (0.054 g, 99%).

¹H-NMR (CDCl₃) δ 8.18 (1H, m), 7.59 (1H, m), 7.48 (1H, m), 7.41 (1H, m), 7.14 (2H, m), 6.98 (1H, m), 6.47 (1H, m), 5.33 (2H, s), 4.23 (2H, t), 2.67 (2H, t), 2.11 (2H, m)

Example 220

4-[2,6-difluoro-4-[2-(2-furylmethoxy)-3-pyridyl]phenoxy]butanoic acid

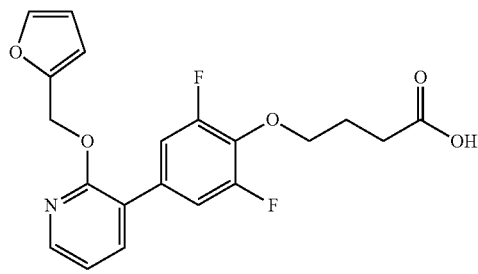 [SMILES: O=C(O)CCCOc1c(F)cc(-c2cccnc2OCc2ccco2)cc1F]

Step A: ethyl 4-[2,6-difluoro-4-[2-(2-furylmethoxy)-3-pyridyl]phenoxy]butanoate 2-(2-Furylmethoxy)-3-iodo-pyridine (0.12 g, 0.4 mmol) obtained in Preparation Example 209 and 4-[2,6-difluoro-4-(4,4,5,5-tetramethyl-1,3,2-dioxaborolan-2-yl)phenoxy]butyric acid ethyl ester (0.18 g, 0.49 mmol) obtained in Preparation Example 2 were used to react in the same manner as in Step A of Example 28 to obtain the title compound (0.108 g, 65%).

¹H-NMR (CDCl₃) δ 8.17 (1H, m), 7.59 (1H, m), 7.23 (1H, m), 7.13 (2H, m), 7.00 (1H, m), 6.41 (1H, m), 6.35 (1H, m), 5.42 (2H, s), 4.20 (2H, m), 4.14 (2H, q), 2.57 (2H, t), 2.10 (2H, m), 1.27 (3H, t)

Step B: 4-[2,6-difluoro-4-[2-(2-furylmethoxy)-3-pyridyl]phenoxy]butanoic acid Ethyl 4-[2,6-difluoro-4-[2-(2-furylmethoxy)-3-pyridyl]phenoxy]butanoate (0.108 g, 0.26 mmol) obtained in Step A was used to react in the same manner as in Step B of Example 1 to obtain the title compound (0.077 g, 76%).

¹H-NMR (CDCl₃) δ 8.17 (1H, m), 7.58 (1H, m), 7.43 (1H, m), 7.14 (2H, m), 7.00 (1H, m), 6.42 (1H, m), 6.35 (1H, m), 5.42 (2H, s), 4.21 (2H, t), 2.66 (2H, t), 2.10 (2H, m)

Example 221

4-[2,6-difluoro-4-[2-[(3-methyloxetan-3-yl)methoxy]-3-pyridyl]phenoxy]butanoic acid

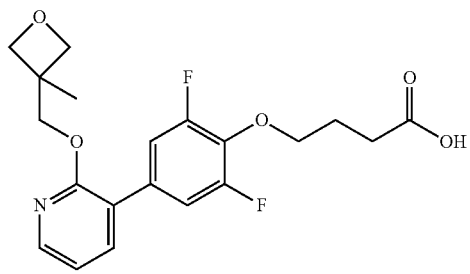 [SMILES: CC1(COc2ncccc2-c2cc(F)c(OCCCC(=O)O)c(F)c2)COC1]

Step A: ethyl 4-[2,6-difluoro-4-[2-[(3-methyloxetan-3-yl)methoxy]-3-pyridyl]phenoxy]butanoate 3-Iodo-2-[(3-methyloxetan-3-yl)methoxy]pyridine (0.12 g, 0.4 mmol) obtained in Preparation Example 210 and 4-[2,6-difluoro-4-(4,4,5,5-tetramethyl-1,3,2-dioxaborolan-2-yl)phenoxy]butyric acid ethyl ester (0.18 g, 0.49 mmol) obtained in Preparation Example 2 were used to react in the same manner as in Step A of Example 28 to obtain the title compound (0.10 g, 59%).

¹H-NMR (CDCl₃) δ 8.15 (1H, m), 7.61 (1H, m), 7.15 (2H, m), 7.00 (1H, m), 4.58 (2H, d), 4.48 (2H, s), 4.42 (2H, d), 4.23 (2H, t), 4.16 (2H, q), 2.59 (2H, t), 2.11 (2H, m), 1.39 (3H, s), 1.27 (3H, t)

Step B: 4-[2,6-difluoro-4-[2-[(3-methyloxetan-3-yl)methoxy]-3-pyridyl]phenoxy]butanoic acid Ethyl 4-[2,6-difluoro-4-[2-[(3-methyloxetan-3-yl)methoxy]-3-pyridyl]phenoxy]butanoate (0.10 g, 0.24 mmol) obtained in Step A was used to react in the same manner as in Step B of Example 1 to obtain the title compound (0.047 g, 48%).

¹H-NMR (CDCl₃) δ 8.15 (1H, m), 7.60 (1H, m), 7.13 (2H, m), 7.00 (1H, m), 4.62 (2H, d), 4.43 (4H, m), 4.27 (2H, t), 2.63 (2H, t), 2.10 (2H, m), 1.40 (3H, s)

Example 222

4-[2,6-difluoro-4-[2-(tetrahydrofuran-3-ylmethoxy)-3-pyridyl]phenoxy]butanoic acid

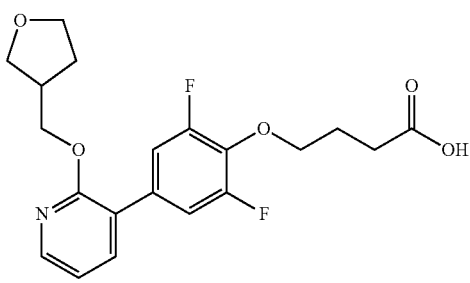 [SMILES: O=C(O)CCCOc1c(F)cc(-c2cccnc2OCC2CCOC2)cc1F]

Step A: ethyl 4-[2,6-difluoro-4-[2-(tetrahydrofuran-3-ylmethoxy)-3-pyridyl]phenoxy]butanoate 3-Iodo-2-(tetrahydrofuran-3-ylmethoxy)pyridine (0.12 g, 0.4 mmol) obtained in Preparation Example 211 and 4-[2,6-difluoro-4-(4,4,5,5-tetramethyl-1,3,2-dioxaborolan-2-yl)phenoxy]butyric acid ethyl ester (0.18 g, 0.49 mmol) obtained in Preparation Example 2 were used to react in the same manner as in Step A of Example 28 to obtain the title compound (0.15 g, 89%).

$^1$H-NMR (CDCl$_3$) δ 8.14 (1H, m), 7.59 (1H, m), 7.13 (2H, m), 6.98 (1H, m), 4.38 (1H, m), 4.28 (1H, m), 4.22 (2H, t), 4.16 (2H, q), 3.88 (2H, m), 3.78 (1H, m), 3.65 (1H, m), 2.75 (1H, m), 2.59 (2H, t), 2.11 (3H, m), 1.73 (1H, m), 1.27 (3H, t)

Step B: 4-[2,6-difluoro-4-[2-(tetrahydrofuran-3-ylmethoxy)-3-pyridyl]phenoxy]butanoic acid Ethyl 4-[2,6-difluoro-4-[2-(tetrahydrofuran-3-ylmethoxy)-3-pyridyl]phenoxy]butanoate (0.15 g, 0.36 mmol) obtained in Step A was used to react in the same manner as in Step B of Example 1 to obtain the title compound (0.11 g, 79%).

$^1$H-NMR (CDCl$_3$) δ 8.14 (1H, m), 7.58 (1H, m), 7.11 (2H, m), 6.99 (1H, m), 4.38 (1H, m), 4.26 (3H, m), 3.89 (2H, m), 3.78 (1H, m), 3.64 (1H, m), 2.74 (1H, m), 2.67 (2H, t), 2.12 (3H, m), 1.74 (1H, m)

Example 223

4-[2,6-difluoro-4-[2-(tetrahydrofuran-2-ylmethoxy)-3-pyridyl]phenoxy]butanoic acid

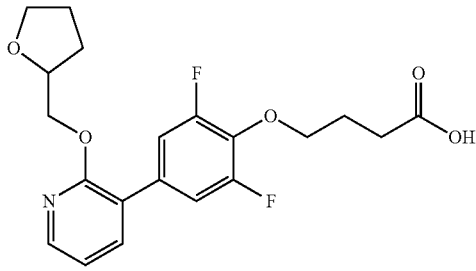 [SMILES: O=C(O)CCCOc1c(F)cc(-c2cccnc2OCC2CCCO2)cc1F]

Step A: ethyl 4-[2,6-difluoro-4-[2-(tetrahydrofuran-2-ylmethoxy)-3-pyridyl]phenoxy]butanoate 3-Iodo-2-(tetrahydrofuran-2-ylmethoxy)pyridine (0.12 g, 0.4 mmol) obtained in Preparation Example 212 and 4-[2,6-difluoro-4-(4,4,5,5-tetramethyl-1,3,2-dioxaborolan-2-yl)phenoxy]butyric acid ethyl ester (0.18 g, 0.49 mmol) obtained in Preparation Example 2 were used to react in the same manner as in Step A of Example 28 to obtain the title compound (0.13 g, 77%).

$^1$H-NMR (CDCl$_3$) δ 8.31 (1H, m), 7.58 (1H, m), 7.20 (2H, m), 6.96 (1H, m), 4.40 (2H, m), 4.29 (1H, m), 4.21 (2H, t), 4.16 (2H, q), 3.89 (1H, m), 3.79 (1H, m), 2.59 (2H, t), 2.10 (2H, m), 2.01 (1H, m), 1.90 (2H, m), 1.77 (1H, m), 1.27 (3H, t)

Step B: 4-[2,6-difluoro-4-[2-(tetrahydrofuran-2-ylmethoxy)-3-pyridyl]phenoxy]butanoic acid Ethyl 4-[2,6-difluoro-4-[2-(tetrahydrofuran-2-ylmethoxy)-3-pyridyl]phenoxy]butanoate (0.13 g, 0.31 mmol) obtained in Step A was used to react in the same manner as in Step B of Example 1 to obtain the title compound (0.10 g, 82%).

$^1$H-NMR (CDCl$_3$) δ 8.13 (1H, m), 7.58 (1H, m), 7.18 (2H, m), 6.97 (1H, m), 4.42 (1H, m), 4.36 (1H, m), 4.30 (1H, m), 4.24 (2H, t), 3.88 (1H, m), 3.81 (1H, m), 2.66 (2H, t), 2.11 (2H, m), 2.03 (1H, m), 1.90 (2H, m), 1.77 (1H, m)

Example 224

4-[4-(2-cyclobutylmethoxy-pyridin-3-yl)-2,6-difluoro-phenoxy]-butyric acid

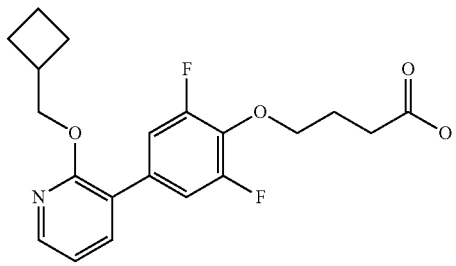 [SMILES: O=C(O)CCCOc1c(F)cc(-c2cccnc2OCC2CCC2)cc1F]

2-Cyclobutylmethoxy-3-iodo-pyridine (0.040 g, 0.14 mmol) obtained in Preparation Example 61 and 4-[2,6-difluoro-4-(4,4,5,5-tetramethyl-1,3,2-dioxaborolan-2-yl)phenoxy]butyric acid ethyl ester (0.051 g, 0.14 mmol) obtained in Preparation Example 2 were used to react in the same manner as in Example 1 to obtain the title compound (0.025 g, 48%).

1H NMR (CDCl$_3$) δ 8.14 (1H, m), 7.58 (1H, m), 7.16 (2H, m), 6.94 (1H, m), 4.32 (2H, t), 4.24 (2H, t), 2.77 (1H, m), 2.69 (2H, t), 2.13 (4H, m), 1.88 (4H, m)

Example 225

4-[4-(2-cyclopropoxy-pyridin-3-yl)-2,6-difluoro-phenoxy]-butyric acid

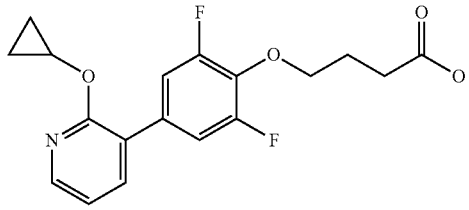 [SMILES: O=C(O)CCCOc1c(F)cc(-c2cccnc2OC2CC2)cc1F]

2-Cyclopropoxy-3-iodo-pyridine (0.040 g, 0.14 mmol) obtained in Preparation Example 62 and 4-[2,6-difluoro-4-(4,4,5,5-tetramethyl-1,3,2-dioxaborolan-2-yl)phenoxy]butyric acid ethyl ester (0.051 g, 0.14 mmol) obtained in Preparation Example 2 were used to react in the same manner as in Example 1 to obtain the title compound (0.025 g, 52%).

1H NMR (CDCl$_3$) δ 8.23 (1H, m), 7.57 (1H, m), 7.07 (2H, m), 6.98 (1H, m), 4.35 (1H, m), 4.24 (2H, t), 2.68 (2H, t), 2.12 (2H, m), 0.82 (4H, m)

Example 226

4-(4-{2-[3-(tert-butyl-dimethyl-silanyloxy)-cyclopentyloxy]-pyridin-3-yl}-2,6-difluoro-phenoxy)-butyric acid

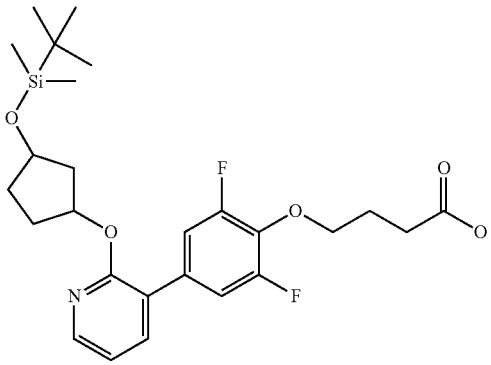 [SMILES: CC(C)(C)[Si](C)(C)OC1CCC(Oc2ncccc2-c2cc(F)c(OCCCC(=O)O)c(F)c2)C1]

Step A: 4-(4-{2-[3-(tert-butyl-dimethyl-silanyloxy)-cyclopentyloxy]-pyridin-3-yl}-2,6-difluoro-phenoxy)-butyric acid ethyl ester 2-[3-(tert-butyl-dimethyl-silanyloxy)-cyclopentyloxy]-3-iodo-pyridine (0.10 g, 0.24 mmol) obtained in Preparation Example 213 and 4-[2,6-difluoro-4-(4,4,5,5-tetramethyl-1,3,2-dioxaborolan-2-yl)phenoxy]butyric acid ethyl ester (0.088 g, 0.24 mmol) obtained in Preparation Example 2 were used to react in the same manner as in Step A of Example 1 to obtain the title compound (0.12 g, 94%).

Step B: 4-(4-{2-[3-(tert-butyl-dimethyl-silanyloxy)-cyclopentyloxy]-pyridin-3-yl}-2,6-difluoro-phenoxy)-butyric acid 4-(4-{2-[3-(tert-butyl-dimethyl-silanyloxy)-cyclopentyloxy]-pyridin-3-yl}-2,6-difluoro-phenoxy)-butyric acid ethyl ester (20 mg, 0.04 mmol) obtained in Step A was used to react in the same manner as in Step B of Example 1 to obtain the title compound (15 mg, 79%).

1H NMR (CDCl$_3$) δ 8.14 (1H, m), 7.54 (1H, m), 7.13 (2H, m), 6.92 (1H, m), 5.59 (1H, m), 4.41 (1H, m), 4.24 (2H, t), 2.69 (2H, t), 2.28 (1H, m), 2.13 (2H, m), 2.03 (3H, m), 1.75 (1H, m), 1.61 (1H, m), 0.91 (9H, s), 0.08 (6H, s)

Example 227

4-{2,6-difluoro-4-[2-(3-hydroxy-cyclopentyloxy)-pyridin-3-yl]-phenoxy}-butyric acid

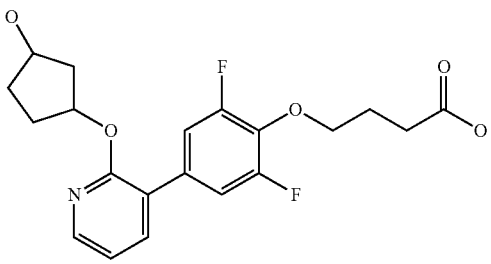 [SMILES: O=C(O)CCCOc1c(F)cc(-c2cccnc2OC2CCC(O)C2)cc1F]

Step A: 4-{2,6-difluoro-4-[2-(3-hydroxy-cyclopentyloxy)-pyridin-3-yl]-phenoxy}-butyric acid ethyl ester 4-(4-{2-[3-(tert-butyl-dimethyl-silanyloxy)-cyclopentyloxy]-pyridin-3-yl}-2,6-difluoro-phenoxy)-butyric acid ethyl ester (0.10 g, 0.19 mmol) obtained in Step A of Example 226 was dissolved in 1 mL of tetrahydrofuran. TBAF (0.28 mL, 0.28 mmol, 1.0 M in THF) was added thereto, and the resultant was agitated at room temperature for 3 hours. Extraction was carried out with water and ethyl acetate, and the resultant was washed with brine. The resultant was dried with MgSO$_4$, concentrated and purified by column chromatography to obtain the title compound (60 mg, 76%).

Step B: 4-{2,6-difluoro-4-[2-(3-hydroxy-cyclopentyloxy)-pyridin-3-yl]-phenoxy}-butyric acid 4-{2,6-Difluoro-4-[2-(3-hydroxy-cyclopentyloxy)-pyridin-3-yl]-phenoxy}-butyric acid ethyl ester (55 mg, 0.13 mmol) obtained in Step A was used to react in the same manner as in Step B of Example 1 to obtain the title compound (45 mg, 88%).

1H NMR (CDCl$_3$) δ 8.15 (1H, m), 7.55 (1H, m), 7.11 (2H, m), 6.94 (1H, m), 5.64 (1H, m), 4.50 (1H, m), 4.25 (2H, t), 2.68 (2H, t), 2.28 (1H, m), 2.13 (5H, m), 1.83 (1H, m), 1.66 (1H, m)

Example 228

4-[4-(2-cyclohexyloxy-pyridin-3-yl)-2,6-difluoro-phenoxy]-butyric acid

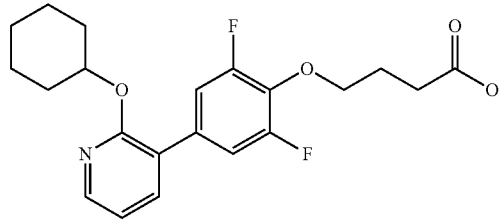 [SMILES: O=C(O)CCCOc1c(F)cc(-c2cccnc2OC2CCCCC2)cc1F]

Cyclohexanol (45 mg, 0.45 mmol) and 4-[2,6-difluoro-4-(2-fluoro-3-pyridyl)phenoxy]butyric acid (70 mg, 0.22 mmol) obtained in Preparation Example 56 were used to react in the same manner as in Preparation Example 37 to obtain the title compound (40 mg, 45%).

1H NMR (CDCl$_3$) δ 8.13 (1H, m), 7.56 (1H, m), 7.18 (2H, m), 6.92 (1H, m), 5.18 (1H, m), 4.24 (2H, t), 2.69 (2H, t), 2.13 (2H, m), 1.96 (2H, m), 1.70 (2H, m), 1.58 (3H, m), 1.45 (2H, m), 1.35 (1H, m)

Example 229

4-[4-(2-cyclopentylmethoxy-pyridin-3-yl)-2,6-difluoro-phenoxy]-butyric acid

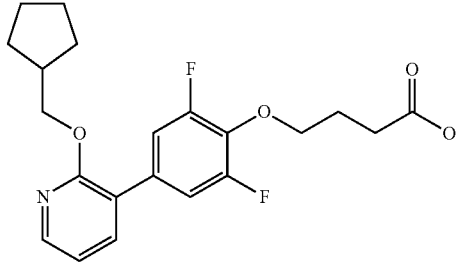 [SMILES: O=C(O)CCCOc1c(F)cc(-c2cccnc2OCC2CCCC2)cc1F]

Cyclopentyl-methanol (45 mg, 0.45 mmol) and 4-[2,6-difluoro-4-(2-fluoro-3-pyridyl)phenoxy]butyric acid (70 mg, 0.22 mmol) obtained in Preparation Example 56 were used to react in the same manner as in Preparation Example 37 to obtain the title compound (55 mg, 62%).

1H NMR (CDCl₃) δ 8.14 (1H, m), 7.57 (1H, m), 7.18 (2H, m), 6.95 (1H, m), 4.24 (4H, m), 2.69 (2H, t), 2.37 (1H, m), 2.13 (2H, m), 1.80 (2H, m), 1.62 (4H, m), 1.36 (2H, m)

Example 230

4-[2,6-difluoro-4-(2-isobutoxy-pyridin-3-yl)-phenoxy]-butyric acid

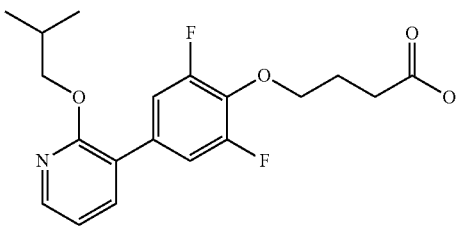 [SMILES: CC(C)COc1ncccc1-c1cc(F)c(OCCCC(=O)O)c(F)c1]

2-Methyl-propan-1-ol (33 mg, 0.45 mmol) and 4-[2,6-difluoro-4-(2-fluoro-3-pyridyl)phenoxy]butyric acid (70 mg, 0.22 mmol) obtained in Preparation Example 56 were used to react in the same manner as in Preparation Example 37 to obtain the title compound (50 mg, 61%).

1H NMR (CDCl₃) δ 8.14 (1H, m), 7.58 (1H, m), 7.17 (2H, m), 6.95 (1H, m), 4.25 (2H, t), 4.13 (2H, d), 2.69 (2H, t), 2.13 (3H, m), 1.00 (6H, d)

Example 231

4-{4-[2-(2,2-dimethy-propoxy)-pyridin-3-yl]-2,6-difluoro-phenoxy}-butyric acid

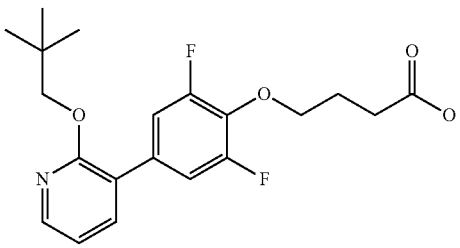 [SMILES: CC(C)(C)COc1ncccc1-c1cc(F)c(OCCCC(=O)O)c(F)c1]

2,2-Dimethyl-propan-1-ol (40 mg, 0.45 mmol) and 4-[2,6-difluoro-4-(2-fluoro-3-pyridyl)phenoxy]butyric acid (70 mg, 0.22 mmol) obtained in Preparation Example 56 were used to react in the same manner as in Preparation Example 37 to obtain the title compound (40 mg, 47%).

1H NMR (CDCl₃) δ 8.15 (1H, m), 7.58 (1H, m), 7.18 (2H, m), 6.95 (1H, m), 4.25 (2H, t), 4.02 (2H, s), 2.69 (2H, t), 2.13 (2H, m), 0.98 (9H, s)

Example 232

5-[4-(2-cyclopentyloxy-pyridin-3-yl)-2,6-difluoro-phenoxy]-pentanoic acid

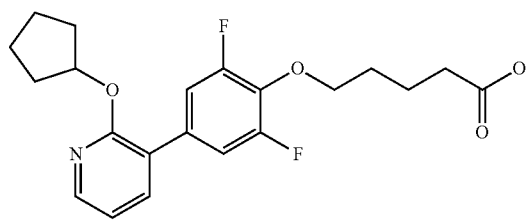 [SMILES: O=C(O)CCCCOc1c(F)cc(-c2cccnc2OC2CCCC2)cc1F]

Step A: 5-[4-(2-cyclopentyloxy-pyridin-3-yl)-2,6-difluoro-phenoxy]-pentanoic acid ethyl ester 5-Bromo-pentanoic acid ethyl ester (43 mg, 0.21 mmol) and 4-(2-cyclopentyloxy-pyridin-3-yl)-2,6-difluoro-phenol (50 mg, 0.17 mmol) obtained in Preparation Example 55 were used to react in the same manner as in Step C of Preparation Example 2 to obtain the title compound (50 mg, 69%).

Step B: 5-[4-(2-cyclopentyloxy-pyridin-3-yl)-2,6-difluoro-phenoxy]-pentanoic acid 5-[4-(2-Cyclopentyloxy-pyridin-3-yl)-2,6-difluoro-phenoxy]-pentanoic acid ethyl ester (45 mg, 0.11 mmol) obtained in Step A was used to react in the same manner as in Step B of Example 1 to obtain the title compound (36 mg, 86%).

1H NMR (CDCl₃) δ 8.15 (1H, m), 7.56 (1H, m), 7.15 (2H, m), 6.92 (1H, m), 5.51 (1H, m), 4.19 (2H, t), 2.47 (2H, t), 2.00-1.70 (10H, m), 1.64 (2H, m)

Example 233

5-[4-(2-cyclobutylsulfanyl-3-pyridyl)-2,6-difluoro-phenoxy]pentanoic acid

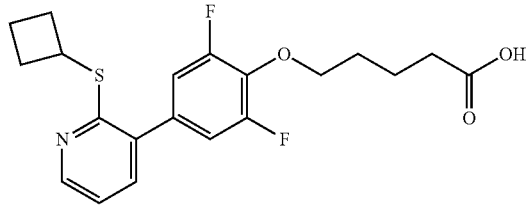 [SMILES: O=C(O)CCCCOc1c(F)cc(-c2cccnc2SC2CCC2)cc1F]

Step A: ethyl 5-[4-(2-cyclobutylsulfanyl-3-pyridyl)-2,6-difluoro-phenoxy]pentanoate 2-Cyclobutylsulfanyl-3-iodo-pyridine (0.064 g, 0.22 mmol) obtained in Preparation Example 44 and ethyl 5-[2,6-difluoro-4-(4,4,5,5-tetramethyl-1,3,2-dioxaborolan-2-yl)phenoxy]pentanoate (0.095 g, 0.247 mmol) obtained in Preparation Example 225 were used to react in the same manner as in Step A of Example 28 to obtain the title compound (0.07 g, 75%).

¹H-NMR (CDCl₃) δ 8.40 (1H, m), 7.32 (1H, m), 7.02 (1H, m), 6.98 (2H, m), 4.42 (1H, m), 4.21 (2H, t), 4.15 (2H, q), 2.51 (2H, m), 2.41 (2H, t), 2.04 (4H, m), 1.86 (4H, m), 1.27 (3H, t)

Step B: 5-[4-(2-cyclobutylsulfanyl-3-pyridyl)-2,6-difluoro-phenoxy]pentanoic acid Ethyl 5-[4-(2-cyclobutylsulfanyl-3-pyridyl)-2,6-difluoro-phenoxy]pentanoate (0.07 g, 0.16 mmol) obtained in Step A was used to react in the same manner as in Step B of Example 1 to obtain the title compound (0.065 g, 99%).
¹H-NMR (CDCl₃) δ 8.41 (1H, m), 7.31 (1H, m), 7.03 (1H, m), 6.97 (2H, m), 4.43 (1H, m), 4.21 (2H, t), 2.52 (4H, m), 2.10 (4H, m), 1.90 (4H, m)

Example 234

5-[4-(2-cyclopentylsulfanyl-3-pyridyl)-2,6-difluoro-phenoxy]pentanoic acid

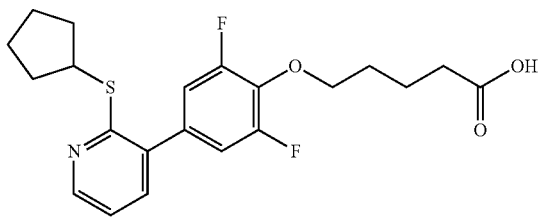 [SMILES: O=C(O)CCCCOc1c(F)cc(-c2cccnc2SC2CCCC2)cc1F]

Step A: ethyl 5-[4-(2-cyclopentylsulfanyl-3-pyridyl)-2,6-difluoro-phenoxy]pentanoate 2-Cyclopentylsulfanyl-3-iodo-pyridine (0.067 g, 0.22 mmol) obtained in Preparation Example 39 and ethyl 5-[2,6-difluoro-4-(4,4,5,5-tetramethyl-1,3,2-dioxaborolan-2-yl)phenoxy]pentanoate (0.095 g, 0.25 mmol) obtained in Preparation Example 225 were used to react in the same manner as in Step A of Example 28 to obtain the title compound (0.057 g, 59%).
¹H-NMR (CDCl₃) δ 8.43 (1H, m), 7.32 (1H, m), 7.02 (1H, m), 6.98 (2H, m), 4.20 (2H, t), 4.16 (2H, q), 4.11 (1H, m), 2.40 (2H, t), 2.20 (2H, m), 1.86 (4H, m), 1.73 (2H, m), 1.62 (4H, m), 1.27 (3H, t)

Step B: 5-[4-(2-cyclopentylsulfanyl-3-pyridyl)-2,6-difluoro-phenoxy]pentanoic acid Ethyl 5-[4-(2-cyclopentylsulfanyl-3-pyridyl)-2,6-difluoro-phenoxy]pentanoate (0.057 g, 0.13 mmol) obtained in Step A was used to react in the same manner as in Step B of Example 1 to obtain the title compound (0.051 g, 97%).
¹H-NMR (CDCl₃) δ 8.43 (1H, m), 7.31 (1H, m), 7.03 (1H, m), 6.97 (2H, m), 4.21 (2H, t), 4.10 (2H, t), 2.48 (2H, t), 2.20 (2H, m), 1.89 (4H, m), 1.72 (2H, m), 1.60 (4H, m)

Example 235

5-[2,6-difluoro-4-(2-isopropylsulfanyl-3-pyridyl)phenoxy]pentanoic acid

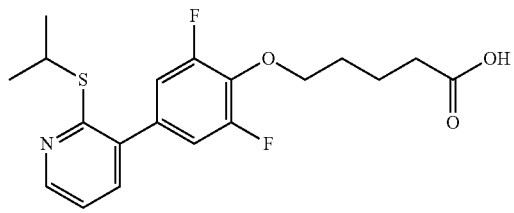 [SMILES: CC(C)Sc1ncccc1-c1cc(F)c(OCCCCC(=O)O)c(F)c1]

Step A: ethyl 5-[2,6-difluoro-4-(2-isopropylsulfanyl-3-pyridyl)phenoxy]pentanoate 3-Iodo-2-isopropylsulfanyl-pyridine (0.062 g, 0.22 mmol) obtained in Preparation Example 226 and ethyl 5-[2,6-difluoro-4-(4,4,5,5-tetramethyl-1,3,2-dioxaborolan-2-yl)phenoxy]pentanoate (0.095 g, 0.25 mmol) obtained in Preparation Example 225 were used to react in the same manner as in Step A of Example 28 to obtain the title compound (0.063 g, 70%).
¹H-NMR (CDCl₃) δ 8.44 (1H, m), 7.33 (1H, m), 7.03 (1H, m), 6.97 (2H, m), 4.20 (2H, t), 4.15 (2H, q), 4.07 (1H, m), 2.41 (2H, t), 1.87 (4H, m), 1.37 (6H, d), 1.27 (3H, t)

Step B: 5-[2,6-difluoro-4-(2-isopropylsulfanyl-3-pyridyl)phenoxy]pentanoic acid

Ethyl 5-[2,6-difluoro-4-(2-isopropylsulfanyl-3-pyridyl)phenoxy]pentanoate (0.063 g, 0.155 mmol) obtained in Step A was used to react in the same manner as in Step B of Example 1 to obtain the title compound (0.058 g, 98%).
¹H-NMR (CDCl₃) δ 8.44 (1H, m), 7.34 (1H, m), 7.02 (1H, m), 6.96 (2H, m), 4.21 (2H, t), 4.06 (1H, m), 2.48 (2H, t), 1.89 (4H, m), 1.36 (6H, d)

Example 236

5-[2,6-difluoro-4-(2-propylsulfanyl-3-pyridyl)phenoxy]pentanoic acid

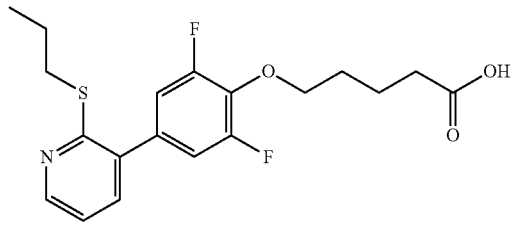 [SMILES: CCCSc1ncccc1-c1cc(F)c(OCCCCC(=O)O)c(F)c1]

Step A: ethyl 5-[2,6-difluoro-4-(2-propylsulfanyl-3-pyridyl)phenoxy]pentanoate

3-Iodo-2-propylsulfanyl-pyridine (0.062 g, 0.22 mmol) obtained in Preparation Example 203 and ethyl 5-[2,6-difluoro-4-(4,4,5,5-tetramethyl-1,3,2-dioxaborolan-2-yl)phenoxy]pentanoate (0.095 g, 0.25 mmol) obtained in Preparation Example 225 were used to react in the same manner as in Step A of Example 28 to obtain the title compound (0.04 g, 44%).

¹H-NMR (CDCl₃) (8.43 (1H, m), 7.33 (1H, m), 7.03 (1H, m), 6.99 (2H, m), 4.20 (2H, t), 4.14 (2H, q), 3.15 (2H, t), 2.39 (2H, t), 1.86 (4H, m), 1.69 (2H, m), 1.27 (3H, t), 1.02 (3H, t)

Step B: 5-[2,6-difluoro-4-(2-propylsulfanyl-3-pyridyl)phenoxy]pentanoic acid

Ethyl 5-[2,6-difluoro-4-(2-propylsulfanyl-3-pyridyl)phenoxy]pentanoate (0.04 g, 0.1 mmol) obtained in Step A was used to react in the same manner as in Step B of Example 1 to obtain the title compound (0.022 g, 58%).

¹H-NMR (CDCl₃) δ 8.43 (1H, m), 7.34 (1H, m), 7.03 (1H, m), 6.99 (2H, m), 4.2 (2H, t), 3.14 (2H, t), 2.49 (2H, t), 1.89 (4H, m), 1.67 (2H, m), 1.02 (3H, t)

Example 237

5-[2,6-difluoro-4-(6-isopropylsulfanyl-2-pyridyl)phenoxy]pentanoic acid

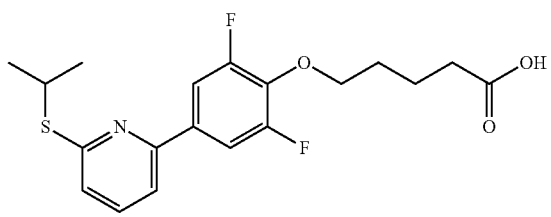 [SMILES: CC(C)Sc1cccc(-c2cc(F)c(OCCCCC(=O)O)c(F)c2)n1]

Step A: ethyl 5-[2,6-difluoro-4-(6-isopropylsulfanyl-2-pyridyl)phenoxy]pentanoate 2-Chloro-6-isopropylsulfanyl-pyridine (0.05 g, 0.26 mmol) obtained in Preparation Example 125 and ethyl 5-[2,6-difluoro-4-(4,4,5,5-tetramethyl-1,3,2-dioxaborolan-2-yl)phenoxy]pentanoate (0.098 g, 0.25 mmol) obtained in Preparation Example 225 were used to react in the same manner as in Step A of Example 29 to obtain the title compound (0.068 g, 65%).

¹H-NMR (CDCl₃) δ 7.58 (2H, m), 7.52 (1H, t), 7.31 (1H, d), 7.08 (1H, d), 4.20 (2H, t), 4.14 (3H, m), 2.40 (2H, t), 1.85 (4H, m), 1.47 (6H, d), 1.26 (3H, t)

Step B: 5-[2,6-difluoro-4-(6-isopropylsulfanyl-2-pyridyl)phenoxy]pentanoic acid

Ethyl 5-[2,6-difluoro-4-(6-isopropylsulfanyl-2-pyridyl)phenoxy]pentanoate (0.068 g, 0.16 mmol) obtained in Step A was used to react in the same manner as in Step B of Example 1 to obtain the title compound (0.046 g, 73%).

¹H-NMR (CDCl₃) δ 7.59 (2H, m), 7.52 (1H, t), 7.31 (1H, d), 7.08 (1H, d), 4.22 (2H, t), 4.14 (1H, m), 2.47 (2H, t), 1.87 (4H, m), 1.48 (6H, d)

Example 238

5-[2,6-difluoro-4-(6-isopropoxy-2-pyridyl)phenoxy]pentanoic acid

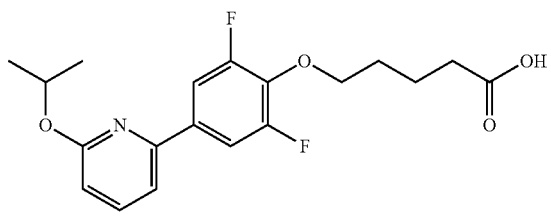 [SMILES: CC(C)Oc1cccc(-c2cc(F)c(OCCCCC(=O)O)c(F)c2)n1]

Step A: ethyl 5-[2,6-difluoro-4-(6-isopropoxy-2-pyridyl)phenoxy]pentanoate

2-Chloro-6-isopropoxy-pyridine (0.039 g, 0.22 mmol) obtained in Preparation Example 21 and ethyl 5-[2,6-difluoro-4-(4,4,5,5-tetramethyl-1,3,2-dioxaborolan-2-yl)phenoxy]pentanoate (0.098 g, 0.25 mmol) obtained in Preparation Example 225 were used to react in the same manner as in Step A of Example 29 to obtain the title compound (0.079 g, 89%).

¹H-NMR (CDCl₃) δ 7.57 (3H, m), 7.19 (1H, d), 6.63 (1H, d), 5.45 (1H, m), 4.19 (2H, t), 4.14 (2H, q), 2.40 (2H, t), 1.85 (4H, m), 1.40 (6H, d), 1.27 (3H, t)

Step B: 5-[2,6-difluoro-4-(6-isopropoxy-2-pyridyl)phenoxy]pentanoic acid

Ethyl 5-[2,6-difluoro-4-(6-isopropoxy-2-pyridyl)phenoxy]pentanoate (0.079 g, 0.2 mmol) obtained in Step A was used to react in the same manner as in Step B of Example 1 to obtain the title compound (0.070 g, 96%).

¹H-NMR (CDCl₃) δ 7.58 (3H, m), 7.19 (1H, d), 6.63 (1H, d), 5.44 (1H, m), 4.20 (2H, t), 2.47 (2H, t), 1.87 (4H, m), 1.40 (6H, d)

Example 239

5-[4-[2-(cyclopropylmethoxy)-3-pyridyl]-2,6-difluoro-phenoxy]pentanoic acid

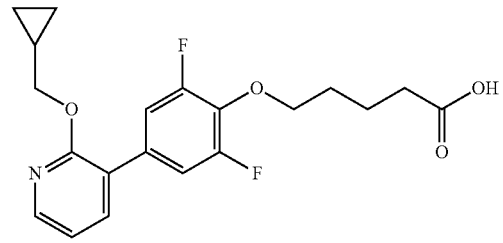 [SMILES: O=C(O)CCCCOc1c(F)cc(-c2cccnc2OCC2CC2)cc1F]

Step A: ethyl 5-[4-[2-(cyclopropylmethoxy)-3-pyridyl]-2,6-difluoro-phenoxy]pentanoate 2-Cyclopropylmethoxy-3-iodo-pyridine (0.062 g, 0.22 mmol) obtained in Preparation Example 40 and ethyl 5-[2,6-difluoro-4-(4,4,5,5-tetramethyl-1,3,2-dioxaborolan-2-yl)

phenoxy]pentanoate (0.095 g, 0.25 mmol) obtained in Preparation Example 225 were used to react in the same manner as in Step A of Example 28 to obtain the title compound (0.072 g, 79%).

¹H-NMR (CDCl₃) δ 8.12 (1H, m), 7.58 (1H, m), 7.22 (2H, m), 6.95 (1H, m), 4.22 (2H, d), 4.19 (2H, t), 4.14 (2H, q), 2.40 (2H, t), 1.85 (4H, m), 1.26 (4H, m), 0.60 (2H, m), 0.35 (2H, m)

Step B: 5-[4-[2-(cyclopropylmethoxy)-3-pyridyl]-2,6-difluoro-phenoxy]pentanoic acid Ethyl 5-[4-[2-(cyclopropylmethoxy)-3-pyridyl]-2,6-difluoro-phenoxy]pentanoate (0.072 g, 0.18 mmol) obtained in Step A was used to react in the same manner as in Step B of Example 1 to obtain the title compound (0.067 g, 99%).

¹H-NMR (CDCl₃) δ 8.13 (1H, m), 7.58 (1H, m), 7.21 (2H, m), 6.94 (1H, m), 4.21 (4H, m), 2.48 (2H, t), 1.88 (4H, m), 1.30 (1H, m), 0.60 (2H, m), 0.34 (2H, m)

Example 240

5-[2,6-difluoro-4-(2-tetrahydrofuran-3-yloxy-3-pyridyl)phenoxy]pentanoic acid

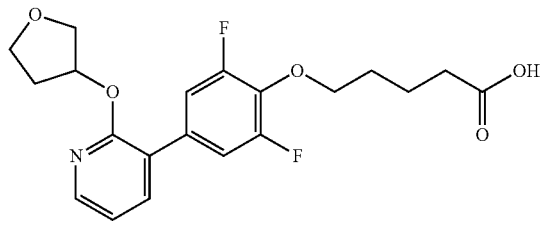 [SMILES: O=C(O)CCCCOc1c(F)cc(-c2cccnc2OC2CCOC2)cc1F]

Step A: ethyl 5-[2,6-difluoro-4-(2-tetrahydrofuran-3-yloxy-3-pyridyl)phenoxy]pentanoate 3-Iodo-2-(tetrahydrofuran-3-yloxy)-pyridine (0.066 g, 0.22 mmol) obtained in Preparation Example 59 and ethyl 5-[2,6-difluoro-4-(4,4,5,5-tetramethyl-1,3,2-dioxaborolan-2-yl)phenoxy]pentanoate (0.095 g, 0.25 mmol) obtained in Preparation Example 225 were used to react in the same manner as in Step A of Example 28 to obtain the title compound (0.06 g, 63%).

¹H-NMR (CDCl₃) δ 8.12 (1H, m), 7.58 (1H, m), 7.14 (2H, m), 6.97 (1H, m), 5.63 (1H, m), 4.19 (2H, t), 4.14 (2H, q), 4.10 (1H, m), 3.93 (3H, m), 2.40 (2H, t), 2.25 (1H, m), 2.15 (1H, m), 1.85 (4H, m), 1.26 (3H, t)

Step B: 5-[2,6-difluoro-4-(2-tetrahydrofuran-3-yloxy-3-pyridyl)phenoxy]pentanoic acid Ethyl 5-[2,6-difluoro-4-(2-tetrahydrofuran-3-yloxy-3-pyridyl)phenoxy]pentanoate (0.06 g, 0.14 mmol) obtained in Step A was used to react in the same manner as in Step B of Example 1 to obtain the title compound (0.055 g, 99%).

¹H-NMR (CDCl₃) δ 8.12 (1H, m), 7.58 (1H, m), 7.12 (2H, m), 6.98 (1H, m), 5.65 (1H, m), 4.21 (2H, t), 4.07 (1H, m), 3.93 (3H, m), 2.46 (2H, t), 2.25 (1H, m), 2.15 (1H, m), 1.86 (4H, m)

Example 241

5-[2,6-difluoro-4-(2-tetrahydropyran-4-yloxy-3-pyridyl)phenoxy]pentanoic acid

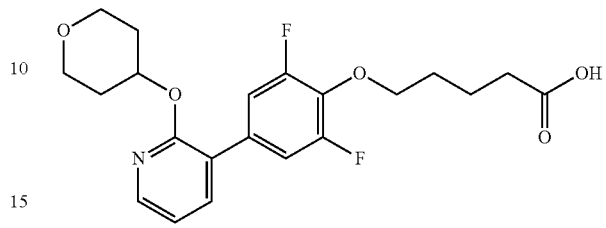

Step A: ethyl 5-[2,6-difluoro-4-(2-tetrahydropyran-4-yloxy-3-pyridyl)phenoxy]pentanoate 3-Iodo-2-(tetrahydropyran-4-yloxy)-pyridine (0.069 g, 0.22 mmol) obtained in Preparation Example 58 and ethyl 5-[2,6-difluoro-4-(4,4,5,5-tetramethyl-1,3,2-dioxaborolan-2-yl)phenoxy]pentanoate (0.095 g, 0.25 mmol) obtained in Preparation Example 225 were used to react in the same manner as in Step A of Example 28 to obtain the title compound (0.071 g, 72%).

¹H-NMR (CDCl₃) δ 8.12 (1H, m), 7.58 (1H, m), 7.15 (2H, m), 6.95 (1H, m), 5.37 (1H, m), 4.20 (2H, t), 4.14 (2H, q), 3.91 (2H, m), 3.63 (2H, m), 2.41 (2H, t), 2.06 (2H, m), 1.85 (6H, m), 1.27 (3H, t)

Step B: 5-[2,6-difluoro-4-(2-tetrahydropyran-4-yloxy-3-pyridyl)phenoxy]pentanoic acid Ethyl 5-[2,6-difluoro-4-(2-tetrahydropyran-4-yloxy-3-pyridyl)phenoxy]pentanoate (0.071 g, 0.16 mmol) obtained in Step A was used to react in the same manner as in Step B of Example 1 to obtain the title compound (0.054 g, 83%).

¹H-NMR (CDCl₃) δ 8.12 (1H, m), 7.58 (1H, m), 7.15 (2H, m), 6.95 (1H, m), 5.38 (1H, m), 4.21 (2H, t), 3.90 (2H, m), 3.64 (2H, m), 2.47 (2H, t), 2.06 (2H, m), 1.88 (4H, m), 1.80 (2H, m)

Example 242

4-[2,6-difluoro-4-(2-isopropoxy-pyridin-3-yl)-phenylsulfanyl]-pentanoic acid

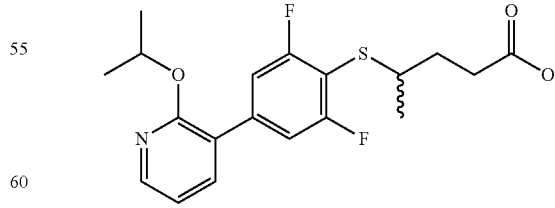

4-[2,6-Difluoro-4-(2-isopropoxy-pyridin-3-yl)-phenylsulfanyl]-pentanoic acid ethyl ester (0.015 g, 0.04 mmol) obtained in Preparation Example 219 was reacted in the same manner as in Step B of Example 1 to obtain the title compound (0.008 g, 57%).

¹H-NMR (CDCl₃) δ 8.16 (1H, m), 7.60 (1H, m), 7.21 (2H, d), 6.93 (1H, m), 5.40 (1H, m), 3.31 (1H, m), 2.62 (2H, m), 1.86 (2H, m), 1.36 (6H, d), 1.31 (3H, d).

Example 243

4-[4-(2-cyclopentylsulfanyl-pyridin-3-yl)-phenylsulfanyl]-pentanoic acid

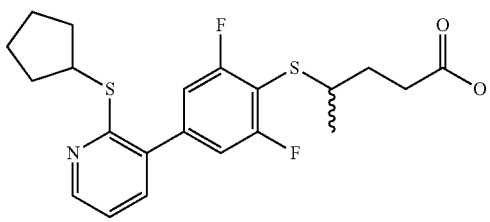 [SMILES: CC(CCC(=O)O)Sc1c(F)cc(-c2cccnc2SC2CCCC2)cc1F]

4-[4-(2-Cyclopentylsulfanyl-pyridin-3-yl)-phenylsulfanyl]-pentanoic acid ethyl ester (0.004 g, 0.01 mmol) obtained in Preparation Example 217 was reacted in the same manner as in Step B of Example 1 to obtain the title compound (0.002 g, 54%).

¹H-NMR (CDCl₃) δ 8.41 (1H, m), 7.42 (2H, d), 7.35 (3H, m), 7.02 (1H, m), 4.06 (1H, m), 3.31 (1H, m), 2.58 (2H, m), 2.17 (2H, m), 1.93 (2H, m), 1.69-1.51 (6H, m), 1.36 (3H, d).

Example 244

4-{2-fluoro-4-[2-(tetrahydropyran-4-yloxy)-pyridin-3-yl]-phenylsulfanyl}-butyric acid

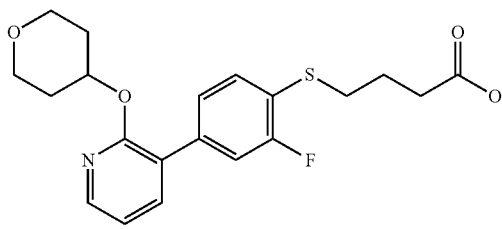 [SMILES: O=C(O)CCCSc1ccc(-c2cccnc2OC2CCOCC2)cc1F]

4-[2-Fluoro-4-(4,4,5,5-tetramethyl-[1,3,2]dioxaborolan-2-yl)-phenylsulfanyl]-butyric acid ethyl ester (0.05 g, 0.14 mmol) obtained in Preparation Example 180 and 3-iodo-2-(tetrahydropyran-4-yloxy)-pyridine (0.06 g, 0.2 mmol) obtained in Preparation Example 58 were used to react sequentially in the same manner as in Steps A and B of Example 1 to obtain the title compound (0.03 g, 66%).

¹H-NMR (CDCl₃) δ 8.13 (1H, m), 7.62 (1H, m), 7.42 (1H, m), 7.32 (2H, m), 6.96 (1H, m), 5.37 (1H, m), 3.88 (2H, m), 3.63 (2H, m), 3.02 (2H, t), 2.56 (2H, t), 2.08 (2H, m), 1.98 (2H, m), 1.80 (2H, m)

Example 245

4-{2-fluoro-4-[2-(tetrahydrofuran-3-yloxy)-pyridin-3-yl]-phenylsulfanyl}-butyric acid

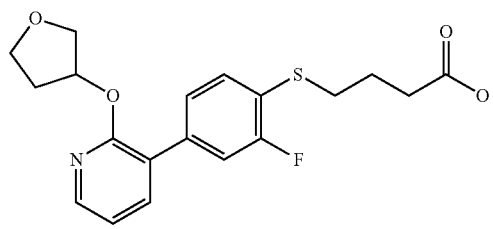 [SMILES: O=C(O)CCCSc1ccc(-c2cccnc2OC2CCOC2)cc1F]

4-[2-Fluoro-4-(4,4,5,5-tetramethyl-[1,3,2]dioxaborolan-2-yl)-phenylsulfanyl]-butyric acid ethyl ester (0.05 g, 0.14 mmol) obtained in Preparation Example 180 and 3-iodo-2-(tetrahydrofuran-3-yloxy)-pyridine (0.06 g, 0.2 mmol) obtained in Preparation Example 59 were used to react sequentially in the same manner as in Steps A and B of Example 1 to obtain the title compound (0.028 g, 54%).

¹H-NMR (CDCl₃) δ 8.13 (1H, m), 7.62 (1H, m), 7.42 (1H, m), 7.29 (2H, m), 6.98 (1H, m), 5.66 (1H, m), 4.02 (2H, m), 3.93 (2H, m), 3.03 (2H, t), 2.54 (2H, t), 2.26 (1H, m), 2.14 (1H, m), 1.95 (2H, m)

Example 246

4-[4-(2-cyclobutylmethoxy-pyridin-3-yl)-2-fluoro-phenylsulfanyl]-butyric acid

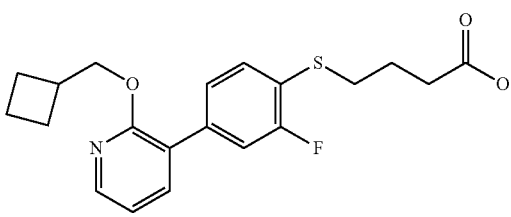 [SMILES: O=C(O)CCCSc1ccc(-c2cccnc2OCC2CCC2)cc1F]

4-[2-Fluoro-4-(4,4,5,5-tetramethyl-[1,3,2]dioxaborolan-2-yl)-phenylsulfanyl]-butyric acid ethyl ester (0.05 g, 0.14 mmol) obtained in Preparation Example 180 and 2-cyclobutylmethoxy-3-iodo-pyridine (0.06 g, 0.2 mmol) obtained in Preparation Example 61 were used to react sequentially in the same manner as in Steps A and B of Example 1 to obtain the title compound (0.03 g, 60%).

¹H-NMR (CDCl₃) δ 8.14 (1H, m), 7.62 (1H, m), 7.42-7.29 (3H, m), 6.96 (1H, m), 4.32 (2H, d), 3.01 (2H, t), 2.77 (1H, m), 2.56 (2H, t), 2.09 (2H, m), 2.01-1.83 (6H, m)

Example 247

4-{2,6-difluoro-4-[2-(2,2,2-trifluoro-ethoxy)-pyridin-3-yl]-phenylsulfanyl}-butyric acid

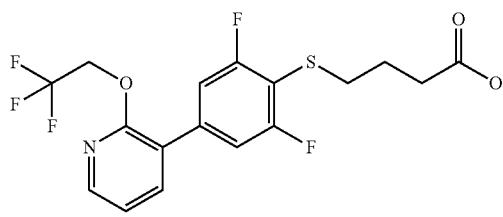 [SMILES: O=C(O)CCCSc1c(F)cc(-c2cccnc2OCC(F)(F)F)cc1F]

4-[2,6-Difluoro-4-(4,4,5,5-tetramethyl-[1,3,2]dioxaborolan-2-yl)-phenylsulfanyl]-butyric acid ethyl ester (0.04 g, 0.1 mmol) obtained in Preparation Example 170 and 3-iodo-2-(2,2,2-trifluoro-ethoxy)-pyridine (0.05 g, 0.15 mmol) obtained in Preparation Example 220 were used to react sequentially in the same manner as in Steps A and B of Example 1 to obtain the title compound (0.019 g, 45%).

$^1$H-NMR (CDCl$_3$) δ 8.17 (1H, m), 7.69 (1H, m), 7.16 (2H, d), 7.09 (1H, m), 4.82 (2H, q), 2.97 (2H, t), 2.56 (2H, t), 1.88 (2H, m)

Example 248

4-[4-(2-cyclobutylmethoxy-pyridin-3-yl)-2,6-difluoro-phenylsulfanyl]-butyric acid

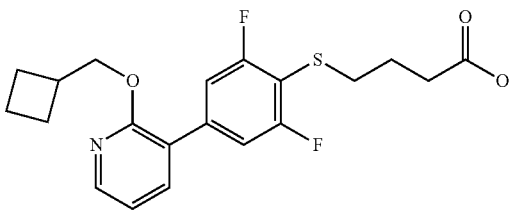 [SMILES: O=C(O)CCCSc1c(F)cc(-c2cccnc2OCC2CCC2)cc1F]

4-[2,6-Difluoro-4-(4,4,5,5-tetramethyl-[1,3,2]dioxaborolan-2-yl)-phenylsulfanyl]-butyric acid ethyl ester (0.04 g, 0.1 mmol) obtained in Preparation Example 170 and 2-cyclobutylmethoxy-3-iodo-pyridine (0.045 g, 0.15 mmol) obtained in Preparation Example 61 were used to react sequentially in the same manner as in Steps A and B of Example 1 to obtain the title compound (0.022 g, 55%).

$^1$H-NMR (CDCl$_3$) δ 8.16 (1H, m), 7.61 (1H, m), 7.20 (2H, d), 6.96 (1H, m), 4.32 (2H, d), 2.95 (2H, t), 2.77 (1H, m), 2.54 (2H, t), 2.09 (2H, m), 2.01-1.83 (6H, m)

Example 249

4-[4-(2-cyclopentylamino-pyridin-3-yl)-2,6-difluoro-phenylsulfanyl]-butyric acid

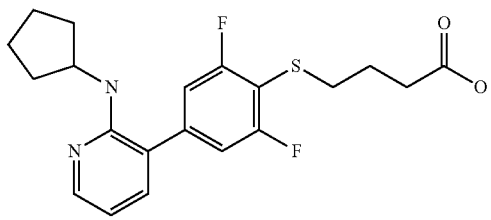 [SMILES: O=C(O)CCCSc1c(F)cc(-c2cccnc2NC2CCCC2)cc1F]

4-[2,6-Difluoro-4-(4,4,5,5-tetramethyl-[1,3,2]dioxaborolan-2-yl)-phenylsulfanyl]-butyric acid ethyl ester (0.04 g, 0.1 mmol) obtained in Preparation Example 170 and N-cyclopentyl-3-iodo-pyridin-2-amine (0.045 g, 0.15 mmol) obtained in Preparation Example 64 were used to react sequentially in the same manner as in Steps A and B of Example 1 to obtain the title compound (0.02 g, 49%).

$^1$H-NMR (CDCl$_3$) δ 8.16 (1H, m), 7.23 (1H, m), 7.01 (2H, d), 6.63 (1H, m), 4.34 (1H, m), 2.99 (2H, t), 2.55 (2H, t), 2.07 (2H, m), 1.92 (2H, m), 1.64 (4H, m), 1.35 (2H, m)

Example 250

4-[2,6-difluoro-4-(2-isopropylamino-pyridin-3-yl)-phenylsulfanyl]-butyric acid

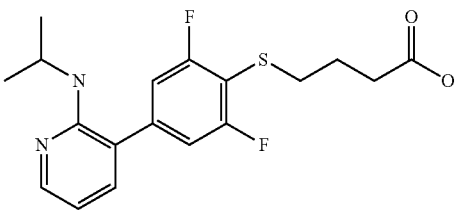

4-[2,6-Difluoro-4-(4,4,5,5-tetramethyl-[1,3,2]dioxaborolan-2-yl)-phenylsulfanyl]-butyric acid ethyl ester (0.04 g, 0.1 mmol) obtained in Preparation Example 170 and 3-iodo-N-isopropyl-pyridin-2-amine (0.04 g, 0.15 mmol) obtained in Preparation Example 66 were used to react sequentially in the same manner as in Steps A and B of Example 1 to obtain the title compound (0.017 g, 44%).

$^1$H-NMR (CDCl$_3$) δ 8.16 (1H, m), 7.23 (1H, m), 7.01 (2H, d), 6.62 (1H, m), 4.26 (1H, m), 3.00 (2H, t), 2.58 (2H, t), 1.92 (2H, m), 1.20 (6H, d)

Example 251

4-{4-[2-(cyclopropylmethyl-amino)-pyridin-3-yl]-2,6-difluoro-phenylsulfanyl}-butyric acid

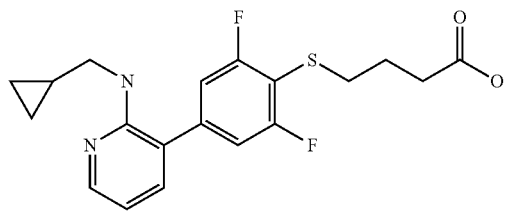 [SMILES: O=C(O)CCCSc1c(F)cc(-c2cccnc2NCC2CC2)cc1F]

4-[2,6-Difluoro-4-(4,4,5,5-tetramethyl-[1,3,2]dioxaborolan-2-yl)-phenylsulfanyl]-butyric acid ethyl ester (0.04 g, 0.1 mmol) obtained in Preparation Example 170 and cyclopropylmethyl-(3-iodo-pyridin-2-yl)-amine (0.043 g, 0.15 mmol) obtained in Preparation Example 235 were used to react sequentially in the same manner as in Steps A and B of Example 1 to obtain the title compound (0.013 g, 31%).

$^1$H-NMR (CDCl$_3$) δ 8.15 (1H, m), 7.25 (1H, m), 7.02 (2H, d), 6.65 (1H, m), 3.26 (2H, d), 3.00 (2H, t), 2.57 (2H, t), 1.90 (2H, m), 1.05 (1H, m), 0.50 (2H, m), 0.21 (2H, m).

Example 252

5-[4-(2-cyclopentyloxy-pyridin-3-yl)-2,6-difluoro-phenylsulfanyl]-pentanoic acid

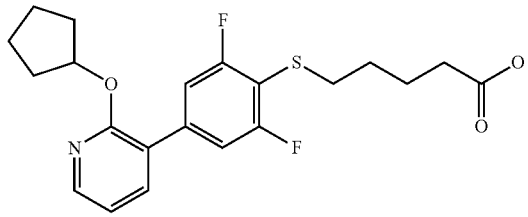 [SMILES: O=C(O)CCCCSc1c(F)cc(-c2cccnc2OC2CCCC2)cc1F]

5-[2,6-Difluoro-4-(4,4,5,5-tetramethyl-[1,3,2]dioxaborolan-2-yl)-phenylsulfanyl]-pentanoic acid ethyl ester (0.055 g, 0.14 mmol) obtained in Preparation Example 222 and 2-cyclopentoxy-3-iodo-pyridine (0.06 g, 0.21 mmol) obtained in Preparation Example 38 were used to react sequentially in the same manner as in Steps A and B of Example 1 to obtain the title compound (0.029 g, 51%).

$^1$H-NMR (CDCl$_3$) δ 8.17 (1H, m), 7.59 (1H, m), 7.16 (2H, d), 6.92 (1H, m), 5.52 (1H, m), 2.92 (2H, t), 2.36 (2H, t), 1.95 (2H, m), 1.76 (6H, m), 1.64 (4H, m)

Example 253

5-[2,6-difluoro-4-(2-isopropoxy-pyridin-3-yl)-phenylsulfanyl]-pentanoic acid

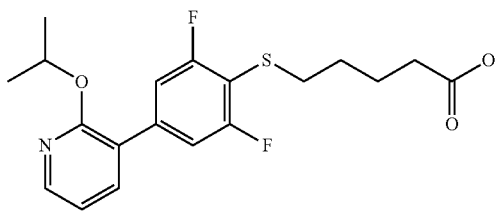 [SMILES: CC(C)Oc1ncccc1-c1cc(F)c(SCCCCC(=O)O)c(F)c1]

5-[2,6-Difluoro-4-(4,4,5,5-tetramethyl-[1,3,2]dioxaborolan-2-yl)-phenylsulfanyl]-pentanoic acid ethyl ester (0.05 g, 0.12 mmol) obtained in Preparation Example 222 and 3-iodo-2-isopropoxy-pyridine (0.05 g, 0.19 mmol) obtained in Preparation Example 37 were used to react sequentially in the same manner as in Steps A and B of Example 1 to obtain the title compound (0.023 g, 48%).

$^1$H-NMR (CDCl$_3$) δ 8.16 (1H, m), 7.59 (1H, m), 7.18 (2H, d), 6.92 (1H, m), 5.40 (1H, m), 2.92 (2H, t), 2.36 (2H, t), 1.79 (2H, m), 1.66 (2H, m), 1.35 (6H, d)

Example 254

5-[4-(2-cyclopentyloxy-pyridin-3-yl)-phenylsulfanyl]-pentanoic acid

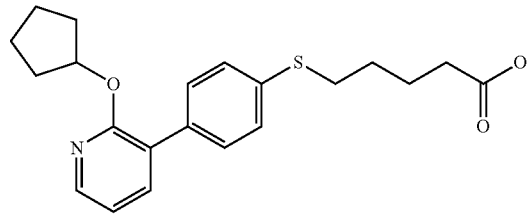 [SMILES: O=C(O)CCCCSc1ccc(-c2cccnc2OC2CCCC2)cc1]

5-[4-(4,4,5,5-Tetramethyl-[1,3,2]dioxaborolan-2-yl)-phenylsulfanyl]-pentanoic acid ethyl ester (0.05 g, 0.14 mmol) obtained in Preparation Example 224 and 2-cyclopentoxy-3-iodo-pyridine (0.06 g, 0.2 mmol) obtained in Preparation Example 38 were used to react sequentially in the same manner as in Steps A and B of Example 1 to obtain the title compound (0.026 g, 51%).

$^1$H-NMR (CDCl$_3$) δ 8.12 (1H, m), 7.56 (1H, m), 7.47 (2H, d), 7.32 (2H, d), 6.90 (1H, m), 5.49 (1H, m), 2.97 (2H, t), 2.37 (2H, t), 1.93 (2H, m), 1.82-1.65 (8H, m), 1.60 (2H, m)

Example 255

5-[4-(2-isopropoxy-pyridin-3-yl)-phenylsulfanyl]-pentanoic acid

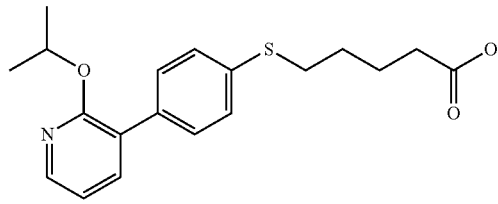 [SMILES: CC(C)Oc1ncccc1-c1ccc(SCCCCC(=O)O)cc1]

5-[4-(4,4,5,5-Tetramethyl-[1,3,2]dioxaborolan-2-yl)-phenylsulfanyl]-pentanoic acid ethyl ester (0.05 g, 0.14 mmol) obtained in Preparation Example 224 and 3-iodo-2-isopropoxy-pyridine (0.054 g, 0.2 mmol) obtained in Preparation Example 37 were used to react sequentially in the same manner as in Steps A and B of Example 1 to obtain the title compound (0.026 g, 55%).

$^1$H-NMR (CDCl$_3$) δ 8.11 (1H, m), 7.58 (1H, m), 7.49 (2H, d), 7.32 (2H, d), 6.90 (1H, m), 5.39 (1H, m), 2.97 (2H, t), 2.39 (2H, t), 1.82-1.69 (4H, m), 1.34 (6H, d)

Example 256

5-[4-(2-cyclopentylsulfanyl-pyridin-3-yl)-2,6-difluoro-phenylsulfanyl]-pentanoic acid

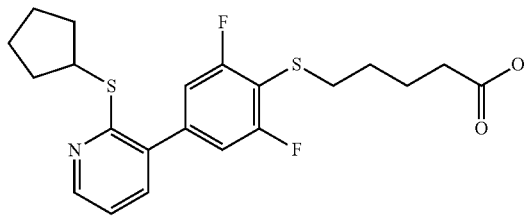

5-[2,6-Difluoro-4-(4,4,5,5-tetramethyl-[1,3,2]dioxaborolan-2-yl)-phenylsulfanyl]-pentanoic acid ethyl ester (0.05 g, 0.12 mmol) obtained in Preparation Example 222 and 2-cyclopentylsulfanyl-3-iodo-pyridine (0.057 g, 0.19 mmol) obtained in Preparation Example 39 were used to react sequentially in the same manner as in Steps A and B of Example 1 to obtain the title compound (0.014 g, 26%).

$^1$H-NMR (CDCl$_3$) δ 8.45 (1H, m), 7.34 (1H, m), 7.03 (3H, m), 4.09 (1H, m), 2.93 (2H, t), 2.37 (2H, t), 2.20 (2H, m), 1.79-1.52 (10H, m)

Example 257

5-[2,6-difluoro-4-(2-propylsulfanyl-pyridin-3-yl)-phenylsulfanyl]-pentanoic acid

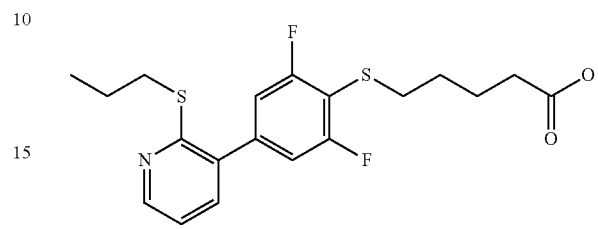

5-[2,6-Difluoro-4-(4,4,5,5-tetramethyl-[1,3,2]dioxaborolan-2-yl)-phenylsulfanyl]-pentanoic acid ethyl ester (0.05 g, 0.12 mmol) obtained in Preparation Example 222 and 3-iodo-2-propylsulfanyl-pyridine (0.052 g, 0.19 mmol) obtained in Preparation Example 203 were used to react sequentially in the same manner as in Steps A and B of Example 1 to obtain the title compound (0.023 g, 46%).

$^1$H-NMR (CDCl$_3$) δ 8.44 (1H, m), 7.35 (1H, m), 7.03 (3H, m), 3.15 (2H, t), 2.93 (2H, t), 2.37 (2H, t), 1.80 (2H, m), 1.65 (4H, m), 1.02 (3H, t)

Example 258

5-[4-(2-cyclopentylsulfanyl-pyridin-3-yl)-phenylsulfanyl]-pentanoic acid

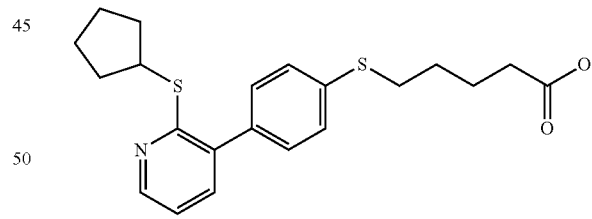

5-[4-(4,4,5,5-Tetramethyl-[1,3,2]dioxaborolan-2-yl)-phenylsulfanyl]-pentanoic acid ethyl ester (0.05 g, 0.14 mmol) obtained in Preparation Example 224 and 2-cyclopentylsulfanyl-3-iodo-pyridine (0.062 g, 0.2 mmol) obtained in Preparation Example 39 were used to react sequentially in the same manner as in Steps A and B of Example 1 to obtain the title compound (0.029 g, 54%).

$^1$H-NMR (CDCl$_3$) δ 8.40 (1H, m), 7.34 (5H, m), 7.01 (1H, m), 4.08 (1H, m), 2.98 (2H, t), 2.39 (2H, t), 2.18 (2H, m), 1.81-1.52 (10H, m)

Example 259

5-[4-(2-cyclobutylsulfanyl-pyridin-3-yl)-phenylsulfanyl]-pentanoic acid

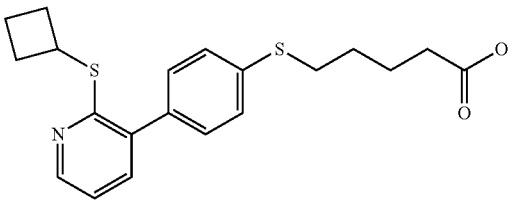 [SMILES: O=C(O)CCCCSc1ccc(-c2cccnc2SC2CCC2)cc1]

5-[4-(4,4,5,5-Tetramethyl-[1,3,2]dioxaborolan-2-yl)-phenylsulfanyl]-pentanoic acid ethyl ester (0.05 g, 0.14 mmol) obtained in Preparation Example 224 and 2-cyclobutylsulfanyl-3-iodo-pyridine (0.06 g, 0.2 mmol) obtained in Preparation Example 44 were used to react sequentially in the same manner as in Steps A and B of Example 1 to obtain the title compound (0.03 g, 58%).

$^1$H-NMR (CDCl$_3$) δ 8.39 (1H, m), 7.35 (5H, m), 7.01 (1H, m), 4.42 (1H, m), 2.98 (2H, t), 2.48 (2H, m), 2.40 (2H, t), 2.02 (4H, m), 1.79 (4H, m)

Example 260

5-[4-(2-cyclobutylmethoxy-pyridin-3-yl)-2,6-difluoro-phenylsulfanyl]-pentanoic acid

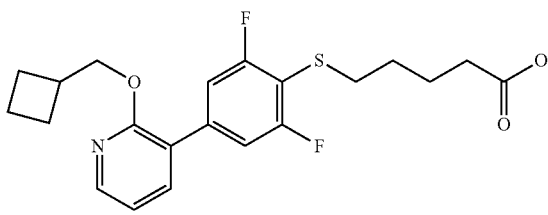 [SMILES: O=C(O)CCCCSc1c(F)cc(-c2cccnc2OCC2CCC2)cc1F]

5-[2,6-Difluoro-4-(4,4,5,5-tetramethyl-[1,3,2]dioxaborolan-2-yl)-phenylsulfanyl]-pentanoic acid ethyl ester (0.05 g, 0.12 mmol) obtained in Preparation Example 222 and 2-cyclobutylmethoxy-3-iodo-pyridine (0.054 g, 0.19 mmol) obtained in Preparation Example 61 were used to react sequentially in the same manner as in Steps A and B of Example 1 to obtain the title compound (0.019 g, 38%).

$^1$H-NMR (CDCl$_3$) δ 8.16 (1H, m), 7.62 (1H, m), 7.20 (2H, d), 6.96 (1H, m), 4.33 (2H, d), 2.92 (2H, t), 2.77 (1H, m), 2.34 (2H, t), 2.09 (2H, m), 1.87 (4H, m), 1.78 (2H, m), 1.64 (2H, m)

Example 261

5-[4-(2-cyclobutoxy-pyridin-3-yl)-2,6-difluoro-phenylsulfanyl]-pentanoic acid

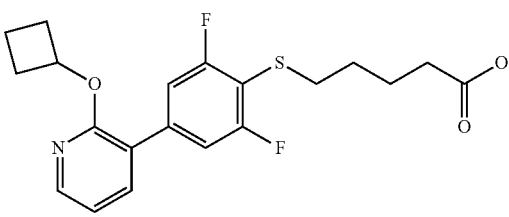 [SMILES: O=C(O)CCCCSc1c(F)cc(-c2cccnc2OC2CCC2)cc1F]

5-[2,6-Difluoro-4-(4,4,5,5-tetramethyl-[1,3,2]dioxaborolan-2-yl)-phenylsulfanyl]-pentanoic acid ethyl ester (0.05 g, 0.12 mmol) obtained in Preparation Example 222 and 2-cyclobutoxy-3-iodo-pyridine (0.052 g, 0.19 mmol) obtained in Preparation Example 200 were used to react sequentially in the same manner as in Steps A and B of Example 1 to obtain the title compound (0.019 g, 38%).

$^1$H-NMR (CDCl$_3$) δ 8.14 (1H, m), 7.60 (1H, m), 7.21 (2H, d), 6.94 (1H, m), 5.27 (1H, m), 2.92 (2H, t), 2.47 (2H, m), 2.36 (2H, t), 2.12 (2H, m), 1.80 (3H, m), 1.65 (3H, m)

Example 262

6-[4-(2-cyclopentyloxy-pyridin-3-yl)-2,6-difluoro-phenoxy]-hexanoic acid

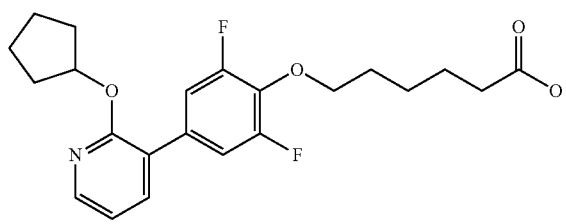 [SMILES: O=C(O)CCCCCOc1c(F)cc(-c2cccnc2OC2CCCC2)cc1F]

6-Bromo-hexanoic acid ethyl ester (46 mg, 0.21 mmol) and 4-(2-cyclopentyloxy-pyridin-3-yl)-2,6-difluoro-phenol (50 mg, 0.17 mmol) obtained in Preparation Example 55 were used to react in the same manner as in Steps A and B of Example 232 to obtain the title compound (43 mg, 62%).

1H NMR (CDCl$_3$) δ 8.15 (1H, m), 7.56 (1H, m), 7.14 (2H, m), 6.91 (1H, m), 5.51 (1H, m), 4.19 (2H, t), 2.41 (2H, t), 1.95 (2H, m), 1.83 (4H, m), 1.74 (4H, m), 1.57 (4H, m)

Example 263

7-[4-(2-cyclopentyloxy-pyridin-3-yl)-2,6-difluoro-phenoxy]-heptanoic acid

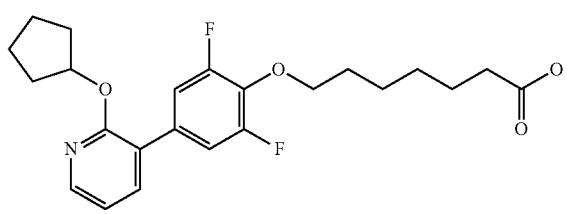 [SMILES: O=C(O)CCCCCCOc1c(F)cc(-c2cccnc2OC2CCCC2)cc1F]

7-Bromo-heptanoic acid ethyl ester (49 mg, 0.21 mmol) and 4-(2-cyclopentyloxy-pyridin-3-yl)-2,6-difluoro-phenol (50 mg, 0.17 mmol) obtained in Preparation Example 55 were used to react in the same manner as in Step C of Preparation Example 2 to obtain the title compound (45 mg, 59%).

1H NMR (CDCl$_3$) δ 8.14 (1H, m), 7.57 (1H, m), 7.14 (2H, m), 6.91 (1H, m), 5.52 (1H, m), 4.18 (2H, t), 2.39 (2H, t), 1.95 (2H, m), 1.85-1.40 (14H, m)

Example 264

5-[2-fluoro-4-(2-isopropoxy-pyridin-3-yl)-phenoxy]-pentanoic acid

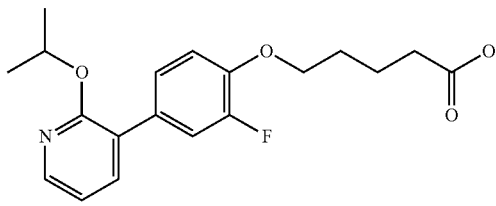 [SMILES: CC(C)Oc1ncccc1-c1ccc(OCCCCC(=O)O)c(F)c1]

3-Iodo-2-isopropoxy-pyridine (0.030 g, 0.11 mmol) obtained in Preparation Example 37 and 5-[2-fluoro-4-(4,4,5,5-tetramethyl-[1,3,2]dioxaborolan-2-yl)-phenoxy]-pentanoic acid ethyl ester (0.042 g, 0.11 mmol) obtained in Preparation Example 147 were used to react in the same manner as in Steps A and B of Example 1 to obtain the title compound (0.023 g, 58%).

1H NMR (CDCl$_3$) δ 8.10 (1H, m), 7.55 (1H, m), 7.38 (1H, m), 7.25 (1H, d), 6.97 (1H, t), 6.90 (1H, m), 5.40 (1H, m), 4.10 (2H, t), 2.49 (2H, t), 1.91 (4H, m), 1.43 (6H, d)

Example 265

5-[4-(2-cyclopentylsulfanyl-pyridin-3-yl)-2-fluoro-phenoxy]-pentanoic acid

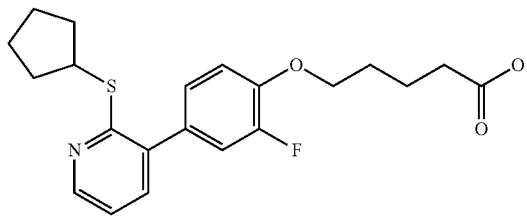

2-Cyclopentylsulfanyl-3-iodo-pyridine (0.030 g, 0.10 mmol) obtained in Preparation Example 39 and 5-[2-fluoro-4-(4,4,5,5-tetramethyl-[1,3,2]dioxaborolan-2-yl)-phenoxy]-pentanoic acid ethyl ester (0.036 g, 0.10 mmol) obtained in Preparation Example 147 were used to react in the same manner as in Steps A and B of Example 1 to obtain the title compound (0.026 g, 68%).

1H NMR (CDCl$_3$) δ 8.41 (1H, m), 7.32 (1H, m), 7.17 (1H, m), 7.12 (1H, d), 7.01 (2H, m), 4.10 (3H, m), 2.49 (2H, t), 2.19 (2H, m), 1.91 (4H, m), 1.75-1.50 (6H, m)

Example 266

5-[4-(2-cyclobutylsulfanyl-pyridin-3-yl)-2-fluoro-phenoxy]-pentanoic acid

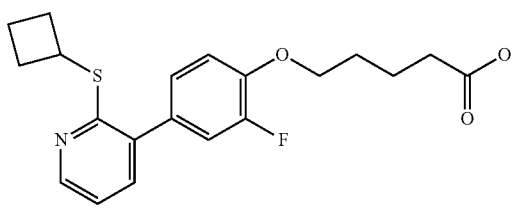 [SMILES: O=C(O)CCCCOc1ccc(-c2cccnc2SC2CCC2)cc1F]

2-Cyclobutylsulfanyl-3-iodo-pyridine (0.030 g, 0.10 mmol) obtained in Preparation Example 44 and 5-[2-fluoro-4-(4,4,5,5-tetramethyl-[1,3,2]dioxaborolan-2-yl)-phenoxy]-pentanoic acid ethyl ester (0.038 g, 0.10 mmol) obtained in Preparation Example 147 were used to react in the same manner as in Steps A and B of Example 1 to obtain the title compound (0.024 g, 62%).

1H NMR (CDCl$_3$) δ 8.39 (1H, m), 7.34 (1H, m), 7.15 (2H, m), 7.02 (2H, m), 4.43 (1H, m), 4.11 (2H, t), 2.50 (4H, m), 2.04 (4H, m), 1.92 (4H, m)

Example 267

5-[4-(2-cyclopentyloxy-pyridin-3-yl)-2-fluoro-phenoxy]-pentanoic acid

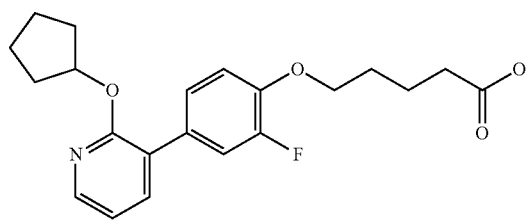 [SMILES: O=C(O)CCCCOc1ccc(-c2cccnc2OC2CCCC2)cc1F]

2-Cyclopentoxy-3-iodo-pyridine (0.030 g, 0.10 mmol) obtained in Preparation Example 38 and 5-[2-fluoro-4-(4,4,5,5-tetramethyl-[1,3,2]dioxaborolan-2-yl)-phenoxy]-pentanoic acid ethyl ester (0.038 g, 0.10 mmol) obtained in Preparation Example 147 were used to react in the same manner as in Example 1 to obtain the title compound (0.026 g, 67%).

1H NMR (CDCl$_3$) δ 8.11 (1H, m), 7.57 (1H, m), 7.34 (1H, m), 7.25 (1H, m), 6.96 (1H, t), 6.90 (1H, m), 5.51 (1H, m), 4.10 (2H, t), 2.49 (2H, t), 2.00-1.60 (12H, m)

Example 268

4-[2,6-difluoro-4-(2-methoxy-pyridin-3-yl)-phenoxy]-butyric acid

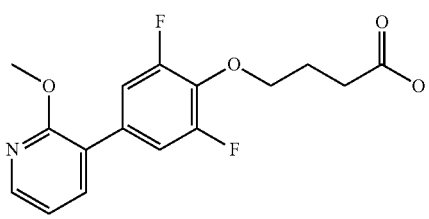 [SMILES: COc1ncccc1-c1cc(F)c(OCCCC(=O)O)c(F)c1]

Methanol (26 mg, 0.80 mmol) and 4-[2,6-difluoro-4-(2-fluoro-3-pyridyl)phenoxy]butyric acid (50 mg, 0.16 mmol) obtained in Preparation Example 56 were used to react in the same manner as in Preparation Example 37 to obtain the title compound (35 mg, 67%).

1H NMR (CDCl$_3$) δ 8.17 (1H, m), 7.57 (1H, m), 7.14 (2H, m), 6.98 (1H, m), 4.24 (2H, t), 3.98 (3H, s), 2.68 (2H, t), 2.13 (2H, m)

Example 269

4-[4-(2-allyloxy-pyridin-3-yl)-2,6-difluoro-phenoxy]-butyric acid

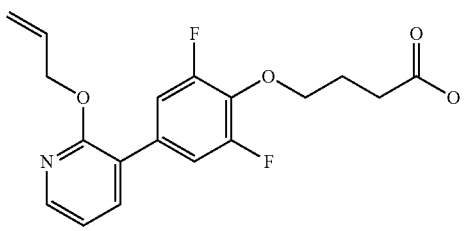 [SMILES: C=CCOc1ncccc1-c1cc(F)c(OCCCC(=O)O)c(F)c1]

Prop-2-en-1-ol (47 mg, 0.80 mmol) and 4-[2,6-difluoro-4-(2-fluoro-3-pyridyl)phenoxy]butyric acid (50 mg, 0.16 mmol) obtained in Preparation Example 56 were used to react in the same manner as in Preparation Example 37 to obtain the title compound (7 mg, 12%).

1H NMR (CDCl₃) δ 8.15 (1H, m), 7.58 (1H, m), 7.15 (2H, m), 6.98 (1H, m), 6.09 (1H, m), 5.36 (1H, m), 5.24 (1H, m), 4.91 (2H, m), 4.24 (2H, t), 2.68 (2H, t), 2.13 (2H, m)

Example 270

4-[4-(2-but-2-ynyloxy-pyridin-3-yl)-2,6-difluoro-phenoxy]-butyric acid

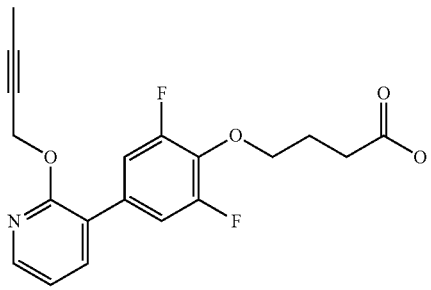 [SMILES: CC#CCOc1ncccc1-c1cc(F)c(OCCCC(=O)O)c(F)c1]

But-2-yn-1-ol (47 mg, 0.80 mmol) and 4-[2,6-difluoro-4-(2-fluoro-3-pyridyl)phenoxy]butyric acid (50 mg, 0.16 mmol) obtained in Preparation Example 56 were used to react in the same manner as in Preparation Example 37 to obtain the title compound (35 mg, 60%).

1H NMR (CDCl₃) δ 8.17 (1H, m), 7.58 (1H, m), 7.17 (2H, m), 7.00 (1H, m), 5.00 (2H, m), 4.24 (2H, t), 2.68 (2H, t), 2.13 (2H, m), 1.85 (3H, t)

Example 271

6-[4-[2-(cyclobutoxy)-3-pyridyl]-2,6-difluoro-phenoxy]hexanoic acid

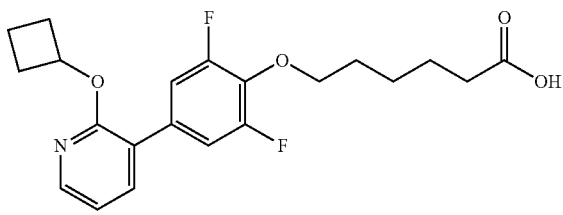 [SMILES: O=C(O)CCCCCOc1c(F)cc(-c2cccnc2OC2CCC2)cc1F]

Step A: ethyl 6-[4-[2-(cyclobutoxy)-3-pyridyl]-2,6-difluoro-phenoxy]hexanoate

2-Cyclobutoxy-3-iodo-pyridine (0.072 g, 0.26 mmol) obtained in Preparation Example 200 and ethyl 6-[2,6-difluoro-4-(4,4,5,5-tetramethyl-1,3,2-dioxaborolan-2-yl)phenoxy]hexanoate (0.11 g, 0.27 mmol) obtained in Preparation Example 146 were used to react in the same manner as in Step A of Example 28 to obtain the title compound (0.064 g, 59%).

¹H-NMR (CDCl₃) δ 8.11 (1H, m), 7.56 (1H, m), 7.20 (2H, m), 6.93 (1H, m), 5.28 (1H, m), 4.15 (4H, m), 2.49 (2H, m), 2.44 (2H, t), 2.14 (2H, m), 1.82 (3H, m), 1.72 (3H, m), 1.55 (2H, m), 1.26 (3H, t)

Step B: 6-[4-[2-(cyclobutoxy)-3-pyridyl]-2,6-difluoro-phenoxy]hexanoic acid

Ethyl 6-[4-[2-(cyclobutoxy)-3-pyridyl]-2,6-difluoro-phenoxy]hexanoate (0.064 g, 0.15 mmol) obtained in Step A was used to react in the same manner as in Step B of Example 1 to obtain the title compound (0.058 g, 97%).

¹H-NMR (CDCl₃) δ 8.12 (1H, m), 7.57 (1H, m), 7.17 (2H, m), 6.93 (1H, m), 5.27 (1H, m), 4.18 (2H, t), 2.48 (2H, m), 1.41 (2H, t), 2.14 (2H, m), 1.83 (3H, m), 1.71 (3H, m), 1.59 (2H, m),

Example 272

6-[4-[2-(cyclobutylmethoxy)-3-pyridyl]-2,6-difluoro-phenoxy]hexanoic acid

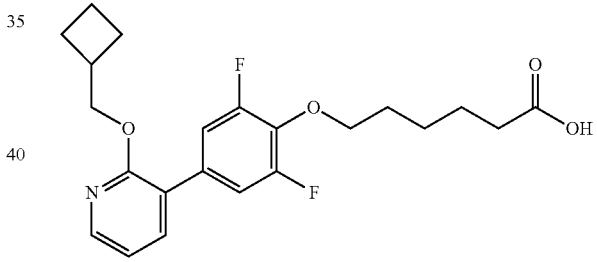

Step A: ethyl 6-[4-[2-(cyclobutylmethoxy)-3-pyridyl]-2,6-difluoro-phenoxy]hexanoate 2-Cyclobutylmethoxy-3-iodo-pyridine (0.076 g, 0.26 mmol) obtained in Preparation Example 61 and ethyl 6-[2,6-difluoro-4-(4,4,5,5-tetramethyl-1,3,2-dioxaborolan-2-yl)phenoxy]hexanoate (0.11 g, 0.27 mmol) obtained in Preparation Example 146 were used to react in the same manner as in Step B of Example 1 to obtain the title compound (0.058 g, 97%).

¹H-NMR (CDCl₃) δ 8.14 (1H, m), 7.58 (1H, m), 7.17 (2H, m), 6.95 (1H, m), 4.32 (2H, d), 4.15 (4H, m), 2.80 (1H, m), 2.34 (2H, t), 2.10 (2H, m), 1.92 (4H, m), 1.82 (2H, m), 1.75 (2H, m), 1.54 (2H, m), 1.26 (3H, t)

Step B: 6-[4-[2-(cyclobutylmethoxy)-3-pyridyl]-2,6-difluoro-phenoxy]hexanoic acid Ethyl 6-[4-[2-(cyclobutylmethoxy)-3-pyridyl]-2,6-difluoro-phenoxy]hexanoate (0.064 g, 0.15 mmol) obtained in Step A was used to react in the same manner as in Step B of Example 1 to obtain the title compound (0.067 g, 99%).

¹H-NMR (CDCl₃) δ 8.14 (1H, m), 7.58 (1H, m), 7.17 (2H, m), 6.93 (1H, m), 4.32 (2H, d), 4.17 (2H, t), 2.78 (1H, m), 2.41 (2H, t), 2.10 (2H, m), 1.89 (2H, m), 1.96 (1H, m), 1.88 (3H, m), 1.82 (2H, m), 1.73 (2H, m)

Example 273

6-[4-[2-(cyclopropylmethoxy)-3-pyridyl]-2,6-difluoro-phenoxy]hexanoic acid

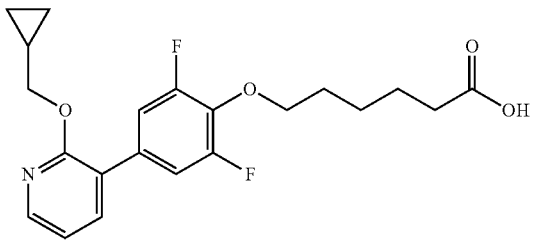 [SMILES: O=C(O)CCCCCOc1c(F)cc(-c2cccnc2OCC2CC2)cc1F]

Step A: ethyl 6-[4-[2-(cyclopropylmethoxy)-3-pyridyl]-2,6-difluoro-phenoxy]hexanoate 2-Cyclopropylmethoxy-3-iodo-pyridine (0.072 g, 0.26 mmol) obtained in Preparation Example 40 and ethyl 6-[2,6-difluoro-4-(4,4,5,5-tetramethyl-1,3,2-dioxaborolan-2-yl)phenoxy]hexanoate (0.11 g, 0.27 mmol) obtained in Preparation Example 146 were used to react in the same manner as in Step A of Example 28 to obtain the title compound (0.075 g, 69%).

¹H-NMR (CDCl₃) δ 8.12 (1H, m), 7.59 (1H, m), 7.23 (2H, m), 6.94 (1H, m), 4.22 (2H, d), 4.15 (4H, m), 2.34 (2H, t), 1.80 (2H, m), 1.72 (2H, m), 1.55 (2H, m), 1.26 (4H, m), 0.60 (2H, m), 0.35 (2H, m)

Step B: 6-[4-[2-(cyclopropylmethoxy)-3-pyridyl]-2,6-difluoro-phenoxy]hexanoic acid Ethyl 6-[4-[2-(cyclopropylmethoxy)-3-pyridyl]-2,6-difluoro-phenoxy]hexanoate (0.075 g, 0.18 mmol) obtained in Step A was used to react in the same manner as in Step B of Example 1 to obtain the title compound (0.049 g, 69%).

¹H-NMR (CDCl₃) δ 8.12 (1H, m), 7.58 (1H, m), 7.22 (2H, m), 6.95 (1H, m), 4.22 (2H, d), 4.18 (2H, t), 2.41 (2H, t), 1.82 (2H, m), 1.73 (2H, m), 1.58 (2H, m), 1.31 (1H, m), 0.60 (2H, m), 0.35 (2H, m)

Example 274

6-[4-(2-cyclobutylsulfanyl-3-pyridyl)-2,6-difluoro-phenoxy]hexanoic acid

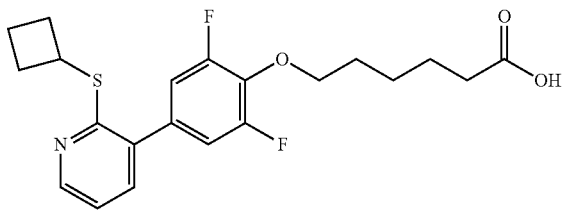 [SMILES: O=C(O)CCCCCOc1c(F)cc(-c2cccnc2SC2CCC2)cc1F]

Step A: ethyl 6-[4-(2-cyclobutylsulfanyl-3-pyridyl)-2,6-difluoro-phenoxy]hexanoate 2-Cyclobutylsulfanyl-3-iodo-pyridine (0.076 g, 0.26 mmol) obtained in Preparation Example 44 and ethyl 6-[2,6-difluoro-4-(4,4,5,5-tetramethyl-1,3,2-dioxaborolan-2-yl)phenoxy]hexanoate (0.11 g, 0.27 mmol) obtained in Preparation Example 146 were used to react in the same manner as in Step A of Example 28 to obtain the title compound (0.067 g, 59%).

¹H-NMR (CDCl₃) δ 8.41 (1H, m), 7.33 (1H, m), 7.03 (1H, m), 6.95 (2H, m), 4.43 (1H, m), 4.19 (2H, t), 4.14 (2H, q), 2.52 (2H, m), 2.35 (2H, t), 2.06 (4H, m), 1.82 (2H, m), 1.73 (2H, m), 1.55 (2H, m), 1.26 (3H, t)

Step B: 6-[4-(2-cyclobutylsulfanyl-3-pyridyl)-2,6-difluoro-phenoxy]hexanoic acid Ethyl 6-[4-(2-cyclobutylsulfanyl-3-pyridyl)-2,6-difluoro-phenoxy]hexanoate (0.067 g, 0.15 mmol) obtained in Step A was used to react in the same manner as in Step B of Example 1 to obtain the title compound (0.057 g, 91%).

¹H-NMR (CDCl₃) δ 8.41 (1H, m), 7.32 (1H, m), 7.02 (1H, m), 6.99 (2H, m), 4.42 (1H, m), 4.19 (2H, t), 2.52 (2H, m), 2.42 (2H, t), 2.05 (4H, m), 1.82 (2H, m), 1.74 (2H, m), 1.58 (2H, m)

Example 275

6-[4-(2-cyclopentylsulfanyl-3-pyridyl)-2,6-difluoro-phenoxy]hexanoic acid

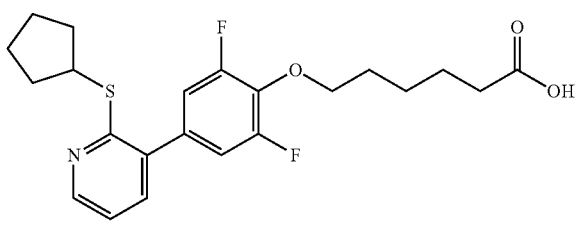 [SMILES: O=C(O)CCCCCOc1c(F)cc(-c2cccnc2SC2CCCC2)cc1F]

Step A: ethyl 6-[4-(2-cyclopentylsulfanyl-3-pyridyl)-2,6-difluoro-phenoxy]hexanoate 2-Cyclopentylsulfanyl-3-iodo-pyridine (0.079 g, 0.26 mmol) obtained in Preparation Example 39 and ethyl 6-[2,6-difluoro-4-(4,4,5,5-tetramethyl-1,3,2-dioxaborolan-2-yl)phenoxy]hexanoate (0.11 g, 0.27 mmol) obtained in Preparation Example 146 were used to react in the same manner as in Step A of Example 28 to obtain the title compound (0.080 g, 68%).

¹H-NMR (CDCl₃) δ 8.43 (1H, m), 7.32 (1H, m), 7.03 (1H, m), 6.98 (2H, m), 4.20 (2H, t), 4.13 (3H, m), 2.34 (2H, t), 2.20 (2H, m), 1.82 (2H, m), 1.72 (4H, m), 1.65 (2H, m), 1.59 (4H, m), 1.26 (3H, t)

Step B: 6-[4-(2-cyclopentylsulfanyl-3-pyridyl)-2,6-difluoro-phenoxy]hexanoic acid Ethyl 6-[4-(2-cyclopentylsulfanyl-3-pyridyl)-2,6-difluoro-phenoxy]hexanoate (0.080 g, 0.17 mmol) obtained in Step A was used to react in the same manner as in Step B of Example 1 to obtain the title compound (0.067 g, 89%).

¹H-NMR (CDCl₃) δ 8.43 (1H, m), 7.33 (1H, m), 7.03 (1H, m), 6.98 (2H, m), 4.19 (2H, t), 4.10 (1H, m), 2.41 (2H, t), 2.20 (2H, m), 1.83 (2H, m), 1.73 (4H, m), 1.63 (2H, m), 1.56 (4H, m)

Example 276

6-[4-(2-cyclopentyloxy-pyridin-3-yl)-2,6-difluoro-phenylsulfanyl]-hexanoic acid

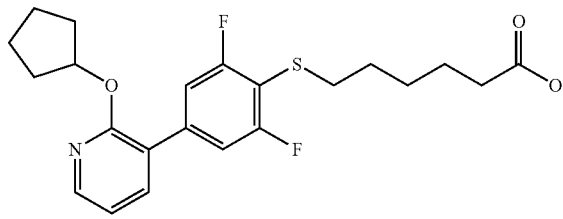 [SMILES: O=C(O)CCCCCSc1c(F)cc(-c2cccnc2OC2CCCC2)cc1F]

6-[2,6-Difluoro-4-(4,4,5,5-tetramethyl-[1,3,2]dioxaborolan-2-yl)-phenylsulfanyl]-hexanoic acid ethyl ester (0.05 g, 0.12 mmol) obtained in Preparation Example 237 and 2-cyclopentoxy-3-iodo-pyridine (0.052 g, 0.18 mmol) obtained in Preparation Example 38 were used to react sequentially in the same manner as in Steps A and B of Example 1 to obtain the title compound (0.029 g, 58%).

¹H-NMR (CDCl₃) δ 8.17 (1H, m), 7.59 (1H, m), 7.16 (2H, d), 6.92 (1H, m), 5.52 (1H, m), 2.90 (2H, t), 2.33 (2H, t), 1.94 (2H, m), 1.82-1.71 (4H, m), 1.63 (6H, m), 1.48 (2H, m).

Example 277

6-[4-(2-cyclopentylsulfanyl-pyridin-3-yl)-2,6-difluoro-phenylsulfanyl]-hexanoic acid

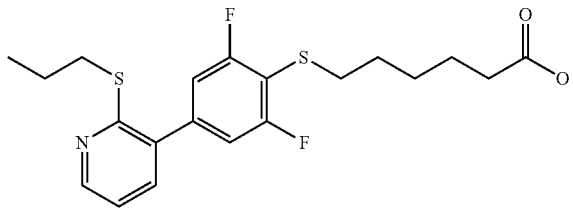 [SMILES: CCCSc1ncccc1-c1cc(F)c(SCCCCCC(=O)O)c(F)c1]

6-[2,6-Difluoro-4-(4,4,5,5-tetramethyl-[1,3,2]dioxaborolan-2-yl)-phenylsulfanyl]-hexanoic acid ethyl ester (0.05 g, 0.12 mmol) obtained in Preparation Example 237 and 2-cyclopentylsulfanyl-3-iodo-pyridine (0.055 g, 0.18 mmol) obtained in Preparation Example 39 were used to react sequentially in the same manner as in Steps A and B of Example 1 to obtain the title compound (0.032 g, 60%).

¹H-NMR (CDCl₃) δ 8.44 (1H, m), 7.34 (1H, m), 7.02 (3H, m), 4.08 (1H, m), 2.91 (2H, t), 2.34 (2H, t), 2.19 (2H, m), 1.78-1.48 (12H, m).

Example 278

6-[4-(2-cyclobutylsulfanyl-pyridin-3-yl)-2,6-difluoro-phenylsulfanyl]-hexanoic acid

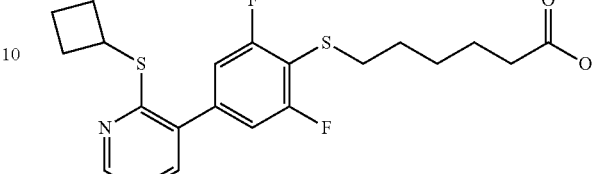

6-[2,6-Difluoro-4-(4,4,5,5-tetramethyl-[1,3,2]dioxaborolan-2-yl)-phenylsulfanyl]-hexanoic acid ethyl ester (0.05 g, 0.12 mmol) obtained in Preparation Example 237 and 2-cyclobutylsulfanyl-3-iodo-pyridine (0.053 g, 0.18 mmol) obtained in Preparation Example 44 were used to react sequentially in the same manner as in Steps A and B of Example 1 to obtain the title compound (0.029 g, 56%).

¹H-NMR (CDCl₃) δ 8.42 (1H, m), 7.35 (1H, m), 7.02 (3H, m), 4.42 (1H, m), 2.92 (2H, t), 2.49 (2H, t), 2.35 (2H, t), 2.03 (4H, m), 1.63 (4H, m), 1.49 (2H, m).

Example 279

6-[2,6-difluoro-4-(2-propylsulfanyl-pyridin-3-yl)-phenylsulfanyl]-hexanoic acid

6-[2,6-Difluoro-4-(4,4,5,5-tetramethyl-[1,3,2]dioxaborolan-2-yl)-phenylsulfanyl]-hexanoic acid ethyl ester (0.05 g, 0.12 mmol) obtained in Preparation Example 237 and 3-iodo-2-propylsulfanyl-pyridine (0.05 g, 0.18 mmol) obtained in Preparation Example 203 were used to react sequentially in the same manner as in Steps A and B of Example 1 to obtain the title compound (0.027 g, 55%).

¹H-NMR (CDCl₃) δ 8.44 (1H, m), 7.35 (1H, m), 7.03 (3H, m), 3.14 (2H, t), 2.92 (2H, t), 2.34 (2H, t), 1.69-1.62 (6H, m), 1.49 (2H, m), 1.02 (3H, t).

Experimental Example 1

Measurement of Activity of GPR120 Agonist (Cell-Based Assay)

CHO-K1 cells expressing Gα16 and hGPR120 were dispensed into each well of a 96-well plate (3×10⁴ cells/100 μl/well) and then incubated in 5% CO₂, 37° C. incubator for 18 hours. Each well was treated with 100 μl of Calcium 5 dye (Molecular Devices) solution including 2% DMSO and then incubated in 5% CO₂, 37° C. incubator for 1 hour. Serially diluted GPR120 agonists were prepared to a final concentration of 0.5% DMSO in a 96-well plate. Each well was treated with 50 µl of the agonist compounds using Plexstation II, and then fluorescence was measured at Ex 485 nm, Em 525 nm.

Fluorescence increased by the serially diluted GPR120 agonists is calculated as a relative percent (%) value based on the fluorescence represented by the treatment of 1% DMSO only. $EC_{50}$ refers to the concentration of agonist which shows 50% of maximum fluorescence increased by the treatment of agonist. The calculation of measurement was carried out by using statistical software (Prizm).

The agonistic effects of the Example compounds obtained by the above experiment are shown in the following Table 1 with $EC_{50}$ unit (M). Activity is denoted based on the following criteria:

A=>20 µM, B=20~2 µM, C=2~0.2 µM, D=<0.2 µM

As shown in the table, most of the novel compounds according to the present invention have superior GPR120 agonistic effects ($EC_{50}$), less than 0.2 µM.

TABLE 1

| Example | $EC_{50}$ | Example | $EC_{50}$ | Example | $EC_{50}$ | Example | $EC_{50}$ |
|---|---|---|---|---|---|---|---|
| 1 | C | 2 | D | 3 | D | 4 | C |
| 5 | C | 6 | D | 7 | B | 8 | A |
| 9 | 0.097 | 10 | D | 11 | 0.050 | 12 | D |
| 13 | C | 14 | C | 15 | C | 16 | C |
| 17 | C | 18 | 0.144 | 19 | 0.040 | 20 | D |
| 21 | D | 22 | 0.030 | 23 | D | 24 | D |
| 25 | D | 26 | D | 27 | D | 28 | D |
| 29 | D | 30 | A | 31 | C | 32 | A |
| 33 | C | 34 | 0.253 | 35 | C | 36 | C |
| 37 | D | 38 | C | 39 | D | 40 | 0.085 |
| 41 | C | 42 | 1.421 | 43 | C | 44 | C |
| 45 | 0.057 | 46 | C | 47 | D | 48 | D |
| 49 | C | 50 | 0.031 | 51 | D | 52 | C |
| 53 | D | 54 | D | 55 | D | 56 | C |
| 57 | C | 58 | C | 59 | D | 60 | D |
| 61 | C | 62 | C | 63 | B | 64 | D |
| 65 | D | 66 | 0.088 | 67 | C | 68 | C |
| 69 | 0.147 | 70 | 0.036 | 71 | B | 72 | C |
| 73 | C | 74 | C | 75 | C | 76 | C |
| 77 | A | 78 | C | 79 | D | 80 | D |
| 81 | D | 82 | D | 83 | C | 84 | 0.043 |
| 85 | C | 86 | C | 87 | D | 88 | C |
| 89 | D | 90 | D | 91 | D | 92 | D |
| 93 | 0.064 | 94 | C | 95 | C | 96 | D |
| 97 | D | 98 | C | 99 | D | 100 | D |
| 101 | D | 102 | D | 103 | D | 104 | D |
| 105 | D | 106 | B | 107 | C | 108 | D |
| 109 | C | 110 | A | 111 | A | 112 | A |
| 113 | 0.281 | 114 | D | 115 | 0.052 | 116 | D |
| 117 | 0.029 | 118 | D | 119 | 0.019 | 120 | 0.028 |
| 121 | D | 122 | D | 123 | D | 124 | C |
| 125 | D | 126 | D | 127 | D | 128 | D |
| 129 | C | 130 | D | 131 | C | 132 | D |
| 133 | C | 134 | D | 135 | 0.348 | 136 | D |
| 137 | D | 138 | D | 139 | D | 140 | D |
| 141 | D | 142 | D | 143 | C | 144 | D |
| 145 | D | 146 | D | 147 | D | 148 | D |
| 149 | D | 150 | 0.043 | 151 | 0.043 | 152 | D |
| 153 | D | 154 | D | 155 | D | 156 | D |
| 157 | 0.037 | 158 | D | 159 | D | 160 | D |
| 161 | D | 162 | D | 163 | D | 164 | D |
| 165 | D | 166 | D | 167 | 0.034 | 168 | D |
| 169 | D | 170 | D | 171 | D | 172 | D |
| 173 | C | 174 | C | 175 | D | 176 | D |
| 177 | C | 178 | 0.066 | 179 | C | 180 | C |
| 181 | C | 182 | 0.208 | 183 | C | 184 | C |
| 185 | D | 186 | D | 187 | D | 188 | D |
| 189 | C | 190 | D | 191 | D | 192 | B |
| 193 | C | 194 | A | 195 | C | 196 | D |
| 197 | C | 198 | D | 199 | D | 200 | C |
| 201 | D | 202 | C | 203 | A | 204 | D |
| 205 | C | 206 | D | 207 | D | 208 | D |

TABLE 1-continued

| Example | $EC_{50}$ | Example | $EC_{50}$ | Example | $EC_{50}$ | Example | $EC_{50}$ |
|---|---|---|---|---|---|---|---|
| 209 | D | 210 | D | 211 | 0.024 | 212 | A |
| 213 | D | 214 | D | 215 | C | 216 | A |
| 217 | B | 218 | A | 219 | 0.335 | 220 | C |
| 221 | A | 222 | B | 223 | 1.99 | 224 | 0.018 |
| 225 | C | 226 | A | 227 | B | 228 | D |
| 229 | D | 230 | D | 231 | C | 232 | D |
| 233 | D | 234 | D | 235 | D | 236 | D |
| 237 | D | 238 | D | 239 | D | 240 | C |
| 241 | C | 242 | D | 243 | D | 244 | C |
| 245 | C | 246 | D | 247 | D | 248 | D |
| 249 | D | 250 | C | 251 | C | 252 | D |
| 253 | C | 254 | D | 255 | C | 256 | 0.052 |
| 257 | D | 258 | D | 259 | D | 260 | D |
| 261 | D | 262 | D | 263 | B | 264 | C |
| 265 | D | 266 | D | 267 | D | 268 | C |
| 269 | C | 270 | B | 271 | C | 272 | D |
| 273 | C | 274 | D | 275 | C | 276 | C |
| 277 | C | 278 | C | 279 | C | | |

The invention claimed is:

1. A biaryl derivative of Formula 1, or a pharmaceutically acceptable salt or isomer thereof:

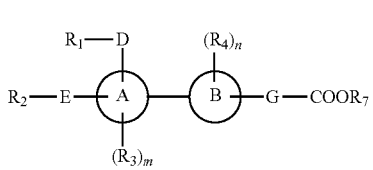

[Formula 1]

wherein,

A and B represent independently phenyl or pyridine, provided that when B is phenyl, -G-COOR$_7$ is substituted at the para position of phenyl, and when B is pyridine, -G-COOR$_7$ is substituted at the 3 position of pyridine, wherein R$_2$-E may optionally not exist, D and E represent independently carbon, nitrogen, oxygen or sulfur, or represent direct bond, or R$_1$ represents halogen; $C_1$-$C_6$-alkyl optionally substituted by halogen, $C_3$-$C_{10}$-cycloalkyl, $C_1$-$C_6$-alkoxy, $C_1$-$C_6$-alkylamino, $C_3$-$C_{10}$-heterocycloalkyl or $C_1$-$C_6$-alkyl-$C_3$-$C_{10}$-heterocycloalkyl; $C_3$-$C_{10}$-cycloalkyl optionally substituted by $C_3$-$C_{10}$-alkylsilanyloxy or hydroxy; $C_2$-$C_6$-alkenyl; $C_2$-$C_6$-alkynyl; $C_3$-$C_{10}$-heterocycloalkyl optionally substituted by $C_1$-$C_6$-alkylamino or halogen; $C_1$-$C_6$-alkyl-$C_3$-$C_{10}$-cycloalkyl; $C_1$-$C_6$-alkyl-$C_3$-$C_{10}$-heterocycloalkyl; aryl; $C_1$-$C_6$-alkylaryl; unsubstituted heteroaryl or $C_1$-$C_6$-alkyl-$C_5$-$C_6$-heteroaryl, R$_2$ represents hydrogen; halogen; $C_1$-$C_6$-alkyl optionally substituted by halogen, $C_3$-$C_{10}$-cycloalkyl, $C_1$-$C_6$-alkoxy, $C_1$-$C_6$-alkylamino, $C_3$-$C_{10}$-heterocycloalkyl or $C_1$-$C_6$-alkyl-$C_3$-$C_{10}$-heterocycloalkyl; $C_3$-$C_{10}$-cycloalkyl optionally substituted by $C_3$-$C_{10}$-alkylsilanyloxy or hydroxy; $C_2$-$C_6$-alkenyl; $C_2$-$C_6$-alkynyl; $C_3$-$C_{10}$-heterocycloalkyl optionally substituted by $C_1$-$C_6$-alkylamino or halogen; $C_1$-$C_6$-alkyl-$C_3$-$C_{10}$-cycloalkyl; $C_1$-$C_6$-alkyl-$C_3$-$C_{10}$-heterocycloalkyl; aryl; $C_1$-$C_6$-alkylaryl; unsubstituted heteroaryl or $C_1$-$C_6$-alkyl-$C_5$-$C_6$-heteroaryl, and when D and E represent nitrogen or carbon, R$_1$ and R$_2$ can represent two or three $C_1$-$C_6$-alkyl optionally substituted by $C_3$-$C_{10}$-cycloalkyl or $C_3$-$C_{10}$-heterocycloalkyl; $C_3$-$C_{10}$-cycloalkyl; $C_2$-$C_6$-alkenyl; $C_2$-$C_6$- alkynyl; $C_1$-$C_6$-alkyl-$C_3$-$C_{10}$-cycloalkyl; aryl or $C_1$-$C_6$-alkylaryl which may be the same or different, G represents -J-$(CR_5R_6)_p$, wherein J represents oxygen or sulfur, $R_5$ and $R_6$ represent independently hydrogen, halogen, alkyl, cycloalkyl, hydroxyl or amine, and $R_5$ and $R_6$ which are substituted at the same or different carbon may be connected to form cycloalkyl, $R_3$ and $R_4$ cannot independently exist depending on the number of m or n, or represent independently hydrogen, halogen, or optionally substituted $C_1$-$C_6$-alkyl or $C_1$-$C_6$-alkoxy, $R_7$ represents hydrogen, alkyl or cycloalkyl, m and n represent independently an integer of 0 to 5, p represents an integer of 2 to 6, and wherein the isomer is at least one selected from the group consisting of an E-isomer, Z-isomer, R-isomer, S-isomer, racemic mixture and a diastereoisomer mixture.

2. A biaryl derivative, or a pharmaceutically acceptable salt or isomer thereof, which is selected from the following compounds:

4-[4-(6-phenoxy-2-pyridyl)phenoxy]butyric acid;
4-[2,6-difluoro-4-(6-isopropylsulfanyl-2-pyridyl)phenoxy]butyric acid;
4-[2,6-difluoro-4-(6-phenoxy-2-pyridyl)phenoxy]butyric acid;
4-[2-chloro-4-(6-isopropylsulfanyl-2-pyridyl)phenoxy]butyric acid;
4-[2-fluoro-4-(6-isopropylsulfanyl-2-pyridyl)phenoxy]butyric acid;
4-[4-(6-cyclopentylsulfanyl-2-pyridyl)-2,6-difluoro-phenoxy]butyric acid;
4-[4-(2-cyclobutylsulfanyl-pyridin-3-yl)-2-methoxy-phenoxy]-butyric acid;
4-[2,6-difluoro-4-(2-isopropylsulfanyl-4-pyridyl)phenoxy]butyric acid;
4-[4-[6-(cyclopentoxy)-2-pyridyl]-2,6-difluoro-phenoxy]butyric acid;
4-[4-(2-cyclobutylsulfanyl-pyridin-3-yl)-2,6-dimethyl-phenoxy]-butyric acid;
4-[4-[3-(cyclopentoxy)phenyl]-2,6-difluoro-phenoxy]butyric acid;
4-[2,6-difluoro-4-(6-pyrrolidin-1-yl-2-pyridyl)phenoxy]butyric acid;
4-[4-(2-sec-butylsulfanyl-pyridin-3-yl)-2,6-difluoro-phenoxy]-butyric acid;
4-[4-[3-(cyclopentoxy)phenyl]-2,3-difluoro-phenoxy]butyric acid;
4-[2,6-difluoro-4-[6-(1-piperidyl)-2-pyridyl]phenoxy]butyric acid;
4-[4-(6-anilino-2-pyridyl)-2,6-difluoro-phenoxy]butyric acid;
4-[2,6-difluoro-4-[6-(N-methylanilino)-2-pyridyl]phenoxy]butyric acid;
4-[4-[6-(cyclopentylamino)-2-pyridyl]-2,6-difluoro-phenoxy]butyric acid;
4-[4-[6-(cyclopropylmethylsulfanyl)-2-pyridyl]-2,6-difluoro-phenoxy]butyric acid;
4-[4-(6-cyclobutylsulfanyl-2-pyridyl)-2,6-difluoro-phenoxy]butyric acid;
4-[2,6-difluoro-4-(6-propylsulfanyl-2-pyridyl)phenoxy]butyric acid;
4-[2,6-difluoro-4-(6-isopropoxy-2-pyridyl)phenoxy]butyric acid;
4-[2,6-difluoro-4-(6-propoxy-2-pyridyl)phenoxy]butyric acid;
4-[4-[6-(cyclopropylmethoxy)-2-pyridyl]-2,6-difluoro-phenoxy]butyric acid;
4-[4-[6-(cyclobutoxy)-2-pyridyl]-2,6-difluoro-phenoxy]butyric acid;
4-[4-[6-(cyclobutoxy)-2-pyridyl]-2-methyl-phenoxy]butyric acid;
4-[4-[6-(cyclobutoxy)-2-pyridyl]-2-(trifluoromethyl)phenoxy]butyric acid;
4-[4-(2-cyclobutylsulfanyl-3-pyridyl)-2,6-difluoro-phenoxy]pentanoic acid;
4-[4-[6-(cyclobutoxy)-2-pyridyl]-2,6-difluoro-phenoxy]pentanoic acid;
4-[[5-(2-cyclobutylsulfanyl-3-pyridyl)-2-pyridyl]oxy]pentanoic acid;
4-{2,6-difluoro-4-[2-(3-methyl-butylsulfanyl)-pyridin-3-yl]-phenoxy}-butyric acid
4-{2,6-difluoro-4-[2-(2-fluoro-ethoxy)-pyridin-3-yl]-phenoxy}-butyric acid;
2-[1-[[4-(2-cyclobutylsulfanyl-3-pyridyl)-2,6-difluoro-phenoxy]methyl]cyclopropyl]acetic acid;
2-[1-[[4-[3-(cyclobutoxy)phenyl]-2,6-difluoro-phenoxy]methyl]cyclopropyl]acetic acid;
4-[[6-[3-(cyclobutoxy)phenyl]-3-pyridyl]oxy]butyric acid;
4-[[6-[3-(cyclopentoxy)phenyl]-3-pyridyl]oxy]butyric acid;
4-(2'-phenoxy-biphenyl-4-yloxy)-butyric acid;
4-[4-(2-isopropylsulfanyl-pyridin-3-yl)-phenoxy]-butyric acid;
4-(3,5-difluoro-2'-phenoxy-biphenyl-4-yloxy)-butyric acid;
4-[4-(2-cyclopentylsulfanyl-pyridin-3-yl)-phenoxy]-butyric acid;
4-[2,6-difluoro-4-(2-isopropylsulfanyl-pyridin-3-yl)-phenoxy]-butyric acid;
4-[2,6-difluoro-4-(2-phenoxy-pyridin-3-yl)-phenoxy]-butyric acid;
4-[2,6-difluoro-4-(2-isopropoxy-pyridin-3-yl)-phenoxy]-butyric acid;
4-[4-(2-cyclopentyloxy-pyridin-3-yl)-2,6-difluoro-phenoxy]-butyric acid;
4-[4-(2-cyclopentylsulfanyl-pyridin-3-yl)-2,6-difluoro-phenoxy]-butyric acid;
4-[4-(2-cyclopropylmethoxy-pyridin-3-yl)-2,6-difluoro-phenoxy]-butyric acid;
4-[4-(2-cyclopropylmethylsulfanyl-pyridin-3-yl)-2,6-difluoro-phenoxy]-butyric acid;
4-[4-(2-cyclobutylsulfanyl-pyridin-3-yl)-phenoxy]-butyric acid;
4-[4-(2-cyclopropylmethylsulfanyl-pyridin-3-yl)-phenoxy]-butyric acid;
4-[4-(2-cyclobutylsulfanyl-pyridin-3-yl)-2,6-difluoro-phenoxy]-butyric acid;
4-[4-(2-propylsulfanyl-pyridin-3-yl)-phenoxy]-butyric acid;
4-(3,5-difluoro-2'-isopropoxy-biphenyl-4-yloxy)-butyric acid;
4-(2'-cyclobutoxy-3,5-difluoro-biphenyl-4-yloxy)-butyric acid;
4-(2'-cyclopropylmethoxy-3,5-difluoro-biphenyl-4-yloxy)-butyric acid;
4-(2'-cyclopentyloxy-3,5-difluoro-biphenyl-4-yloxy)-butyric acid;
4-(2'-cyclopentyloxy-biphenyl-4-yloxy)-butyric acid;
4-(2'-isopropoxy-biphenyl-4-yloxy)-butyric acid;
4-(2'-cyclopropylmethoxy-biphenyl-4-yloxy)-butyric acid;
4-[4-(2-cyclobutylsulfanyl-pyridin-3-yl)-2,6-difluoro-phenoxy]-2-methyl-butyric acid;

2-[4-(2-cyclobutylsulfanyl-pyridin-3-yl)-2,6-difluoro-phenoxymethyl]-cyclopropanecarboxylic acid;
4-[4-(2-cyclobutylsulfanyl-pyridin-3-yl)-2,5-difluoro-phenoxy]-butyric acid;
4-[4-(6-cyclobutylsulfanyl-pyridin-2-yl)-2,5-difluoro-phenoxy]-butyric acid;
4-[4-(2-tert-butylsulfanyl-pyridin-3-yl)-2,6-difluoro-phenoxy]-butyric acid;
6-[2,6-difluoro-4-(2-propylsulfanyl-3-pyridyl)phenoxy]hexanoic acid;
4-{2,6-difluoro-4-[6-(2-methyl-propenyl)-pyridin-2-yl]-phenoxy}-butyric acid;
4-[2,6-difluoro-4-(6-isobutyl-pyridin-2-yl)-phenoxy]-butyric acid;
4-[4-(2-cyclobutylsulfanyl-pyridin-3-yl)-3,5-difluoro-phenoxy]-butyric acid;
4-{2,6-difluoro-4-[2-(tetrahydro-pyran-4-yloxy)-pyridin-3-yl]-phenoxy}-butyric acid;
4-{2,6-difluoro-4-[2-(tetrahydro-furan-3-yloxy)-pyridin-3-yl]-phenoxy}-butyric acid;
4-[4-(2-cyclobutoxy-pyridin-3-yl)-2,6-difluoro-phenoxy]-butyric acid;
4-{2,6-difluoro-4-[2-(2-methoxy-ethoxy)-pyridin-3-yl]-phenoxy}-butyric acid;
4-[2,6-difluoro-4-(2-pyrrolidin-1-yl-3-pyridyl)phenoxy]butanoic acid;
4-[4-[2-(cyclopentylamino)-3-pyridyl]-2,6-difluoro-phenoxy]butanoic acid;
4-[4-[2-(cyclopropylmethylamino)-3-pyridyl]-2,6-difluoro-phenoxy]butanoic acid;
4-[4-[6-(cyclopropylmethylamino)-2-pyridyl]-2,6-difluoro-phenoxy]butanoic acid;
4-[2,6-difluoro-4-[2-(isopropylamino)-3-pyridyl]phenoxy]butanoic acid;
4-[4-[2-(cyclopropylamino)-3-pyridyl]-2,6-difluoro-phenoxy]butanoic acid;
4-[2,6-difluoro-4-[6-(isopropylamino)-2-pyridyl]phenoxy]butanoic acid;
4-[4-[2-(cyclopentylamino)phenyl]-2,6-difluoro-phenoxy]butanoic acid;
4-[4-[3-(cyclopentylamino)phenyl]-2,6-difluoro-phenoxy]butanoic acid;
4-[2,6-difluoro-4-[2-(propylamino)phenyl]phenoxy]butanoic acid;
4-[4-[2-(cyclopropylmethylamino)phenyl]-2,6-difluoro-phenoxy]butanoic acid;
4-[2,6-difluoro-4-[2-(isopropylamino)phenyl]phenoxy]butanoic acid;
4-[4-[2-(cyclopentylamino)phenyl]phenoxy]butanoic acid;
4-[4-[2-(cyclopropylmethylamino)phenyl]phenoxy]butanoic acid;
4-[4-[2-(propylamino)phenyl]phenoxy]butanoic acid;
4-[4-[2-(isopropylamino)phenyl]phenoxy]butanoic acid;
4-[4-[2-(cyclobutylamino)phenyl]phenoxy]butanoic acid;
4-[4-[2-(cyclobutylamino)phenyl]-2,6-difluoro-phenoxy]butanoic acid;
4-[4-[3-(cyclopropylmethylamino)phenyl]-2,6-difluoro-phenoxy]butanoic acid;
4-[2,6-difluoro-4-[3-(isopropylamino)phenyl]phenoxy]butanoic acid;
4-[2,6-difluoro-4-(3-pyrrolidin-1-ylphenyl)phenoxy]butanoic acid;
4-[4-[3-(cyclobutylamino)phenyl]-2,6-difluoro-phenoxy]butanoic acid;
4-[2,6-difluoro-4-[3-(propylamino)phenyl]phenoxy]butanoic acid;
4-[4-[5-chloro-2-(cyclopentylamino)phenyl]-2,6-difluoro-phenoxy]butanoic acid;
4-[4-[2-(cyclopentylamino)-5-fluoro-phenyl]-2,6-difluoro-phenoxy]butanoic acid;
4-[4-(3-cyclopentylphenyl)-2,6-difluoro-phenoxy]butanoic acid;
4-[4-[3-(cyclopentylmethyl)phenyl]-2,6-difluoro-phenoxy]butanoic acid;
4-[4-[2-(cyclopentylmethyl)phenyl]-2,6-difluoro-phenoxy]butanoic acid;
4-[4-[6-(cyclopentylmethyl)-2-pyridyl]-2,6-difluoro-phenoxy]butanoic acid;
4-[4-[2-(cyclobutylmethyl)phenyl]-2,6-difluoro-phenoxy]butanoic acid;
4-[4-[3-(cyclobutylmethyl)phenyl]-2,6-difluoro-phenoxy]butanoic acid;
4-[4-[6-(cyclobutylmethyl)-2-pyridyl]-2,6-difluoro-phenoxy]butanoic acid;
4-[4-(2-cyclopentylphenyl)-2,6-difluoro-phenoxy]butanoic acid;
4-[4-(6-cyclopentyl-2-pyridyl)-2,6-difluoro-phenoxy]butanoic acid;
4-[2,6-difluoro-4-(2-isobutyl-3-pyridyl)phenoxy]butanoic acid;
4-[4-(2-cyclopentyl-3-pyridyl)-2,6-difluoro-phenoxy]butanoic acid;
4-[4-[2-(cyclopentylmethyl)-3-pyridyl]-2,6-difluoro-phenoxy]butanoic acid;
4-[2,6-difluoro-4-(2-pyrrol-1-yl-3-pyridyl)phenoxy]butanoic acid;
4-[2,6-difluoro-4-[2-(4-methylpyrazol-1-yl)-3-pyridyl]phenoxy]butanoic acid;
4-[2,6-difluoro-4-(2-morpholino-3-pyridyl)phenoxy]butanoic acid;
4-[2,6-difluoro-4-[2-(tetrahydropyran-4-ylmethylamino)-3-pyridyl]phenoxy]butanoic acid;
4-[2,6-difluoro-4-[2-(1-piperidyl)-3-pyridyl]phenoxy]butanoic acid;
(4S)-4-[4-(2-cyclobutylsulfanyl-3-pyridyl)-2,6-difluoro-phenoxy]pentanoic acid;
(4R)-4-[4-(2-cyclobutylsulfanyl-3-pyridyl)-2,6-difluoro-phenoxy]pentanoic acid;
(4R)-4-[4-[3-(cyclobutoxy)phenyl]-2,6-difluoro-phenoxy]pentanoic acid;
(4R)-4-[4-(2-cyclopentylsulfanyl-3-pyridyl)-2,6-difluoro-phenoxy]pentanoic acid;
(4R)-4-[2,6-difluoro-4-(3-phenoxyphenyl)phenoxy]pentanoic acid;
4-(3'-cyclobutoxy-biphenyl-4-ylsulfanyl)-butyric acid;
4-(3'-isopropoxy-biphenyl-4-ylsulfanyl)-butyric acid;
[1-(3,5-difluoro-3'-isopropoxy-biphenyl-4-ylsulfanylmethyl)-cyclopropyl]-acetic acid;
4-(3'-cyclopentyloxy-3,5-difluoro-biphenyl-4-ylsulfanyl)-butyric acid;
4-[4-(2-cyclopentyloxy-pyridin-3-yl)-phenylsulfanyl]-butyric acid;
4-[4-(2-cyclopropylmethoxy-pyridin-3-yl)-phenylsulfanyl]-butyric acid;
4-(3'-phenoxy-biphenyl-4-ylsulfanyl)-butyric acid;
4-(3'-cyclopentyloxy-biphenyl-4-ylsulfanyl)-butyric acid;
4-(3'-propoxy-biphenyl-4-ylsulfanyl)-butyric acid;
4-[4-(6-cyclobutoxy-pyridin-2-yl)-phenylsulfanyl]-butyric acid;
4-[4-(6-cyclopentyloxy-pyridin-2-yl)-phenylsulfanyl]-butyric acid;
4-[4-(6-isopropoxy-pyridin-2-yl)-phenylsulfanyl]-butyric acid;

4-[4-(2-isopropoxy-pyridin-3-yl)-phenylsulfanyl]-butyric acid;
4-[4-(6-propoxy-pyridin-2-yl)-phenylsulfanyl]-butyric acid;
4-[4-(6-cyclopentylsulfanyl-pyridin-2-yl)-phenylsulfanyl]-butyric acid;
4-(3'-cyclobutoxy-3,5-difluoro-biphenyl-4-ylsulfanyl)-butyric acid;
4-(3,5-difluoro-3'-isopropoxy-biphenyl-4-ylsulfanyl)-butyric acid;
4-[2,6-difluoro-4-(6-propoxy-pyridin-2-yl)-phenylsulfanyl]-butyric acid;
4-[2,6-difluoro-4-(6-isopropoxy-pyridin-2-yl)-phenylsulfanyl]-butyric acid;
4-[2,6-difluoro-4-(2-isopropoxy-pyridin-3-yl)-phenylsulfanyl]-butyric acid;
4-[2,6-difluoro-4-(2-propoxy-pyridin-3-yl)-phenylsulfanyl]-butyric acid;
4-[2,6-difluoro-4-(6-isopropylsulfanyl-pyridin-2-yl)-phenylsulfanyl]-butyric acid;
4-[2,6-difluoro-4-(6-propylsulfanyl-pyridin-2-yl)-phenylsulfanyl]-butyric acid;
4-[4-(2-cyclobutylsulfanyl-pyridin-3-yl)-2,6-difluoro-phenylsulfanyl]-butyric acid;
4-[4-(2-cyclobutoxy-pyridin-3-yl)-phenylsulfanyl]-butyric acid;
4-[4-(2-cyclobutoxy-pyridin-3-yl)-2,6-difluoro-phenylsulfanyl]-butyric acid;
4-[4-(2-cyclopentyloxy-pyridin-3-yl)-2,6-difluoro-phenylsulfanyl]-butyric acid;
4-[2,6-difluoro-4-(2-isopropylsulfanyl-pyridin-3-yl)-phenylsulfanyl]-butyric acid;
4-[4-(2-cyclopentylsulfanyl-pyridin-3-yl)-2,6-difluoro-phenylsulfanyl]-butyric acid;
4-[4-(2-isopropylsulfanyl-pyridin-3-yl)-phenylsulfanyl]-butyric acid;
4-[4-(2-cyclopentylsulfanyl-pyridin-3-yl)-phenylsulfanyl]-butyric acid;
4-[2-fluoro-4-(6-isopropoxy-pyridin-2-yl)-phenylsulfanyl]-butyric acid;
4-[4-(2-cyclopentyloxy-pyridin-3-yl)-2-fluoro-phenylsulfanyl]-butyric acid;
4-[4-(2-cyclobutylsulfanyl-pyridin-3-yl)-2-fluoro-phenylsulfanyl]-butyric acid;
4-[4-(2-cyclobutylsulfanyl-pyridin-3-yl)-phenylsulfanyl]-butyric acid;
4-[4-(6-cyclobutoxy-pyridin-2-yl)-2,6-difluoro-phenylsulfanyl]-butyric acid;
4-[4-(6-cyclopentyloxy-pyridin-2-yl)-2,6-difluoro-phenylsulfanyl]-butyric acid;
4-[4-(6-cyclobutylsulfanyl-pyridin-2-yl)-phenylsulfanyl]-butyric acid;
4-[4-(6-cyclopropylmethoxy-pyridin-2-yl)-2,6-difluoro-phenylsulfanyl]-butyric acid;
4-[4-(6-cyclobutylsulfanyl-pyridin-2-yl)-2,6-difluoro-phenylsulfanyl]-butyric acid;
4-[4-(6-cyclopentylsulfanyl-pyridin-2-yl)-2,6-difluoro-phenylsulfanyl]-butyric acid;
4-(2'-cyclopentylamino-3-fluoro-biphenyl-4-ylsulfanyl)-butyric acid;
4-(2'-cyclopentylamino-3,5-difluoro-biphenyl-4-ylsulfanyl)-butyric acid;
4-[2'-(cyclopropylmethyl-amino)-3,5-difluoro-biphenyl-4-ylsulfanyl]-butyric acid;
4-[2-fluoro-4-(2-isopropylsulfanyl-pyridin-3-yl)-phenylsulfanyl]-butyric acid;
4-[4-(2-cyclopentylsulfanyl-pyridin-3-yl)-2-fluoro-phenylsulfanyl]-butyric acid;
4-(3,5-difluoro-2'-isopropylamino-biphenyl-4-ylsulfanyl)-butyric acid;
4-(3,5-difluoro-2'-propylamino-biphenyl-4-ylsulfanyl)-butyric acid;
4-[4-(2-cyclopropylmethoxy-pyridin-3-yl)-2,6-difluoro-phenylsulfanyl]-butyric acid;
4-[2,6-difluoro-4-(2-propylsulfanyl-pyridin-3-yl)-phenylsulfanyl]-butyric acid;
4-[4-(6-cyclobutylsulfanyl-pyridin-2-yl)-2-fluoro-phenylsulfanyl]-butyric acid;
4-[4-(2-cyclopentylamino-pyridin-3-yl)-2-fluoro-phenylsulfanyl]-butyric acid;
4-[2-fluoro-4-(2-isopropoxy-pyridin-3-yl)-phenylsulfanyl]-butyric acid;
4-[4-(2-cyclobutoxy-pyridin-3-yl)-2-fluoro-phenylsulfanyl]-butyric acid;
4-[2-fluoro-4-(2-pyrrolidin-1-yl-pyridin-3-yl)-phenylsulfanyl]-butyric acid;
4-[2-fluoro-4-(2-isopropylamino-pyridin-3-yl)-phenylsulfanyl]-butyric acid;
4-(2'-cyclopentylamino-3,5'-difluoro-biphenyl-4-ylsulfanyl)-butyric acid;
4-(2'-cyclopentylamino-5'-fluoro-biphenyl-4-ylsulfanyl)-butyric acid;
4-(2'-cyclopentyloxy-5'-methyl-biphenyl-4-ylsulfanyl)-butyric acid;
4-(2'-cyclopentyloxy-4'-methoxy-biphenyl-4-ylsulfanyl)-butyric acid;
4-(2'-cyclopentyloxy-5'-fluoro-biphenyl-4-ylsulfanyl)-butyric acid;
4-(2'-cyclopentyloxy-3,5-difluoro-biphenyl-4-ylsulfanyl)-butyric acid;
4-[4-(2-cyclopentyloxy-5-methyl-pyridin-3-yl)-phenylsulfanyl]-butyric acid;
4-(2'-cyclopentyloxy-3,5,5'-trifluoro-biphenyl-4-ylsulfanyl)-butyric acid;
4-(2'-cyclopentyloxy-3-fluoro-4'-methoxy-biphenyl-4-ylsulfanyl)-butyric acid;
4-(2'-cyclopentyloxy-3,5-difluoro-4'-methoxy-biphenyl-4-ylsulfanyl)-butyric acid;
4-(3-fluoro-2'-isopropoxy-4'-methoxy-biphenyl-4-ylsulfanyl)-butyric acid;
4-[4-(2-cyclopentyloxy-5-methyl-pyridin-3-yl)-2-fluoro-phenylsulfanyl]-butyric acid;
4-[2-fluoro-4-(2-isopropoxy-5-methyl-pyridin-3-yl)-phenylsulfanyl]-butyric acid;
4-(3,5'-difluoro-2'-isopropoxy-biphenyl-4-ylsulfanyl)-butyric acid;
4-[4-(2-cyclopentyloxy-6-methyl-pyridin-3-yl)-2-fluoro-phenylsulfanyl]-butyric acid;
4-(3,3'-difluoro-2'-isopropoxy-5'-methyl-biphenyl-4-ylsulfanyl)-butyric acid;
4-(3,3'-difluoro-5'-methyl-2'-propoxy-biphenyl-4-ylsulfanyl)-butyric acid;
4-(3-fluoro-2',4'-dipropoxy-biphenyl-4-ylsulfanyl)-butyric acid;
4-(6'-cyclopentyloxy-3,2'-difluoro-3'-methyl-biphenyl-4-ylsulfanyl)-butyric acid;
4-(2'-cyclopentyloxy-3,3'-difluoro-biphenyl-4-ylsulfanyl)-butyric acid;
4-(2'-cyclopentyloxy-3,3'-difluoro-5'-methyl-biphenyl-4-ylsulfanyl)-butyric acid;
5-[4-(2-cyclobutylmethoxy-pyridin-3-yl)-2,6-difluoro-phenoxy]-pentanoic acid;

5-[4-(2-cyclopropoxy-pyridin-3-yl)-2,6-difluoro-phenoxy]-pentanoic acid;
4-[4-(2-cyclopentyloxy-5-methyl-pyridin-3-yl)-2,6-difluoro-phenylsulfanyl]-butyric acid;
4-[4-(2-cyclopentyloxy-pyridin-3-yl)-phenylsulfanyl]-pentanoic acid;
4-[4-(2-isopropoxy-pyridin-3-yl)-phenylsulfanyl]-pentanoic acid;
4-[4-(2-cyclopentyloxy-pyridin-3-yl)-2,6-difluoro-phenylsulfanyl]-pentanoic acid;
4-[4-(2-cyclopentylsulfanyl-pyridin-3-yl)-2,6-difluoro-phenylsulfanyl]-pentanoic acid;
4-[4-[2-(2-dimethylaminoethyloxy)-3-pyridyl]-2,6-difluoro-phenoxy]butanoic acid;
4-[2,6-difluoro-4-(2-propylsulfanyl-pyridin-3-yl)-phenoxy]-butanoic acid;
4-[4-(2-cyclopropylsulfanyl-pyridin-3-yl)-2,6-difluoro-phenoxy]-butanoic acid;
4-[4-(2-ethylsulfanyl-pyridin-3-yl)-2,6-difluoro-phenoxy]-butanoic acid;
4-[4-(2-butylsulfanyl-pyridin-3-yl)-2,6-difluoro-phenoxy]-butanoic acid;
4-(2'-cyclopentylamino-biphenyl-4-ylsulfanyl)-butyric acid;
4-[4-(2-cyclopentyloxy-5-methyl-pyridin-3-yl)-2,6-difluoro-phenoxy]-butyric acid;
4-[4-(6-isopropylsulfanyl-2-pyridyl)phenoxy]butanoic acid;
4-[2,6-difluoro-4-(3-phenoxyphenyl)phenoxy]butanoic acid;
4-[4-[6-[3-(dimethylamino)pyrrolidin-1-yl]-2-pyridyl]-2,6-difluoro-phenoxy]butanoic acid;
5-[2,6-difluoro-4-(2-isopropoxy-pyridin-3-yl)-phenoxy]-pentanoic acid
5-[4-(2-cyclobutoxy-pyridin-3-yl)-2,6-difluoro-phenoxy]-pentanoic acid
4-[4-[2-(3,3-difluoropyrrolidin-1-yl)-3-pyridyl]-2,6-difluoro-phenoxy]butanoic acid;
4-[2,6-difluoro-4-[2-(4-methylpiperazin-1-yl)-3-pyridyl]phenoxy]butanoic acid;
4-[2,6-difluoro-4-[2-(5-methylisoxazol-3-yl)oxy-3-pyridyl]phenoxy]butanoic acid;
4-[4-[2-[2-(aziridin-1-yl)ethoxy]-3-pyridyl]-2,6-difluoro-phenoxy]butanoic acid;
4-[2,6-difluoro-4-[2-(3-furylmethoxy)-3-pyridyl]phenoxy]butanoic acid;
4-[2,6-difluoro-4-[2-(2-furylmethoxy)-3-pyridyl]phenoxy]butanoic acid;
4-[2,6-difluoro-4-[2-[(3-methyloxetan-3-yl)methoxy]-3-pyridyl]phenoxy]butanoic acid;
4-[2,6-difluoro-4-[2-(tetrahydrofuran-3-ylmethoxy)-3-pyridyl]phenoxy]butanoic acid;
4-[2,6-difluoro-4-[2-(tetrahydrofuran-2-ylmethoxy)-3-pyridyl]phenoxy]butanoic acid;
4-[4-(2-cyclobutylmethoxy-pyridin-3-yl)-2,6-difluoro-phenoxy]-butyric acid;
4-[4-(2-cyclopropoxy-pyridin-3-yl)-2,6-difluoro-phenoxy]-butyric acid;
4-(4-{2-[3-(tert-butyl-dimethyl-silanyloxy)-cyclopentyloxy]-pyridin-3-yl}-2,6-difluoro-phenoxy)-butyric acid;
4-{2,6-difluoro-4-[2-(3-hydroxy-cyclopentyloxy)-pyridin-3-yl]-phenoxy}-butyric acid;
4-[4-(2-cyclohexyloxy-pyridin-3-yl)-2,6-difluoro-phenoxy]-butyric acid;
4-[4-(2-cyclopentylmethoxy-pyridin-3-yl)-2,6-difluoro-phenoxy]-butyric acid;
4-[2,6-difluoro-4-(2-isobutoxy-pyridin-3-yl)-phenoxy]-butyric acid;
4-{4-[2-(2,2-dimethy-propoxy)-pyridin-3-yl]-2,6-difluoro-phenoxy}-butyric acid;
5-[4-(2-cyclopentyloxy-pyridin-3-yl)-2,6-difluoro-phenoxy]-pentanoic acid;
5-[4-(2-cyclobutylsulfanyl-3-pyridyl)-2,6-difluoro-phenoxy]pentanoic acid;
5-[4-(2-cyclopentylsulfanyl-3-pyridyl)-2,6-difluoro-phenoxy]pentanoic acid;
5-[2,6-difluoro-4-(2-isopropylsulfanyl-3-pyridyl)phenoxy]pentanoic acid;
5-[2,6-difluoro-4-(2-propylsulfanyl-3-pyridyl)phenoxy]pentanoic acid;
5-[2,6-difluoro-4-(6-isopropylsulfanyl-2-pyridyl)phenoxy]pentanoic acid;
5-[2,6-difluoro-4-(6-isopropoxy-2-pyridyl)phenoxy]pentanoic acid;
5-[4-[2-(cyclopropylmethoxy)-3-pyridyl]-2,6-difluoro-phenoxy]pentanoic acid;
5-[2,6-difluoro-4-(2-tetrahydrofuran-3-yloxy-3-pyridyl)phenoxy]pentanoic acid;
5-[2,6-difluoro-4-(2-tetrahydropyran-4-yloxy-3-pyridyl)phenoxy]pentanoic acid;
4-[2,6-difluoro-4-(2-isopropoxy-pyridin-3-yl)-phenylsulfanyl]-pentanoic acid;
4-[4-(2-cyclopentylsulfanyl-pyridin-3-yl)-phenylsulfanyl]-pentanoic acid;
4-{2-fluoro-4-[2-(tetrahydro-pyran-4-yloxy)-pyridin-3-yl]-phenylsulfanyl}-butyric acid;
4-{2-fluoro-4-[2-(tetrahydrofuran-3-yloxy)-pyridin-3-yl]-phenylsulfanyl}-butyric acid;
4-[4-(2-cyclobutylmethoxy-pyridin-3-yl)-2-fluoro-phenylsulfanyl]-butyric acid;
4-{2,6-difluoro-4-[2-(2,2,2-trifluoro-ethoxy)-pyridin-3-yl]-phenylsulfanyl}-butyric acid;
4-[4-(2-cyclobutylmethoxy-pyridin-3-yl)-2,6-difluoro-phenylsulfanyl]-butyric acid;
4-[4-(2-cyclopentylamino-pyridin-3-yl)-2,6-difluoro-phenylsulfanyl]-butyric acid;
4-[2,6-difluoro-4-(2-isopropylamino-pyridin-3-yl)-phenylsulfanyl]-butyric acid;
4-{4-[2-(cyclopropylmethyl-amino)-pyridin-3-yl]-2,6-difluoro-phenylsulfanyl}-butyric acid;
5-[4-(2-cyclopentyloxy-pyridin-3-yl)-2,6-difluoro-phenylsulfanyl]-pentanoic acid;
5-[2,6-difluoro-4-(2-isopropoxy-pyridin-3-yl)-phenylsulfanyl]-pentanoic acid;
5-[4-(2-cyclopentyloxy-pyridin-3-yl)-phenylsulfanyl]-pentanoic acid;
5-[4-(2-isopropoxy-pyridin-3-yl)-phenylsulfanyl]-pentanoic acid;
5-[4-(2-cyclopentylsulfanyl-pyridin-3-yl)-2,6-difluoro-phenylsulfanyl]-pentanoic acid;
5-[2,6-difluoro-4-(2-propylsulfanyl-pyridin-3-yl)-phenylsulfanyl]-pentanoic acid;
5-[4-(2-cyclopentylsulfanyl-pyridin-3-yl)-phenylsulfanyl]-pentanoic acid;
5-[4-(2-cyclobutylsulfanyl-pyridin-3-yl)-phenylsulfanyl]-pentanoic acid;
5-[4-(2-cyclobutylmethoxy-pyridin-3-yl)-2,6-difluoro-phenylsulfanyl]-pentanoic acid;
5-[4-(2-cyclobutoxy-pyridin-3-yl)-2,6-difluoro-phenylsulfanyl]-pentanoic acid;
6-[4-(2-cyclopentyloxy-pyridin-3-yl)-2,6-difluoro-phenoxy]-hexanoic acid;

7-[4-(2-cyclopentyloxy-pyridin-3-yl)-2,6-difluoro-phenoxy]-heptanoic acid;
5-[2-fluoro-4-(2-isopropoxy-pyridin-3-yl)-phenoxy]-pentanoic acid;
5-[4-(2-cyclopentylsulfanyl-pyridin-3-yl)-2-fluoro-phenoxy]-pentanoic acid;
5-[4-(2-cyclobutylsulfanyl-pyridin-3-yl)-2-fluoro-phenoxy]-pentanoic acid;
5-[4-(2-cyclopentyloxy-pyridin-3-yl)-2-fluoro-phenoxy]-pentanoic acid;
4-[2,6-difluoro-4-(2-methoxy-pyridin-3-yl)-phenoxy]-butyric acid;
4-[4-(2-allyloxy-pyridin-3-yl)-2,6-difluoro-phenoxy]-butyric acid;
4-[4-(2-but-2-ynyloxy-pyridin-3-yl)-2,6-difluoro-phenoxy]-butyric acid;
6-[4-[2-(cyclobutoxy)-3-pyridyl]-2,6-difluoro-phenoxy] hexanoic acid;
6-[4-[2-(cyclobutylmethoxy)-3-pyridyl]-2,6-difluoro-phenoxy]hexanoic acid;
6-[4-[2-(cyclopropylmethoxy)-3-pyridyl]-2,6-difluoro-phenoxy]hexanoic acid;
6-[4-(2-cyclobutylsulfanyl-3-pyridyl)-2,6-difluoro-phenoxy]hexanoic acid;
6-[4-(2-cyclopentylsulfanyl-3-pyridyl)-2,6-difluoro-phenoxy]hexanoic acid;
6-[4-(2-cyclopentyloxy-pyridin-3-yl)-2,6-difluoro-phenylsulfanyl]-hexanoic acid;
6-[4-(2-cyclopentylsulfanyl-pyridin-3-yl)-2,6-difluoro-phenylsulfanyl]-hexanoic acid;
6-[4-(2-cyclobutylsulfanyl-pyridin-3-yl)-2,6-difluoro-phenylsulfanyl]-hexanoic acid; and
6-[2,6-difluoro-4-(2-propylsulfanyl-pyridin-3-yl)-phenylsulfanyl]-hexanoic acid, and
wherein the isomer is at least one selected from the group consisting of an E-isomer, Z-isomer, R-isomer, S-isomer, racemic mixture and a diastereoisomer mixture.

3. A pharmaceutical composition as GPR120 agonists, comprising the biaryl derivative, pharmaceutically acceptable salt or isomer thereof according to claim 1 and a pharmaceutically acceptable carrier.

4. A pharmaceutical composition for treating diabetes, complications of diabetes, obesity, non-alcoholic fatty liver, steatohepatitis, osteoporosis or inflammation, comprising the biaryl derivative, pharmaceutically acceptable salt or isomer thereof according to claim 1 and a pharmaceutically acceptable carrier.

5. A composition for lowering blood glucose level, comprising the biaryl derivative, pharmaceutically acceptable salt or isomer thereof according to claim 1 and a pharmaceutically acceptable carrier.

6. A method for preparing a composition for treating diabetes, complications of diabetes, obesity, non-alcoholic fatty liver, steatohepatitis, osteoporosis or inflammation, which comprises the step of mixing the biaryl derivative, pharmaceutically acceptable salt or isomer thereof according to claim 1 with a pharmaceutically acceptable carrier.

7. A pharmaceutical composition as GPR120 agonists, comprising the biaryl derivative, pharmaceutically acceptable salt or isomer thereof according to claim 2 and a pharmaceutically acceptable carrier.

8. A pharmaceutical composition for treating diabetes, complications of diabetes, obesity, non-alcoholic fatty liver, steatohepatitis, osteoporosis or inflammation, comprising the biaryl derivative, pharmaceutically acceptable salt or isomer thereof according to claim 2 and a pharmaceutically acceptable carrier.

9. A composition for lowering blood glucose level, comprising the biaryl derivative, pharmaceutically acceptable salt or isomer thereof according to claim 2 and a pharmaceutically acceptable carrier.

10. A method for preparing a composition for treating diabetes, complications of diabetes, obesity, non-alcoholic fatty liver, steatohepatitis, osteoporosis or inflammation, which comprises the step of mixing the biaryl derivative, pharmaceutically acceptable salt or isomer thereof according to claim 2 with a pharmaceutically acceptable carrier.

* * * * *